(12) United States Patent
Frohlich et al.

(10) Patent No.: US 11,491,137 B2
(45) Date of Patent: Nov. 8, 2022

(54) METHODS OF IMPROVING RENAL FUNCTION

(71) Applicant: Chinook Therapeutics, Inc., Seattle, WA (US)

(72) Inventors: Philip Thomas Frohlich, Vancouver (CA); Andrew James King, Dublin, CA (US); Chidambaram Ramachandran, Vancouver (CA); Sarah Beth Noonberg, Seattle, WA (US)

(73) Assignee: Chinook Therapeutics, Inc., Seattle, WA (US)

( * ) Notice: Subject to any disclaimer, the term of this patent is extended or adjusted under 35 U.S.C. 154(b) by 0 days.

(21) Appl. No.: 17/826,843

(22) Filed: May 27, 2022

(65) Prior Publication Data

US 2022/0288027 A1    Sep. 15, 2022

Related U.S. Application Data

(63) Continuation of application No. PCT/US2020/065311, filed on Dec. 16, 2020.

(60) Provisional application No. 63/125,205, filed on Dec. 14, 2020, provisional application No. 63/084,739, filed on Sep. 29, 2020, provisional application No. 63/072,699, filed on Aug. 31, 2020, provisional application No. 63/005,003, filed on Apr. 3, 2020, provisional application No. 62/949,115, filed on Dec. 17, 2019.

(51) Int. Cl.
| | | |
|---|---|---|
| *A61K 31/41* | (2006.01) | |
| *A61P 31/12* | (2006.01) | |
| *A61K 31/4025* | (2006.01) | |
| *A61P 13/12* | (2006.01) | |
| *A61K 45/06* | (2006.01) | |
| *A61P 7/12* | (2006.01) | |

(52) U.S. Cl.
CPC .......... *A61K 31/4025* (2013.01); *A61K 45/06* (2013.01); *A61P 7/12* (2018.01); *A61P 13/12* (2018.01); *A61K 31/41* (2013.01)

(58) Field of Classification Search
CPC ................................ A61K 31/41; A61P 31/12
USPC ........................................................ 514/422
See application file for complete search history.

(56) References Cited

U.S. PATENT DOCUMENTS

| | | | |
|---|---|---|---|
| 5,236,940 A | 8/1993 | Audiau et al. | |
| 6,946,481 B1 | 9/2005 | Winn et al. | |
| 7,208,517 B1 | 4/2007 | Winn et al. | |
| 7,365,093 B2 | 4/2008 | Winn et al. | |
| 8,623,819 B2 | 1/2014 | Roden et al. | |
| 8,865,650 B2 | 10/2014 | Roden et al. | |
| 8,962,675 B1 | 2/2015 | Gong et al. | |
| 9,051,301 B2 | 6/2015 | Zhang | |
| 9,255,931 B2 | 2/2016 | Newman et al. | |
| 9,364,458 B2 | 6/2016 | Huang et al. | |
| 9,365,445 B2 | 6/2016 | Wada et al. | |
| 9,592,231 B2 | 3/2017 | Roden et al. | |
| 9,637,476 B2 | 5/2017 | Gong et al. | |
| 9,855,245 B2 | 1/2018 | Coll Crespo et al. | |
| 10,016,393 B2 | 7/2018 | Huang et al. | |
| 2016/0015701 A1 | 1/2016 | Andress et al. | |
| 2016/0128980 A1 | 5/2016 | Kohan et al. | |
| 2017/0014386 A1 | 1/2017 | Brennan et al. | |
| 2017/0079978 A1 | 3/2017 | Roden et al. | |
| 2017/0190692 A1 | 7/2017 | Gong et al. | |
| 2018/0140587 A1 | 5/2018 | Miao et al. | |
| 2019/0262317 A1 | 8/2019 | Komers et al. | |
| 2021/0247406 A1 | 8/2021 | Newman et al. | |

FOREIGN PATENT DOCUMENTS

| | | |
|---|---|---|
| CN | 101454018 | 6/2009 |
| CN | 105324395 | 2/2016 |
| CN | 110049764 | 7/2019 |
| WO | WO 1997/030045 | 8/1997 |
| WO | WO 2006/034084 | 3/2006 |
| WO | WO 2006/034085 | 3/2006 |
| WO | WO 2006/034094 | 3/2006 |
| WO | WO 2006/034234 | 3/2006 |
| WO | WO 2011/070049 | 6/2011 |
| WO | WO 2011/163085 | 12/2011 |
| WO | WO 2018/071784 | 4/2018 |
| WO | WO 2019/075086 | 4/2019 |
| WO | WO 2019/106066 | 6/2019 |
| WO | WO 2021/207723 | 10/2021 |

OTHER PUBLICATIONS

ADA, "Improving Care and Promoting Health in Populations: Standards of Medical Care in Diabetes," Diabetes Care, Jan. 2019, 42(1):S7-S12.

ADA, "Summary of Revisions: Standards of Medical Care in Diabetes," Diabetes Care, Jan. 2020, 43(1):S4-S6.

Afkarian et al., "Kidney disease and increased mortality risk in type 2 diabetes," J Am Soc Nephrol, Feb. 2013, 24(2):302-308.

Akilesh et al., "Arhgap24 inactivates Rac1 in mouse podocytes, and a mutant form is associated with familial focal segmental glomerulosclerosis," The Journal of Clinical Investigation, Oct. 2011, 121(10):4127-4137.

Alicic et al, "Diabetic Kidney Disease: Challenges, Progress, and Possibilities," Clin J Am Soc Nephrol, Dec. 2017, 12(12):2032-2045.

(Continued)

*Primary Examiner* — Raymond J Henley, III

(74) *Attorney, Agent, or Firm* — Fish & Richardson P.C.

(57) ABSTRACT

Provided herein are methods of improving kidney function in a subject in need thereof.

30 Claims, 20 Drawing Sheets

(56) References Cited

OTHER PUBLICATIONS

Anguiano et al., "Endothelin blockade in diabetic kidney disease," J. or Clin. Med., 2015, 4:1171-1192.
Barratt et al., "IgA nephropathy," J Am Soc Nephrol, Jul. 2005, 16(7):2088-2097.
Barton et al., "Endothelin: 20 years from discovery to therapy," Review/Synthese, 2008, 867/7/2021485-498.
Bartram et al., "Three-layered proteomic characterization of a novel ACTN4 mutation unravels its pathogenic potential in FSGS," Human Molecular Genetics, Jan. 5, 2016, 25(6):1152-1164.
Barua et al., "Mutations in PAX2 Associate with Adult-Onset FSGS," J Am Soc Nephrol, Sep. 2014, 25:1942-1953.
Battistini et al., "Profile of past and current clinical trials Involving endothelin receptor antagonists: The novel "—Sentan" class drug," Exp. Biol. Med., 2006, 231:6:653-695.
Boute et al., "NPHS2, encoding the glomerular protein podocin, is mutated in autosomal recessive steroid-resistant nephrotic syndrome," Nat Genet., Apr. 2000, 24(4):349-354.
Boyer et al., "LMX1B Mutations Cause Hereditary FSGS without Extrarenal Involvement," J Am Soc Nephrol, Aug. 2013, 24:1216-1222.
Boyer et al., "Mutational analysis of the PLCE1 gene in steroid resistant nephrotic syndrome," Journal of Medical Genetics, Jul. 2010, 47(7):445-452.
Boyer et al., "Mutations in INF2 Are a Major Cause of Autosomal Dominant Focal Segmental Glomerulosclerosis," J Am Soc Nephrol, Feb. 2011, 22:239-245.
Breyer et al., "The next generation of therapeutics for chronic kidney disease," Nat. Rev. Drug Discov., 2016, 15(8):568-588.
Brown et al., "Mutations in the formin protein INF2 cause focal segmental glomerulosclerosis," Nat Genet., Jan. 2010, 42(1):72-76.
Cahn et al., "The SONAR study is there a future for endothelin receptor antagonists in diabetic kidney disease," Annals of Trans Med., Dec. 2019, 7:1-5.
canada.ca [online], "Management of clinical trials during the COVID-19 pandemic: Notice to clinical trial sponsors," updated on Mar. 2, 2022, retrieved on May 13, 2022, retrieved from URL<https://www.canada.ca/en/health-canada/services/drugs-health-products/drug-products/announcements/management-clinical-trials-during-covid-19-pandemic.html>, 12 pages.
Canney et al., "Quantifying Duration of Proteinuria Remission and Association with Clinical Outcome in IgA Nephropathy," J Am Soc Nephrol, Feb. 2021, 32(2):436-447.
Caridi et al., "Prevalence, genetics, and clinical features of patients carrying podocin mutations in steroid-resistant nonfanrilial focal segmental glomerulosclerosis," J Am Soc Nephrol., Dec. 2001, 12(12):2742-2746.
Chou et al., "Quantitative analysis of dose-effect relationships: the combined effects of multiple drugs or enzyme inhibitors," Advances in Enzyme Regulation, 1984, 22:27-55.
Cravedi et al., "Recent progress in the pathophysiology and treatment of FSGS recurrence," Am J Transplant, 2013, 13(2):266-274.
Daneshpajouhnejad et al., "The evolving story of apolipoprotein L1 nephropathy: the end of the beginning," Nature Reviews, May 2022, 18:307-320.
Dattani et al., "Secondary glomerular disease," Medicine, 47(10), Oct. 2019, 644-648, 5 pages.
Davenport et al., "Endothelin," Pharmacol. Rev., Apr. 2016, 68(2):357-418.
De Vriese et al., "Differentiating Primary, Genetic, and Secondary FSGS in Adults: A Clinicopathologic Approach," Journal of the American Society of Nephrology, Mar. 2018, 29(3):759-774.
De Zeeuw et al., "The endothelin antagonist atrasentan lowers residual albuminuria in patients with type 2 diabetic nephropathy," J Am Soc Nephrol, May 2014, 25(5):1083-1093.
Dhaun et al., "Endothelin-1 and the kidney—beyond BP," British journal of pharmacology, Jun. 6, 2012, 167(4):720-731.
Dhaun et al., "Selective endothelin-A receptor antagonism reduces proteinuria, blood pressure, and arterial stiffness in chronic proteinuric kidney disease," Hypertension, Apr. 2011, 57(4):772-779, 11 pages.
Dufek et al., "Endothelin A receptor activation on mesangial cells initiates Alport glomerular disease," Kidney Int, Aug. 2016, 90(2):300-310.
Dummer et al., "APOL1 Kidney Disease Risk Variants: An Evolving Landscape," Semin Nephrol, May 2015, 35(3): 222-236.
Duru et al., "The Landscape of Diabetic Kidney Disease in the United States," Curr Diab Rep, Feb. 19, 2018, 18(3):14.
Ebarasi et al., "Defects of CRB2 Cause Steroid-Resistant Nephrotic Syndrome," The American Journal of Human Genetics, Jan. 8, 2015, 96:153-161.
EMA (Apr. 2020). Guidance on the management of clinical trials during the COVID-19 (Coronavirus) pandemic, version 5, Oct. 2, 2022, 22 pages.
fda.gov [online], "Conduct of Clinical Trials of Medical Products during COVID-19 Public Health Emergency—Guidance for Industry, Investigators and Institutional Review Boards," updated on Aug. 30, 2021, retrieved on May 13, 2022, retrieved from URL<https://www.fda.gov/media/136238/download>, 39 pages.
Fizazi et al., "Phase III, randomized, placebo-controlled study of docetaxel in combination with zibotentan in patients with metastatic castration-resistant prostate cancer," J. Clin. Oncol., May 2013, 31(14):1740-1747, 10 pages.
Freireich et al., "Quantitative comparison of toxicity of anticancer agents in mouse, rat, hamster, dog, monkey, and man," Cancer Chemother. Rep., May 1966, 50(4):219-244.
Funk et al., "Alport syndrome and Pierson syndrome: Diseases of the glomerular basement membrane," Matrix Biol, Oct. 2018, 71-72:250-261.
Galie et al., "Liver toxicity of sitaxentan in pulmonary arterial hypertension," Eur. Resp. J., Feb. 2011, 37(2):475-477.
Galla, "IgA nephropathy," Kidney Int, Feb. 1995, 47(2):377-387.
Gbadegesin et al., "Mutations in the Gene That Encodes the F-Actin Binding Protein Anillin Cause FSGS," J Am Soc Nephrol, Sep. 2014, 25:1991-2002.
Geddes et al., "A tricontinental view of IgA nephropathy," Nephrol Dial Transplant, Aug. 2003, 18(8):1541-1548.
GenBank Acession No. M95549, "*Homo sapiens* sodium/glucose cotransporter-like protein mRNA, complete cds," Aug. 3, 1993, 2 pages.
Genovese et al., "Association of Trypanolytic ApoL1 Variants with Kidney Disease in African-Americans," Aug. 13, 2010; 329(5993): 841-845.
Girgis et al., "Selective endothelin A receptor antagonism with sitaxsentan for pulmonary arterial hypertension associated with connective tissue disease," Ann Rheum Dis., Nov. 2007, 66(11):1467-1472.
Goodard et al., "Endothelin-A receptor antagonism reduces blood pressure and increases renal blood flow in hypertensive patients with chronic renal failure: a comparison of selective and combined endothelin receptor blockade," Circulation, 2004, 109(9): 1186-93.
gov.uk [online], "Guidance: Managing clinical trials during Coronavirus (COVID-19)," last updated Nov. 16, 2021, retrieved on May 16, 2022, retrieved from URL<https://www.gov.uk/guidance/managing-clinical-trials-during-coronavirus-covid-19>, 14 pages.
Hall et al., "A Novel Missense Mutation of Wilms' Tumor 1 Causes Autosomal Dominant FSGS," J Am Soc Nephrol, Apr. 2015, 26:831-843.
Hall et al., "Dysregulation of WTI (—KTS) is Associated with the Kidney-Specific Effects of the LMX1B R246Q Mutation," Scientific Reports, Jan. 6, 2017, 7:39933, 9 pages.
Hasselbacher et al., "Recessive missense mutations in LAMB2 expand the clinical spectrum of LAMB2-associated disorders," Kidney International, Aug. 16, 2006, 70:1008-1012.
health.gov.au [online], "COVID-19: Guidance on clinical trials for institutions, HRECs, researchers and sponsors," Apr. 9, 2020, retrieved on May 13, 2022, retrieved from URL<https://www1.health.gov.au/internet/main/publishing.nsf/Content/Clinical-Trials>, 11 pages.

(56) References Cited

OTHER PUBLICATIONS

Heeringa et al., "COQ6 mutations in human patients produce nephrotic syndrome with sensorineural deafness," The Journal of Clinical Investigation, May 2011, 121(5):2013-2024.

Heerspink et al., "Atrasentan and renal events in patients with type 2 diabetes and chronic kidney disease (SONAR): a double-blind, randomised, placebo-controlled trial," The Lancet, May 2019, 393(10184):1937-1947, 11 pages.

Heerspink et al., "Baseline characteristics and enrichment results from the SONAR trial," Diabetes Obes Metab., Aug. 2018, 20(8):1829-1835.

Heerspink et al., "Comparison of exposure response relationship of atrasentan between North American and Asian populations," Diabetes, Obesity and Metabolism, Apr. 2017, 19(4):545-552.

Heerspink et al., "Rationale and protocol of the Study of diabetic Nephropathy with AtRasentan (SONAR) trial: A clinical trial design novel to diabetic nephropathy," Diabetes Obes. Metab., Jun. 2018, 20:6:1369-1376.

Heerspink et al., "Sodium Glucose Cotransporter 2 Inhibitors in the Treatment of Diabetes Mellitus: Cardiovascular and Kidney Effects, Potential Mechanisms, and Clinical Applications," Circulation, Sep. 6, 2016, 134(10):752-772.

Hesselink et al., "Genetic polymorphisms of the CYP3A4, CYP3A5, and MDR-1 genes and pharmacokinetics of the calcineurin inhibitors cyclosporine and tacrolimus," Clin Pharmacol Ther, Sep. 17, 2003, 74(3):245-254.

Hinkes et al., "Positional cloning uncovers mutations in PLCE1 responsible for a nephrotic syndrome variant that may be reversible," Nat Genet., Dec. 2006, 38(12):1397-1405.

Hoekman et al., "Predictors of congestive heart failure after treatment with an endothelin receptor antagonist," Clin J Am Soc Nephrol, Mar. 2014, 9(3):490-498.

Ieiri et al., "Genetic polymorphisms of uptake (OATP1B1, 1B3) and efflux (MRP2, BCRP) transporters: implications for inter-individual differences in the pharmacokinetics and pharmacodynamics of statins and other clinically relevant drugs," Expert Opin Dmg Metab Toxicol, May 15, 2009, 5(7):703-729.

International Search Report and Written Opinion in Appln. No. PCT/US2021/026803, dated Nov. 9, 2021, 13 pages.

Isojima et al., "LMX1B mutation with residual transcriptional activity as a cause of isolated glomerulopathy," Nephrol Dial Transplant, Jan. 2014, 29(1):81-88.

Jandeleit-Dahm et al., "The endothelin system and endothelin receptor antagonists," Curr. Opin. Nephrol. Hypertens., 2012, 21:1:66-71.

Jefferson et al., "The pathogenesis of focal segmental glomerulosclerosis," Adv Chronic Kidney Dis, Sep. 2014, 21(5):408-416.

Jin et al., "Cytochrome P450 3A5 genotype is associated with verapamil response in healthy subjects," Clin Pharmacol Ther, Nov. 2007, 82(5):579-585.

Kaplan et al., "Mutations in ACTN4, encoding alpha-actinin-4, cause familial focal segmental glomerulosclerosis," Nat Genet., Mar. 2000, 24(3):251-256.

Kashtan et al., "Alport syndrome: a unified classification of genetic disorders of collagen IV α345: a position paper of the Alport Syndrome Classification Working Group," Kidney Int, May 2018, 93(5):1045-1051.

Kashtan et al., "Clinical practice recommendations for the treatment of Alport syndrome: a statement of the Alport Syndrome Research Collaborative," Pediatr Nephrol, 2013, 28(1):5-11.

KDOQI, "KDOQI Clinical Practice Guidelines and Clinical Practice Recommendations for Diabetes and Chronic Kidney Disease," Am J Kidney Dis, Feb. 2007, 49(2 Suppl 2):S12-154.

Kestila et al., "Positionally Cloned Gene for a Novel Glomerular Protein—Nephrin—Is Mutated in Congenital Nephrotic Syndrome," Molecular Cell, Mar. 1998, 1:575-582.

Khalifa et al., "Pattern of Glomerulonephritis in Sudan: Histopathological andImmunofluorescence Study," Saudi J. Kidney Dis. Transplant, 2004, 15:2:176-179.

Kim et al., "CD2-associated protein haploinsufficiency is linked to glomerular disease susceptibility," Science, May 23, 2003, 300(5623):1298-1300.

Knoppova et al., "The Origin and Activities of IgA1-Containing Immune Complexes in IgA Nephropathy," Front. Immunol., Apr. 2016, 7:117, 1-25.

Kohan et al., "Addition of Atrasentan to Renin-Angiotensin System Blockade Reduces Albuminuria in Diabetic Nephropathy," Soc. Nephrol., 2011, 22:763-772.

Kohan, "Endothelin and endothelin antagonists in chronic kidney disease," Kidney Int., Nov. 2014, 86(5):896-904, 9 pages.

Komers et al., "Dual inhibition of renin-angiotensin-aldosterone system and endothelin-1 in treatment of chronic kidney disease,". Am. J. Physiol. Regul. Comp. Physiol., 2016, 310:R877-R884.

Koomen et al., "Determining the optimal dose of atrasentan by evaluating the exposure-response relationships of albuminuria and body weight," Diabetes Obes Metab, Mar. 30, 2018, 20(8):2019-2022.

Korbet, "Treatment of primary FSGS in adults," J Am Soc Nephrol, Nov. 2012, 23(11):1769-1776.

Korotkevich et al., "Fast gene set enrichment analysis," BioRxiv, 2016, 1-29.

Koziell et al., "Genotype/phenotype correlations of NPHS1 and NPHS2 mutations in nephrotic syndrome advocate a functional inter-relationship in glomerular filtration," Hum Mol Genet., Feb. 15, 2002, 11(4):379-388.

Lai et al., "IgA nephropathy," Nat Rev Dis Primers, Feb. 11, 2016, 2:16001, 20 pages.

Lai et al., "IgA nephropathy," Nature Reviews Disease Primers, Feb. 2016, 2:16001, 1-20.

Lake et al., "A single-nucleus RNA-sequencing pipeline to decipher the molecular anatomy and pathophysiology of human kidneys," Nat. Comm, Jun. 2019, 10(1):2832, 1-15.

Lake et al., "Integrative single-cell analysis of transcriptional and epigenetic states in the human adult brain,"Nat. Biotechnol., 2018, 36:1:70-80.

Lepist et al., "Evaluation of the Endothelin Receptor Antagonists Ambrisentan, Bosentan, Macitentan, and Sitaxsentan as Hepatobiliary Transporter Inhibitors and Substrates in Sandwich-Cultured Human Hepatocytes," Plos One, Jan. 2014, 9(1):e87548, 1-10.

Liang et al., "Proliferation and Cytokine Production of Human Mesangial Cells Stimulated by Secretory IgA Isolated from Patients with IgA Nephropathy," Cell Physiol. Biochem., 2015, 36(5):1793-1808.

Liao et al., "The R package Rsubread is easier, faster, cheaper and better for alignment and quantification of RNA sequencing reads," Nucleic Acids Res., May 2019, 47(8):e47, 1-9.

Liberzon et al., "The Molecular Signatures Database (MSigDB) hallmark gene set collection," Cell Systems, Dec. 2015,1(6):417-425, 10 pages.

Lin et al., "Update of pathophysiology and management of diabetic kidney disease," Sci Direct., 2018, 117:662-675.

Lin et al., "Relationship between atrasentan concentrations and urinary albumin to creatinine ratio in Western and Japanese patients with diabetic Nephropathy," Clinical Therapeutics, Feb. 2018, 40(2):242-251.

Lowik et al., "Focal segmental glomerulosclerosis in a patient homozygous for a CD2AP mutation," Kidney International, Aug. 22, 2007, 72:1198-1203.

Mallett et al., "End-stage kidney disease due to Alport syndrome: outcomes in 296 consecutive Australia and New Zealand Dialysis and Transplant Registry cases," Nephrol Dial Transplant, Jul. 24, 2014, 29(12):2277-2286.

Mann et al., "Avosentan for Overt Diabetic Nephropathy," J Am Soc Nephrol., 2010, 21: 527-535.

Markowitz, "Glomerular disease: Updated Oxford Classification of IgA nephropathy: a new MEST-C score," Nature Reviews Nephrology, Jul. 2017, 13(7):385-386.

McGrogan et al., "The incidence of primary glomerulonephritis worldwide: a systematic review of the literature," Nephrol Dial Transplant, Feb. 2011, 26(2):414-430.

(56) References Cited

OTHER PUBLICATIONS

Meehan et al., "Endothelin-1 mediated induction of extracellular matrix genes in strial marginal cells underlies strial pathology in Alport mice," Hear Res, Nov. 2016, 341:100-108.

Mele et al., "MYO1E Mutations and Childhood Familial Focal Segmental Glomerulosclerosis," The New England Journal of Medicine, Jul. 28, 2011, 365(4):295-306.

Nakamura et al., "Effect of a specific endothelin receptor A antagonist on glomerulonephritis of ddY mice with IgA nephropathy," Nephron, 1996,72(3):454-460.

Newman et al., "Development of the Tinnitus Handicap Inventory," Arch Otolaryngol Head Neck Surg, Feb. 1996, 122(2): 143-148.

Newman et al., "Psychometric adequacy of the Tinnitus Handicap Inventory (THI) for evaluating treatment outcome," J Am Acad Audiol, Apr. 1998, 9(2):153-160.

Nguyen et al., "Higher serum galactose-deficient immunoglobulin A1 concentration is associated with stronger mesangial cellular inflammatory response and more severe histologic findings in immunoglobulin A nephropathy," Clin. Kidney J, Aug. 2018, 12(2):232-238.

Novak et al., "IgA1 immune complexes from pediatric patients with IgA nephropathy activate cultured human mesangial cells," Nephrol. Dial. Transplant, Nov. 2011, 26(11):3451-3457.

Novak et al., "IgA1-containing immune complexes in IgA nephropathy differentially affect proliferation of mesangial cells," Kidney International, Feb. 2005, 67(2):504-513.

Nozu et al., "A review of clinical characteristics and genetic backgrounds in Alport syndrome," Clin Exp Nephrol, Feb. 2019, 23(2):158-168.

O'Dwyer et al., "Uridine diphosphate glucuronosyltransferase (UGT) 1A1 and irinotecan: practical pharmacogenomics arrives in cancer therapy," J Clin Oncol, Oct. 1, 2006, 24(28): 4534-4538.

Okazaki et al., "Development of a model of early-onset IgA nephropathy," J Am Soc Nephrol, Aug. 2012, 23(8):1364-1374.

Papeta et al., "APOL1 Variants Increase Risk for FSGS and HIVAN but Not IgA Nephropathy," J. Am. Soc. Nephrol., 2011, 2991-1996.

Park et al., "COQ6 Mutations in Children With Steroid-Resistant Focal Segmental Glomerulosclerosis and Sensorineural Hearing Loss," Am J Kidney Dis., Jul. 2017, 70(1):139-144.

Parsa et al., "APOL1 Risk Variants, Race, and Progression of Chronic Kidney Disease," The New England Journal of Medicine, Dec. 5, 2013, 369(23):2183-2196.

PCT International Search Report and Written Opinion in International Appln. No. PCTUS2020/65311, dated Mar. 9, 2021, 15 pages.

Penfold et al., "Primary IgA nephropathy: current challenges and future prospects," Int. J. Nephrol. and Renovascular Dis., 2018, 11:137-148.

Persson et al., "Diagnosis of diabetic kidney disease: state of the art and future perspective," Kidney international supplements, Jan. 2018, 8(1):2-7.

Rajasekeran et al. "Do effects of sodium-glucose cotransporter-2 inhibitors in patients with diabetes give insight into potential use in non-diabetic kidney disease?," Current Opinion in Nephrology and hypertension, 2017, vol. 26, No. 5, pp. 358-367 (Year: 2017).

Reiser et al., "TRPC6 is a glomerular slit diaphragm-associated channel required for normal renal function," Nat Genet., Jul. 2005, 37(7):739-744.

Robinson et al., "A Bioconductor package for differential expression analysis of digital gene expression data," Bioinformatics, Jan. 2010, 26(1):139-140.

Rood et al., "Genetic causes of focal segmental glomerulosclerosis: implications for clinical practice," Nephrology Dialysis Transplantation, Mar. 2012, 27(3):882-890.

Rosenberg et al., "Focal Segmental Glomerulosclerosis," Clin J Am Soc Nephrol, Mar. 7, 2017, 12(3):502-517.

Ryan et al., "HK-2: an immortalized proximal tubule epithelial cell line from normal adult human kidney," Kidney International, Jan. 1994, 45(1):48-57.

Saleh et al., "Distinct actions of endothelin A-selective versus combined endothelin A/B receptor antagonists in early diabetic kidney disease," J. Pharm. Exp. Ther., 2011, 338(1):263-270.

Salim, [online], "IgA Nephropathy," May 19, 2020, retrived on Jul. 7, 2021, retrieved from URL:https://emedicine.medscape.com/article/239927-print., 20pages.

Scheen, "Cardiovascular Effects of New Oral Glucose-Lowering Agents: DPP-4 and SGLT-2 Inhibitors," Circ Res, May 2018, 122(10):1439-1459, 22 pages.

Schneider et al., "Endothelin antagonism for patients with chronic kidney disease: still a hope for the future," Nephrol, Dial. Transplant, Feb. 2014, 29 (Suppl. 1):i69-i73.

Shao et al., "Focal segmental glomerulosclerosis ACTN4 mutants binding to actin: regulation by phosphomimetic mutations," Scientific Reports, Oct. 29, 2019, 9:15517, 12 pages.

Subramanian et al., "Gene set enrichment analysis: a knowledge-based approach for interpreting genome-wide expression profiles," Proc. Nat. Acad. Sci. USA, Oct. 2005, 102(43):15545-15550.

Sugiyama et al., "Pharmacokinetics of gemcitabine in Japanese cancer patients: the impact of a cytidine deaminase polymorphism," J Clin Oncol, Jan. 1, 2007, 25(1):32-42.

Suzuki et al., "The pathophysiology of IgA nephropathy," J. Am Soc. Nephrol., Oct. 2011, 22(10):1795-1803.

Thomas et al., "Diabetic kidney disease," Nat. Rev. Disease Primers., Jul. 2015, 1:15018, 20 pages.

Tomino, "Diagnosis and treatment of patients with IgA nephropathy in Japan," Kidney Research and Clinical Practice, Dec. 2016, 35(4):197-203.

Toth-Manikowski et al., "Diabetic Kidney Disease: Pathophysiology and Therapeutic Targets," J Diabetes Res, Apr. 30, 2015, 2015:697010, 17 pages.

Trachtman et al., "Duet: A Phase 2 Study Evaluating the Efficacy and Safety of Sparsentan in Patients with Fsgs," J Am Soc Nephrol, Nov. 2018, 29(11):2745-2754.

Tsukaguchi et al., "NPHS2 mutations in late-onset focal segmental glomerulosclerosis: R229Q is a common disease-associated allele," J. Clin. Invest., Dec. 2002, 110(11):1659-1666.

Tuttle et al., "Diabetic kidney disease: a report from an ADA Consensus Conference," Diabetes Care, Oct. 2014, 37(10):2864-2883.

Tuttle et al., "Sodium glucose cotransporter 2 inhibition heralds a call to action for diabetickidney disease," Clin. J. of Amer. Soc of Nephrology, Feb. 2020, 15:285-288.

Vairo et al., "Nail-patella-like renal disease masquerading as Fabry disease on kidney biopsy: a case report," BMC Nephrology, Aug. 13, 2020, 21:341, 5 pages.

Vignon-Zellweger et al., "Endothelin and endothelin receptors in the renal and cardiovascular systems," Life sciences, Oct. 15, 2012, 91(13-14):490-500.

Weins et al., "Mutational and Biological Analysis of—Actinin-4 in Focal Segmental Glomerulosclerosis," J Am Soc Nephrol, 2005, 16:3694-3701.

Winn et al., "A mutation in the TRPC6 cation channel causes familial focal segmental glomerulosclerosis," Science, Jun. 17, 2005, 308(5729):1801-1804.

Working Group of the International IgA Nephropathy Network and the Renal Pathology Society et al., "The Oxford classification of IgA nephropathy: pathology definitions, correlations, and reproducibility," Kidney International, Sep. 2009, 76(5):546-556.

Wright, "Renal Na(+)-glucose cotransporters," Am. J. Physiol. Renal Physiol., Jan. 2001, 280(1):F10-F18.

Wu-Wong et al., "Pharmacology of endothelin receptor antagonists ABT-627, ABT-546, A-182086 and A-192621: in vitro studies" Clin. Sci.(Lond. ),2002, 103:48:1075-1115.

www.uptodate.com[online] "Cattran et al., Membranous nephropathy: Treatment and prognosis," May 2019, last accessed Oct. 18, 2012, retrieved from URL<https://www.uptodate.com/contents/membranous-nephropathy-treatment-and-prognosis/>,40 pages.

Wyatt et al., "IgA nephropathy," N Engl J Med, Jun. 20, 2013, 368(25):2402-2414.

Zanatta et al., "Endothelin-1 and endothelin a receptor immunoreactivity is increased in patients with diabetic nephropathy," Renal Failure, 2012, 34(3):308-315.

(56) References Cited

OTHER PUBLICATIONS

Zelnick et al., "Diabetes and CKD in the United States Population, 2009-2014," Clin J Am Soc Nephrol, Dec. 2017, 12(12):1984-1990.

Zhao et al., "Measures of Urinary Protein and Albumin in the Prediction of Progression of IgA Nephropathy," Clin J Am Soc Nephrol, Jun. 2016, 11(6):947-955.

Heerspink et al., "New insights from SONAR indicate adding sodium glucose co-transporter 2 inhibitors to an endothelin receptor antagonist mitigates fluid retention and enhances albuminuria reduction", Kidney International, 2021, 99:346-349.

Nakamura et al. "Endothelin-1 mRNA expression by peripheral blood monocytes in IgA nephropathy," The Lancet, Nov. 6, 1993, 342(8880):1147-1148.

| Symbol Entrez Gene Name | | Human | Mouse | Plasma/Serum | Urine |
|---|---|---|---|---|---|
| ALPL | alkaline phosphatase, biomineralization associated | X | X | X | X |
| AMIN | amnion associated transmembrane protein | X | X | | X |
| ASL | argininosuccinate lyase | X | X | X | X |
| CRYL1 | crystallin lamda 1 | X | X | | X |
| DPEP1 | dipeptidase 1 | X | X | | X |
| GAPDH | glyceraldehyde-3-phosphate dehydrogenase | X | X | X | X |
| IGF1 | insulin like growth factor 1 | X | X | X | X |
| PDZK1IP1 | PDZK1 interacting protein 1 | X | X | | X |
| PEBP1 | phosphatidylethanolamine binding protein 1 | X | X | | X |
| SELENBP1 | selenium binding protein 1 | X | X | X | X |
| SLC19A1 | solute carrier family 19 member 1 | X | X | X | |
| SLC6A19 | solute carrier family 6 member 19 | X | X | | X |

FIG. 12A

METHODS OF IMPROVING RENAL FUNCTION

CROSS-REFERENCE TO RELATED APPLICATIONS

This application is a continuation of PCT/US2020/065311, filed on Dec. 16, 2020, which claims priority to U.S. Provisional Application No. 62/949,115, filed on Dec. 17, 2019, U.S. Provisional Application No. 63/005,003, filed on Apr. 3, 2020, U.S. Provisional Application No. 63/072,699, filed Aug. 31, 2020, U.S. Provisional Application No. 63/084,739, filed on Sep. 29, 2020 and U.S. Provisional Application No. 63/125,205, filed on Dec. 14, 2020, which are incorporated by reference in their entirety.

BACKGROUND

IgA nephropathy (IgAN) is the most common primary glomerulonephritis worldwide. Aberrant glycosylation of IgA1 results in increased serum levels of galactose-deficient IgA1 (Gd-IgA1) that are recognized by glycan-specific IgA and IgG autoantibodies. Aggregates of the immune complexes are formed in situ and/or deposited in the glomerular mesangium. This promotes proliferation of mesangial cells, increased synthesis of extracellular matrix proteins, cytokines, chemokines, and infiltration of immune cells into the surrounding tissue. Accordingly, disease progression involves (1) production of Gd-IgA1; and (2) its recognition by antiglycan autoantibodies; which (3) form immune complexes in the kidney; and (4) activate mesangial cells. See, e.g., Penfold et al., Int. J. Nephrol. and Renovascular Dis. 11, pp. 137-148 (2017).

Unlike other progressive kidney diseases such as diabetic nephropathy, IgAN occurs primarily in subjects in their 20s and 30s who are otherwise healthy. Patients present with a range of symptoms, typically including micro- or macro-hematuria and increased protein excretion in the urine. Patients may also present with hypertension as a result of sustained renal damage. Current therapeutic approaches merely provide supportive care, including administration of the maximum tolerable dose of an angiotensin converting enzyme inhibitor or angiotensin-receptor blocker, or administration of immunosuppressive drugs, whose benefits are largely outweighed by adverse reactions. Ultimately, 30-40% of patients will develop end-stage renal disease (ESRD) within 20-30 years of diagnosis of IgAN. In the interim, patients experience numerous symptoms that significantly degrade their quality of life, in addition to declining renal function. Patients with IgAN often exhibit significantly increased expressions of endothelin 1 (ET-1) and ET-RA in the kidney. Increased expression of endothelins positively correlates with proteinuria, one of the hallmark symptoms of IgAN.

SUMMARY

Atrasentan is a selective endothelin A (ETA) receptor antagonist (ETA Ki~34 pM; ETB Ki~63 nM, ETA selectivity ~1800×). See, e.g. Wu-Wong et al., Clin. Sci. (Lond.), 103(48), pp. 107s-111 (2002). Selective ETA receptor antagonists block ETA function, while minimally effecting the ETB receptor, providing beneficial renal effects including vasodilation and reduction of inflammation, while still enabling ET-1 clearance. See e.g., Jandeleit-Dahm and Watson, Curr. Opin. Nephrol. Hypertens., 21(1), pp. 66-71 (2012); see also, Nakamura, et al., Nephron, Vol. 72, pp. 454-460 (1996). While ETA receptor antagonists increase sodium and water retention by the kidney, this is typically clinically manageable. See, e.g., Saleh, et al., J. Pharm. Exp. Ther., 338(1), pp. 263-270 (2011). Atrasentan has been shown to be effective in patients with diabetic kidney disease (DKD), significantly reducing the risk of renal events defined as a doubling of serum creatinine or end-stage kidney disease. See, e.g., Heerspink, et al., The Lancet, 393, pp 1937-1947 (2019). DKD is considered a secondary glomerular disease, where kidney disease develops secondarily to an identified systemic cause, in the case of DKD as a microvascular complication to long standing diabetes. See, e.g. Dattani and McAdoo, Medicine, 47(10), pp. 644-648 (2019). The pathogenesis of DKD is multifactorial and complex. Chronically elevated blood glucose levels due to diabetes which causes glucose toxicity to renal cells, especially kidney endothelial cells, and systemic and renal hemodynamic factors associated with hypertension that result in shear stress being transmitted to resident glomerular cells are the key pathogenic drivers of DKD. See, e.g. Thomas et al., Nat. Rev. Disease Primers. 1, pp. 15018-15026 (2015). Multiple factors dysregulated in the diabetic milieu, including metabolic components such as hyperglycemia, dyslipidemia and oxidative stress, and hemodynamic factors such as vasoactive substances associated with hypertension, all stimulate renal ET-1 formation. In addition, DKD is typically observed in older populations due to the requirement for long-standing diabetes prior to the manifestation of DKD, and aging is also associated with increased ET-1 production in the kidney. See, e.g. Kohan, Kidney Int., 86(5), pp. 896-904 (2014). Combined, this all provides a sound scientific rationale for the treatment of DKD with the ETA receptor blocker atrasentan. See Dhaun, et al., Hypertension, Vol. 57, pp. 772-779 (2011).

In contrast to DKD, IgA nephropathy is considered a primary glomerular disease where localized or intrinsic renal pathology is present. The peak incidence of IgA nephropathy is in young individuals in their second or third decade of life and is a disease that is auto-immune in origin, unlike DKD. IgA nephropathy results from pathogenic IgA/immune complex deposition in the glomerular mesangium. See, e.g., Lai, et al., Nature Reviews Disease Primers, 2, pp. 16001, 2016. Definitive diagnosis requires kidney biopsy and demonstration of mesangial IgA deposition by immunofluorescence microscopy. Recent advances in the understanding of the initiating events triggering IgA nephropathy have revealed that an aberrant mucosal immune response stimulates the production of galactose deficient IgA1 which is recognized as an autoantigen by circulating antiglycan autoantibodies. Immune recognition results in the formation of nephritogenic immune complexes that deposit in the kidney and activate mesangial cells. Activated mesangial cells proliferate and produce excess amounts of extracellular matrix components, cytokines and chemokines. See, e.g., Suzuki, et al., J. Am. Soc. Nephrol., Vol. 22, pp. 1795-1803 (2011). Up to 40% of patients with biopsy-proven IgA nephropathy progress to end stage kidney disease at some point during long term follow up. The role of ET-1 or the ETA receptor in mesangial cell activation has not been previously reported and atrasentan has not been previously tested in IgA nephropathy. As further described herein, atrasentan can be administered at an efficacious dose with acceptable toxicity, and has the appropriate selectivity to minimize undesired side effects while still treating the underlying IgAN and improving subjects' quality of life. Some embodiments provide a method of inhibiting mesangial cell activation in a subject having IgA nephropathy, comprising administering a therapeutically effective amount of atrasentan, or a pharmaceutically acceptable salt thereof, to the subject; wherein the subject has not been previously diagnosed with one or more of diabetic nephropathy, HIV/AIDS, or acute kidney failure.

Some embodiments provide a method of inhibiting PDGF signaling (e.g., decreasing the activity and/or expression of one or more of PIK3R1, PDGFRA, NFKBIA, PIK3CG, PLA2G4 Å, TIAM1, PDGFB, NFKB1, and MAP3K1) in a mesangial cell in a subject having IgA nephropathy, comprising administering a therapeutically effective amount of atrasentan, or a pharmaceutically acceptable salt thereof, to the subject; wherein the subject has not been previously diagnosed with one or more of diabetic nephropathy, HIV/AIDS, or acute kidney failure.

Some embodiments provide a method of treating IgA nephropathy, comprising administering a therapeutically effective amount of atrasentan, or a pharmaceutically acceptable salt thereof, to a subject in need thereof; wherein the subject has not been previously diagnosed with one or more of diabetic nephropathy, HIV/AIDS, or acute kidney failure.

Some embodiments provide a method of treating IgA nephropathy, comprising administering a therapeutically effective amount of atrasentan, or a pharmaceutically acceptable salt thereof, to a subject in need thereof, wherein the subject does not have one or more of diabetic nephropathy, HIV/AIDS, or acute kidney failure.

Some embodiments provide a method of treating IgA nephropathy, comprising administering a therapeutically effective amount of atrasentan, or a pharmaceutically acceptable salt thereof, to a subject in need thereof; wherein the subject does not suffer from one or more of diabetic nephropathy, HIV/AIDS, or acute kidney failure.

Some embodiments provide a method of treating IgA nephropathy, comprising administering a therapeutically effective amount of atrasentan, or a pharmaceutically acceptable salt thereof, to a subject in need thereof; wherein the subject has not been previously diagnosed with one or more of diabetic nephropathy, HIV/AIDS, prostate cancer, or acute kidney failure.

Some embodiments provide a method of treating IgA nephropathy, comprising administering a therapeutically effective amount of atrasentan, or a pharmaceutically acceptable salt thereof, to a subject in need thereof; wherein the subject has not been previously diagnosed with one or more of diabetic nephropathy, HIV-related nephropathy, prostate cancer, or acute kidney failure.

Some embodiments provide a method of treating IgA nephropathy, comprising administering a therapeutically effective amount of atrasentan, or a pharmaceutically acceptable salt thereof, to a subject in need thereof; wherein the subject has not been previously diagnosed with one or more of diabetic nephropathy, HIV-related nephropathy, or acute kidney failure.

Some embodiments provide a method of treating IgA nephropathy, comprising administering a therapeutically effective amount of atrasentan, or a pharmaceutically acceptable salt thereof, to a subject in need thereof, wherein the subject is not being treated for one or more of diabetic nephropathy, HIV-related nephropathy, or acute kidney failure.

Some embodiments provide a method of treating IgA nephropathy, comprising administering a therapeutically effective amount of atrasentan, or a pharmaceutically acceptable salt thereof, to a subject in need thereof; wherein the subject has been determined to have controlled serum glucose levels; and wherein the subject has not been diagnosed with one or more of HIV-related nephropathy or acute kidney failure.

Some embodiments provide a method of decreasing renal inflammation and/or fibrosis in a subject having IgA nephropathy, comprising administering a therapeutically effective amount of atrasentan, or a pharmaceutically acceptable salt thereof, to a subject in need thereof.

Some embodiments provide a method of decreasing the occurrence of hematuria in a subject having IgA nephropathy, comprising administering a therapeutically effective amount of atrasentan, or a pharmaceutically acceptable salt thereof, to a subject in need thereof.

Some embodiments provide a method of stabilizing eGFR in a subject having IgA nephropathy, comprising administering a therapeutically effective amount of atrasentan, or a pharmaceutically acceptable salt thereof, to a subject in need thereof.

Some embodiments provide a method of decreasing the number of IgA-nephropathy associated disease flares in a subject having IgA nephropathy, comprising administering a therapeutically effective amount of atrasentan, or a pharmaceutically acceptable salt thereof, to a subject in need thereof.

Some embodiments provide a method of delaying the onset of ESRD in a subject having IgA nephropathy, comprising administering a therapeutically effective amount of atrasentan, or a pharmaceutically acceptable salt thereof, to a subject in need thereof.

Some embodiments provide a method of decreasing proteinuria in a subject having IgA nephropathy, comprising administering a therapeutically effective amount of atrasentan, or a pharmaceutically acceptable salt thereof, to a subject in need thereof.

Some embodiments provide a method of decreasing fatigue in a subject having IgA nephropathy, comprising administering a therapeutically effective amount of atrasentan, or a pharmaceutically acceptable salt thereof, to a subject in need thereof; wherein the subject has been determined not to suffer from one or more of diabetic nephropathy, HIV-related nephropathy, prostate cancer, or acute kidney failure.

Some embodiments provide a method of inhibiting mesangial cell activation, comprising contacting a mesangial cell with an effective amount of atrasentan, or a pharmaceutically acceptable salt thereof.

Some embodiments provide a method of reducing activation of a mesangial cell in contact with an IgA immune complex, comprising contacting a mesangial cell with an effective amount of atrasentan, or a pharmaceutically acceptable salt thereof.

Some embodiments provide a method of treating IgA nephropathy in a subject in need thereof, comprising: a) determining that the subject has elevated serum Gd-IgA1 levels; and b) administering a therapeutically effective amount of atrasentan, or a pharmaceutically acceptable salt thereof, to the subject.

Some embodiments provide a method of treating IgA nephropathy in a subject in need thereof, comprising: a) determining that the subject has elevated levels of mesangial activation; and b) administering a therapeutically effective amount of atrasentan, or a pharmaceutically acceptable salt thereof, to the subject.

Some embodiments provide a method of treating IgA nephropathy in a subject in need thereof, comprising: a) determining that the subject has elevated levels of IgA-immune complexes in the kidney; and b) administering a therapeutically effective amount of atrasentan, or a pharmaceutically acceptable salt thereof, to the subject.

BRIEF DESCRIPTION OF THE FIGURES

FIG. 12A illustrates a comparison between potential biomarkers based on human and mouse with an "x" indicating translatability and whether the potential biomarker is in plasma/serum and/or urine. Notably, each of the relevant markers are found in both humans and mice (e.g., g-ddY mice).

Figure 1A:
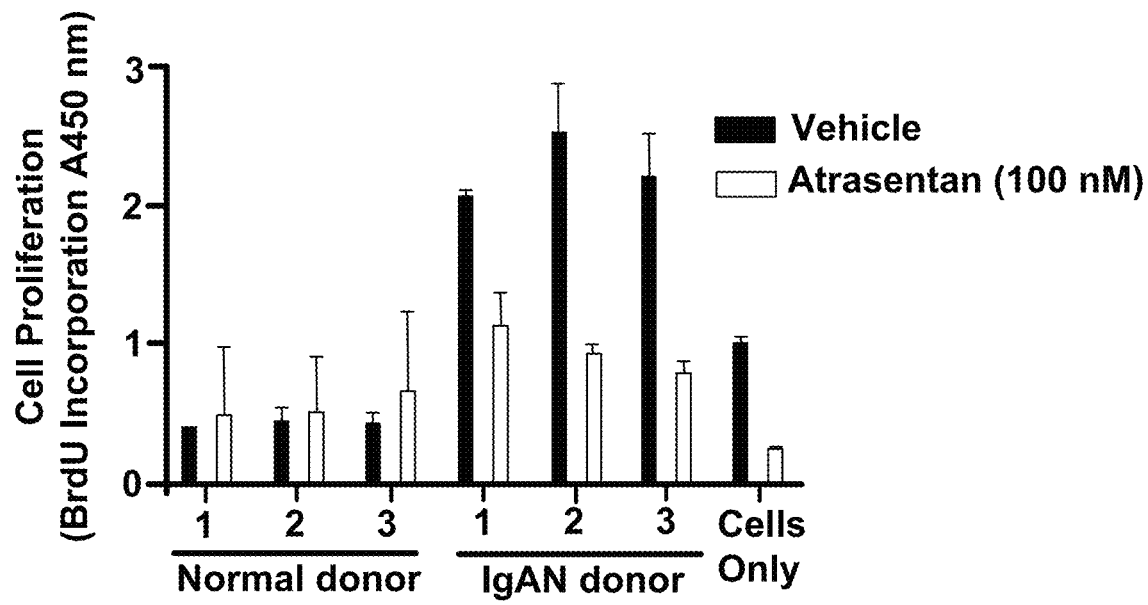
FIG. 1A illustrates that treatment with atrasentan reduces the proliferation of primary human mesangial cells exposed to immune complexes derived from subjects with IgAN.

Table 1 Top 40 DEGs (25 upregulated and 15 downregulated) in treatment of g-ddY mice with atrasentan at 10 mg/kg/day compared to atrasentan at 0 mg/kg/day (control).

Table 2 Top 50 DEGs (25 upregulated and 25 downregulated) in treatment of g-ddY mice with atrasentan at 20 mg/kg/day compared to atrasentan at 0 mg/kg/day (control).

Table 3 Top 50 DEGs (25 upregulated and 25 downregulated) in treatment of g-ddY mice with atrasentan at 30 mg/kg/day compared to atrasentan at 0 mg/kg/day (control).

Table 4 The enriched signaling pathways following treatment of g-ddY mice with atrasentan at 10, 20 or 30 mg/kg/day compared to atrasentan at 0 mg/kg/day (control). Z-score values indicate the magnitude of the effect seen at each dosage.

Table 5 Gene Set Enrichment Analysis showing the enrichment in hallmark gene sets following treatment of g-ddY mice with atrasentan at 10, 20 or 30 mg/kg/day compared to atrasentan at 0 mg/kg/day (control). NES is the normalized enrichment score indicating the representation of DEGs in the gene set and accounted for gene set size. NES of <−1.5 or >1.5 is considered to be biologically significant. Adj p-value is the estimated probability that the calculated NES of the given enriched gene set is a false positive result.

Table 6 list of upstream regulators grouped by cytokine and growth factor molecular types. P-value of overlap indicates the significance of enrichment based on the number of overlapping genes between the dataset and the gene targets in IPKB. Activation z-score threshold of <−2 or >2 and p-value of overlap threshold of <0.05 was considered significant.

Table 7 List of upstream regulators grouped by transmembrane receptor, G-protein coupled receptor, and protein complexes molecular types. P-value of overlap indicates the significance of enrichment based on the number of overlapping genes between the dataset and the gene targets in IPKB. Activation z-score threshold of <−2 or >2 and p-value of overlap threshold of <0.05 was considered significant.

Table 8 List of upstream regulators grouped by transcription regulator and ligand-dependent nuclear receptor molecular types. P-value of overlap indicates the significance of enrichment based on the number of overlapping genes between the dataset and the gene targets in IPKB. Activation z-score threshold of <−2 or >2 and p-value of overlap threshold of <0.05 was considered significant.

Table 9 Gene expression of the components of the NF-kB signaling pathways following treatment of g-ddY mice with atrasentan at 10, 20 or 30 mg/kg/day compared to atrasentan at 0 mg/kg/day (control).

Table 10 Gene expression of the components of the IL6 signaling pathways following treatment of g-ddY mice with atrasentan at 10, 20 or 30 mg/kg/day compared to atrasentan at 0 mg/kg/day (control).

Table 11 Gene expression of the components of the PDGF signaling pathways following treatment of g-ddY mice with atrasentan at 10, 20 or 30 mg/kg/day compared to atrasentan at 0 mg/kg/day (control).

Table 12 Gene expression of the components of the cell proliferation signaling pathways (mitotic spindle and G2M cell cycle checkpoint) following treatment of g-ddY with atrasentan at 10, 20, or 30 mg/kg/day compared to atrasentan at 0 mg/kg/day (control).

Table 13 Gene expression of the components of the inflammatory response signaling pathways following treatment of g-ddY with atrasentan at 10, 20, or 30 mg/kg/day compared to atrasentan at 0 mg/kg/day (control).

Table 14 Gene expression of the 44 genes associated with mesangial cell signature following treatment of g-ddY with atrasentan at 10, 20, or 30 mg/kg/day compared to atrasentan at 0 mg/kg/day (control).

DETAILED DESCRIPTION

A. Definitions

In order that the present disclosure can be more readily understood, certain terms are first defined. As used in this application, except as otherwise expressly provided herein, each of the following terms shall have the meaning set forth below. Additional definitions are set forth throughout the application.

Unless defined otherwise, all technical and scientific terms used herein have the same meaning as commonly understood by one of ordinary skill in the art to which this disclosure is related. For example, the Concise Dictionary of Biomedicine and Molecular Biology, Juo, Pei-Show, 2nd ed., 2002, CRC Press; The Dictionary of Cell and Molecular Biology, 3rd ed., 1999, Academic Press; and the Oxford Dictionary Of Biochemistry And Molecular Biology, Revised, 2000, Oxford University Press, provide one of skill with a general dictionary of many of the terms used in this disclosure. For purposes of the present disclosure, the following terms are defined.

Units, prefixes, and symbols are denoted in their Système International de Unites (SI) accepted form. Numeric ranges are inclusive of the numbers defining the range. The headings provided herein are not limitations of the various aspects of the disclosure, which can be had by reference to the specification as a whole. Accordingly, the terms defined immediately below are more fully defined by reference to the specification in its entirety.

The terms "a," "an," or "the" as used herein not only include aspects with one member, but also include aspects with more than one member. For instance, the singular forms "a," "an," and "the" include plural referents unless the context clearly dictates otherwise. Thus, for example, reference to "a cell" includes a plurality of such cells and reference to "the agent" includes reference to one or more agents known to those skilled in the art, and so forth.

The term "or" as used herein should in general be construed non-exclusively. For example, a claim to "a composition comprising A or B" would typically present an aspect with a composition comprising both A and B. "Or" should, however, be construed to exclude those aspects presented that cannot be combined without contradiction (e.g., a composition pH that is between 9 and 10 or between 7 and 8).

The group "A or B" is typically equivalent to the group "selected from the group consisting of A and B."

The term "and/or" where used herein is to be taken as specific disclosure of each of the two specified features or components with or without the other. Thus, the term "and/or" as used in a phrase such as "A and/or B" herein is intended to include "A and B," "A or B," "A" (alone), and "B" (alone). Likewise, the term "and/or" as used in a phrase such as "A, B, and/or C" is intended to encompass each of the following aspects: A, B, and C; A, B, or C; A or C; A or B; B or C; A and C; A and B; B and C; A (alone); B (alone); and C (alone).

The terms "about" and "approximately" as used herein shall generally mean an acceptable degree of error for the quantity measured given the nature or precision of the measurements. Typical, exemplary degrees of error are within 20 percent (%), within 10%, or within 5% of a given value or range of values. Any reference to "about X" specifically indicates at least the values X, 0.95X, 0.96X, 0.97X, 0.98X, 0.99X, 1.01X, 1.02X, 1.03X, 1.04X, and 1.05X. Thus, "about X" is intended to provide written description support for a claim limitation of, e.g., "0.98X." The terms "about" and "approximately," particularly in reference to a given quantity, encompass and describe the given quantity itself.

When "about" is applied to the beginning of a numerical range, it applies to both ends of the range. Thus, "from about 5 to 20%" is equivalent to "from about 5% to about 20%." When "about" is applied to the first value of a set of values, it applies to all values in that set. Thus, "about 0.5, 0.75, or 1.0 mg" is equivalent to "about 0.5, about 0.75, or about 1.0 mg."

As used herein, the term "about", when preceding a series of peak positions for X-ray powder diffraction (e.g., 2θ values), means that all of the peaks of the group which it precedes are reported in terms of angular positions with a variability of ±0.1°. Accordingly, for example, the phrase about 8.3°, 9.7°, 10.0°, 13.0°, 15.6°, 17.2° or 19.5° means 8.3°±0.1°, 9.7°±0.1°, 10.0°±0.1°, 13.0°±0.1°, 15.6°±0.1°, 17.2°±0.1°, or 19.5°+0.1°.

"Treatment" or "therapy" of a subject refers to any type of intervention or process performed on, or the administration of an active agent to, the subject with the objective of reversing, alleviating, ameliorating, inhibiting, or slowing down, the onset, progression, development, severity, or recurrence of a symptom, complication, condition, or biochemical indicia associated with a disease.

"Administering" or "administration" refer to the physical introduction of a therapeutic agent to a subject, using any of the various methods and delivery systems known to those skilled in the art. Routes of administration can include oral, intravenous, intramuscular, subcutaneous, intraperitoneal, spinal or other parenteral routes of administration, for example by injection or infusion (e.g., intravenous infusion). Administration can also be performed, for example, once, a plurality of times, and/or over one or more extended periods.

The term "prophylactic" or "prophylactically" refers to any type of intervention or process performed on, or the administration of an active agent to, the subject with the objective of protecting or preventing a disease or condition from developing or at least not developing fully (e.g., to reduce the symptoms or severity of the disease or condition) such as in the development of a side effect.

A "subject" includes any human or non-human animal. The term "non-human animal" includes, but is not limited to, vertebrates such as non-human primates, sheep, dogs, and rodents such as mice, rats, and guinea pigs. In some embodiments, the subject is a human. The terms "subject" and "patient" and "individual" are used interchangeably herein.

An "effective amount" or "therapeutically effective amount" or "therapeutically effective dosage" of a drug or therapeutic agent is any amount of the drug that, when used alone or in combination with another therapeutic agent, slowing down the onset of a disease or promotes disease regression evidenced by a decrease in severity of disease symptoms, an increase in frequency and duration of disease symptom-free periods, or a ameliorating an impairment or disability due to the disease affliction. The ability of a therapeutic agent to promote disease regression can be evaluated using a variety of methods known to the skilled practitioner, such as in human subjects during clinical trials, in animal model systems predictive of efficacy in humans, or by assaying the activity of the agent in in vitro assays.

The phrase "pharmaceutically acceptable" indicates that the substance or composition must be compatible chemically and/or toxicologically, with the other ingredients comprising a formulation, and/or the mammal being treated therewith.

As used herein, "polymorphs" refer to distinct solids sharing the same molecular formula, yet each polymorph may have distinct solid state physical properties. A single compound may give rise to a variety of polymorphic forms where each form has different and distinct solid state physical properties, such as different solubility profiles, melting point temperatures, flowability, dissolution rates and/or different X-ray diffraction peaks. These practical physical characteristics are influenced by the conformation and orientation of molecules in the unit cell, which defines a particular polymorphic form of a substance. Polymorphic forms of a compound can be distinguished in a laboratory by X-ray diffraction spectroscopy, such as X-ray powder diffraction ("XRPD"), and by other methods, such as infrared spectrometry. Additionally, polymorphic forms of the same drug substance or active pharmaceutical ingredient can be administered by itself or formulated as a drug product (pharmaceutical composition) and are well known in the pharmaceutical art to affect, for example, the solubility, stability, flowability, tractability and compressibility of drug substances and the safety and efficacy of drug products. For more, see Hilfiker, Rolf (ed.), *Polymorphism in the Pharmaceutical Industry*. Weinheim, Germany: Wiley-VCH 2006.

As used herein, the term "amorphous" means a solid in a solid state that is a non-crystalline state. Amorphous solids generally possess crystal-like short range molecular arrangement, but no long range order of molecular packing as found in crystalline solids. The solid state form of a solid may be determined by polarized light microscopy, X-ray powder diffraction ("XRPD"), differential scanning calorimetry ("DSC"), or other standard techniques known to those of skill in the art.

As used herein, the term "crystalline" means a solid in a solid state having a regularly repeating arrangement of molecules or external face planes. The solid state form of a solid may be determined by polarized light microscopy, X-ray powder diffraction ("XRPD"), differential scanning calorimetry ("DSC"), or other standard techniques known to those of skill in the art. Accordingly, the term "crystalline purity," as used herein, means the percentage of a certain crystalline polymorph of atrasentan or pharmaceutically acceptable salt thereof in a sample that may contain amorphous atrasentan or a pharmaceutically acceptable salt thereof, one or more additional crystalline polymorphs of atrasentan or a pharmaceutically acceptable salt thereof, or mixtures thereof. When a crystalline polymorph of atrasentan or a pharmaceutically acceptable salt thereof is described as having "substantial crystalline purity", it means the polymorph is substantially free (e.g., contains <10%, <5%, <2%, <1%, <0.5%, <0.1%, or <0.05%) of other polymorphs (amorphous and/or crystalline).

The term "chemical purity," as used herein, means percentage of a particular compound (e.g., atrasentan or a pharmaceutically acceptable salt thereof) in a sample. Accordingly, atrasentan or a pharmaceutically acceptable salt thereof and compositions comprising or made therefrom may contain one or more impurity, including but not limited to: water, ethyl acetate, ethanol, (2R,3R,4S)-2-(4-methoxyphenyl)-4-(1,3-benzodioxol-5-yl)-1-(N-(n-butyl)aminocarbonylmethyl)pyrrolidine-3-carboxylic acid, (2R,3R,4S)-2-(4-methoxyphenyl)-4-(1,3-benzodioxol-5-yl)-1-((N-(n-butyl)-N-ethyl)aminocarbonylmethyl)pyrrolidine-3-carboxylic acid, (2R,4S)-2-(4-methoxyphenyl)-4-(1,3-benzodioxol-5-yl)-1-(N,N-di(n-butyl) aminocarbonylmethyl)pyrrolidine, or ethyl (2R,3R,4S)-2-(4-methoxyphenyl)-4-(1,3-benzodioxol-5-yl)-1-(N,N-di(n- butyl)aminocarbonylmethyl)pyrrolidine-3-carboxylate.

When a sample of atrasentan or a pharmaceutically acceptable salt thereof is described as having "substantial purity", the sample is substantially free of impurities (e.g., contains <10%, <5%, <2%, <1%, <0.5%, <0.1%, or <0.05%).

The term "diastereomeric excess," as used herein, means the amount of one diastereomer of a compound (e.g., atrasentan or a pharmaceutically acceptable salt thereof) in a mixture which may have other diastereomers of the same compound in the mixture. The term "substantial diastereomeric purity," as used herein, means diastereomeric excess greater than about 90%, 95%, 99%, 99.5%, 99.9%, or 100%.

As used herein, the term "pharmaceutically acceptable carrier" refers to a substance that aids the administration of an active agent to a cell, an organism, or a subject. "Pharmaceutically acceptable carrier" refers to a carrier or excipient that can be included in the compositions of the disclosure and that causes no significant adverse toxicological effect on the subject. Non-limiting examples of pharmaceutically acceptable carriers include water, NaCl, normal saline solutions, lactated Ringer's, normal sucrose, normal glucose, binders, fillers, disintegrants, lubricants, coatings, sweeteners, flavors and colors, liposomes, dispersion media, microcapsules, cationic lipid carriers, isotonic and absorption delaying agents, and the like. The carrier may also be substances for providing the formulation with stability, sterility and isotonicity (e.g., antimicrobial preservatives, antioxidants, chelating agents and buffers), for preventing the action of microorganisms (e.g. antimicrobial and antifungal agents, such as parabens, chlorobutanol, phenol, sorbic acid and the like) or for providing the formulation with an edible flavor etc. In some instances, the carrier is an agent that facilitates the delivery of a small molecule drug or antibody to a target cell or tissue. One of skill in the art will recognize that other pharmaceutical carriers are useful in the present disclosure.

The term "expression" as used herein refers the level of protein or mRNA in a mammalian cell.

The term "activity" as used herein refers to one or more activities of a protein, such as binding or enzymatic activity (e.g., one or more of phosphorylation, dephosphorylation, nuclear import, transcriptional activation, transcriptional repression, and/or binding activity to a substrate or a binding partner).

The term "IL-6 signaling" as used herein means the expression and/or activity of one or more proteins in a signaling pathway beginning with activation of an IL-6 receptor and ending in gene expression. Non-limiting examples of proteins in a signaling pathway beginning with activation of an IL-6 receptor and ending in gene expression include an IL-6 receptor, JAK, STAT3, PI3K, Akt/PKB, IKKs, IkBs, NF-kB, MAPK, Ras, Raf, MEK, and ERK.

The term "NF-kB signaling" as used herein means the expression and/or activity of one or more of IKKα, IKKβ, IkB, and NF-kB, and/or one or more genes upregulated by activity of NF-kB (e.g., one or more of TNF-α, IL-1, CAM, COX-2, and iNOS).

The term "PDGF signaling" as used herein means the expression and/or activity of one or more of PDGF receptor, PKC, PI3K, Src, Ras, ERKT1/2, Rho, Rac, Akt, mTOR, NAPDH oxidase, MAPK, and cPLA$_2$.

The term "SGLT-2 inhibitor" as used herein refers to a compound that inhibits the Sodium Glucose Co-Transporter-2 (SGLT-2). SGLT-2 inhibitors disrupt reabsorption of glucose by the kidneys and thus exert a glucose-lowering effect. By enhancing glucosuria, independently of insulin, SGLT-2 inhibitors have been shown to treat Type 2 diabetes and to improve cardiovascular outcomes. See Wright, 2001, Am. J. Physiol. Renal Physiol. 280:F10; and Scheen, 2018, Circ. Res. 122:1439. In some embodiments, the term "SGLT-2 inhibitor" refers to compounds whose primary effect is inhibition of SGLT-2, but is not limited to compounds that only inhibit SGLT-2, thus including compounds that have other activities in addition to SGLT-2 inhibition (e.g., SGLT-1 inhibition).

In some embodiments, SGLT-2 inhibitors include compounds of a class of drugs known as gliflozins. In some embodiments, SGLT-2 inhibitors include compounds that are approved as SGLT-2 inhibitors by a regulatory agency such as the FDA or EMA. Non-limiting examples of SGLT-2 inhibitors include bexagliflozin, canagliflozin (INVOKANA®), dapagliflozin (FARXIGA®), empagliflozin (JARDIANCE®), ertugliflozin (STEGLATRO™) ipragliflozin (SUGLAT®), luseogliflozin (LUSEFI®), remogliflozin, sergliflozin, licogliflozin, sotagliflozin (ZYNQUISTA™), and tofogliflozin.

In some embodiments, the SGLT-2 inhibitors include, but are not limited to dapagliflozin, canagliflozin, ipragliflozin, empagliflozin, bexagliflozin, licogliflozin, janagliflozin (XZP-5695), tofogliflozin, ertugliflozin, henagliflozin (SHR-3824), enavogliflozin (DWP-16001), TA-1887 (3-(4-cyclopropylbenzyl)-4-fluoro-1-(β-D-glucopyranosyl)-1H-indole), indole-N-glycoside 18 (3-(4-ethylbenzyl)-1-(β-D-glucopyranosyl)-1H-indole), sotagliflozin, luseogliflozin, sergliflozin etabonate (ethyl carbonate), remogliflozin, remogliflozin etabonate, and T-1095 (((2R,3S,4S,5R,6S)-6-(2-(3-(benzofuran-5-yl)propanoyl)-3-hydroxy-5-methylphenoxy)-3,4,5-trihydroxytetrahydro-2H-pyran-2-yl) etabonate).

In some embodiments, the SGLT-2 inhibitors include C-glycosides such as dapagliflozin, canagliflozin, ipragliflozin, empagliflozin, bexagliflozin, licogliflozin, janagliflozin (XZP-5695), tofogliflozin, ertugliflozin, henagliflozin (SHR-3824), enavogliflozin (DWP-16001). In some embodiments, the SGLT-2 inhibitors include C-glycosides with a bicyclic or spiro pyran group, such as tofogliflozin, ertugliflozin, and henagliflozin (SHR-3824). In some embodiments, the SGLT-2 inhibitors include C-glycosides that do not have a bicyclic or spiro pyran group, such as dapagliflozin, canagliflozin, ipragliflozin, empagliflozin, bexagliflozin, licogliflozin, janagliflozin (XZP-5695), and enavogliflozin (DWP-16001).

In some embodiments, the SGLT-2 inhibitors include N-glycosides such as TA-1887 (3-(4-cyclopropylbenzyl)-4-fluoro-1-(β-D-glucopyranosyl)-1H-indole) and indole-N-glycoside 18 (3-(4-ethylbenzyl)-1-(β-D-glucopyranosyl)-1H-indole).

In some embodiments, the SGLT-2 inhibitors include 2-methylthio-C-glycosides, such as sotagliflozin.

In some embodiments, the SGLT-2 inhibitors include thiopyran-C-glycosides, such as luseogliflozin.

In some embodiments, the SGLT-2 inhibitors include O-glycosides and O-glycoside prodrugs, such as sergliflozin etabonate (ethyl carbonate), remogliflozin, remogliflozin etabonate, and T-1095 (((2R,3S,4S,5R,6S)-6-(2-(3-(benzofuran-5-yl)propanoyl)-3-hydroxy-5-methylphenoxy)-3,4,5-trihydroxytetrahydro-2H-pyran-2-yl) etabonate).

In some embodiments, an SGLT-2 inhibitor, as defined herein, includes any compound exhibiting SGLT-2 inhibition activity. In some embodiments, an SGLT-2 inhibitor is selective for SGLT-2 over SGLT-1, for example, by having about 2-fold, about 5-fold, about 10-fold, about 20-fold, about 50-fold, about 100-fold, about 200-fold, about 300-fold, about 400-fold, about 500-fold, about 750-fold, about 1,000-fold, about 1,250-fold, about 1,500-fold, about 1,750-fold, about 2,000-fold, about 2,500-fold, or any value in between, greater activity against SGLT-2 than against SGLT-1. Exemplary SGLT-2 inhibitors can exhibit inhibition activity ($IC_{50}$) against SGLT-2 of less than about 1000 nM, less than about 500 nM, less than about 200 nM, less than about 100 nM, less than about 50 nM, less than about 25 nM, less than about 10 nM, or less than about 1 nM as measured in an assay as described herein. In some embodiments, SGLT-2 inhibitors can exhibit inhibition activity ($IC_{50}$) against SGLT-2 of less than about 25 nM, less than about 10 nM, less than about 5 nM, or less than about 1 nM as measured in an assay as provided herein. An exemplary assay for determining SGLT-2 inhibitory activity is described in Ryan, et al., Kidney International, Vol. 45, pp. 48-57 (1994). Briefly, CHO cells are stably transfected with cDNA encoding human SGLT-2 (GenBank #M95549). Cells are washed and then incubated with 10 µM [$^{14}C$]alpha-methyl glucopyranoside (AMG), and 10 µM inhibitor. The uptake of [$^{14}C$] AMG is quenched with cold buffer containing phlorizin, and cells are lysed. Suitable reagents are then used to quantify the uptake of [$^{14}C$]AMG.

SGLT-2 inhibitors include pharmaceutically acceptable salts, solvates, complexes, and salts of solvates thereof, for example, "dapagliflozin" includes salts of dapagliflozin (such as the hydrochloride salt) as well as solvates (such as the propylene glycol hydrate); likewise, "canagliflozin" includes solvates (such as canagliflozin hemihydrate) and salts of solvates (such as the hydrochloride salt of the hydrate). Similarly, henagliflozin (SHR-3824) and dapagliflozin include complexes (such as the complexes henagliflozin proline and dapagliflozin proline, respectively).

As used herein, when a subject is described as having "controlled serum glucose levels", it means the subject has a serum glucose level within the normal or healthy ranges. In some embodiments, the subject has a fasting serum glucose level of between about 70 mg/dL and about 130 mg/dL. For example, the subject has been determined to have a fasting serum glucose level of below about 130 mg/dL, 125 mg/dL, 120 mg/dL, 115 mg/dL, 110 mg/dL, 105 mg/dL, 100 mg/dL, 95 mg/dL, 90 mg/dL, 85 mg/dL, 80 mg/dL, or 75 mg/dL.

As used in the methods described herein, the term "reducing" refers to a reduction in the indicated parameter relative to the baseline measurement (or measurements) of the same parameter in the subject taken prior to the initiation of administration with atrasentan or a pharmaceutically acceptable salt thereof, or a reduction in the indicated parameter relative to the baseline measurement (or measurements) of the same parameter in a healthy subject (for example, a subject that does not have IgA nephropathy). Similarly, the term "increasing," as used herein, refers to an increase in the indicated parameter relative to the baseline measurement (or measurements) of the same parameter in the subject taken prior to the initiation of administration with atrasentan or a pharmaceutically acceptable salt thereof, or an increase in the indicated parameter relative to the baseline measurement (or measurements) of the same parameter in a healthy subject (for example, a subject that does not have IgA nephropathy).

The term "glomerular filtration rate (GFR)" is defined as the volume of fluid filtered from the renal (kidney) glomerular capillaries into the Bowman's capsule per unit time. It is indicative of overall kidney function. The glomerular filtration rate (GFR) can be calculated by measuring any chemical that has a steady level in the blood, and is freely filtered but neither reabsorbed nor secreted by the kidneys. The rate therefore measured is the quantity of the substance in the urine that originated from a calculable volume of blood. The GFR is typically recorded in units of volume per time, e.g., milliliters per minute and the formula below can be used: GFR=(Urine Concentration×Urine Volume)/Plasma Concentration. The GFR can be determined by injecting inulin into the plasma. Since inulin is neither reabsorbed nor secreted by the kidney after glomerular filtration, its rate of excretion is directly proportional to the rate of filtration of water and solutes across the glomerular filter. A normal value is: GFR=90-125 mL/min/1.73 $m^2$, in particular GFR=100-125 mL/min/1.73 $m^2$. Other principles to determine GFR involve measuring 51Cr-EDTA, [125I] iothalamate or iohexol. The "estimated glomerular filtration rate (eGFR)" is defined as derived at screening from serum creatinine values based on e.g., the Chronic Kidney Disease Epidemiology Collaboration (CKD-EPI) equation, the Cockcroft-Gault formula or the Modification of Diet in Renal Disease (MDRD) formula, which are all known in the art. "Stabilizing eGFR" as used herein means reducing the rate of decrease of eGFR and/or attenuating the rate of decline of eGFR. For example, the rate of decline of eGFR can be attenuated by at least about 20%; by at least about 30%; by at least about 40%; by at least about 50%; by at least about 60%; by at least about 70%; by at least about 80%; by at least about 90%; or by at least about 95%; or any value in between after treatment with atrasentan, or a pharmaceutically acceptable salt thereof. This attenuation can be after treatment, for example, for about 1 week, about 2 weeks, about 3 weeks, about 4 weeks, about 5 weeks, about 6 weeks, about 7 weeks, about 8 weeks, about 9 weeks, about 10 weeks, about 20 weeks, about 30 weeks, about 40 weeks, about 50 weeks, about 60 weeks, about 70 weeks, about 80 weeks, about 90 weeks, about 100 weeks, about 110 weeks, about 120 weeks, about 130 weeks, about 140 weeks, about 150 weeks, about 160 weeks, about 170 weeks, about 180 weeks, about 190 weeks, or about 200 weeks, or any value in between. In some embodiments, the subject has been treated with atrasentan or a pharmaceutically acceptable salt thereof for between about 15 days and about 30 days. In some embodiments, the subject has been treated with atrasentan or a pharmaceutically acceptable salt thereof for between about 6 months and about 1 year.

"ESRD" is the abbreviation for end-stage renal disease. As used herein, the onset of ESRD is defined as the time point when the subject has an eGFR of below about 15 mL/min/1.73 $m^2$ and/or when the subject has initiated chronic dialysis. When a subject is defined to be "at a high risk of progression to ESRD", the subject has >1 g/day protein in the urine and/or eGFR<60 for at least about 3 months before the first administration of atrasentan or a pharmaceutically acceptable salt thereof.

"IgA-nephropathy associated disease flares" as used herein refer to disease flares associated with hematuria, worsening proteinuria, systemic manifestations, and declines in eGFR. Other symptoms associated with disease flares include: increased edema, fatigue, increased hematuria, gross hematuria, and other symptoms which generally negatively impact disease progression.

As used herein, when a subject is described to "maintain a potassium level within the normal physiologic range", the subject has a blood potassium level of from about 3.5 mEq/L to about 5.2 mEq/L.

As used herein, when a subject is described to "maintain a sodium level within the normal physiologic range", the subject has a blood sodium level of from about 135 to about 145 mEq/L.

As used herein, the term "proteinuria" refers to the presence of protein in the urine in excess of normal levels. "Proteinuria" includes "albuminuria" and "microalbuminuria". Normal human levels of protein appear in the urine in the range of about 0 to 30 mg/L, although for any given urine sample, the level may reach about 80 mg/L. For a 24 hour urine collection, normal human levels of urinary protein are in the range of about 0 to 150 mg. Proteinuria can be indicated by the ratio of total protein/creatinine in the urine (UPCR), or by the ration of a specific protein, such as a urinary albumin/creatinine ratio (ACR) of greater than about 30 mg/g. Typically, the urinary UACR value in mg/g approximately equals to the albumin excretion by the subject in mg/day. Proteinuria, including albuminuria and microalbuminuria, often leads to or is indicative of a disease, but is not limited to production of a disease. Proteinuria is intended to encompass all forms of proteinuria, including but not limited to physiological proteinuria; functional proteinuria; and athletic proteinuria, which relates to a form of functional proteinuria following excessive muscular exertion. Further, proteinuria covers benign proteinuria (also known as "essential" proteinuria), which refers to types or proteinuria that are not the result of pathologic changes in the kidneys. Proteinuria also covers pathologic proteinuria, for example levels of protein in the urine greater than normal physiological levels.

As used herein, the term "albuminuria" (also known as "microalbuminuria") refers to the presence of albumin in the urine in excess of normal levels. Since urinary protein is predominantly albumin, normal human levels of urinary UACR are in the range of about 0 to 30 mg/mmol. As used herein, the term "microalbuminuria" refers to the presence of albumin in the urine, excreted at a rate of about 20 to 200 µg/min or at a level of about 30 to 300 mg/L in humans. When defined by the urinary ACR, "microalbuminuria" refers to a urinary UACR of greater than about 30 mg/g, or a urinary UACR of about 3.5 mg/mmol or greater for women and about 2.5 mg/mmol or greater for men. Microalbuminuria is often an early warning of kidney disease, but can also be present for other reasons.

As used herein, the term "hematuria" refers to the presence of blood in the urine. It may present as macroscopic hematuria (visible traces of blood cells) or microscopic hematuria (microscopic traces of blood) within the urine. A confirmed indication of microhematuria is defined as 3 or more red blood cells present per microscopic high-powered field (HPF) on a minimum of 3 properly collected urine samples. Microhematuria may also be detected by urine dipstick (colorimetric comparison estimate) at clinic. Hematuria (either microscopic or macroscopic) may be asymptomatic (no additional symptoms associated with hematuria) or symptomatic. Additional symptoms include dysuria (painful urination), a feeling of incomplete emptying of the bladder or increased frequency or urination, or flank pain.

"ALT" as used herein refers to alanine transaminase. "AST" as used herein refers to aspartate transaminase.

The term "synergy" or "synergistic" is used herein to mean that the effect of a combination of two or more therapeutic agents is greater than the sum of the effect of each agent when administered alone. See, e.g., Chou and Talalay, Advances in Enzyme Regulation (1984), 22, 27-55. A "synergistically effective amount" is an amount of the combination of the two or more therapeutic agents that results in a synergistic effect (as "synergistic" is defined herein). In some embodiments, a synergistically effective amount of a combination may be therapeutically effective even when one or more of the compounds in the combination is administered at a dose that would be sub-therapeutic when the compound is administered alone.

It will be appreciated that different concentrations of each compound may be employed for various art-recognized factors, for example, the patient's height, weight, sex, age and medical history. Exemplary synergistic effects includes, but are not limited to, enhanced therapeutic efficacy, decreased dosage at equal or increased level of efficacy, reduced or delayed development of drug resistance, and simultaneous enhancement or equal therapeutic actions (e.g., the same therapeutic effect as at least one of the therapeutic agents) and a reduction of unwanted drug effects (e.g. side effects and adverse events) of at least one of the therapeutic agents.

In some embodiments, "synergistic effect" as used herein refers to a combination of atrasentan, or a pharmaceutically acceptable salt thereof, and one or more additional therapeutic agents (for example, a SGLT-2 inhibitor), producing an effect, for example, any of the beneficial or desired results including clinical results as described herein, which is greater than the sum of effect observed when the atrasentan, or a pharmaceutically acceptable salt thereof, and the SGLT-2 inhibitor are administered alone. Such clinical results include, but are not limited to treating IgA nephropathy, decreasing renal inflammation and/or fibrosis, decreasing hematuria, decreasing proteinuria (e.g., albuminuria), stabilizing eGFR, decreasing the number of IgA-nephropathy associated disease flares, delaying the onset of ESRD, decreasing fatigue, reducing activation of a mesangial cell.

In some embodiments, "synergistic effect" as used herein refers to a combination of atrasentan, or a pharmaceutically acceptable salt thereof and a SGLT-2 inhibitor, providing a greater reduction in proteinuria, such as albuminuria, than the sum of effect observed when the atrasentan, or a pharmaceutically acceptable salt thereof, and the SGLT-2 inhibitor are administered alone.

In some embodiments, "synergistic effect" as used herein refers to a combination of atrasentan, or a pharmaceutically acceptable salt thereof, and an SGLT-2 inhibitor, producing a desired therapeutic effect and a reduction in the occurrence and/or severity of an unwanted drug effect, side effect, or adverse event. In some embodiments, the unwanted drug effect, side effect, or adverse event is associated with or observed in monotherapy of atrasentan, or a pharmaceutically acceptable salt thereof, or a SGLT-2 inhibitor. In some embodiments, the unwanted drug effect, side effect, or adverse event is one or more of fluid retention, anemia, nausea, constipation, thirst, bone fractures, increased urination, urinary tract infection, yeast infection, vaginal itching, increased LDL cholesterol levels, increased brain natriuretic peptide (BNP) levels, acute sodium retention, and acute increases in creatinine levels. In some embodiments, the fluid retention is associated with a weight gain of greater than about 3 kg. In some embodiments, the increased BNP levels are greater than about 300 pg/mL.

As described herein, any concentration range, percentage range, ratio range, or integer range is to be understood to include the value of any integer within the recited range and, when appropriate, fractions thereof (such as one tenth and one hundredth of an integer), unless otherwise indicated.

Unless otherwise stated, any reference to an amount of atrasentan in this disclosure is based on the free equivalent weight of atrasentan. For example, 0.75 mg of atrasentan refers to 0.75 mg of atrasentan in the free form or an equivalent amount of a salt form of atrasentan.

Various aspects of the disclosure are described in further detail in the following subsections.

B. Introduction

Most subjects with IgAN first present with either single or episodic macroscopic hematuria, or after detection of microscopic hematuria and/or proteinuria during routine urine testing. In some cases, subjects present with acute kidney injury, such as a result of crescentic IgAN or gross hematuria causing tubular obstruction. Definitive diagnosis of IgAN is typically is established by kidney biopsy, with immunofluorescence and/or immunoperoxidase studies for IgA deposits. Prominent, globular deposits of IgA (sometimes accompanied by C3 and IgG) in the mesangium and less prominently along the glomerular capillary wall are a hallmark of IgAN. Certain histopathological features that correlate with long-term outcome include mesangial proliferation, endocapillary proliferation, segmental scarring, and tubular atrophy.

C. Methods of Treatment

In a normal and healthy human kidney, expressions of ET-1 and ET-RA are more intense in vascular tissue and less intense in glomerular structures. In contrast, subjects with IgAN show increased expressions of ET-1 and ET-RA in the kidney. In that population, ET-1 expression positively correlates with proteinuria, which is at least partially ameliorated by administration of ACE inhibitors. Indeed, the currently therapy for IgAN is optimization of antihypertensive and antiproteinuric agents (e.g., angiotensin converting enzyme inhibitors and/or angiotensin II receptor blockers), along with a course of corticosteroids, to inhibit disease progression. See, e.g., Penfold et al., Int. J. Nephrol. and Renovascular Dis. 11, pp. 137-148 (2017). However, these combinations of agents may exhibit significant dose-limiting side effects such as hyperkalemia, and further immunosuppression may be necessary in more serious cases.

Clinically, IgAN is diagnosed by kidney biopsy indicating the presence of mesangial cell proliferation and/or matrix expansion (or focal segmental glomerular sclerosis in advanced stages) with predominant mesangial granular deposits of IgA (2+ or more) on immunofluorescence. This pathology is distinct from other progressive kidney diseases such as diabetic nephropathy, which typically present with a diffuse capillary basement membrane thickening with peripheral hyaline PAS-positive nodules, with segmental or global glomerular sclerosis at advanced stages, and thickened arterioles with hyaline deposits. See, e.g., Zanatta, et al., Renal Failure, 34(3), pp. 308-315 (2012).

Accordingly, in one aspect, provided herein is a method of treating IgA nephropathy, comprising administering a therapeutically effective amount of atrasentan, or a pharmaceutically acceptable salt thereof, to a subject in need thereof.

In some embodiments, the subject has not been previously diagnosed with one or more of diabetic nephropathy, HIV/AIDS, HIV-related nephropathy, prostate cancer, or acute kidney failure. In some embodiments, the subject has not been previously diagnosed with any of diabetic nephropathy, HIV/AIDS, HIV-related nephropathy, prostate cancer, or acute kidney failure. In some embodiments, the subject has not been previously diagnosed with diabetic nephropathy. In some embodiments, the subject has not been previously diagnosed with HIV/AIDS. In some embodiments, the subject has not been previously diagnosed with HIV-related nephropathy. In some embodiments, the subject has not been previously diagnosed with prostate cancer. In some embodiments, the subject has not been previously diagnosed with acute kidney failure. In some embodiments, the subject has not been previously diagnosed with one or more of diabetic nephropathy, HIV/AIDS, HIV-related nephropathy, cancer, or acute kidney failure. In some embodiments, the subject has not been previously diagnosed with diabetes (i.e., Type 1 or Type 2 diabetes). In some embodiments, the subject has been previously diagnosed with diabetes (i.e., Type 1 or Type 2 diabetes). In some embodiments, the subject has been previously diagnosed with diabetes, and has not been previously diagnosed with diabetic nephropathy. In some embodiments, the subject has not been previously diagnosed with Type 2 diabetes. In some embodiments, the subject has been previously diagnosed with Type 2 diabetes. In some embodiments, the subject has been previously diagnosed with Type 2 diabetes, and has not been previously diagnosed with diabetic nephropathy.

In some embodiments, the subject is not currently diagnosed with cancer. In some embodiments, the subject is not currently being treated for cancer. In some embodiments, the cancer is lung cancer or prostate cancer.

In some embodiments, the subject does not have one or more of diabetic nephropathy, HIV/AIDS, HIV-related nephropathy, prostate cancer, or acute kidney failure. In some embodiments, the subject does not have any of diabetic nephropathy, HIV/AIDS, HIV-related nephropathy, prostate cancer, or acute kidney failure. In some embodiments, the subject does not have diabetic nephropathy. In some embodiments, the subject does not have HIV/AIDS. In some embodiments, the subject does not have HIV-related nephropathy. In some embodiments, the subject does not have cancer. In some embodiments, the cancer is prostate cancer. In some embodiments, the cancer is lung cancer. In some embodiments, the subject does not have acute kidney failure. In some embodiments, the subject does not have one or more of diabetic nephropathy, HIV/AIDS, HIV-related nephropathy, cancer, or acute kidney failure. In some embodiments, the cancer is lung cancer or prostate cancer. In some embodiments, the subject has diabetes (i.e., Type 1 or Type 2 diabetes). In some embodiments, the subject does not have diabetes (i.e., Type 1 or Type 2 diabetes). In some embodiments, the subject has diabetes, and does not have diabetic nephropathy. In some embodiments, the subject has Type 2 diabetes. In some embodiments, the subject does not have Type 2 diabetes. In some embodiments, the subject has Type 2 diabetes, and does not have diabetic nephropathy.

In some embodiments, the subject does not suffer from one or more of diabetic nephropathy, HIV/AIDS, HIV-related nephropathy, prostate cancer, or acute kidney failure. In some embodiments, the subject does not suffer from any of diabetic nephropathy, HIV/AIDS, HIV-related nephropathy, prostate cancer, or acute kidney failure. In some embodiments, the subject does not suffer from diabetic nephropathy. In some embodiments, the subject does not suffer from HIV/AIDS. In some embodiments, the subject does not suffer from HIV-related nephropathy. In some embodiments, the subject does not suffer from cancer. In some embodiments, the cancer is prostate cancer. In some embodiments, the cancer is lung cancer. In some embodiments, the subject does not suffer from acute kidney failure. In some embodiments, the subject does not suffer from one or more of diabetic nephropathy, HIV/AIDS, HIV-related nephropathy, cancer, or acute kidney failure. In some embodiments, the cancer is lung cancer or prostate cancer. In some embodiments, the subject does not suffer from diabetes (i.e., Type 1 or Type 2 diabetes). In some embodiments, the subject does suffer from diabetes (i.e., Type 1 or Type 2 diabetes). In some embodiments, the subject does suffer from diabetes, such as Type 1 diabetes or Type 2 diabetes, but does not suffer from diabetic nephropathy. In some embodiments, the subject does not suffer from Type 2 diabetes. In some embodiments, the subject does suffer from Type 2 diabetes. In some embodiments, the subject does suffer from Type 2 diabetes, but does not suffer from diabetic nephropathy.

In some embodiments, the subject is not being treated for one or more of diabetic nephropathy, HIV/AIDS, HIV-related nephropathy, prostate cancer, or acute kidney failure. In some embodiments, the subject is not being treated for any of diabetic nephropathy, HIV/AIDS, HIV-related nephropathy, prostate cancer, or acute kidney failure. In some embodiments, the subject is not being treated for diabetic nephropathy. In some embodiments, the subject is not being treated for HIV/AIDS. In some embodiments, the subject is not being treated for HIV-related nephropathy. In some embodiments, the subject is not being treated for prostate cancer. In some embodiments, the subject is not being treated for acute kidney failure. In some embodiments, the subject is not being treated for one or more of diabetic nephropathy, HIV/AIDS, HIV-related nephropathy, cancer, or acute kidney failure. In some embodiments, the cancer is lung cancer or prostate cancer. In some embodiments, the subject is not being treated for diabetes (i.e., Type 1 or Type 2 diabetes). In some embodiments, the subject is being treated for diabetes (i.e., Type 1 or Type 2 diabetes). In some embodiments, the subject is being treated for diabetes, such as Type 1 diabetes or Type 2 diabetes, but is not being treated for diabetic nephropathy. In some embodiments, the subject is not being treated for Type 2 diabetes. In some embodiments, the subject is being treated for Type 2 diabetes. In some embodiments, the subject is being treated for Type 2 diabetes, but is not being treated for diabetic nephropathy.

In certain embodiments, the subject has been determined to have controlled serum glucose levels. In some embodiments, the subject with controlled serum glucose levels is not being treated for diabetes. In some embodiments, the subject with controlled serum glucose levels is being treated for diabetes. In some embodiments, the subject with controlled serum glucose levels is not being treated for Type 2 diabetes. In some embodiments, the subject with controlled serum glucose levels is being treated for Type 2 diabetes. In some embodiments, the subject has been determined to have controlled serum glucose levels; where the subject has not been diagnosed with one or more of HIV-related nephropathy or acute kidney failure. For example, the subject has been determined to have a fasting serum glucose level of below about 130 mg/dL, about 125 mg/dL, about 120 mg/dL, about 115 mg/dL, about 110 mg/dL, about 105 mg/dL, about 100 mg/dL, about 95 mg/dL, about 90 mg/dL, about 85 mg/dL, about 80 mg/dL, or about 75 mg/dL, or any value in between. In certain embodiments, the subject has not been diagnosed with one or more of HIV-related nephropathy or acute kidney failure. In certain embodiments, the subject has been determined to have controlled serum glucose levels as described anywhere herein; and the subject has not been diagnosed with one or more of HIV-related nephropathy or acute kidney failure. In certain embodiments, the subject has been determined to have controlled serum glucose levels; and the subject has not been diagnosed with one or more of HIV-related nephropathy or acute kidney failure.

In another aspect, provided herein is a method of decreasing renal inflammation and/or fibrosis in a subject having IgA nephropathy, comprising administering a therapeutically effective amount of atrasentan, or a pharmaceutically acceptable salt thereof, to a subject in need thereof.

In some embodiments, the renal inflammation in the subject having IgA nephropathy is decreased by at least about 10% after treatment with atrasentan or a pharmaceutically acceptable salt thereof (e.g., after treatment for about 1 week, about 2 weeks, about 3 weeks, about 4 weeks, about 5 weeks, about 6 weeks, about 7 weeks, about 8 weeks, about 9 weeks, about 10 weeks, about 20 weeks, about 30 weeks, about 40 weeks, about 50 weeks, about 60 weeks, about 70 weeks, about 80 weeks, about 90 weeks, about 100 weeks, about 110 weeks, about 120 weeks, about 130 weeks, about 140 weeks, about 150 weeks, about 160 weeks, about 170 weeks, about 180 weeks, about 190 weeks, or about 200 weeks, or any value in between). In certain embodiments, the renal inflammation in the subject is decreased by at least about 20%, about 30%, about 40%, about 50%, about 60%, about 70%, about 80%, about 90%, or about 95%, or any value in between. In certain of the foregoing embodiments, the subject has been treated with atrasentan or a pharmaceutically acceptable salt thereof for between about 15 days and about 30 days.

In some embodiments, renal fibrosis in the subject having IgA nephropathy is decreased by at least about 10% after treatment with atrasentan or a pharmaceutically acceptable salt thereof (e.g., after treatment for about 1 week, about 2 weeks, about 3 weeks, about 4 weeks, about 5 weeks, about 6 weeks, about 7 weeks, about 8 weeks, about 9 weeks, about 10 weeks, about 20 weeks, about 30 weeks, about 40 weeks, about 50 weeks, about 60 weeks, about 70 weeks, about 80 weeks, about 90 weeks, about 100 weeks, about 110 weeks, about 120 weeks, about 130 weeks, about 140 weeks, about 150 weeks, about 160 weeks, about 170 weeks, about 180 weeks, about 190 weeks, or about 200 weeks, or any value in between). In certain embodiments, the renal fibrosis in the subject is decreased by at least about 20%, about 30%, about 40%, about 50%, about 60%, about 70%, about 80%, about 90%, or about 95%, or any value in between. In certain of the foregoing embodiments, the subject has been treated with atrasentan or a pharmaceutically acceptable salt thereof for between about 15 days and about 30 days.

In some embodiments, renal fibrosis in the subject having IgA nephropathy is decreased to less than about 50% of the cortical area of the affected kidney(s) after treatment with atrasentan or a pharmaceutically acceptable salt thereof (e.g., after treatment for about 1 week, about 2 weeks, about 3 weeks, about 4 weeks, about 5 weeks, about 6 weeks, about 7 weeks, about 8 weeks, about 9 weeks, about 10 weeks, about 20 weeks, about 30 weeks, about 40 weeks, about 50 weeks, about 60 weeks, about 70 weeks, about 80 weeks, about 90 weeks, about 100 weeks, about 110 weeks, about 120 weeks, about 130 weeks, about 140 weeks, about 150 weeks, about 160 weeks, about 170 weeks, about 180 weeks, about 190 weeks, or about 200 weeks, or any value in between). In certain embodiments, about renal fibrosis in the subject is decreased to less than about 40% of the cortical area. For example, in some embodiments, renal fibrosis in the subject is decreased to less than about 35%, about 30%, about 25%, about 20%, about 15%, or about 10%, or any value in between, of the cortical area. In certain of the foregoing embodiments, the subject has been treated with atrasentan or a pharmaceutically acceptable salt thereof for between about 15 days and about 30 days.

In another aspect, provided herein is a method of decreasing the occurrence of hematuria in a subject having IgA nephropathy, comprising administering a therapeutically effective amount of atrasentan, or a pharmaceutically acceptable salt thereof, to a subject in need thereof.

In some embodiments, the number of urinary red blood cells per high powered (microscope) field (rbc/hpf) in the subject having IgA nephropathy is decreased by at least about 10% after treatment with atrasentan or a pharmaceutically acceptable salt thereof (e.g., after treatment for about 1 week, about 2 weeks, about 3 weeks, about 4 weeks, about 5 weeks, about 6 weeks, about 7 weeks, about 8 weeks, about 9 weeks, about 10 weeks, about 20 weeks, about 30 weeks, about 40 weeks, about 50 weeks, about 60 weeks, about 70 weeks, about 80 weeks, about 90 weeks, about 100 weeks, about 110 weeks, about 120 weeks, about 130 weeks, about 140 weeks, about 150 weeks, about 160 weeks, about 170 weeks, about 180 weeks, about 190 weeks, or about 200 weeks, or any value in between). In certain embodiments, the urinary rbc/hpf in the subject is decreased by at least about 20%, about 30%, about 40%, about 50%, about 60%, about 70%, about 80%, about 90%, or about 95%, or any value in between. In certain of the foregoing embodiments, the subject has been treated with atrasentan or a pharmaceutically acceptable salt thereof for between about 15 days and about 30 days.

In another aspect, provided herein is a method of stabilizing eGFR, in a subject having IgA nephropathy comprising administering a therapeutically effective amount of atrasentan, or a pharmaceutically acceptable salt thereof, to a subject in need thereof.

In some embodiments, provided herein is a method for reducing the rate of decrease of eGFR in a subject having IgA nephropathy, the method comprising administering a therapeutically effective amount of atrasentan, or a pharmaceutically acceptable salt thereof, to a subject in need thereof. In some embodiments, the rate of decrease of eGFR of the subject is reduced by at least about 10% after treatment with atrasentan or a pharmaceutically acceptable salt thereof (e.g., after treatment for 1 week, about 2 weeks, about 3 weeks, about 4 weeks, about 5 weeks, about 6 weeks, about 7 weeks, about 8 weeks, about 9 weeks, about 10 weeks, about 20 weeks, about 30 weeks, about 40 weeks, about 50 weeks, about 60 weeks, about 70 weeks, about 80 weeks, about 90 weeks, about 100 weeks, about 110 weeks, about 120 weeks, about 130 weeks, about 140 weeks, about 150 weeks, about 160 weeks, about 170 weeks, about 180 weeks, about 190 weeks, or about 200 weeks, or any value in between). In some embodiments, the rate of decrease of eGFR of the subject is reduced by at least about 20%; by at least about 30%; by at least about 40%; by at least about 50%; by at least about 60%; by at least about 70%; by at least about 80%; by at least about 90%; or by at least about 95%; or any value in between. In certain of the foregoing embodiments, the subject has been treated with atrasentan or a pharmaceutically acceptable salt thereof for between about 15 days and about 30 days. In certain of the foregoing embodiments, the subject has been treated with atrasentan or a pharmaceutically acceptable salt thereof for between about 6 months and about 1 year.

In some embodiments, the rate of decrease of eGFR of the subject having IgA nephropathy is reduced to below about 10 mL/min/1.73 m$^2$ after treatment with atrasentan or a pharmaceutically acceptable salt thereof. For example, after treatment for 1 week, about 2 weeks, about 3 weeks, about 4 weeks, about 5 weeks, about 6 weeks, about 7 weeks, about 8 weeks, about 9 weeks, about 10 weeks, about 20 weeks, about 30 weeks, about 40 weeks, about 50 weeks, about 60 weeks, about 70 weeks, about 80 weeks, about 90 weeks, about 100 weeks, about 110 weeks, about 120 weeks, about 130 weeks, about 140 weeks, about 150 weeks, about 160 weeks, about 170 weeks, about 180 weeks, about 190 weeks, or about 200 weeks, or any value in between. In certain embodiments, the rate of decrease of eGFR of the subject is reduced to below about 9 mL/min/1.73 m$^2$, about 8 mL/min/1.73 m$^2$, about 7 mL/min/1.73 m$^2$, about 6 mL/min/1.73 m$^2$, about 5 mL/min/1.73 m$^2$, about 4 mL/min/1.73 m$^2$, about 3 mL/min/1.73 m$^2$, about 2 mL/min/1.73 m$^2$, about 1 mL/min/1.73 m$^2$, or about 0.75 mL/min/1.73 m$^2$, or any value in between after treatment with atrasentan, or a pharmaceutically acceptable salt thereof, for between about 6 months to about 1 year. The typical decline in eGFR with age, for example, in a subject between about 20 to about 30 years of age, is about 1 mL/min/1.73 m$^2$ per year.

In another aspect, provided herein is method of decreasing the number of IgA-nephropathy associated disease flares in a subject having IgA nephropathy, comprising administering a therapeutically effective amount of atrasentan, or a pharmaceutically acceptable salt thereof, to a subject in need thereof. In some embodiments, the method decreases disease flares associated with hematuria. In some embodiments, the method decreases disease flares associated with proteinuria. In some embodiments, the method decreases IgA-nephropathy associated disease flares which are associated with systemic manifestations. In some embodiments, the method decreases declines in eGFR as described anywhere herein. In some embodiments, the method decreases one or more of edema, fatigue, hematuria, or gross hematuria. In some embodiments, the method positively impacts disease progression.

In another aspect, provided herein is a method of delaying the onset of ESRD in a subject having IgA nephropathy, comprising administering a therapeutically effective amount of atrasentan, or a pharmaceutically acceptable salt thereof, to a subject in need thereof.

In some embodiments, the method increases the time between the diagnosis of IgA nephropathy in the subject and the time when eGFR of the subject falls below 15 mL/min/1.73 m$^2$. In certain embodiments, the method increases the time between the diagnosis of IgA nephropathy in the subject and the time when eGFR of the subject falls below 15 mL/min/1.73 m$^2$ by at least about 10%. For example, in some embodiments, the method increases the time between the diagnosis of IgA nephropathy in the subject and the time when eGFR of the subject falls below 15 mL/min/1.73 m$^2$ by at least about 20%, about 30%, about 40%, about 50%, about 60%, about 70%, about 80%, about 90%, about 100%, about 150%, about 200%, about 250%, about 300%, about 350%, about 400%, about 450%, or about 500%, or any value in between.

In certain embodiments, the method increases the time between the diagnosis of IgA nephropathy in the subject and the time when eGFR of the subject falls below 15 mL/min/1.73 m$^2$ by at least about 1 year. For example, the method can delay the time when eGFR of the subject falls below 15 mL/min/1.73 m$^2$ by at least about 1.5 years, 2 years, 2.5 years, 3 years, 3.5 years, 4 years, 4.5 years, 5 years, 5.5 years, 6 years, 6.5 years, 7 years, 7.5 years, 8 years, 8.5 years, 9 years, 9.5 years, 10 years, 11 years, 12 years, 13 years, 15 years, 15 years, 16 years, 17 years, 18 years, 19 years, or 20 years.

In another aspect, provided herein is a method of decreasing proteinuria in a subject having IgA nephropathy, comprising administering a therapeutically effective amount of atrasentan, or a pharmaceutically acceptable salt thereof, to a subject in need thereof.

In some embodiments, the amount of proteins (e.g., albumin) in the urine of the subject having IgA nephropathy is reduced by at least about 10% after treatment with atrasentan or a pharmaceutically acceptable salt thereof (e.g., after treatment for 1 week, about 2 weeks, about 3 weeks, about 4 weeks, about 5 weeks, about 6 weeks, about 7 weeks, about 8 weeks, about 9 weeks, about 10 weeks, about 20 weeks, about 30 weeks, about 40 weeks, about 50 weeks, about 60 weeks, about 70 weeks, about 80 weeks, about 90 weeks, about 100 weeks, about 110 weeks, about 120 weeks, about 130 weeks, about 140 weeks, about 150 weeks, about 160 weeks, about 170 weeks, about 180 weeks, about 190 weeks, or about 200 weeks, or any value in between). In some embodiments, the amount of proteins in the urine of the subject is reduced by at least about 15%, about 20%, about 25%, about 30%, about 35%, about 40%, about 50%, about 55%, about 60%, about 65%, about 70%, about 75%, about 80%, about 85%, about 90%, or about 95%, or any value in between. In certain of the foregoing embodiments, the subject has been treated with atrasentan or a pharmaceutically acceptable salt thereof for between about 15 days and about 30 days.

In certain embodiments, the amount of proteins (e.g., albumin) in the urine of the subject having IgA nephropathy is reduced by about 20% to about 80% after between about 2 days and about 30 days of treatment with atrasentan, or a pharmaceutically acceptable salt thereof. In certain embodiments, the amount of proteins (e.g., albumin) in the urine of the subject having IgA nephropathy is reduced by about 20% to about 80% after between about 15 days and about 30 days of treatment with atrasentan, or a pharmaceutically acceptable salt thereof. In certain of these embodiments, the amount of proteins in the urine of the subject is reduced by about 25% to about 80%. In certain of these embodiments, the amount of proteins in the urine of the subject is reduced by about 30% to about 80%. In certain of these embodiments, the amount of proteins in the urine of the subject is reduced by about 35% to about 80%. In certain of these embodiments, the amount of proteins in the urine of the subject is reduced by about 40% to about 80%. In certain of these embodiments, the amount of proteins in the urine of the subject is reduced by about 45% to about 80%. In certain of these embodiments, the amount of proteins in the urine of the subject is reduced by about 50% to about 80%. In the aforementioned embodiments, the reduction of the amount of proteins (e.g., albumin) in the urine of the subject having IgA nephropathy is relative to the amount of proteins (e.g., albumin) in the urine prior to initiation of treatment with atrasentan, or a pharmaceutically acceptable salt thereof.

In some embodiments, the amount of proteins (e.g., albumin) in the urine of the subject having IgA nephropathy is reduced by about 100 mg/dL to about 3,000 mg/dL after treatment with atrasentan or a pharmaceutically acceptable salt thereof (e.g., after treatment for 1 week, about 2 weeks, about 3 weeks, about 4 weeks, about 5 weeks, about 6 weeks, about 7 weeks, about 8 weeks, about 9 weeks, about 10 weeks, about 20 weeks, about 30 weeks, about 40 weeks, about 50 weeks, about 60 weeks, about 70 weeks, about 80 weeks, about 90 weeks, about 100 weeks, about 110 weeks, about 120 weeks, about 130 weeks, about 140 weeks, about 150 weeks, about 160 weeks, about 170 weeks, about 180 weeks, about 190 weeks, or about 200 weeks, or any value in between). In certain embodiments, the amount of proteins in the urine of the subject is reduced by about 100 mg/dL to about 2,500 mg/dL. In certain embodiments, the amount of proteins in the urine of the subject is reduced by about 100 mg/dL to about 2,000 mg/dL. In certain embodiments, the amount of proteins in the urine of the subject is reduced by about 100 mg/dL to about 1,500 mg/dL. In certain embodiments, the amount of proteins in the urine of the subject is reduced by about 100 mg/dL to about 1,000 mg/dL. In certain embodiments, the amount of proteins in the urine of the subject is reduced by about 100 mg/dL to about 500 mg/dL. In certain embodiments, the amount of proteins in the urine of the subject is reduced by about 100 mg/dL to about 400 mg/dL. In certain embodiments, the amount of proteins in the urine of the subject is reduced by about 100 mg/dL to about 300 mg/dL. In certain embodiments, the amount of proteins in the urine of the subject is reduced by about 100 mg/dL to about 200 mg/dL. In certain embodiments, the amount of proteins in the urine of the subject is reduced by about 500 mg/dL to about 2,500 mg/dL. In certain embodiments, the amount of proteins in the urine of the subject is reduced by about 500 mg/dL to about 2,000 mg/dL. In certain embodiments, the amount of proteins in the urine of the subject is reduced by about 500 mg/dL to about 1,500 mg/dL. In certain embodiments, the amount of proteins in the urine of the subject is reduced by about 500 mg/dL to about 1,000 mg/dL. In certain embodiments, the amount of proteins in the urine of the subject is reduced by about 500 mg/dL to about 900 mg/dL. In certain embodiments, the amount of proteins in the urine of the subject is reduced by about 500 mg/dL to about 800 mg/dL. In certain embodiments, the amount of proteins in the urine of the subject is reduced by about 600 mg/dL to about 900 mg/dL. In certain embodiments, the amount of proteins in the urine of the subject is reduced by about 700 mg/dL to about 900 mg/dL. In certain embodiments, the amount of proteins in the urine of the subject is reduced by about 1,000 mg/dL to about 2,000 mg/dL. In certain of the foregoing embodiments, the subject has been treated with atrasentan or a pharmaceutically acceptable salt thereof for between about 15 days and about 30 days. In the aforementioned embodiments, the reduction of the amount of proteins (e.g., albumin) in the urine of the subject having IgA nephropathy is relative to the amount of proteins (e.g., albumin) in the urine prior to initiation of treatment with atrasentan, or a pharmaceutically acceptable salt thereof.

In certain embodiments, the amount of proteins (e.g., albumin) in the urine of the subject having IgA nephropathy is reduced by about 100 mg/dL to about 500 mg/dL after between about 15 days and about 30 days of treatment with atrasentan, or a pharmaceutically acceptable salt thereof. In certain embodiments, the amount of proteins in the urine of the subject is reduced by about 200 mg/dL to about 500 mg/dL after between about 15 days and about 30 days of treatment with atrasentan, or a pharmaceutically acceptable salt thereof. In certain embodiments, the amount of proteins in the urine of the subject is reduced by about 300 mg/dL to about 500 mg/dL after between about 15 days and about 30 days of treatment with atrasentan, or a pharmaceutically acceptable salt thereof. In the aforementioned embodiments, the reduction of the amount of proteins (e.g., albumin) in the urine of the subject having IgA nephropathy is relative to the amount of proteins (e.g., albumin) in the urine prior to initiation of treatment with atrasentan, or a pharmaceutically acceptable salt thereof.

In certain embodiments, the amount of proteins (e.g., albumin) in the urine of the subject having IgA nephropathy is reduced by about 500 mg/dL to about 900 mg/dL after between about 15 days and about 30 days of treatment with atrasentan, or a pharmaceutically acceptable salt thereof. In certain embodiments, the amount of proteins in the urine of the subject is reduced by about 600 mg/dL to about 900 mg/dL after between about 15 days and about 30 days of treatment with atrasentan, or a pharmaceutically acceptable salt thereof. In certain embodiments, the amount of proteins in the urine of the subject is reduced by about 700 mg/dL to about 900 mg/dL after between about 15 days and about 30 days of treatment with atrasentan, or a pharmaceutically acceptable salt thereof. In the aforementioned embodiments, the reduction of the amount of proteins (e.g., albumin) in the urine of the subject having IgA nephropathy is relative to the amount of proteins (e.g., albumin) in the urine prior to initiation of treatment with atrasentan, or a pharmaceutically acceptable salt thereof.

In some embodiments, the subject having IgA nephropathy has a reduced level of proteins (e.g., albumin) in the urine of below about 1.0 gram/day after treatment with atrasentan or a pharmaceutically acceptable salt thereof (e.g., after treatment for 1 week, 2 weeks, 3 weeks, 4 weeks, 5 weeks, 6 weeks, 7 weeks, 8 weeks, 9 weeks, 10 weeks, 20 weeks, 30 weeks, 40 weeks, 50 weeks, 60 weeks, 70 weeks, 80 weeks, 90 weeks, 100 weeks, 110 weeks, 120 weeks, 130 weeks, 140 weeks, 150 weeks, 160 weeks, 170 weeks, 180 weeks, 190 weeks, or 200 weeks). In certain embodiments, the subject has a reduced level of proteins in the urine of below about 0.9 gram/day. In certain embodiments, the subject has a reduced level of proteins in the urine of below about 0.8 gram/day. In certain embodiments, the subject has a reduced level of proteins in the urine of below about 0.7 gram/day. In certain embodiments, the subject has a reduced level of proteins in the urine of below about 0.6 gram/day. In certain embodiments, the subject has a reduced level of proteins in the urine of below about 0.5 gram/day. In certain embodiments, the subject has a reduced level of proteins in the urine of below about 0.4 gram/day. In certain embodiments, the subject has a reduced level of proteins in the urine of below about 0.3 gram/day. In certain embodiments, the subject has a reduced level of proteins in the urine of below about 0.2 gram/day. In certain of the foregoing embodiments, the subject has been treated with atrasentan or a pharmaceutically acceptable salt thereof for between about 15 days and about 30 days. In the aforementioned embodiments, the reduction of the amount of proteins (e.g., albumin) in the urine of the subject having IgA nephropathy is relative to the amount of proteins (e.g., albumin) in the urine prior to initiation of treatment with atrasentan, or a pharmaceutically acceptable salt thereof.

In another aspect, provided herein is a method of decreasing fatigue in a subject having IgA nephropathy, comprising administering a therapeutically effective amount of atrasentan, or a pharmaceutically acceptable salt thereof, to a subject in need thereof. In some embodiments, the subject has been determined not to suffer from one or more of diabetic nephropathy, HIV-related nephropathy, prostate cancer, or acute kidney failure. In certain embodiments, the subject has been determined not to suffer from diabetic nephropathy. In certain embodiments, the subject has been determined not to suffer from HIV-related neuropathy. In certain embodiments, the subject has been determined not to suffer from prostate cancer. In certain embodiments, the subject has been determined not to suffer from acute kidney failure.

In some embodiments, the fatigue of the subject having IgA nephropathy is reduced by about 5% to about 80% after treatment with atrasentan or a pharmaceutically acceptable salt thereof (e.g., after treatment for 1 week, about 2 weeks, about 3 weeks, about 4 weeks, about 5 weeks, about 6 weeks, about 7 weeks, about 8 weeks, about 9 weeks, about 10 weeks, about 20 weeks, about 30 weeks, about 40 weeks, about 50 weeks, about 60 weeks, about 70 weeks, about 80 weeks, about 90 weeks, about 100 weeks, about 110 weeks, about 120 weeks, about 130 weeks, about 140 weeks, about 150 weeks, about 160 weeks, about 170 weeks, about 180 weeks, about 190 weeks, or about 200 weeks, or any value in between). In certain embodiments, the fatigue is reduced by about 10% to about 75%. In certain embodiments, the fatigue is reduced by about 10% to about 70%. In certain embodiments, the fatigue is reduced by about 10% to about 65%. In certain embodiments, the fatigue is reduced by about 10% to about 60%. In certain embodiments, the fatigue is reduced by about 10% to about 55%. In certain embodiments, the fatigue is reduced by about 10% to about 50%. In certain embodiments, the fatigue is reduced by about 10% to about 45%. In certain embodiments, the fatigue is reduced by about 10% to about 40%. In certain embodiments, the fatigue is reduced by about 10% to about 35%. In certain embodiments, the fatigue is reduced by about 10% to about 30%. In certain embodiments, the fatigue is reduced by about 10% to about 25%. In certain embodiments, the fatigue is reduced by about 10% to about 20%. In certain embodiments, the fatigue is reduced by about 10% to about 15%. In certain embodiments, the fatigue is reduced by about 20% to about 75%. In certain embodiments, the fatigue is reduced by about 20% to about 70%. In certain embodiments, the fatigue is reduced by about 20% to about 65%. In certain embodiments, the fatigue is reduced by about 20% to about 60%. In certain embodiments, the fatigue is reduced by about 20% to about 55%. In certain embodiments, the fatigue is reduced by about 20% to about 50%. In certain embodiments, the fatigue is reduced by about 20% to about 45%. In certain embodiments, the fatigue is reduced by about 20% to about 40%. In certain embodiments, the fatigue is reduced by about 20% to about 35%. In certain embodiments, the fatigue is reduced by about 20% to about 30%. In certain embodiments, the fatigue is reduced by about 30% to about 75%. In certain embodiments, the fatigue is reduced by about 30% to about 70%. In certain embodiments, the fatigue is reduced by about 30% to about 65%. In certain embodiments, the fatigue is reduced by about 30% to about 60%. In certain embodiments, the fatigue is reduced by about 30% to about 55%. In certain embodiments, the fatigue is reduced by about 30% to about 50%. In certain embodiments, the fatigue is reduced by about 30% to about 45%. In certain embodiments, the fatigue is reduced by about 30% to about 40%. In certain embodiments, the fatigue is reduced by about 40% to about 75%. In certain embodiments, the fatigue is reduced by about 40% to about 70%. In certain embodiments, the fatigue is reduced by about 40% to about 65%. In certain embodiments, the fatigue is reduced by about 40% to about 60%. In certain embodiments, the fatigue is reduced by about 40% to about 55%. In certain embodiments, the fatigue is reduced by about 40% to about 50%. In certain embodiments, the fatigue is reduced by about 50% to about 75%. In certain embodiments, the fatigue is reduced by about 50% to about 70%. In certain embodiments, the fatigue is reduced by about 50% to about 65%. In certain embodiments, the fatigue is reduced by about 50% to about 60%. In certain of the foregoing embodiments, the subject has been treated with atrasentan or a pharmaceutically acceptable salt thereof for between about 15 days and about 30 days. In certain embodiments, the decrease in fatigue comprises a decrease in the score on one or more of the Fatigue Severity Scale, the Chalder Fatigue Scale, the FACIT Fatigue Scale, the Brief Fatigue Inventory, the FACT-F Subscale, Global Vigor and Affect, the May and Kline Adjective Checklist, the Pearson-Byars Fatigue Feeling Checklist, the Rhoten Fatigue Scale, the Schedule of Fatigue and Anergia, the Visual Analog Scale, or the Checklist Individual Strength. In the aforementioned embodiments, the reduction of fatigue experienced by the subject having IgA nephropathy is relative to the fatigue experienced by the subject prior to initiation of treatment with atrasentan, or a pharmaceutically acceptable salt thereof. In some embodiments, the decrease in fatigue comprises a decrease in the score on the Brief Fatigue Inventory.

Subject Selection

The subject having IgA nephropathy as described anywhere herein can be diagnosed using one or more methods known in the art. Non-limiting examples include: kidney biopsy, detecting galactose-deficient IgA (e.g., Gd-IgA1), detecting anti-glycan antibodies, detecting deposition of IgA-immune complexes in the kidney, or a combination of any of the foregoing. In some embodiments, the diagnosis of IgA nephropathy comprises detecting deposition of IgA-immune complexes in the kidney. In certain embodiments, the diagnosis of IgA nephropathy comprises a kidney biopsy. In certain embodiments, the diagnosis of IgA nephropathy comprises detecting galactose-deficient IgA. In certain embodiments, the diagnosis of IgA nephropathy comprises detecting anti-glycan antibodies (e.g., KM55). In certain embodiments, the diagnosis of IgA nephropathy comprises a kidney biopsy followed by detecting deposition of IgA-immune complexes in the kidney (for example, by light microscopy and/or immunofluorescence microscopy).

In some embodiments, the presence and/or level of a particular protein in a subject is determined prior to administration of atrasentan, or a pharmaceutically acceptable salt thereof. For example, serum levels of Gd-IgA1, serum levels of autoantibodies specific for Gd-IgA1, and/or serum and/or urine levels of IgA1-containing immune complexes. See, e.g., Knoppova, et al., *Front. Immunol.*, Vol. 17, Art. 117 (2016), which is hereby incorporated by reference in its entirety. In some embodiments, the subject has Gd-IgA levels in the $90^{th}$ percentile or above prior to administration of atrasentan or a pharmaceutically acceptable salt thereof. In some embodiments, the subject has Gd-IgA levels in the $95^{th}$ percentile or above prior to administration of atrasentan or a pharmaceutically acceptable salt thereof. In some embodiments, the subject's Gd-IgA levels decrease to below the $90^{th}$ percentile after treatment with atrasentan, or a pharmaceutically acceptable salt thereof, for between about 6 months to 1 year.

In certain embodiments, the subject has mesangial cellularity in about ≥50% (e.g., about ≥60%, about ≥70%, or about ≥80%) of the glomeruli, wherein mesangial cellularity is defined as more than four mesangial cells in any mesangial area of a glomerulus. In certain embodiments, endocapillary hypercellularity is present in the subject, wherein endocapillary hypercellularity is defined as hypercellularity due to an increased number of cells within glomerular capillary lumina. In certain embodiments, segmental sclerosis is present in the subject, wherein segmental sclerosis is defined as adhesion or sclerosis (obliteration of capillary lumina by matrix) in part of but not the whole glomerular tuft. In certain embodiments, the subject has tubular atrophy/interstitial fibrosis in about ≥50% (e.g., about ≥60%, about ≥65%, about ≥70%, about ≥75%, or about ≥80%) of the cortical area, wherein tubular atrophy/interstitial fibrosis is defined as the estimated percentage of cortical area showing tubular atrophy or interstitial fibrosis. In certain embodiments, the subject has crescents present on the glomeruli. In certain of these embodiments, the subject has crescents present on below about 25% (e.g., below about 20%, about 15%, about 10%, or about 5%) of the glomeruli. In certain embodiments, the subject has a MEST-C score of M1; E1; S1; T1 or T2; and/or C0 or C1 under the Oxford MEST-C classification system. The Oxford MEST-C classification system is defined in *Kidney International* (2009) 76, 546-556 and *Nature Reviews Nephrology* (2017) 13, 385-386, each of which is incorporated herein by reference in its entirety (Also see: *Kidney Research and Clinical Practice* (2016) 35, 197-203; and IgA Nephropathy in Medscape (accessed Nov. 4, 2019), each of which is incorporated herein by reference in its entirety)).

In some embodiments, the subject is at a high risk of progression to ESRD. In certain of these embodiments, the subject is excreting an average of about 1 gram or more of protein in the urine per day for at least about 3 months prior to the first administration of atrasentan, or a pharmaceutically acceptable salt thereof. In certain embodiments, the subject has an average eGFR≤60 mL/min/1.73 m$^2$ (e.g., about ≤55, about ≤50, about ≤45, about ≤40, about ≤35) for at least about 3 months prior to the first administration of atrasentan, or a pharmaceutically acceptable salt thereof. In certain of these embodiments, the subject has eGFR>30 mL/min/1.73 m$^2$ prior to the first administration of atrasentan or a pharmaceutically acceptable salt thereof.

In some embodiments, the subject is excreting an average of about 1 gram or more of protein in the urine per day for at least about 3 months (e.g., at least about 4 months, at least about 5 months, at least about 6 months, at least about 7 months, at least about 8 months, at least about 9 months, at least about 10 months, at least about 11 months, at least about a year, at least about 1.5 years, or at least about 2 years) prior to the first administration of atrasentan, or a pharmaceutically acceptable salt thereof. For example, the subject can be excreting an average of about 1.1 gram, 1.2 grams, 1.3 grams, 1.4 grams, 1.5 grams, 1.6 grams, 1.7 grams, 1.8 grams, 1.9 grams, 2.0 grams, 2.1 grams, 2.2 grams, 2.3 grams, 2.4 grams, 2.5 grams, 2.6 grams, 2.7 grams. 2.8 grams, 2.9 grams, 3.0 grams, 3.1 grams, 3.2 grams, 3.3 grams, 3.4 grams, 3.5 grams, 5 grams, or 7.5 grams, or 10 grams, or any value in between, of protein in the urine per day for at least 3 months prior to the first administration of atrasentan, or a pharmaceutically acceptable salt thereof.

In some embodiments, the subject is excreting an average of from about 0.3 grams to about 2 grams of protein in the urine per day for at least about 3 months (e.g., at least about 4 months, at least about 5 months, at least about 6 months, at least about 7 months, at least about 8 months, at least about 9 months, at least about 10 months, at least about 11 months, at least about a year, at least about 1.5 years, or at least about 2 years) prior to the first administration of atrasentan, or a pharmaceutically acceptable salt thereof. For example, the subject can be excreting from about 0.3 grams to 0.5 grams, 0.5 grams to 1 gram, from about 0.5 grams to 1.5 grams, from about 1 gram to 1.5 grams, or from about 1.5 grams to 2 grams of protein in the urine per day for at least 3 months.

In some embodiments, the subject is excreting at least about 1 gram of protein in the urine per day on at least two of three consecutive measurements a year prior to the first administration of atrasentan or a pharmaceutically acceptable salt thereof. For example, the subject can be excreting about 1.1 grams, 1.2 grams, 1.3 grams, 1.4 grams, 1.5 grams, 1.6 grams, 1.7 grams, 1.8 grams, 1.9 grams, 2.0 grams, 2.1 grams, 2.2 grams, 2.3 grams, 2.4 grams, 2.5 grams, 2.6 grams, 2.7 grams. 2.8 grams, 2.9 grams, 3.0 grams, 3.1 grams, 3.2 grams, 3.3 grams, 3.4 grams, 3.5 grams, 5 grams, or 7.5 grams, or 10 grams of protein, or any value in between, in the urine per day on at least two of three consecutive measurements a year prior to the first administration of atrasentan or a pharmaceutically acceptable salt thereof.

In some embodiments, the subject has an UACR value of at least about 300 mg/g for at least three months prior to the first administration of atrasentan or a pharmaceutically acceptable salt thereof, for example, 300 mg/g to about 5,000 mg/g. In some embodiments, the subject has an UACR value of about 800 mg/g for at least three months prior to the first administration of atrasentan or a pharmaceutically acceptable salt thereof, for example, 800 mg/g to about 5,000 mg/g. In some embodiments, the subject has an UACR value of at least about 500 mg/g, about 600 mg/g, about 700 mg/g, about 800 mg/g, about 900 mg/g, about 1,000 mg/g, about 1,500 mg/g, about 2,000 mg/g, about 2,500 mg/g, about 3,000 mg/g, about 3,500 mg/g, about 4,000 mg/g, about 4,500 mg/g, or about 5,000 mg/g, or any value in between, for at least three months prior to the first administration of atrasentan or a pharmaceutically acceptable salt thereof.

In some embodiments, the subject has a decrease in UACR value of at least about 30% relative to the subject's average UACR value for at least three months prior to the first administration of atrasentan or a pharmaceutically acceptable salt thereof, for example, a decrease of about 30% to about 100%, relative to the subject's average UACR value for at least three months prior to the first administration of atrasentan or a pharmaceutically acceptable salt thereof. In some embodiments, the subject has a decrease in UACR value of at least about 30%, about 40%, about 50%, about 60%, about 70%, about 80%, about 90%, or about 100%, or any value in between, relative to the subject's average UACR value for at least three months prior to the first administration of atrasentan or a pharmaceutically acceptable salt thereof. In some embodiments, the subject having a decrease in UACR value does not also experience significant sodium retention and/or significant fluid retention. In some embodiments, significant fluid retention can be about 1 kg to about 4 kg over six weeks, for example, about 4 kg, about 3.5 kg, about 3 kg, about 2.5 kg, about 2 kg, about 1.5 kg, or about 1 kg, or any value in between over 6 weeks. In some embodiments, a subject having significant fluid retention exhibits clinical symptoms of edema.

In certain embodiments, the subject has an average eGFR of about 20 to about 90 mL/min/1.73 m$^2$ for at least about 3 months prior to the first administration of atrasentan, or a pharmaceutically acceptable salt thereof (e.g., about 3 months, about 4 months, about 5 months, about 6 months, about 7 months, about 8 months, about 9 months, about 10 months, about 11 months, about 12 months, about 1.5 years, or about 2 years). For example, about 20 to about 50 mL/min/1.73 m$^2$; about 30 to about 60 mL/min/1.73 m$^2$; about 40 to about 70 mL/min/1.73 m$^2$; about 50 to about 80 mL/min/1.73 m$^2$; or about 60 to about 90 mL/min/1.73 m$^2$; for at least about 3 months prior to the first administration of atrasentan, or a pharmaceutically acceptable salt thereof. In some embodiments, the subject has an average eGFR≤60 mL/min/1.73 m$^2$ for at least about 3 months prior to the first administration of atrasentan, or a pharmaceutically acceptable salt thereof. In certain embodiments, the subject has an average eGFR≤55 mL/min/1.73 m$^2$ for at least about 3 months. In certain embodiments, the subject has an average eGFR≤50 mL/min/1.73 m$^2$ for at least about 3 months. In certain embodiments, the subject has an average eGFR≤45 mL/min/1.73 m$^2$ for at least about 3 months. In certain embodiments, the subject has an average eGFR≤40 mL/min/ 1.73 m$^2$ for at least about 3 months. In certain embodiments, the subject has an average eGFR≤35 mL/min/1.73 m$^2$ for at least about 3 months. In certain embodiments, the subject has an average eGFR≤25 mL/min/1.73 m$^2$ for at least about 3 months. In certain embodiments, the subject has an average eGFR≤20 mL/min/1.73 m$^2$ for at least about 3 months. In certain of the foregoing embodiments, the subject has an average eGFR between about 30 mL/min/1.73 m$^2$ and about 60 mL/min/1.73 m$^2$ for at least 3 months before the administration of atrasentan or a pharmaceutically acceptable salt thereof. For example, the subject can have an average eGFR of between about 30 mL/min/1.73 m$^2$ and about 55 mL/min/1.73 m$^2$, between about 30 mL/min/1.73 m$^2$ and about 50 mL/min/1.73 m$^2$, between about 30 mL/min/1.73 m$^2$ and about 45 mL/min/1.73 m$^2$, or between about 30 mL/min/1.73 m$^2$ and about 40 mL/min/1.73 m$^2$.

In certain embodiments, the subject has an average eGFR of about 30 mL/min/1.73 m$^2$ to about 45 mL/min/1.73 m$^2$, for example, about ≤45, about ≤40, about ≤35 or about ≤30, for at least about 3 months (e.g., at least about 4 months, at least about 5 months, at least about 6 months, at least about 7 months, at least about 8 months, at least about 9 months, at least about 10 months, at least about 11 months, at least about a year, at least about 1.5 years, or at least about 2 years) prior to the first administration of atrasentan, or a pharmaceutically acceptable salt thereof. In some embodiments, the subject has an average eGFR of about 25 mL/min/1.73 m$^2$ to about 75 mL/min/1.73 m$^2$ for at least about 3 months prior to the first administration of atrasentan, or a pharmaceutically acceptable salt thereof. For example, about 25 mL/min/1.73 m$^2$, about 30 mL/min/1.73 m$^2$, about 35 mL/min/1.73 m$^2$, about 40 mL/min/1.73 m$^2$, about 45 mL/min/1.73 m$^2$, about 50 mL/min/1.73 m$^2$, about 55 mL/min/1.73 m$^2$, about 60 mL/min/1.73 m$^2$, about 65 mL/min/1.73 m$^2$, about 70 mL/min/1.73 m$^2$, about 75 mL/min/1.73 m$^2$, or any value in between, for at least about 3 months prior to the first administration of atrasentan, or a pharmaceutically acceptable salt thereof.

In some embodiments, the subject has an average HbA1c of about 4% to about 6% for at least about 3 months (e.g., at least about 4 months, at least about 5 months, at least about 6 months, at least about 7 months, at least about 8 months, at least about 9 months, at least about 10 months, at least about 11 months, at least about a year, at least about 1.5 years, or at least about 2 years) prior to the first administration of atrasentan, or a pharmaceutically acceptable salt thereof. For example, the subject can have an average HbA1c of about 4.2%, about 4.4%, about 4.6%, about 4.8%, about 5.0%, about 5.2%, about 5.4%, about 5.6%, about 5.8%, or about 6%, or any value in between.

In some embodiments, the subject has an average fasting blood glucose level of about 125 mg/dL or less for at least about 3 months (e.g., at least about 4 months, at least about 5 months, at least about 6 months, at least about 7 months, at least about 8 months, at least about 9 months, at least about 10 months, at least about 11 months, at least about a year, at least about 1.5 years, or at least about 2 years) prior to the first administration of atrasentan, or a pharmaceutically acceptable salt thereof. For example, the subject can have an average fasting blood glucose level of about 120 mg/dL, about 115 mg/dL, about 110 mg/dL, about 105 mg/dL, about 100 mg/dL, about 95 mg/dL, about 90 mg/dL, about 85 mg/dL, about 80 mg/dL, or about 75 mg/dL, or any value in between.

In some embodiments, the subject maintains a potassium level within the normal physiologic range. In certain embodiments, the subject maintains a potassium level within the normal physiologic range for at least about 3 months (e.g., at least about 4 months, at least about 5 months, at least about 6 months, at least about 7 months, at least about 8 months, at least about 9 months, at least about 10 months, at least about 11 months, at least about a year, at least about 1.5 years, or at least about 2 years) prior to the first administration of atrasentan or a pharmaceutically acceptable salt thereof. In certain embodiments, the subject maintains a potassium level within 3.5 to 5.2 mEq/L. For example, the subject maintains an average potassium level at about 3.5 mEq/L, about 3.6 mEq/L, about 3.7 mEq/L, about 3.8 mEq/L, about 3.9, about mEq/L, about 4.0 mEq/L, about 4.1 mEq/L, about 4.2 mEq/L, about 4.3 mEq/L, about 4.4 mEq/L, about 4.5 mEq/L, about 4.6 mEq/L, about 4.7 mEq/L, about 4.8 mEq/L, about 4.9 mEq/L, about 5.0 mEq/L, about 5.1 mEq/L, or about 5.2 mEq/L, or any value in between.

In some embodiments, the subject maintains a sodium level within the normal physiologic range. In certain embodiments, the subject maintains a potassium level within the normal physiologic range for at least about 3 months (e.g., at least about 4 months, at least about 5 months, at least about 6 months, at least about 7 months, at least about 8 months, at least about 9 months, at least about 10 months, at least about 11 months, at least about a year, at least about 1.5 years, or at least about 2 years) prior to the first administration of atrasentan or a pharmaceutically acceptable salt thereof. In certain embodiments, the subject maintains a sodium level within 135 to 145 mEq/L. For example, the subject maintains an average sodium level of about 135 mEq/L, about 136 mEq/L, about 137 mEq/L, about 138 mEq/L, about 139 mEq/L, about 140 mEq/L, about 141 mEq/L, about 142 mEq/L, about 143 mEq/L, about 144 mEq/L, about or 145 mEq/L, or any value in between.

In some embodiments, the subject has ALT/AST levels during the administration of atrasentan, or a pharmaceutically acceptable salt thereof, that are about the same as the ALT/AST levels prior to the first administration of atrasentan, or a pharmaceutically acceptable salt thereof. For example, the subject has ALT/AST levels during the administration of atrasentan or a pharmaceutically acceptable salt thereof within about 25%, about 20%, about 15%, about 10%, about 5%, about or 2.5%, or any value in between, of the levels prior to the first administration of atrasentan, or a pharmaceutically acceptable salt thereof.

In some embodiments, the subject has bilirubin levels during the administration of atrasentan, or a pharmaceutically acceptable salt thereof, that are about the same as the bilirubin levels prior to the first administration of atrasentan, or a pharmaceutically acceptable salt thereof. For example, the subject has bilirubin levels during the administration of atrasentan or a pharmaceutically acceptable salt thereof within about 25%, about 20%, about 15%, about 10%, about 5%, or about 2.5%, or any value in between, of the levels prior to the first administration of atrasentan, or a pharmaceutically acceptable salt thereof.

In some embodiments, the fluid retention in the subject is manageable with diuretics (e.g., during the treatment with atrasentan or a pharmaceutically acceptable salt thereof and/or prior to the first administration of atrasentan or a pharmaceutically acceptable salt thereof). For example, the fluid retention can be less than about 3 kilograms (kg) of weight gain over 6 weeks. In some embodiments, the fluid retention is less than about 4 kg, about 3.5 kg, about 3 kg, about 2.5 kg, about 2 kg, about 1.5 kg, or about 1 kg, or any value in between over 6 weeks.

In some embodiments, the subject undergoes surgery, and/or other regimens prior to, substantially at the same time as, or following the administration of atrasentan, or a pharmaceutically acceptable salt thereof, as disclosed herein. In some embodiments, the subject is administered other chemical and/or biological therapeutic agents prior to, substantially at the same time as, or following the administration of atrasentan, or a pharmaceutically acceptable salt thereof, as disclosed herein.

In some embodiments, the subject has been receiving one or more inhibitors of the renin-angiotensin system for at least about 60 weeks prior to the first administration of atrasentan or a pharmaceutically acceptable salt thereof. For example, in some embodiments, the subject has been receiving one or more inhibitors of the renin-angiotensin system for at least about 12 weeks, about 24 weeks, about 48 weeks, or about 60 weeks, or any value in between, prior to the first administration of atrasentan or a pharmaceutically acceptable salt thereof.

In some embodiments, the subject has been receiving a maximally tolerated stable dose of the one or more renin-angiotensin system inhibitors. For example, the subject can be receiving a maximally tolerated stable dose of the one or more renin-angiotensin system inhibitor for at least about 12 weeks, about 14 weeks, about 16 weeks, about 18 weeks, about 20 weeks, about 25 weeks, about 30 weeks, about 35 weeks, about 40 weeks, about 45 weeks, or about 50 weeks, or any value in between, prior to the first administration of atrasentan or a pharmaceutically acceptable salt thereof. In some embodiments, the one or more inhibitors of the renin-angiotensin system is selected from the group consisting of angiotensin converting enzyme (ACE) inhibitors, angiotensin II receptor blockers (ARBs), renin inhibitors, and aldosterone antagonists. For example, the one or more inhibitors of the renin-angiotensin system can be ACE inhibitor, ARB, or a combination thereof, wherein the ACE inhibitor or ARB can be described anywhere herein. For example, the ACE inhibitor can be selected from: quinapril, fosinopril perindopril, captopril, enalapril, enalaprilat, ramipril, cilazapril, delapril, fosenopril, zofenopril, indolapril, benazepril, lisinopril, spirapril, trandolapril, perindep, pentopril, moexipril, rescinnamine, and pivopril. For example, the ARB can be selected from: candesartan, candesartan cilexetil, eprosartan, irbesartan, losartan, olmesartan, olmesartan medoxomil, telmisartan, valsartan, azilsartan medoxomil, and BRA-657.

In some embodiments, the subject is also being administered one or more additional agents. In some embodiments, the one or more additional agents are selected from calcineurin inhibitors, proteasome inhibitors, aminoquinolines, complement inhibitors, B-cell inhibitors, cytotoxic agents, mTOR inhibitors, and steroids. In some embodiments, the dosage of the one or more additional agents is decreased after between about 15 days to about 30 days of treatment with atrasentan, or a pharmaceutically acceptable salt thereof. In some embodiments, the one or more additional agents are immunosuppressants.

In some embodiments, the subject is not currently receiving one or more additional agents. In certain embodiments, the subject has not used one or more additional agent for two or more weeks within the 6 months prior to the first administration of atrasentan or a pharmaceutically acceptable salt thereof.

In some embodiments, the one or more additional agents are selected from calcineurin inhibitors, proteasome inhibitors, aminoquinolines, complement inhibitors, B-cell inhibitors, cytotoxic agents, mTOR inhibitors, and steroids.

In certain embodiments, the one or more additional agents are steroids. For example, the one or more additional agents can be selected from the group consisting of prednisone, dexamethasone, hydrocortisone, ciclosporin, and combinations of any of the foregoing.

In certain embodiments, the one or more additional agents are aminoquinolines. For example, the one or more additional agents can be hydroxychloroquine.

In some embodiments, the subject is receiving one or more additional agents at the time of treatment with atrasentan. In certain embodiments, the dosage of the one or more additional agents is decreased after treatment with atrasentan, or a pharmaceutically acceptable salt thereof (e.g., after 1 week, 2 weeks, 3 weeks, 4 weeks, 5 weeks, 6 weeks, 7 weeks, 8 weeks, 9 weeks, 10 weeks, 20 weeks, 30 weeks, 40 weeks, 50 weeks, 60 weeks, 70 weeks, 80 weeks, 90 weeks, 100 weeks, 110 weeks, 120 weeks, 130 weeks, 140 weeks, 150 weeks, 160 weeks, 170 weeks, 180 weeks, 190 weeks, or 200 weeks of treatment). In certain of these embodiments, the dosage of the one or more additional agents is decreased after between about 15 days to about 30 days of treatment with atrasentan, or a pharmaceutically acceptable salt thereof. In certain of the foregoing embodiments, the additional agent dosage is decreased by about 10% to about 100%. In certain embodiments, the additional agent dosage is decreased by about 15% to about 100%. In certain embodiments, the additional agent dosage is decreased by about 20% to about 100%. In certain embodiments, the additional agent dosage is decreased by about 25% to about 100%. In certain embodiments, the additional agent dosage is decreased by about 30% to about 100%. In certain embodiments, the additional agent dosage is decreased by about 35% to about 100%. In certain embodiments, the additional agent dosage is decreased by about 40% to about 100%. In certain embodiments, the additional agent dosage is decreased by about 45% to about 100%. In certain embodiments, the additional agent dosage is decreased by about 50% to about 100%. In certain embodiments, the additional agent dosage is decreased by about 55% to about 100%. In certain embodiments, the additional agent dosage is decreased by about 60% to about 100%. In certain embodiments, the additional agent dosage is decreased by about 65% to about 100%. In certain embodiments, the additional agent dosage is decreased by about 70% to about 100%. In certain embodiments, the additional agent dosage is decreased by about 75% to about 100%. In certain embodiments, the additional agent dosage is decreased by about 80% to about 100%. In certain embodiments, the additional agent dosage is decreased by about 85% to about 100%. In certain embodiments, the additional agent dosage is decreased by about 90% to about 100%. In certain of the foregoing embodiments, the dosage of the one or more additional agents is decreased after between about 15 days to about 30 days (e.g., about 15 days, about 20 days, about 25 days, or about 30 days) of treatment with atrasentan, or a pharmaceutically acceptable salt thereof. When the dosage of additional agent is decreased by 100% as described herein, the subject is no longer needing additional agent.

In certain embodiments, the dosage of one or more steroids is decreased after treatment with atrasentan, or a pharmaceutically acceptable salt thereof, for example, after between about 15 days to about 30 days of treatment with atrasentan, or a pharmaceutically acceptable salt thereof. In some embodiments, the steroid dosage is decreased by about 10% to about 100%, as described herein. In some embodiments, the dosage of prednisone, dexamethasone, hydrocortisone, ciclosporin, or a combination of any of the foregoing is reduced by about 10% to about 100% after treatment with atrasentan, or a pharmaceutically acceptable salt thereof.

In certain embodiments, the dosage of one or more aminoquinolines is decreased after treatment with atrasentan, or a pharmaceutically acceptable salt thereof, for example, after between about 15 days to about 30 days of treatment with atrasentan, or a pharmaceutically acceptable salt thereof. In some embodiments, the aminoquinoline dosage is decreased by about 10% to about 100%, as described herein. In some embodiments, the dosage of hydroxychloroquine is reduced by about 10% to about 100% after treatment with atrasentan, or a pharmaceutically acceptable salt thereof.

In some embodiments, the subject is concomitantly receiving one or more additional therapeutic agents. The one or more additional therapeutic agents are described herein. For example, the subject is concomitantly receiving an inhibitor of one or more elements of the renin-angiotensin-aldosterone system. In certain embodiments, the subject is concomitantly receiving a SGLT-2 inhibitor, an ACE inhibitor, an ARB, a statin, a diuretic, a calcium channel blocker, a beta blocker, an aldosterone antagonist, fish oil, hydroxychloroquine, or a combination of any of the foregoing. In certain of these embodiments, the subject is concomitantly receiving a SGLT-2 inhibitor. In certain of these embodiments, the subject is concomitantly receiving an ACE inhibitor, an ARB, or a combination thereof. In certain embodiments, the subject is concomitantly receiving one or more statins, such as atorvastatin, fluvastatin, lovastatin, pravastatin, rosuvastatin, simvastatin, and pitavastatin. In certain embodiments, the subject is concomitantly receiving one or more diuretics, such as hydrochlorothiazide, trichloromethiazide, hydroflumethiazide, quinethazone, metolazone, chlorothiazide, chlorthalidone, indapamide, methylclothiazide bemetanide, torsemide, piretanide, ethacrynic acid, bumetanide, furosemide, triamterene, spironolactone, eplerenone, and amiloride. In certain embodiments, the subject is concomitantly receiving a SGLT-2 inhibitor, such as canagliflozin, dapagliflozin, empagliflozin, or ertugliflozin. In certain embodiments, the subject is concomitantly receiving one or more ACE inhibitors, such as quinapril, fosinopril perindopril, captopril, enalapril, enalaprilat, ramipril, cilazapril, delapril, fosenopril, zofenopril, indolapril, benazepril, lisinopril, spirapril, trandolapril, perindep, pentopril, moexipril, rescinnamine, and pivopril. In certain embodiments, the subject is concomitantly receiving an ARB, such as candesartan, candesartan cilexetil, eprosartan, irbesartan, losartan, olmesartan, olmesartan medoxomil, telmisartan, valsartan, azilsartan medoxomil, and BRA-657. In certain embodiments, the subject is concomitantly receiving a diuretic and an ACE inhibitor or an ARB. In certain embodiments, the subject is concomitantly receiving a diuretic, an ACE inhibitor, and an ARB. In certain embodiments, the subject is concomitantly receiving a diuretic and a SGLT-2 inhibitor, and an ACE inhibitor or an ARB. In certain embodiments, the subject is concomitantly receiving a diuretic, a SGLT-2 inhibitor, an ACE inhibitor, and an ARB. In certain embodiments, the subject concomitantly receiving one or more additional therapeutic agents has not previously received the one or more therapeutic agents. For example, a subject that is concomitantly receiving a SGLT-2 inhibitor that has not previously received a SGLT-2 inhibitor.

In some embodiments, the subject has previously received, but is not concomitantly receiving, one or more additional therapeutic agents such as those described herein. For example, the subject is has previously received, but is not concomitantly receiving a SGLT-2 inhibitor, an ACE inhibitor, an ARB, a statin, a diuretic, a calcium channel blocker, a beta blocker, an aldosterone antagonist, fish oil, hydroxychloroquine, or a combination of any of the foregoing, as described herein. In certain of these embodiments, the subject has previously received, but is not concomitantly receiving a SGLT-2 inhibitor.

In some embodiments, the subject has cellular glomerular crescents present in about ≤25% of glomeruli within 6 months prior to the first administration of atrasentan or a pharmaceutically acceptable salt thereof. For example, the subject can have cellular glomerular crescents present in about 25%, about 20%, about 15%, about 10%, about 5%, or about 1%, or any value in between, of glomeruli. In some embodiments, the subject does not have cellular glomerular crescents present in the glomeruli. In certain embodiments, the subject is not under clinical suspicion of rapidly progressive glomerulonephritis (RPGN).

In some embodiments, the subject has not undergone organ transplantation prior to the first administration of atrasentan or a pharmaceutically acceptable salt thereof.

In some embodiments, the subject has a systolic blood pressure of below about 160 mmHg prior to the first administration of atrasentan or a pharmaceutically acceptable salt thereof. For example, the subject can be a systolic blood pressure of below about 155 mmHg, below about 150 mmHg, below about 145 mmHg, or below about 140 mmHg. In some embodiments, the subject has a diastolic blood pressure of below about 100 mmHg prior to the first administration of atrasentan or a pharmaceutically acceptable salt thereof. For example, the subject can have a diastolic blood pressure of below about 100 mmHg, below about 95 mmHg, or below about 90 mmHg. In some embodiments, the subject has a systolic blood pressure of between about 100 mm Hg and about 130 mm Hg and a diastolic blood pressure of about 70 mm Hg to about 90 mm Hg.

In some embodiments, the subject has not been diagnosed with heart failure prior to the first administration of atrasentan or a pharmaceutically acceptable salt thereof. In some embodiments, the subject has not been previously admitted to hospital for conditions relating to fluid overload prior to the first administration of atrasentan or a pharmaceutically acceptable salt thereof. Non-limiting examples of conditions include uncontrolled peripheral edema, pleural effusion, or ascites. In some embodiments, the subject has not been diagnosed with clinically significant liver disease prior to the first administration of atrasentan or a pharmaceutically acceptable salt thereof. In some embodiments, the transaminase or bilirubin values of the subject are no more than twice the normal upper limit prior to the first administration of atrasentan or a pharmaceutically acceptable salt thereof. For example, the ALT level of the subject is below about 110 U/L (e.g., below about 100 U/L, below 90 U/L, below about 80 U/L, below about 70 U/L, below about 60 U/L, below about 50 U/L, or below about 40 U/L, or any value in between). As another example, the AST level of the subject is below 100 U/L (e.g., below 90 U/L, below about 80 U/L, below about 70 U/L, below about 60 U/L, below about 50 U/L, or below about 40 U/L, or any value in between). As yet another example, the bilirubin level of the subject is below about 2.5 mg/dL (e.g., below about 2 mg/dL, below about 1.5 mg/dL, below about 1.4 mg/dL, below about 1.3 mg/dL, below about 1.2 mg/dL, below about 1.1 mg/dL, below about 1.0 mg/dL, or below about 0.9 mg/dL, or any value in between).

In some embodiments, the subject has a hemoglobin level of above about 9 g/dL (e.g., above about 10 g/dL, about 11 g/dL, about 12 g/dL, or about 13 g/dL, or any value in between) prior to the first administration of atrasentan or a pharmaceutically acceptable salt thereof. In some embodiments, the subject has not received blood transfusion for anemia for at least about 3 months (e.g., at least about 4 months, about 5 months, about 6 months, or about one year) prior to the first administration of atrasentan or a pharmaceutically acceptable salt thereof. In some embodiments, the subject has not been diagnosed with cancer for at least 5 years prior to the first administration of atrasentan or a pharmaceutically acceptable salt thereof. In some embodiments, the subject has not been diagnosed with cancer (e.g., lung cancer or prostate cancer) for at least 5 years prior to the first administration of atrasentan or a pharmaceutically acceptable salt thereof. In some embodiments, the subject has not been diagnosed with cancer for at least 5 years prior to the first administration of atrasentan or a pharmaceutically acceptable salt thereof, unless the cancer is nonmelanoma skin cancer not requiring ongoing treatment. In some embodiments, the subject does not have cancer prior to the first administration of atrasentan or a pharmaceutically acceptable salt thereof, unless the cancer is nonmelanoma skin cancer not requiring ongoing treatment. In some embodiments, the subject does not suffer from cancer prior to the first administration of atrasentan or a pharmaceutically acceptable salt thereof, unless the cancer is nonmelanoma skin cancer not requiring ongoing treatment. In some embodiments, the subject is not being treated for cancer for at least 5 years prior to the first administration of atrasentan or a pharmaceutically acceptable salt thereof, unless the cancer is nonmelanoma skin cancer not requiring ongoing treatment.

In some embodiments of the methods, uses, or product for uses herein, the subject has not been previously diagnosed with one or more of diabetic nephropathy, HIV/AIDS, or acute kidney failure. In some embodiments of the methods, uses, or product for uses herein, the subject has not been previously diagnosed with one or more of diabetic nephropathy, HIV/AIDS, cancer (e.g., prostate cancer or lung cancer), or acute kidney failure. In some embodiments, the subject has not been previously diagnosed with one or more of diabetic nephropathy, HIV/AIDS, prostate cancer, or acute kidney failure. In some embodiments, the subject has not been previously diagnosed with one or more of diabetic nephropathy, HIV-related nephropathy, prostate cancer, or acute kidney failure. In some embodiments, the subject has not been previously diagnosed with one or more of diabetic nephropathy, HIV-related nephropathy, cancer (e.g., lung cancer, or prostate cancer), or acute kidney failure. In some embodiments, the subject has not been previously diagnosed with one or more of diabetic nephropathy, HIV-related nephropathy, or acute kidney failure. In certain embodiments, the subject has not been previously diagnosed with diabetic nephropathy. In certain embodiments, the subject has not been previously diagnosed with HIV/AIDS. In certain embodiments, the subject has not been previously diagnosed with acute kidney failure. In certain embodiments, the subject has not been previously diagnosed with HIV-related nephropathy. In certain embodiments, the subject has not been diagnosed with cancer. In certain embodiments, the subject has not been diagnosed with prostate cancer. In certain embodiments, the subject has not been diagnosed with lung cancer. In certain embodiments, the subject has not been previously diagnosed with any one of diabetic nephropathy, HIV/AIDS, and acute kidney failure.

In certain embodiments, the subject has not been previously diagnosed with any one of diabetic nephropathy, HIV/AIDS, prostate cancer, and acute kidney failure. In certain embodiments, the subject has not been previously diagnosed with any one of diabetic nephropathy, HIV-related nephropathy, prostate cancer, and acute kidney failure. In certain embodiments, the subject has not been previously diagnosed with any one of diabetic nephropathy, HIV-related nephropathy, and acute kidney failure. In some embodiments of the methods, uses, or product for uses herein, the subject has not been previously diagnosed with diabetes. In some embodiments of the methods, uses, or product for uses herein, the subject has not been previously diagnosed with Type 2 diabetes. In certain of the foregoing embodiments, the subject has been determined to have controlled serum glucose levels as described anywhere herein.

In some embodiments, the subject does not have one or more of diabetic nephropathy, HIV/AIDS, or acute kidney failure. In some embodiments, the subject does not have one or more of diabetic nephropathy, HIV/AIDS, prostate cancer, or acute kidney failure. In some embodiments, the subject does not have one or more of diabetic nephropathy, HIV-related nephropathy, prostate cancer, or acute kidney failure. In some embodiments, the subject does not have one or more of diabetic nephropathy, HIV-related nephropathy, or acute kidney failure. In certain embodiments, the subject does not have diabetic nephropathy. In certain embodiments, the subject does not have HIV/AIDS. In certain embodiments, the subject does not have acute kidney failure. In certain embodiments, the subject does not have HIV-related nephropathy. In certain embodiments, the subject does not have prostate cancer. In certain embodiments, the subject does not have any one of diabetic nephropathy, HIV/AIDS, and acute kidney failure. In certain embodiments, the subject does not have any one of diabetic nephropathy, HIV/AIDS, prostate cancer, and acute kidney failure. In certain embodiments, the subject does not have any one of diabetic nephropathy, HIV-related nephropathy, prostate cancer, and acute kidney failure. In certain embodiments, the subject does not have any one of diabetic nephropathy, HIV-related nephropathy, and acute kidney failure. In some embodiments, the subject does not have diabetes. In some embodiments, the subject does not have Type 2 diabetes. In certain of the foregoing embodiments, the subject has been determined to have controlled serum glucose levels as described anywhere herein.

In some embodiments, the subject does not suffer from one or more of diabetic nephropathy, HIV/AIDS, or acute kidney failure. In some embodiments, the subject does not suffer from one or more of diabetic nephropathy, HIV/AIDS, prostate cancer, or acute kidney failure. In some embodiments, the subject does not suffer from one or more of diabetic nephropathy, HIV-related nephropathy, prostate cancer, or acute kidney failure. In some embodiments, the subject does not suffer from one or more of diabetic nephropathy, HIV-related nephropathy, or acute kidney failure. In certain embodiments, the subject does not suffer from diabetic nephropathy. In certain embodiments, the subject does not suffer from HIV/AIDS. In certain embodiments, the subject does not suffer from acute kidney failure. In certain embodiments, the subject does not suffer from HIV-related nephropathy. In certain embodiments, the subject does not suffer from prostate cancer. In certain embodiments, the subject does not suffer from any one of diabetic nephropathy, HIV/AIDS, and acute kidney failure. In certain embodiments, the subject does not suffer from any one of diabetic nephropathy, HIV/AIDS, prostate cancer, and acute kidney failure. In certain embodiments, the subject does not suffer from any one of diabetic nephropathy, HIV-related nephropathy, prostate cancer, and acute kidney failure. In certain embodiments, the subject does not suffer from any one of diabetic nephropathy, HIV-related nephropathy, and acute kidney failure. In some embodiments, the subject does not suffer from diabetes. In some embodiments, the subject does not suffer from Type 2 diabetes. In certain of the foregoing embodiments, the subject has been determined to have controlled serum glucose levels as described anywhere herein.

In some embodiments, the subject is not being treated for one or more of diabetic nephropathy, HIV/AIDS, or acute kidney failure. In some embodiments, the subject is not being treated for one or more of diabetic nephropathy, HIV/AIDS, prostate cancer, or acute kidney failure. In some embodiments, the subject is not being treated for one or more of diabetic nephropathy, HIV-related nephropathy, prostate cancer, or acute kidney failure. In some embodiments, the subject is not being treated for one or more of diabetic nephropathy, HIV-related nephropathy, or acute kidney failure. In certain embodiments, the subject is not being treated for diabetic nephropathy. In certain embodiments, the subject is not being treated for HIV/AIDS. In certain embodiments, the subject is not being treated for acute kidney failure. In certain embodiments, the subject is not being treated for HIV-related nephropathy. In certain embodiments, the subject is not being treated for prostate cancer. In certain embodiments, the subject is not being treated for any one of diabetic nephropathy, HIV/AIDS, and acute kidney failure. In certain embodiments, the subject is not being treated for any one of diabetic nephropathy, HIV/AIDS, prostate cancer, and acute kidney failure. In certain embodiments, the subject is not being treated for any one of diabetic nephropathy, HIV-related nephropathy, prostate cancer, and acute kidney failure. In certain embodiments, the subject is not being treated for any one of diabetic nephropathy, HIV-related nephropathy, and acute kidney failure. In some embodiments, the subject is not being treated for diabetes. In some embodiments, the subject is not being treated for Type 2 diabetes. In certain of the foregoing embodiments, the subject has been determined to have controlled serum glucose levels as described anywhere herein.

In some embodiments, the subject has been determined to have controlled serum glucose levels; or the subject has not been diagnosed with one or more of HIV-related nephropathy or acute kidney failure. In certain embodiments, the subject has been determined to have controlled serum glucose levels. For example, the subject has been determined to have a fasting serum glucose level of below about 130 mg/dL, about 125 mg/dL, about 120 mg/dL, about 115 mg/dL, about 110 mg/dL, about 105 mg/dL, about 100 mg/dL, about 95 mg/dL, about 90 mg/dL, about 85 mg/dL, about 80 mg/dL, or about 75 mg/dL, or any value in between. In certain embodiments, the subject has not been diagnosed with one or more of HIV-related nephropathy or acute kidney failure. In certain embodiments, the subject has been determined to have controlled serum glucose levels as described anywhere herein; and the subject has not been diagnosed with one or more of HIV-related nephropathy or acute kidney failure.

In some embodiments, the subject has not been previously diagnosed with a chronic kidney disease that is other than IgA nephropathy. Non-limiting examples include a diabetic kidney disease, a hypertensive kidney disease, or a primary glomerulopathy that is determined to not be associated with IgA nephropathy. In certain embodiments, the subject has not been previously diagnosed with a diabetic kidney disease. In certain embodiments, the subject has not been previously diagnosed with a hypertensive kidney disease. In certain embodiments, the subject has not been diagnosed with a primary glomerulopathy that is determined to not be associated with IgA nephropathy.

In some embodiments, the subject does not have a chronic kidney disease that is other than IgA nephropathy. Non-limiting examples include a diabetic kidney disease, a hypertensive kidney disease, or a primary glomerulopathy that is determined to not be associated with IgA nephropathy. In certain embodiments, the subject does not have a diabetic kidney disease. In certain embodiments, the subject does not have a hypertensive kidney disease. In certain embodiments, the subject does not have a primary glomerulopathy that is determined to not be associated with IgA nephropathy.

In some embodiments, the subject does not suffer from a chronic kidney disease that is other than IgA nephropathy. Non-limiting examples include a diabetic kidney disease, a hypertensive kidney disease, or a primary glomerulopathy that is determined to not be associated with IgA nephropathy. In certain embodiments, the subject does not suffer from a diabetic kidney disease. In certain embodiments, the subject does not suffer from a hypertensive kidney disease. In certain embodiments, the subject does not suffer from a primary glomerulopathy that is determined to not be associated with IgA nephropathy.

In some embodiments, the subject is not being treated for a chronic kidney disease that is other than IgA nephropathy. Non-limiting examples include a diabetic kidney disease, a hypertensive kidney disease, or a primary glomerulopathy that is determined to not be associated with IgA nephropathy. In certain embodiments, the subject is not being treated for a diabetic kidney disease. In certain embodiments, the subject is not being treated for a hypertensive kidney disease. In certain embodiments, the subject is not being treated for a primary glomerulopathy that is determined to not be associated with IgA nephropathy.

Treatment Outcome

In some embodiments of the methods, uses, or product for uses herein, renal inflammation is decreased after treatment with atrasentan or a pharmaceutically acceptable salt thereof. In some embodiments, renal inflammation in the subject is decreased by at least about 10% after treatment with atrasentan or a pharmaceutically acceptable salt thereof (e.g., after treatment for 1 week, about 2 weeks, about 3 weeks, about 4 weeks, about 5 weeks, about 6 weeks, about 7 weeks, about 8 weeks, about 9 weeks, about 10 weeks, about 20 weeks, about 30 weeks, about 40 weeks, about 50 weeks, about 60 weeks, about 70 weeks, about 80 weeks, about 90 weeks, about 100 weeks, about 110 weeks, about 120 weeks, about 130 weeks, about 140 weeks, about 150 weeks, about 160 weeks, about 170 weeks, about 180 weeks, about 190 weeks, or about 200 weeks, or any value in between). In some embodiments, the renal inflammation in the subject is decreased by at least about 20%, about 30%, about 40%, about 50%, about 60% about 70% about 80%, about 90%, or about 95%, or any value in between. In certain of the foregoing embodiments, the subject has been treated with atrasentan or a pharmaceutically acceptable salt thereof for between about 15 days and about 30 days.

In some embodiments, renal fibrosis is decreased after treatment with atrasentan or a pharmaceutically acceptable salt thereof. In some embodiments, renal fibrosis in the subject is decreased by at least about 10% after treatment with atrasentan or a pharmaceutically acceptable salt thereof (e.g., after treatment for 1 week, about 2 weeks, about 3 weeks, about 4 weeks, about 5 weeks, about 6 weeks, about 7 weeks, about 8 weeks, about 9 weeks, about 10 weeks, about 20 weeks, about 30 weeks, about 40 weeks, about 50 weeks, about 60 weeks, about 70 weeks, about 80 weeks, about 90 weeks, about 100 weeks, about 110 weeks, about 120 weeks, about 130 weeks, about 140 weeks, about 150 weeks, about 160 weeks, about 170 weeks, about 180 weeks, about 190 weeks, or about 200 weeks, or any value in between). In certain embodiments, the renal fibrosis in the subject is decreased by at least about 20%, about 30%, about 40%, about 50%, about 60% about 70% about 80%, about 90%, or about 95%, or any value in between. In certain of the foregoing embodiments, the subject has been treated with atrasentan or a pharmaceutically acceptable salt thereof for between about 15 days and about 30 days.

In some embodiments, renal fibrosis in the subject is decreased to less than about 50% of the cortical area after treatment with atrasentan or a pharmaceutically acceptable salt thereof (e.g., after treatment for 1 week, about 2 weeks, about 3 weeks, about 4 weeks, about 5 weeks, about 6 weeks, about 7 weeks, about 8 weeks, about 9 weeks, about 10 weeks, about 20 weeks, about 30 weeks, about 40 weeks, about 50 weeks, about 60 weeks, about 70 weeks, about 80 weeks, about 90 weeks, about 100 weeks, about 110 weeks, about 120 weeks, about 130 weeks, about 140 weeks, about 150 weeks, about 160 weeks, about 170 weeks, about 180 weeks, about 190 weeks, or about 200 weeks, or any value in between). In certain embodiments, renal fibrosis in the subject is decreased to less than about 40% of the cortical area. For example, in some embodiments, renal fibrosis in the subject is decreased to less than about 35%, about 30%, about 25%, about 20%, about 15%, or about 10%, or any value in between, of the cortical area. In certain of the foregoing embodiments, the subject has been treated with atrasentan or a pharmaceutically acceptable salt thereof for between about 15 days and about 30 days.

In some embodiments, the occurrence of hematuria is decreased in a subject after treatment with atrasentan or a pharmaceutically acceptable salt thereof. In some embodiments, the number of urinary red blood cells per high powered (microscope) field (rbc/hpf) in the subject is decreased by at least about 10% after treatment with atrasentan or a pharmaceutically acceptable salt thereof (e.g., after treatment for 1 week, about 2 weeks, about 3 weeks, about 4 weeks, about 5 weeks, about 6 weeks, about 7 weeks, about 8 weeks, about 9 weeks, about 10 weeks, about 20 weeks, about 30 weeks, about 40 weeks, about 50 weeks, about 60 weeks, about 70 weeks, about 80 weeks, about 90 weeks, about 100 weeks, about 110 weeks, about 120 weeks, about 130 weeks, about 140 weeks, about 150 weeks, about 160 weeks, about 170 weeks, about 180 weeks, about 190 weeks, or about 200 weeks). In certain embodiments, the urinary rbc/hpf in the subject is decreased by at least about 20%. For example, in some embodiments, the urinary rbc/hpf in the subject is decreased by at least about 30%, about 40%, about 50%, about 60% about 70% about 80%, about 90%, or about 95%, or any value in between. In certain of the foregoing embodiments, the subject has been treated with atrasentan or a pharmaceutically acceptable salt thereof for between about 15 days and about 30 days.

In some embodiments, the rate of decrease of eGFR of the subject is reduced by at least about 10% after treatment with atrasentan or a pharmaceutically acceptable salt thereof (e.g., after treatment for 1 week, 2 weeks, 3 weeks, about 4 weeks, about 5 weeks, about 6 weeks, about 7 weeks, about 8 weeks, about 9 weeks, about 10 weeks, about 20 weeks, about 30 weeks, about 40 weeks, about 50 weeks, about 60 weeks, about 70 weeks, about 80 weeks, about 90 weeks, about 100 weeks, about 110 weeks, about 120 weeks, about 130 weeks, about 140 weeks, about 150 weeks, about 160 weeks, about 170 weeks, about 180 weeks, about 190 weeks, or about 200 weeks, or any value in between). In certain embodiments, the rate of decrease of eGFR of the subject is reduced by at least about 20%. For example, in some embodiments, the rate of decrease of eGFR of the subject is reduced by at least about 30%, about 40%, about 50%, about 60% about 70% about 80%, about 90%, or about 95%, or any value in between. In certain of the foregoing embodiments, the subject has been treated with atrasentan or a pharmaceutically acceptable salt thereof for between about 15 days and about 30 days. In certain of the foregoing embodiments, the subject has been treated with atrasentan or a pharmaceutically acceptable salt thereof for between about 6 months and about 1 year.

In some embodiments, the rate of decrease of eGFR of the subject is reduced to below about 10 mL/min per year after treatment with atrasentan or a pharmaceutically acceptable salt thereof (e.g., after treatment for about 1 week, about 2 weeks, about 3 weeks, about 4 weeks, about 5 weeks, about 6 weeks, about 7 weeks, about 8 weeks, about 9 weeks, about 10 weeks, about 20 weeks, about 30 weeks, about 40 weeks, about 50 weeks, about 60 weeks, about 70 weeks, about 80 weeks, about 90 weeks, about 100 weeks, about 110 weeks, about 120 weeks, about 130 weeks, about 140 weeks, about 150 weeks, about 160 weeks, about 170 weeks, about 180 weeks, about 190 weeks, or about 200 weeks, or any value in between). In some embodiments, the rate of decrease of eGFR of the subject is reduced to below about 9 mL/min per year. For example, in some embodiments, the rate of decrease of eGFR of the subject is reduced to below about 8 mL/min per year, about 7 mL/min per year, about 6 mL/min per year, about 5 mL/min per year, about 4 mL/min per year, about 3 mL/min per year, about 2 mL/min per year, or about 1 mL/min per year, or any value in between. In certain of the foregoing embodiments, the subject has been treated with atrasentan or a pharmaceutically acceptable salt thereof for between about 15 days and about 30 days. In certain of the foregoing embodiments, the subject has been treated with atrasentan or a pharmaceutically acceptable salt thereof for between about 6 months and about 1 year.

In some embodiments, the risk of the subject developing ESRD is reduced by about 20% to about 99% after treatment with atrasentan or a pharmaceutically acceptable salt thereof (e.g., after treatment for 1 week, about 2 weeks, about 3 weeks, about 4 weeks, about 5 weeks, about 6 weeks, about 7 weeks, about 8 weeks, about 9 weeks, about 10 weeks, about 20 weeks, about 30 weeks, about 40 weeks, about 50 weeks, about 60 weeks, about 70 weeks, about 80 weeks, about 90 weeks, about 100 weeks, about 110 weeks, about 120 weeks, about 130 weeks, about 140 weeks, about 150 weeks, about 160 weeks, about 170 weeks, about 180 weeks, about 190 weeks, or about 200 weeks, or any value in between). For example, the risk of the subject developing ESRD can be reduced by about 20%, about 25%, about 30%, about 35%, about 40%, about 45%, about 50%, about 55%, about 60%, about 65%, about 70%, about 75%, about 80%, about 85%, about 90%, or about 99%, or any value in between. In certain of the foregoing embodiments, the subject has been treated for between about 90 days to about 180 days. In certain embodiments, the risk of the subject developing ESRD is reduced by about 20% to about 99% after between about 90 and about 180 days of treatment with atrasentan, or a pharmaceutically acceptable salt thereof. In certain of the foregoing embodiments, the subject has been treated with atrasentan or a pharmaceutically acceptable salt thereof for between about 6 months and about 1 year.

In some embodiments, the method increases the time between the diagnosis of IgA nephropathy in the subject and the time when eGFR of the subject falls below about 15 mL/min/1.73 m$^2$. In certain embodiments, the method increases the time between the diagnosis of IgA nephropathy in the subject and the time when eGFR of the subject falls below 15 mL/min/1.73 m$^2$ by at least about 10%. For example, in some embodiments, the method increases the time between the diagnosis of IgA nephropathy in the subject and the time when eGFR of the subject falls below about 15 mL/min/1.73 m$^2$ by at least about 20%, about 30%, about 40%, about 50%, about 60%, about 70%, about 80%, about 90%, about 95%, about 100%, about 150%, about 200%, about 250%, about 300%, about 350%, about 400%, about 450%, or about 500%, or any value in between.

In some embodiments, the method increases the time between the diagnosis of IgA nephropathy in the subject and the time when eGFR of the subject falls below 15 mL/min/1.73 m$^2$ by at least about 1 year. For example, the method can delay the time when eGFR of the subject falls below 15 mL/min/1.73 m$^2$ by at least about 1.5 years, about 2 years, about 2.5 years, about 3 years, about 3.5 years, about 4 years, about 4.5 years, about 5 years, about 5.5 years, about 6 years, about 6.5 years, about 7 years, about 7.5 years, about 8 years, about 8.5 years, about 9 years, about 9.5 years, about 10 years, about 11 years, about 12 years, about 13 years, about 15 years, about 15 years, about 16 years, about 17 years, about 18 years, about 19 years, or about 20 years, or any value in between.

In some embodiments, the method reduces the average rate of decrease in eGFR by from about 0.75 mL/min/year to about 6 mL/min/year for at least about 3 months (e.g., at least about 4 months, at least about 5 months, at least about 6 months, at least about 7 months, at least about 8 months, at least about 9 months, at least about 10 months, at least about 11 months, at least about a year, at least about 1.5 years, or at least about 2 years) prior to the first administration of atrasentan, or a pharmaceutically acceptable salt thereof. For example, the method reduces the average rate of decrease in eGFR by about 0.75 mL/min/year, about 1 mL/min/year, about 1.5 mL/min/year, about 2 mL/min/year, about 2.5 mL/min/year, about 3 mL/min/year, about 3.5 mL/min/year, about 4 mL/min/year, about 4.5 mL/min/year, about 5 mL/min/year, about 5.5 mL/min/year, or about 6 mL/min/year. In some embodiments, the method reduces the average rate of decrease in eGFR by from about 4 mL/min/year to about 5 mL/min/year for at least about 3 months prior to the first administration of atrasentan, or a pharmaceutically acceptable salt thereof. In some embodiments, the method reduces the average rate of decrease in eGFR by from about 3 mL/min/year to about 6 mL/min/year for at least about 3 months prior to the first administration of atrasentan, or a pharmaceutically acceptable salt thereof. In some embodiments, the method reduces the average rate of decrease in eGFR by from about 4 mL/min/year to about 5 mL/min/year for at least about 3 months prior to the first administration of atrasentan, or a pharmaceutically acceptable salt thereof. In some embodiments, the decrease in eGFR in mL/min/year refers to units per 1.73 m$^2$.

In some embodiments, the method reduces the average rate of decrease in eGFR by from about 15% to about 30% after between about 6 months and about 24 months of treatment with atrasentan, or a pharmaceutically acceptable salt thereof. In some embodiments, the average rate of decrease in eGFR may be reduced by about 15%, after about 6 months, 9, months, 12 months, 15 months, 18 months, 21 months, or 24 months of treatment with atrasentan, or a pharmaceutically acceptable salt thereof. In some embodiments, the average rate of decrease in eGFR may be reduced by about 20%, after about 6 months, 9, months, 12 months, 15 months, 18 months, 21 months, or 24 months of treatment with atrasentan, or a pharmaceutically acceptable salt thereof. In some embodiments, the average rate of decrease in eGFR may be reduced by about 25%, after about 6 months, 9, months, 12 months, 15 months, 18 months, 21 months, or 24 months of treatment with atrasentan, or a pharmaceutically acceptable salt thereof. In some embodiments, the average rate of decrease in eGFR may be reduced by about 30%, after about 6 months, 9, months, 12 months, 15 months, 18 months, 21 months, or 24 months of treatment with atrasentan, or a pharmaceutically acceptable salt thereof.

In another aspect, provided herein is a method of decreasing proteinuria, comprising administering a therapeutically effective amount of atrasentan, or a pharmaceutically acceptable salt thereof, to a subject in need thereof.

In some embodiments, the amount of proteins (e.g., albumin) in the urine of the subject is reduced by at least about 10% after treatment with atrasentan or a pharmaceutically acceptable salt thereof (e.g., after treatment for about 1 week, about 2 weeks, about 3 weeks, about 4 weeks, about 5 weeks, about 6 weeks, about 7 weeks, about 8 weeks, about 9 weeks, about 10 weeks, about 20 weeks, about 30 weeks, about 40 weeks, about 50 weeks, about 60 weeks, about 70 weeks, about 80 weeks, about 90 weeks, about 100 weeks, about 110 weeks, about 120 weeks, about 130 weeks, about 140 weeks, about 150 weeks, about 160 weeks, about 170 weeks, about 180 weeks, about 190 weeks, or about 200 weeks, or any value in between). In some embodiments, the amount of proteins in the urine of the subject is reduced by at least about 15%. For example, in some embodiments, the amount of proteins in the urine of the subject is reduced by at least about 20%, about 30%, about 40%, about 50%, about 60%, about 70%, about 80%, about 90%, or about 95%, or any value in between. In certain of the foregoing embodiments, the subject has been treated with atrasentan or a pharmaceutically acceptable salt thereof for between about 15 days and about 30 days.

In certain embodiments, the amount of proteins (e.g., albumin) in the urine of the subject is reduced by about 20% to about 80% after between about 15 day and about 30 days of treatment with atrasentan, or a pharmaceutically acceptable salt thereof. In certain of these embodiments, the amount of proteins in the urine of the subject is reduced by about 25% to about 80%. In certain of these embodiments, the amount of proteins in the urine of the subject is reduced by about 30% to about 80%. In certain of these embodiments, the amount of proteins in the urine of the subject is reduced by about 35% to about 80%. In certain of these embodiments, the amount of proteins in the urine of the subject is reduced by about 40% to about 80%. In certain of these embodiments, the amount of proteins in the urine of the subject is reduced by about 45% to about 80%. In certain of these embodiments, the amount of proteins in the urine of the subject is reduced by about 50% to about 80%.

In some embodiments, the amount of proteins (e.g., albumin) in the urine of the subject is reduced by about 100 mg/dL to about 3,000 mg/dL after treatment with atrasentan or a pharmaceutically acceptable salt thereof (e.g., after treatment for about 1 week, about 2 weeks, about 3 weeks, about 4 weeks, about 5 weeks, about 6 weeks, about 7 weeks, about 8 weeks, about 9 weeks, about 10 weeks, about 20 weeks, about 30 weeks, about 40 weeks, about 50 weeks, about 60 weeks, about 70 weeks, about 80 weeks, about 90 weeks, about 100 weeks, about 110 weeks, about 120 weeks, about 130 weeks, about 140 weeks, about 150 weeks, about 160 weeks, about 170 weeks, about 180 weeks, about 190 weeks, or about 200 weeks, or any value in between). In certain embodiments, the amount of proteins in the urine of the subject is reduced by about 100 mg/dL to about 2,500 mg/dL. In certain embodiments, the amount of proteins in the urine of the subject is reduced by about 100 mg/dL to about 2,000 mg/dL. In certain embodiments, the amount of proteins in the urine of the subject is reduced by about 100 mg/dL to about 1,500 mg/dL. In certain embodiments, the amount of proteins in the urine of the subject is reduced by about 100 mg/dL to about 1,000 mg/dL. In certain embodiments, the amount of proteins in the urine of the subject is reduced by about 100 mg/dL to about 500 mg/dL. In certain embodiments, the amount of proteins in the urine of the subject is reduced by about 100 mg/dL to about 400 mg/dL. In certain embodiments, the amount of proteins in the urine of the subject is reduced by about 100 mg/dL to about 300 mg/dL. In certain embodiments, the amount of proteins in the urine of the subject is reduced by about 100 mg/dL to about 200 mg/dL. In certain embodiments, the amount of proteins in the urine of the subject is reduced by about 500 mg/dL to about 2,500 mg/dL. In certain embodiments, the amount of proteins in the urine of the subject is reduced by about 500 mg/dL to about 2,000 mg/dL. In certain embodiments, the amount of proteins in the urine of the subject is reduced by about 500 mg/dL to about 1,500 mg/dL. In certain embodiments, the amount of proteins in the urine of the subject is reduced by about 500 mg/dL to about 1,000 mg/dL. In certain embodiments, the amount of proteins in the urine of the subject is reduced by about 500 mg/dL to about 900 mg/dL. In certain embodiments, the amount of proteins in the urine of the subject is reduced by about 500 mg/dL to about 800 mg/dL. In certain embodiments, the amount of proteins in the urine of the subject is reduced by about 600 mg/dL to about 900 mg/dL. In certain embodiments, the amount of proteins in the urine of the subject is reduced by about 700 mg/dL to about 900 mg/dL. In certain embodiments, the amount of proteins in the urine of the subject is reduced by about 1,000 mg/dL to about 2,000 mg/dL. In certain of the foregoing embodiments, the subject has been treated with atrasentan or a pharmaceutically acceptable salt thereof for between about 15 days and about 30 days.

In certain embodiments, the amount of proteins (e.g., albumin) in the urine of the subject is reduced by about 100 mg/dL to about 500 mg/dL after between about 15 days and about 30 days of treatment with atrasentan, or a pharmaceutically acceptable salt thereof. In certain embodiments, the amount of proteins in the urine of the subject is reduced by about 200 mg/dL to about 500 mg/dL after between about 15 days and about 30 days of treatment with atrasentan, or a pharmaceutically acceptable salt thereof. In certain embodiments, the amount of proteins in the urine of the subject is reduced by about 300 mg/dL to about 500 mg/dL after between about 15 days and about 30 days of treatment with atrasentan, or a pharmaceutically acceptable salt thereof.

In certain embodiments, the amount of proteins (e.g., albumin) in the urine of the subject is reduced by about 500 mg/dL to about 900 mg/dL after between about 15 days and about 30 days of treatment with atrasentan, or a pharmaceutically acceptable salt thereof. In certain embodiments, the amount of proteins in the urine of the subject is reduced by about 600 mg/dL to about 900 mg/dL after between about 15 days and about 30 days of treatment with atrasentan, or a pharmaceutically acceptable salt thereof. In certain embodiments, the amount of proteins in the urine of the subject is reduced by about 700 mg/dL to about 900 mg/dL after between about 15 days and about 30 days of treatment with atrasentan, or a pharmaceutically acceptable salt thereof.

In some embodiments, the subject has a reduced level of proteins (e.g., albumin) in the urine of below about 1.0 gram/day after treatment with atrasentan or a pharmaceutically acceptable salt thereof (e.g., after treatment for about 1 week, about 2 weeks, about 3 weeks, about 4 weeks, about 5 weeks, about 6 weeks, about 7 weeks, about 8 weeks, about 9 weeks, about 10 weeks, about 20 weeks, about 30 weeks, about 40 weeks, about 50 weeks, about 60 weeks, about 70 weeks, about 80 weeks, about 90 weeks, about 100 weeks, about 110 weeks, about 120 weeks, about 130 weeks, about 140 weeks, about 150 weeks, about 160 weeks, about 170 weeks, about 180 weeks, about 190 weeks, or about 200 weeks). In some embodiments, the subject has a reduced level of proteins in the urine of below about 0.9 gram/day. For example, in some embodiments, the subject has a reduced level of proteins in the urine of below about 0.8 gram/day, about 0.7 gram/day, about 0.6 gram/day, 0.5 gram/day, about 0.4 gram/day, about 0.3 gram/day, or about 0.2 gram/day, or any value in between. In certain of the foregoing embodiments, the subject has been treated with atrasentan or a pharmaceutically acceptable salt thereof for between about 15 days and about 30 days.

In some embodiments, the subject is between about 15 and about 40 years old. In some embodiments, the subject is between about 15 to about 25 years old, about 20 to about 30 years old, about 25 to about 35 years old, about 30 to about 40 years old, or any age in between. In some embodiments, the subject is between about 20 to about 30 years old, or any age in between. In some embodiments, the subject is about 20 years old, about 21 years old, about 22 years old, about 23 years old, about 24 years old, about 25 years old, about 26 years old, about 27 years old, about 28 years old, about 29 years old, or about 30 years old.

In some embodiments, the level of fatigue of the patient is reduced following treatment with atrasentan or a pharmaceutically acceptable salt thereof. In some embodiments, the fatigue is reduced by about 5% to about 80% after treatment with atrasentan or a pharmaceutically acceptable salt thereof (e.g., after treatment for about 1 week, about 2 weeks, about 3 weeks, about 4 weeks, about 5 weeks, about 6 weeks, about 7 weeks, about 8 weeks, about 9 weeks, about 10 weeks, about 20 weeks, about 30 weeks, about 40 weeks, about 50 weeks, about 60 weeks, about 70 weeks, about 80 weeks, about 90 weeks, about 100 weeks, about 110 weeks, about 120 weeks, about 130 weeks, about 140 weeks, about 150 weeks, about 160 weeks, about 170 weeks, about 180 weeks, about 190 weeks, or about 200 weeks, or any value in between). In certain embodiments, the fatigue is reduced by about 10% to about 75%. In certain embodiments, the fatigue is reduced by about 10% to about 70%. In certain embodiments, the fatigue is reduced by about 10% to about 65%. In certain embodiments, the fatigue is reduced by about 10% to about 60%. In certain embodiments, the fatigue is reduced by about 10% to about 55%. In certain embodiments, the fatigue is reduced by about 10% to about 50%. In certain embodiments, the fatigue is reduced by about 10% to about 45%. In certain embodiments, the fatigue is reduced by about 10% to about 40%. In certain embodiments, the fatigue is reduced by about 10% to about 35%. In certain embodiments, the fatigue is reduced by about 10% to about 30%. In certain embodiments, the fatigue is reduced by about 10% to about 25%. In certain embodiments, the fatigue is reduced by about 10% to about 20%. In certain embodiments, the fatigue is reduced by about 10% to about 15%. In certain of the foregoing embodiments, the subject has been treated with atrasentan or a pharmaceutically acceptable salt thereof for between about 15 days and about 30 days. In certain embodiments, the decrease in fatigue comprises a decrease in the score on one or more of the Fatigue Severity Scale, the Chalder Fatigue Scale, the FACIT Fatigue Scale, the Brief Fatigue Inventory, the FACT-F Subscale, Global Vigor and Affect, the May and Kline Adjective Checklist, the Pearson-Byars Fatigue Feeling Checklist, the Rhoten Fatigue Scale, the Schedule of Fatigue and Anergia, or the Checklist Individual Strength.

Some embodiments provide a method of inhibiting mesangial cell activation in a subject having IgA nephropathy, comprising administering a therapeutically effective amount of atrasentan, or a pharmaceutically acceptable salt thereof, to the subject; wherein the subject has not been previously diagnosed with one or more of diabetic nephropathy, HIV/AIDS, or acute kidney failure.

Some embodiments provide a method of inhibiting PDGF signaling activity (e.g., decreasing the expression and/or activity of one or more of PIK3R1, PDGFRA, NFKBIA, PIK3CG, PLA2G4 Å, TIAM1, PDGFB, NFKB1, and MAP3K1) in a mesangial cell in a subject having IgA nephropathy, comprising administering a therapeutically effective amount of atrasentan, or a pharmaceutically acceptable salt thereof, to the subject; wherein the subject has not been previously diagnosed with one or more of diabetic nephropathy, HIV/AIDS, or acute kidney failure.

Some embodiments provide a method of inhibiting mesangial cell activation, comprising contacting a mesangial cell with an effective amount of atrasentan, or a pharmaceutically acceptable salt thereof.

In some embodiments, the mesangial activation is induced by IgA immune complexes. In some embodiments, the mesangial activation is associated with the presence of IgA immune complexes. The presence and/or amount of IgA immune complexes can be detected by a variety of methods. For example, the complexes may be detected in serum or urine, and can also be detected in a kidney biopsy sample.

In some embodiments, the inhibiting of mesangial cell activation comprises reducing expression and/or activity of one or more biomarkers indicative of mesangial cell proliferation. In some embodiments, inhibiting of mesangial cell activation comprises reducing mesangial cell inflammation. In some embodiments, reducing mesangial cell inflammation comprises reducing expression and/or activity of one or more of IL6, MCP1, or other biomarkers indicative of mesangial cell inflammation. In some embodiments, reducing mesangial cell inflammation comprises reducing expression and/or activity of IL-6. In some embodiments, the expression and/or activity of one or more biomarkers indicative of mesangial cell inflammation is reduced by about 25% to about 99% after treatment with atrasentan or a pharmaceutically acceptable salt thereof (e.g., after treatment for about 1 week, about 2 weeks, about 3 weeks, about 4 weeks, about 5 weeks, about 6 weeks, about 7 weeks, about 8 weeks, about 9 weeks, about 10 weeks, about 20 weeks, about 30 weeks, about 40 weeks, about 50 weeks, about 60 weeks, about 70 weeks, about 80 weeks, about 90 weeks, about 100 weeks, about 110 weeks, about 120 weeks, about 130 weeks, about 140 weeks, about 150 weeks, about 160 weeks, about 170 weeks, about 180 weeks, about 190 weeks, or about 200 weeks, or any value in between). In some embodiments, the expression and/or activity of one or more biomarkers indicative of mesangial cell inflammation is reduced by about 25% to about 50%, about 40% to about 60%, about 50% to about 75%, about 60% to about 80%, about 75% to about 90%, about 85% to about 99%, or any value in between. For example, in some such embodiments, the one or more biomarkers can be IL-6.

In some embodiments, inhibiting of mesangial cell activation comprises reducing mesangial cell inflammation. In some embodiments, reducing mesangial cell inflammation comprises reducing IL-6 signaling (e.g., reducing the expression and/or activity in one or more proteins involved in an IL-6 signaling pathway, e.g., a reduction in the expression and/or activity of one or more of Cntfr, Il1b, Csf1, Il2ra, Map3k8, and Il1r1). In some embodiments, reducing mesanial cell inflammation comprises reducing the expression and/or activity of one or more (e.g., 1, 2, 3, 4, or 5) of: Cntfr, Il1b, Csf1, Il2ra, Map3k8, Il1r1.

In some embodiments, the inhibiting of mesangial cell activation comprises reducing the pro-fibrotic response in the mesangial cells. In some embodiments, reducing the pro-fibrotic response in the mesangial cells comprises reducing expression and/or activity of one or more of NF-κB, TGF, PDGF, CTGF, MMP, TIMPS, or other biomarkers indicative of mesangial cell fibrosis. In some embodiments, the expression and/or activity of one or more of NF-κB, TGF, PDGF, CTGF, MMP, and TIMPS, is reduced by about 25% to about 99% after treatment with atrasentan or a pharmaceutically acceptable salt thereof (e.g., after treatment for about 1 week, about 2 weeks, about 3 weeks, about 4 weeks, about 5 weeks, about 6 weeks, about 7 weeks, about 8 weeks, about 9 weeks, about 10 weeks, about 20 weeks, about 30 weeks, about 40 weeks, about 50 weeks, about 60 weeks, about 70 weeks, about 80 weeks, about 90 weeks, about 100 weeks, about 110 weeks, about 120 weeks, about 130 weeks, about 140 weeks, about 150 weeks, about 160 weeks, about 170 weeks, about 180 weeks, about 190 weeks, or about 200 weeks, or any value in between), relative to the expression and/or activity prior to administration of atrasentan, or a pharmaceutically acceptable salt thereof. In some embodiments, the expression and/or activity of one or more of NF-κB, TGF, PDGF, CTGF, MMP, and TIMPS is reduced by about 25% to about 50%, about 40% to about 60%, about 50% to about 75%, about 60% to about 80%, about 75% to about 90%, about 85% to about 99%, or any value in between.

In some embodiments, inhibiting of mesangial cell activation comprises reducing the pro-fibrotic response in the mesangial cells. In some embodiments, reducing the the pro-fibrotic response comprises reducing NF-κB signaling. In some embodiments, reducing the pro-fibrotic response comprises reducing the expression and/or activity of one or more (e.g., 1, 2, 3, 4, or 5) of: Pfkfb3, Nr4a1, Gem, Fosl2, Klf4, F3, Nfkbia, Ifit2, Nr4a2, Klf2, Jag1, Dnajb4, Il1b, Spsb1, Btg2, Atf3, Csf1, Trib1, Zbtb10, Btg1, Rhob, Nfat5, Edn1, Rel, Nr4a3, Nfkb1, Serpine1, Ccl20, Per1, Cxcl2, Map3k8, Traf1, and/or increasing the expression and/or activity of one or more (e.g., 1, 2, 3, 4, or 5) of: Ehd1, Snn, Tnfaip8, Ackr3, Id2, Ccn1, Efna1, Ccnd1, Cdkn1a, Pnrc1 (in cases where the component inhibits NF-κB signaling).

In some embodiments, reducing the pro-fibrotic response comprises reducing PDGF signaling. In some embodiments, reducing the pro-fibrotic response comprises reducing the expression and/or activity of one or more (e.g., 1, 2, 3, 4, or 5) of: Pik3r1, Pdgfra, Nfkbia, Pik3cg, Pla2g4a, Tiam1, Pdgfb, Nfkb1, and/or increasing the expression and/or activity of one or more (e.g., 1, 2, 3, 4, or 5) of: Hras (in cases where the component inhibits PDGF signaling).

In some embodiments, the expression and/or activity of NF-κB and/or PDGF expression and/or activity, is reduced by about 25% to about 99% after treatment with atrasentan or a pharmaceutically acceptable salt thereof (e.g., after treatment for about 1 week, about 2 weeks, about 3 weeks, about 4 weeks, about 5 weeks, about 6 weeks, about 7 weeks, about 8 weeks, about 9 weeks, about 10 weeks, about 20 weeks, about 30 weeks, about 40 weeks, about 50 weeks, about 60 weeks, about 70 weeks, about 80 weeks, about 90 weeks, about 100 weeks, about 110 weeks, about 120 weeks, about 130 weeks, about 140 weeks, about 150 weeks, about 160 weeks, about 170 weeks, about 180 weeks, about 190 weeks, or about 200 weeks, or any value in between), relative to the expression and/or activity prior to administration of atrasentan, or a pharmaceutically acceptable salt thereof. In some embodiments, the expression and/or activity of NF-κB and/or PDGF is reduced by about 25% to about 50%, about 40% to about 60%, about 50% to about 75%, about 60% to about 80%, about 75% to about 90%, about 85% to about 99%, or any value in between.

In some embodiments, reducing the pro-fibrotic response in the mesangial cells comprises reducing matrix secretion by mesangial cells. In some embodiments, reducing matrix secretion by mesangial cells comprises reducing expression and/or activity of one or more of excess matrix secretion by mesangial cells.

Some embodiments provide a method of reducing activation of a mesangial cell in contact with an IgA immune complex, comprising contacting a mesangial cell with an effective amount of atrasentan, or a pharmaceutically acceptable salt thereof. In some embodiments, reducing activation of a mesangial cell comprises reducing expression and/or activity of one or more biomarkers indicative of mesangial cell proliferation.

In some embodiments, reducing activation of a mesangial cell comprises reducing mesangial cell inflammation. In some embodiments, reducing mesangial cell inflammation comprises reducing expression and/or activity of one or more of IL6, MCP1, or other biomarkers indicative of mesangial cell inflammation.

In some embodiments, reducing activation of a mesangial cell comprises reducing the pro-fibrotic response in the mesangial cells. In some embodiments, reducing the pro-fibrotic response in the mesangial cells comprises reducing expression and/or activity of one or more of TGF, PDGF, CTGF, MMP, TIMPS, or other biomarkers indicative of mesangial cell fibrosis.

In some embodiments, reducing the pro-fibrotic response in the mesangial cells comprises reducing matrix secretion by mesangial cells. In some embodiments, reducing matrix secretion by mesangial cells comprises reducing expression and/or activity of one or more biomarkers indicative of excess matrix secretion by mesangial cells.

In some embodiments, the reducing activation of a mesangial cell comprises reducing undesired mesangial cell migration. In some embodiments, the reduction in undesired mesangial cell migration occurs after about 15 days to about 30 days after treatment with atrasentan, or a pharmaceutically acceptable salt thereof. In some embodiments, the reduction in undesired mesangial cell migration occurs after about 3 months to about 6 months after treatment with atrasentan, or a pharmaceutically acceptable salt thereof.

In some embodiments, the reducing activation of a mesangial cell comprises reducing undesired mesangial cell proliferation. In some embodiments, the reduction in undesired mesangial cell proliferation occurs after about 15 days to about 30 days after treatment with atrasentan, or a pharmaceutically acceptable salt thereof. In some embodiments, the reduction in undesired mesangial cell proliferation occurs after about 3 months to about 6 months after treatment with atrasentan, or a pharmaceutically acceptable salt thereof.

In some embodiments, the undesired mesangial cell proliferation is reduced by about 25% to about 99% after treatment with atrasentan or a pharmaceutically acceptable salt thereof (e.g., after treatment for about 1 week, about 2 weeks, about 3 weeks, about 4 weeks, about 5 weeks, about 6 weeks, about 7 weeks, about 8 weeks, about 9 weeks, about 10 weeks, about 20 weeks, about 30 weeks, about 40 weeks, about 50 weeks, about 60 weeks, about 70 weeks, about 80 weeks, about 90 weeks, about 100 weeks, about 110 weeks, about 120 weeks, about 130 weeks, about 140 weeks, about 150 weeks, about 160 weeks, about 170 weeks, about 180 weeks, about 190 weeks, or about 200 weeks, or any value in between). In some embodiments, the undesired mesangial cell proliferation is reduced by about 25% to about 50%, about 40% to about 60%, about 50% to about 75%, about 60% to about 80%, about 75% to about 90%, about 85% to about 99%, or any value in between.

In some embodiments, mesangial cell activation can be assessed by one or more of serum analysis, urinalysis, and microscopy of a kidney biopsy sample (e.g., light microscopy and/or immunofluorescence microscopy).

In some embodiments, the contacting occurs in vitro. In some embodiments, the contacting occurs in vivo.

Some embodiments provide a method of treating IgA nephropathy in a subject in need thereof, comprising: a) determining that the subject has elevated serum Gd-IgA1 levels; and b) administering a therapeutically effective amount of atrasentan, or a pharmaceutically acceptable salt thereof, to the subject. In some embodiments, the subject has not been previously diagnosed with one or more of diabetic nephropathy, HIV/AIDS, or acute kidney failure. In some embodiments, the subject has not been previously diagnosed with HIV-related nephropathy. In some embodiments, the subject has not been previously diagnosed with cancer. In some embodiments, the cancer is lung cancer or prostate cancer.

Some embodiments provide a method of treating IgA nephropathy in a subject in need thereof, comprising: a) determining that the subject has elevated levels of mesangial activation; and b) administering a therapeutically effective amount of atrasentan, or a pharmaceutically acceptable salt thereof, to the subject.

In some embodiments, determining of elevated levels of mesangial activation comprises obtaining a sample from the subject and assessing the level of mesangial activation in the same. In some embodiments, the sample is a kidney biopsy sample. In some embodiments, the sample is selected from a blood sample, a urine sample, a kidney biopsy sample, or a combination of two or three of the foregoing.

In some embodiments, the sample exhibits elevated levels of one or more of: matrix secretion by the mesangial cells, IgA-immune complex deposition, mesangial cell proliferation, and endocapillary cell proliferation. In some embodiments, the sample exhibits elevated levels of IgA-immune complex deposition.

In some embodiments, the subject has been determined to have proteinuria of at least about 1 g/day in at least two of three consecutive readings over the year prior to administration of a therapeutically effective amount of atrasentan, or a pharmaceutically acceptable salt thereof. For example, about 1 g/day, about 1.2 g/day, about 1.4 g/day, about 1.6 g/day, about 1.8 g/day, or about at least 2 g/day.

In some embodiments, the subject has been administered a maximally tolerated stable dose of a RAS inhibitor for at least 12 weeks prior to administration of a therapeutically effective amount of atrasentan, or a pharmaceutically acceptable salt thereof. In some embodiments, the subject is concurrently administered a maximally tolerated stable dose of a RAS inhibitor and a therapeutically effective amount of atrasentan, or a pharmaceutically acceptable salt thereof. In some embodiments, the RAS inhibitor is an angiotensin-converting enzyme inhibitor. In some embodiments, the RAS inhibitor is an angiotensin receptor blocker (ARB).

In some embodiments, the subject has been determined to have hematuria prior to administration of a therapeutically effective amount of atrasentan, or a pharmaceutically acceptable salt thereof. In some embodiments, the hematuria is microhematuria. In some embodiments, the hematuria is gross hematuria.

In some embodiments, the subject has been determined to have an eGFR of at least 30 mL/min/1.73 m$^2$ prior to administration of a therapeutically effective amount of atrasentan, or a pharmaceutically acceptable salt thereof. In some embodiments, the subject has been determined to have an eGFR of about 30 mL/min/1.73 m$^2$ to about 60 mL/min/1.73 m$^2$ prior to administration of a therapeutically effective amount of atrasentan, or a pharmaceutically acceptable salt thereof.

In some embodiments, the subject has not been previously diagnosed with one or more of diabetic nephropathy, HIV/AIDS, or acute kidney failure. In some embodiments, the subject has not been previously diagnosed with HIV-related nephropathy. In some embodiments, the subject has not been previously diagnosed with cancer. In some embodiments, the cancer is lung cancer or prostate cancer.

Some embodiments provide a method of treating IgA nephropathy in a subject in need thereof, comprising: a) determining that the subject has elevated levels of IgA-immune complexes in the kidney; and b) administering a therapeutically effective amount of atrasentan, or a pharmaceutically acceptable salt thereof, to the subject.

In some embodiments, determining of elevated levels of IgA-immune complexes in the kidney comprises obtaining a sample from the subject and assessing the level of IgA-immune complexes in the same. In some embodiments, the sample is a kidney biopsy sample. In some embodiments, the sample is selected from a blood sample, a urine sample, a kidney biopsy sample, or a combination of two or three of the foregoing. In some embodiments, the IgA-immune complexes are deposited in the mesangium.

In some embodiments, the levels of IgA-immune complexes can be assessed by one or more of serum analysis, urinalysis, and microscopy of a kidney biopsy sample (e.g., light microscopy and/or immunofluorescence microscopy).

In some embodiments, the sample exhibits elevated levels of one or more of: matrix secretion by the mesangial cells, IgA-immune complex deposition in the mesangium, mesangial cell activation, mesangial cell proliferation, and endocapillary cell proliferation.

In some embodiments, the subject has been determined to have proteinuria of at least about 1 g/day in at least two of three consecutive readings over the year prior to administration of a therapeutically effective amount of atrasentan, or a pharmaceutically acceptable salt thereof. For example, about 1 g/day, about 1.2 g/day, about 1.4 g/day, about 1.6 g/day, about 1.8 g/day, or about at least 2 g/day.

In some embodiments, the subject has been administered a maximally tolerated stable dose of a RAS inhibitor for at least 12 weeks prior to administration of a therapeutically effective amount of atrasentan, or a pharmaceutically acceptable salt thereof. In some embodiments, the subject is concurrently administered a maximally tolerated stable dose of a RAS inhibitor and a therapeutically effective amount of atrasentan, or a pharmaceutically acceptable salt thereof. In some embodiments, the RAS inhibitor is an angiotensin-converting enzyme inhibitor. In some embodiments, the RAS inhibitor is an angiotensin receptor blocker (ARB).

In some embodiments, the subject has been determined to have hematuria prior to administration of a therapeutically effective amount of atrasentan, or a pharmaceutically acceptable salt thereof. In some embodiments, the hematuria is microhematuria. In some embodiments, the hematuria is gross hematuria.

In some embodiments, the subject has been determined to have an eGFR of at least 30 mL/min/1.73 m$^2$ prior to administration of a therapeutically effective amount of atrasentan, or a pharmaceutically acceptable salt thereof. In some embodiments, the subject has been determined to have an eGFR of about 30 mL/min/1.73 m$^2$ to about 60 mL/min/1.73 m$^2$ prior to administration of a therapeutically effective amount of atrasentan, or a pharmaceutically acceptable salt thereof.

In some embodiments, the subject has not been previously diagnosed with one or more of diabetic nephropathy, HIV/AIDS, or acute kidney failure. In some embodiments, the subject has not been previously diagnosed with HIV-related nephropathy. In some embodiments, the subject has not been previously diagnosed with cancer. In some embodiments, the cancer is lung cancer or prostate cancer.

In some embodiments, the methods include determining, in the subject, expression and/or activity of one or more of ET1, TGF, PDGF, CTGF, MMP, TIMPS, IGF1, DPEP1, ASL, AMN, ALPL, SLC6A19, IL-6, and NF-kB. In some embodiments, expression and/or activity are determined prior to administration of a therapeutically effective amount of atrasentan, or a pharmaceutically acceptable salt thereof. In some embodiments, expression and/or activity are determined after administration of a therapeutically effective amount of atrasentan, or a pharmaceutically acceptable salt thereof.

In some embodiments, the determining the expression and/or activity is performed prior to administration of a therapeutically effective amount of atrasentan, or a pharmaceutically acceptable salt thereof. In some embodiments, the determining the expression and/or activity is performed after administration of a therapeutically effective amount of atrasentan, or a pharmaceutically acceptable salt thereof, for example, after treatment for about 1 week, about 2 weeks, about 3 weeks, about 4 weeks, about 5 weeks, about 6 weeks, about 7 weeks, about 8 weeks, about 9 weeks, about 10 weeks, about 20 weeks, about 30 weeks, about 40 weeks, about 50 weeks, about 60 weeks, about 70 weeks, about 80 weeks, about 90 weeks, about 100 weeks, about 110 weeks, about 120 weeks, about 130 weeks, about 140 weeks, about 150 weeks, about 160 weeks, about 170 weeks, about 180 weeks, about 190 weeks, or about 200 weeks, or any value in between.

In some embodiments, the subject has been determined to have elevated expression and/or activity of one or more of ET1, TGF, PDGF, CTGF, MMP, TIMPS, IGF1, DPEP1, ASL, AMN, ALPL, SLC6A19, IL-6, NF-kB, PKC, PI3K, Src, Ras, ERK1/2, Rho, Rac, Akt, mTOR, NAPDH oxidase, MAPK, cPLA$_2$, TNF-α, IL-1, CAM, COX-2, iNOS, JAK, STAT3, PI3K, Akt/PKB, IKKs, IkBs, NF-kB, MAPK, Ras, Raf, MEK, ERK, MCP1, Cntfr, Il1b, Csf1, Il2ra, Map3k8, Il1r1, Pfkfb3, Nr4a1, Gem, Fosl2, Klf4, F3, Nfkbia, Ifit2, Nr4a2, Klf2, Jag1, Dnajb4, Il1b, Spsb1, Btg2, Atf3, Csf1, Trib1, Zbtb10, Btg1, Rhob, Nfat5, Edn1, Rel, Nr4a3, Nfkb1, Serpine1, Ccl20, Per1, Cxcl2, Map3k8, Traf1, Pik3r1, Pdgfra, Nfkbia, Pik3cg, Pla2g4a, Tiam1, and Pdgfb. In some embodiments, the subject has been determined to have elevated expression and/or activity of one or more of ET1, TGF, PDGF, CTGF, MMP, TIMPS, IGF1, DPEP1, ASL, AMN, ALPL, SLC6A19, IL-6, NF-kB, PKC, PI3K, Src, Ras, ERK1/2, Rho, Rac, Akt, mTOR, NAPDH oxidase, MAPK, cPLA$_2$, TNF-α, IL-1, CAM, COX-2, iNOS, JAK, STAT3, PI3K, Akt/PKB, IKKs, IkBs, NF-kB, MAPK, Ras, Raf, MEK, ERK, and MCP1. In some embodiments, the subject has been determined to have elevated expression and/or activity of one or more of Cntfr, Il1b, Csf1, Il2ra, Map3k8, Il1r1, Pfkfb3, Nr4a1, Gem, Fosl2, Klf4, F3, Nfkbia, Ifit2, Nr4a2, Klf2, Jag1, Dnajb4, Il1b, Spsb1, Btg2, Atf3, Csf1, Trib1, Zbtb10, Btg1, Rhob, Nfat5, Edn1, Rel, Nr4a3, Nfkb1, Serpine1, Ccl20, Per1, Cxcl2, Map3k8, Traf1, Pik3r1, Pdgfra, Nfkbia, Pik3cg, Pla2g4a, Tiam1, and Pdgfb. In some embodiments, the subject has been determined to have elevated expression and/or activity of one or more of ET1, TGF, PDGF, CTGF, MMP, TIMPS, IGF1, DPEP1, ASL, AMN, ALPL, SLC6A19, IL-6, and NF-kB. In some embodiments, the subject has been determined to have elevated expression and/or activity of one or more of ET1, TGF, PDGF, CTGF, MMP, TIMPS, IGF1, DPEP1, ASL, AMN, ALPL, and SLC6A19.

Some embodiments provide a method of treating IgA nephropathy in a subject, comprising: (a) determining that the subject has elevated expression and/or activity of one or more of ET1, TGF, PDGF, CTGF, MMP, TIMPS, IGF1, DPEP1, ASL, AMN, ALPL, SLC6A19, IL-6, NF-kB, PKC, PI3K, Src, Ras, ERK1/2, Rho, Rac, Akt, mTOR, NAPDH oxidase, MAPK, cPLA$_2$, TNF-α, IL-1, CAM, COX-2, iNOS, JAK, STAT3, PI3K, Akt/PKB, IKKs, IkBs, NF-kB, MAPK, Ras, Raf, MEK, ERK, MCP1, Cntfr, Il1b, Csf1, Il2ra, Map3k8, Il1r1, Pfkfb3, Nr4a1, Gem, Fosl2, Klf4, F3, Nfkbia, Ifit2, Nr4a2, Klf2, Jag1, Dnajb4, Il1b, Spsb1, Btg2, Atf3, Csf1, Trib1, Zbtb10, Btg1, Rhob, Nfat5, Edn1, Rel, Nr4a3, Nfkb1, Serpine1, Ccl20, Per1, Cxcl2, Map3k8, Traf1, Pik3r1, Pdgfra, Nfkbia, Pik3cg, Pla2g4a, Tiam1, and Pdgfb; and (b) administering to the subject a therapeutically effective amount of atrasentan, or a pharmaceutically acceptable salt thereof.

Some embodiments provide a method of treating IgA nephropathy in a subject determined to have elevated expression and/or activity of one or more of ET1, TGF, PDGF, CTGF, MMP, TIMPS, IGF1, DPEP1, ASL, AMN, ALPL, SLC6A19, IL-6, NF-kB, PKC, PI3K, Src, Ras, ERK1/2, Rho, Rac, Akt, mTOR, NAPDH oxidase, MAPK, cPLA$_2$, TNF-α, IL-1, CAM, COX-2, iNOS, JAK, STAT3, PI3K, Akt/PKB, IKKs, IkBs, NF-kB, MAPK, Ras, Raf, MEK, ERK, MCP1, Cntfr, Il1b, Csf1, Il2ra, Map3k8, Il1r1, Pfkfb3, Nr4a1, Gem, Fosl2, Klf4, F3, Nfkbia, Ifit2, Nr4a2, Klf2, Jag1, Dnajb4, Il1b, Spsb1, Btg2, Atf3, Csf1, Trib1, Zbtb10, Btg1, Rhob, Nfat5, Edn1, Rel, Nr4a3, Nfkb1, Serpine1, Ccl20, Per1, Cxcl2, Map3k8, Traf1, Pik3r1, Pdgfra, Nfkbia, Pik3cg, Pla2g4a, Tiam1, and Pdgfb, comprising administering to the subject a therapeutically effective amount of atrasentan, or a pharmaceutically acceptable salt thereof.

D. Atrasentan

Atrasentan, also known as (2R,3R,4S)-4-(1,3-benzodioxol-5-yl)-1-[2-(dibutylamino)-2-oxoethyl]-2-(4-methoxyphenyl)pyrrolidine-3-carboxylic acid, ABT-627, A-147627, or A-127722, is a small molecule of the following chemical structure:

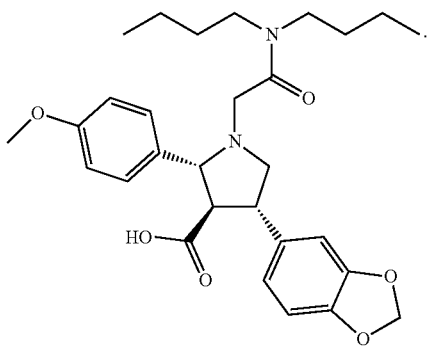

Molecular Weight: 510.62

Atrasentan and methods of preparation thereof are described in U.S. Pat. No. 7,208,517 and International Patent Application Publication No. WO 1997/030045 (see e.g., Example 501), each of which is incorporated herein by reference in its entirety.

In some embodiments, atrasentan is administered as a free base. In some other embodiments, atrasentan is administered as a pharmaceutically acceptable salt as described anywhere herein.

Atrasentan is an ETA inhibitor which is about 1,860 times more selective for ETA relative to ETB. As used herein "ETA" is the abbreviation for endothelin receptor A; and "ETB" is the abbreviation of endothelin receptor B. See, e.g., Ann Rheum Dis., 66(11), pp. 1467-1472 (2007); Eur. Resp. J., 37, pp. 475-476 (2011); Plos One, 9, e87548 (2014); J. Clin. Oncol., 10, 31(14), pp. 1740-7 (2013); Pharmacol. Rev., 68 (2) pp. 357-418 (2016); and Nephrol. Dial. Transplant., 29, pp. i69-i73 (2014).

Salts

In some embodiments, atrasentan is in the form of a pharmaceutically acceptable salt. The phrase "pharmaceutically acceptable salt" as used herein, refers to pharmaceutically acceptable organic or inorganic salts of a compound of the disclosure (e.g., atrasentan). Exemplary salts include acid addition salts formed by the reaction between atrasentan and an acid (e.g., organic acid or inorganic acid). Non-limiting examples include: sulfate, citrate, acetate, oxalate, chloride, bromide, iodide, nitrate, bisulfate, phosphate, acid phosphate, isonicotinate, lactate, salicylate, acid citrate, tartrate, oleate, tannate, pantothenate, bitartrate, ascorbate, succinate, maleate, mandelate (e.g., (S)-mandelate or (R)-mandelate), gentisinate, fumarate, gluconate, glucuronate, saccharate, formate, benzoate, glutamate, methanesulfonate "mesylate", ethanesulfonate, benzenesulfonate, and p-toluenesulfonate, pamoate (i.e., 4,4'-methylene-bis-(2-hydroxy-3-naphthoate)) salts. Exemplary salts also include base addition salts formed by the reaction between atrasentan and a base. Non-limiting examples include: alkali metal (e.g., sodium and potassium) salts, alkaline earth metal (e.g., magnesium) salts, and ammonium salts. A pharmaceutically acceptable salt may involve the inclusion of another molecule such as an acetate ion, a succinate ion or other counter ion. The counter ion may be any organic or inorganic moiety that stabilizes the charge on the parent compound. Furthermore, a pharmaceutically acceptable salt may have more than one charged atom in its structure. Instances where multiple charged atoms are part of the pharmaceutically acceptable salt can have multiple counter ions. Hence, a pharmaceutically acceptable salt can have one or more charged atoms and/or one or more counter ion. When referring to atrasentan, the term "salt" or "salts" is understood to be a salt of atrasentan that can be present alone or in a mixture with free atrasentan.

In some embodiments, atrasentan is in the form of a hydrochloride salt. The hydrochloride salt of atrasentan, also known as atrasentan hydrochloride (CAS Number: 195733-43-8); atrasentan hydrogen chloride; atrasentan hydrochloride salt; atrasentan chloride salt; atrasentan HCl; atrasentan monohydrochloride; (2R,3R,4S)-4-(1,3-benzodioxol-5-yl)-1-[2-(dibutylamino)-2-oxoethyl]-2-(4-methoxyphenyl) pyrrolidine-3-carboxylic acid, monohydrochloride; 3-pyrrolidinecarboxylic acid, 4-(1,3-benzodioxol-5-yl)-1-[2-(dibutylamino)-2-oxoethyl]-2-(4-methoxyphenyl)-, hydrochloride (1:1), (2R, 3R, 4S)-; (2R, 3R, 4S)-1-[(dibutylcarbamoyl)methyl]-2-(p-methoxyphenyl)-4-[3,4-(methylenedioxy)phenyl]-3-pyrrolidinecarboxylic acid, monohydrochloride; 3-pyrrolidinecarboxylic acid, 4-(1,3-benzodioxol-5-yl)-1-[2-(dibutylamino)-2-oxoethyl]-2-(4-methoxyphenyl)-, monohydrochloride, [2R-(2α, 3β, 4α)]; ABT-627; A-147627.1; Abbott-147627.1, has the following structure:

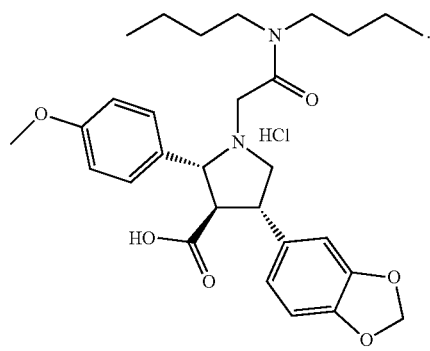

Molecular Weight: 547.08 wherein the molar ratio of atrasentan to chloride is 1:1. Atrasentan hydrochloride and methods of preparation thereof are further described in U.S. Pat. No. 7,208,517 and International Patent Application Publication No. WO 1997/030045 (see e.g., Example 501), each of which is incorporated herein by reference in its entirety.

In some embodiments, atrasentan is in the form of a mandelate salt. In certain embodiments, atrasentan is in the form of a (S)-mandelate salt. In certain embodiments, atrasentan is in the form of a (R)-mandelate salt. In certain embodiments, in the atrasentan mandelate salt, atrasentan and mandelate has a molar ratio of 1:1. In certain embodiments, in the atrasentan mandelate salt, atrasentan and mandelate has a molar ratio of 2:1. Atrasentan mandelate salt and methods of preparation thereof are further described in U.S. Pat. Nos. 8,962,675 and 9,637,476, each of which is incorporated herein by reference in its entirety.

In some embodiments, atrasentan is in the form of a hemisulfate salt. Hemisulfate salt and methods of preparation thereof are further described in U.S. Pat. Nos. 8,962,675 and 9,637,476, each of which is incorporated herein by reference in its entirety.

In some embodiments, the atrasentan or a pharmaceutically acceptable salt thereof is in the form of an anhydrate.

In certain embodiments, the atrasentan or a pharmaceutically acceptable salt thereof is in the form of a hydrate. In certain embodiments, the atrasentan or a pharmaceutically acceptable salt thereof is in the form of a solvate.

Stereochemistry

Atrasentan possesses three asymmetric centers and can be produced as individual stereoisomers (e.g., enantiomers or diastereomers) or as mixtures thereof as described in U.S. Pat. No. 7,208,517 and International Patent Application Publication No. WO 1997/030045. In some embodiments, atrasentan as described herein comprises the (2R,3R,4S)-stereoisomer, that is (2R,3R,4S)-4-(1,3-benzodioxol-5-yl)-1-[2-(dibutylamino)-2-oxoethyl]-2-(4-methoxyphenyl)pyrrolidine-3-carboxylic acid. In certain embodiments, atrasentan is the (2R,3R,4S)-stereoisomer that is substantially free of the other stereoisomers (e.g., contains <10%, <5%, <2%, <1%, <0.5%, <0.1%, or <0.05% of other stereoisomers).

Polymorphs

Atrasentan or a pharmaceutically acceptable salt thereof, as described herein, can be in one or more polymorphic forms. In some embodiments, atrasentan or a pharmaceutically acceptable salt thereof is substantially amorphous (e.g., >75%, >80%, >85%, >90%, >95%, >98%, >99%, or >99.5% amorphous). In some embodiments, atrasentan or a pharmaceutically acceptable salt thereof is substantially crystalline (e.g., >75%, >80%, >85%, >90%, >95%, >98%, >99%, or >99.5% crystalline).

In certain embodiments, the atrasentan or a pharmaceutically acceptable salt thereof comprises Atrasentan Hydrochloride Crystalline Form 1. In certain embodiments, the atrasentan or a pharmaceutically acceptable salt thereof is substantially Atrasentan Hydrochloride Crystalline Form 1 (e.g., >75%, >80%, >85%, >90%, >95%, >98%, >99%, or >99.5% Form 1). Atrasentan Hydrochloride Crystalline Form 1 and methods of making the same are described in International Patent Application Publication No. WO 2006/034094, which is incorporated by reference herein in its entirety.

In some embodiments, Atrasentan Hydrochloride Crystalline Form 1 is characterized, when measured at about 25° C. with Cu-Kα radiation, by an X-ray powder diffraction pattern with at least three peaks (e.g., 3, 4, 5, 6, or 7) having respective 2θ values of about 8.3°, 9.7°, 10.0°, 13.0°, 15.6°, 17.2° or 19.5°. In certain embodiments, Atrasentan Hydrochloride Crystalline Form 1 is characterized, when measured at about 25° C. with Cu-Ku radiation, by an X-ray powder diffraction pattern with at least three peaks having respective 2θ values of about 8.3°, 9.7°, 10.0°, 13.0°, 15.6°, 17.2° or 19.5°, and essentially without peaks having 2θ values below about 6.2° and/or between about 6.6° and 8.0°.

In some embodiments, Atrasentan Hydrochloride Crystalline Form 1 is characterized in the orthorhombic crystal system and P2$_1$2$_1$2$_1$ space group, when measured at about 25° C. with Cu-Kα radiation, by lattice parameters a, b and c of 17.663 Å±0.005 Å, 21.24 Å±0.01 Å and 8.005 Å±0.002 Å, respectively.

In some embodiments, Atrasentan Hydrochloride Crystalline Form 1 has substantial crystalline purity. In some embodiments, Atrasentan Hydrochloride Crystalline Form 1 has substantial chemical purity. In some embodiments, Atrasentan Hydrochloride Crystalline Form 1 has substantial diastereomeric purity.

Representative characteristic peak positions in the X-ray powder diffraction pattern of Atrasentan Hydrochloride Crystalline Form I, expressed as degrees relative to 2θ, are, when measured at about 25° C. with Cu-Ka radiation, about 8.3° ((020), 77.35%); 9.7° ((120), 76.37%); 10.0° ((200), 14.53%); 13.2° ((220), 28.03%); 13.6° ((130), 16.71%); 14.9° ((121), 38.93%); 15.8° ((310), 13.11%); 16.2° ((230), 18.09%); 17.4° ((320), 15.87%); 17.5° ((131), 37.80%); 19.6° ((240), 28.77%); 20.8° ((141), 46.26%); 23.3° ((112), 100.0%); 24.3° ((151), 52.6%); 25.3° ((341), 13.08%); and 25.9° ((132), 33.98%). Each peak position is shown with its accompanying Miller index (hkl) values and its integrated intensity (peak height). It is meant to be understood that peak heights may vary and will be dependent on variables such as the temperature, size of crystal size or morphology, sample preparation, or sample height in the analysis well of the Scintagx2 Diffraction Pattern System. It is also meant to be understood that peak positions may vary when measured with different radiation sources. For example, Cu-Kα1, Mo-Kα, Co-Kα and Fe-Kα radiation, having wavelengths of 1.54060 Å, 0.7107 Å, 1.7902 Å and 1.9373 Å, respectively, may provide peak positions that differ from those measured with Cu-Kα radiation.

In certain embodiments, the atrasentan or a pharmaceutically acceptable salt thereof comprises Atrasentan Hydrochloride Crystalline Form 2. In certain embodiments, the atrasentan or a pharmaceutically acceptable salt thereof is substantially Atrasentan Hydrochloride Crystalline Form 2 (e.g., >75%, >80%, >85%, >90%, >95%, >98%, >99%, or >99.5% Form 2). Atrasentan Hydrochloride Crystalline Form 2 and methods of making the same are described in International Patent Application Publication No. WO 2006/034084, which is incorporated by reference herein in its entirety.

In certain embodiments, Atrasentan Hydrochloride Crystalline Form 2 is characterized, when measured at about 25° C. with Cu-Kα radiation, by an X-ray powder diffraction pattern with peaks having respective 2θ values of about 6.7° and 22.05° and at least one peak having a respective 2θ value of about 8.4°, 15.6°, 18.0°, 18.5°, 19.8° or 20.6°.

In certain embodiments, Atrasentan Hydrochloride Crystalline Form 2 has substantial crystalline purity and is characterized, when measured at about 25° C. with Cu-Kα radiation, by an X-ray powder diffraction pattern with peaks having respective 2θ values of about 6.7° and 22.050 and at least one peak having a respective 2θ value of about 8.4°, 15.6°, 18.0°, 18.5°, 19.8° or 20.6°.

In certain embodiments, Atrasentan Hydrochloride Crystalline Form 2 has substantial crystalline purity and substantial chemical purity; and said Atrasentan Hydrochloride Crystalline Form 2 is characterized, when measured at about 25° C. with Cu-Ku radiation, by an X-ray powder diffraction pattern with peaks having respective 2θ values of about 6.7° and 22.050 and at least one peak having a respective 2θ value of about 8.4°, 15.6°, 18.0°, 18.5°, 19.8° or 20.6°.

In certain embodiments, Atrasentan Hydrochloride Crystalline Form 2 has substantial crystalline purity, substantial chemical purity, and substantial diastereomeric purity; and said Atrasentan Hydrochloride Crystalline Form 2 is characterized, when measured at about 25° C. with Cu-Kα radiation, by an X-ray powder diffraction pattern with peaks having respective 2θ values of about 6.7° and 22.050 and at least one peak having a respective 2θ value of about 8.4°, 15.6°, 18.0°, 18.5°, 19.8° or 20.6°.

In certain embodiments, the atrasentan or a pharmaceutically acceptable salt thereof comprises Atrasentan Hydrochloride Crystalline Form 3. In certain embodiments, the atrasentan or a pharmaceutically acceptable salt thereof is substantially Atrasentan Hydrochloride Crystalline Form 3 (e.g., >75%, >80%, >85%, >90%, >95%, >98%, >99%, or >99.5% Form 3). Atrasentan Hydrochloride Crystalline Form 3 and methods of making the same are described in International Patent Application Publication No. WO 2006/034234 and U.S. Pat. No. 9,051,301, each of which is incorporated by reference herein in its entirety.

In certain embodiments, Atrasentan Hydrochloride Crystalline Form 3 is characterized, when measured at about 25° C. with Cu-Kα radiation, by an X-ray powder diffraction pattern with peaks having respective 2θ values of about 6.7° and 21.95° and at least one peak having a respective 2θ value of about 8.4°, 15.6°, 18.0°, 18.5°, 19.8° or 20.6°.

In certain embodiments, Atrasentan Hydrochloride Crystalline Form 3 has substantial crystalline purity and is characterized, when measured at about 25° C. with Cu-Kα radiation, by an X-ray powder diffraction pattern with peaks having respective 2θ values of about 6.7° and 21.950 and at least one peak having a respective 2θ value of about 8.4°, 15.6°, 18.0°, 18.5°, 19.8° or 20.6°.

In certain embodiments, Atrasentan Hydrochloride Crystalline Form 3 has substantial crystalline purity and substantial chemical purity; and said Atrasentan Hydrochloride Crystalline Form 3 is characterized, when measured at about 25° C. with Cu-Ku radiation, by an X-ray powder diffraction pattern with peaks having respective 2θ values of about 6.7° and 21.950 and at least one peak having a respective 2θ value of about 8.4°, 15.6°, 18.0°, 18.5°, 19.8° or 20.6°.

In certain embodiments, Atrasentan Hydrochloride Crystalline Form 3 has substantial crystalline purity, substantial chemical purity, and substantial diastereomeric purity; and said Atrasentan Hydrochloride Crystalline Form 3 is characterized, when measured at about 25° C. with Cu-Kα radiation, by an X-ray powder diffraction pattern with peaks having respective 2θ values of about 6.7° and 21.950 and at least one peak having a respective 2θ value of about 8.4°, 15.6°, 18.0°, 18.5°, 19.8° or 20.6°.

In certain embodiments, the atrasentan or a pharmaceutically acceptable salt thereof comprises amorphous atrasentan hydrochloride. In certain embodiments, atrasentan hydrochloride is substantially amorphous (e.g., >75%, >80%, >85%, >90%, >95%, >98%, >99%, or >99.5% amorphous). Amorphous atrasentan hydrochloride and methods of making the same are described in International Patent Application Publication No. WO 2006/034085, which is incorporated by reference herein in its entirety.

In certain embodiments, the amorphous atrasentan hydrochloride has substantial chemical purity. In certain embodiments, the amorphous atrasentan hydrochloride has substantial diastereomeric purity.

In some embodiments, the atrasentan or a pharmaceutically acceptable salt thereof comprises a crystalline atrasentan mandelate salt. In certain embodiments, the atrasentan or a pharmaceutically acceptable salt thereof is substantially a crystalline atrasentan mandelate salt (e.g., >75%, >80%, >85%, >90%, >95%, >98%, >99%, or >99.5% crystalline atrasentan mandelate salt).

In certain embodiments, the crystalline atrasentan mandelate salt is a crystalline atrasentan (S)-mandelate salt. In certain embodiments, the atrasentan (S)-mandelate salt is an anhydrous salt. In certain embodiments, the atrasentan (S)-mandelate salt is a solvated salt. In certain embodiments, the atrasentan (S)-mandelate salt is a solvated salt selected from the group consisting of an acetonitrile solvate, an ethanol solvate, and a pyridine solvate. In certain embodiments, the atrasentan (S)-mandelate salt is a hydrated salt.

(a) (S)-Mandelate Salt (1:1 Stoichiometry)

In certain embodiments, the crystalline atrasentan (S)-mandelate salt is a crystalline atrasentan (S)-mandelate salt wherein the molar ratio of atrasentan to (S)-mandelate is about 1:1. In certain embodiments, the atrasentan (S)-mandelate salt is an anhydrous salt. In certain embodiments, the atrasentan (S)-mandelate salt is a solvated salt. In certain embodiments, the atrasentan (S)-mandelate salt is a solvated salt selected from the group consisting of an acetonitrile solvate, an ethanol solvate, and a pyridine solvate. In certain embodiments, the atrasentan (S)-mandelate salt is a hydrated salt. In certain embodiments, the atrasentan or a pharmaceutically acceptable salt thereof is substantially (e.g., >75%, >80%, >85%, >90%, >95%, >98%, >99%, or >99.5%) a crystalline atrasentan (S)-mandelate salt wherein the molar ratio of atrasentan to (S)-mandelate is about 1:1.

In certain embodiments, the crystalline (S)-mandelate salt has an X-ray powder diffraction pattern comprising peaks at 5.5±0.2, 9.7±0.2, and 19.4±0.2 degrees 2θ when measured at about 25° C. with monochromatic Kα1 radiation. In certain embodiments, the crystalline (S)-mandelate salt has an X-ray powder diffraction pattern comprising peaks at 5.5±0.2, 9.7±0.2, 12.1±0.2, and 19.4±0.2 degrees 2θ when measured at about 25° C. with monochromatic Kα1 radiation. In certain embodiments, the crystalline (S)-mandelate salt has an X-ray powder diffraction pattern comprising peaks at 5.5±0.2, 9.7±0.2, 12.1±0.2, 18.0±0.2, 18.4±0.2, and 19.4±0.2 degrees 2θ when measured at about 25° C. with monochromatic Kα1 radiation. In certain embodiments, the experimental error associated with the X-ray powder diffraction peak values recited in the various embodiments above is ±0.1 degrees 2θ. In certain embodiments, the crystalline (S)-mandelate salt is an anhydrous salt. In certain embodiments, the molar ratio of atrasentan to (S)-mandelate is about 1:1.

In certain embodiments, the crystalline (S)-mandelate salt has an orthorhombic lattice type. In certain embodiments, the crystalline (S)-mandelate salt has a $P2_12_12_1$ space group. In certain embodiments, the crystalline (S)-mandelate salt has unit cell a, b and c values of about 9.954 Å, about 11.049 Å, and about 30.861 Å, respectively. In certain embodiments, the crystalline (S)-mandelate salt has unit cell α, β and γ values of about 90°, about 90°, and about 90°, respectively. In certain embodiments, the crystalline (S)-mandelate salt has at least three or more of the following properties: (a) an orthorhombic lattice type, (b) a $P2_12_12_1$ space group, (c) unit cell a, b and c values of about 9.954 Å, about 11.049 Å, and about 30.861 Å, respectively, and/or (d) unit cell α, β and γ values of about 90°, about 90°, and about 90°, respectively. In certain embodiments, the crystalline (S)-mandelate salt has: (a) an orthorhombic lattice type, (b) a $P2_12_12_1$ space group, (c) unit cell a, b and c values of about 9.954 Å, about 11.049 Å, and about 30.861 Å, respectively, and (d) unit cell α, β and γ values of about 90°, about 90°, and about 90°, respectively. In certain embodiments, the crystalline (S)-mandelate salt is an anhydrous salt. In certain embodiments, the molar ratio of atrasentan to (S)-mandelate is about 1:1.

(b) (S)-Mandelate Salt (2:1 Stoichiometry)

In certain embodiments, the crystalline (S)-mandelate salt is a crystalline atrasentan (S)-mandelate salt wherein the molar ratio of atrasentan to (S)-mandelate is about 2:1. In certain embodiments, the crystalline atrasentan (S)-mandelate salt is an anhydrous salt. In certain embodiments, the crystalline atrasentan (S)-mandelate salt is a solvated salt. In certain embodiments, the crystalline atrasentan (S)-mandelate salt is a hydrated salt. In certain embodiments, the atrasentan or a pharmaceutically acceptable salt thereof is substantially (e.g., >75%, >80%, >85%, >90%, >95%, >98%, >99%, or >99.5%) a crystalline atrasentan (S)-mandelate salt wherein the molar ratio of atrasentan to (S)-mandelate is about 2:1.

In certain embodiments, the crystalline (S)-mandelate salt has an X-ray powder diffraction pattern comprising peaks at 4.5±0.2, 8.6±0.2, and 18.1±0.2 degrees 2θ when measured at about 25° C. with monochromatic Kα1 radiation. In certain embodiments, the crystalline (S)-mandelate salt has an X-ray powder diffraction pattern comprising peaks at 4.5±0.2, 8.6±0.2, 18.1±0.2, and 18.7±0.2 degrees 2θ when measured at about 25° C. with monochromatic Kα1 radiation. In certain embodiments, the crystalline (S)-mandelate salt has an X-ray powder diffraction pattern comprising peaks at 4.5±0.2, 8.6±0.2, 9.1±0.2, 18.1±0.2, and 18.7±0.2 degrees 2θ when measured at about 25° C. with monochromatic Kα1 radiation. In certain embodiments, the experimental error associated with the X-ray powder diffraction peak values recited in the various embodiments above is ±0.1 degrees 2θ. In certain embodiments, the crystalline (S)-mandelate salt is an anhydrous salt. In certain embodiments, the crystalline (S)-mandelate salt is a hydrated salt.

In certain embodiments, the crystalline atrasentan mandelate salt is a crystalline atrasentan (R)-mandelate salt. In certain embodiments, the crystalline atrasentan (R)-mandelate salt is an anhydrous salt. In certain embodiments, the crystalline atrasentan (R)-mandelate salt is a solvated salt. In certain embodiments, the crystalline atrasentan (R)-mandelate salt is a hydrated salt.

(c) (R)-Mandelate Salt (1:1 Stoichiometry)

In certain embodiments, the crystalline atrasentan (R)-mandelate salt is a crystalline atrasentan (R)-mandelate salt wherein the molar ratio of atrasentan to (R)-mandelate is about 1:1. In certain embodiments, the crystalline atrasentan (R)-mandelate salt is an anhydrous salt. In certain embodiments, the crystalline atrasentan (R)-mandelate salt is a solvated salt. In certain embodiments, the crystalline atrasentan (R)-mandelate salt is a hydrated salt. In certain embodiments, the atrasentan or a pharmaceutically acceptable salt thereof is substantially (e.g., >75%, >80%, >85%, >90%, >95%, >98%, >99%, or >99.5%) a crystalline atrasentan (R)-mandelate salt wherein the molar ratio of atrasentan to (R)-mandelate is about 1:1.

In certain embodiments, the crystalline atrasentan (R)-mandelate salt has an X-ray powder diffraction pattern comprising peaks at 5.7±0.2, 11.8±0.2, and 20.9±0.2 degrees 2θ when measured at about 25° C. with monochromatic Kα1 radiation. In certain embodiments, the crystalline atrasentan (R)-mandelate salt has an X-ray powder diffraction pattern comprising peaks at 5.7±0.2, 8.2±0.2, 11.8±0.2, and 20.9±0.2 degrees 2θ when measured at about 25° C. with monochromatic Kα1 radiation. In certain embodiments, the crystalline atrasentan (R)-mandelate salt has an X-ray powder diffraction pattern comprising peaks at 5.7±0.2, 8.2±0.2, 8.6±0.2, 11.8±0.2, and 20.9±0.2 degrees 2θ when measured at about 25° C. with monochromatic Kα1 radiation. In certain embodiments, the experimental error associated with the X-ray powder diffraction peak values recited in the various embodiments above is ±0.1 degrees 2θ. In certain embodiments, the crystalline atrasentan (R)-mandelate salt is an anhydrous salt.

In some embodiments, the atrasentan or a pharmaceutically acceptable salt thereof comprises an amorphous atrasentan mandelate salt. In certain embodiments, the atrasentan or a pharmaceutically acceptable salt thereof is substantially an amorphous atrasentan mandelate salt (e.g., >75%, >80%, >85%, >90%, >95%, >98%, >99%, or >99.5% amorphous atrasentan mandelate salt).

In certain embodiments, the amorphous atrasentan mandelate salt is amorphous atrasentan (S)-mandelate salt. In certain embodiments, the amorphous atrasentan (S)-mandelate salt is an anhydrous salt. In certain embodiments, the amorphous atrasentan (S)-mandelate salt is a solvated salt. In certain embodiments, the amorphous atrasentan (S)-mandelate salt is a solvated salt selected from the group consisting of an acetonitrile solvate, an ethanol solvate, and a pyridine solvate. In certain embodiments, the amorphous atrasentan (S)-mandelate salt is a hydrated salt. In certain embodiments, in the amorphous atrasentan (S)-mandelate salt, the molar ratio of atrasentan and (S)-mandelate is about 1:1. In certain embodiments, in the amorphous atrasentan (S)-mandelate salt, the molar ratio of atrasentan and (S)-mandelate is about 2:1.

In certain embodiments, the amorphous atrasentan mandelate salt is amorphous atrasentan (R)-mandelate salt. In certain embodiments, the amorphous atrasentan (R)-mandelate salt is an anhydrous salt. In certain embodiments, the amorphous atrasentan (R)-mandelate salt is a solvated salt. In certain embodiments, the amorphous atrasentan (R)-mandelate salt is a solvated salt selected from the group consisting of an acetonitrile solvate, an ethanol solvate, and a pyridine solvate. In certain embodiments, the amorphous atrasentan (R)-mandelate salt is a hydrated salt. In certain embodiments, in the amorphous atrasentan (R)-mandelate salt, the molar ratio of atrasentan and (R)-mandelate is about 1:1. In certain embodiments, in the amorphous atrasentan (R)-mandelate salt, the molar ratio of atrasentan and (R)-mandelate is about 2:1.

Crystalline and amorphous atrasentan mandelate salts are further described in U.S. Pat. Nos. 8,962,675 and 9,637,476, each of which is incorporated herein by reference in its entirety.

E. Formulation

The term "pharmaceutical composition" as used herein is intended to encompass a product comprising the active ingredient(s), and the inert ingredient(s) that make up the carrier, as well as any product which results, directly or indirectly, from combination, complexation or aggregation of any two or more of the ingredients, or from dissociation of one or more of the ingredients, or from other types of reactions or interactions of one or more of the ingredients. Accordingly, the pharmaceutical compositions of the present disclosure encompass any composition made by admixing a compound of the present disclosure, or a pharmaceutically acceptable salt, or solvate or solvate of the salt thereof, and a pharmaceutically acceptable carrier.

The amount administered depends on the compound formulation, route of administration, etc. and is generally empirically determined, and variations will necessarily occur depending on the target, the host, and the route of administration, etc. Generally, the quantity of active compound in a unit dose of preparation may be varied or adjusted from about 0.1 milligram (mg) to about 10 mg or from about 0.5 mg to about 2 mg, according to the particular application. For convenience, the total daily dosage may be divided and administered in portions during the day.

Pharmaceutical compositions of the present disclosure for injection comprise pharmaceutically acceptable sterile aqueous or non-aqueous solutions, dispersions, suspensions or emulsions as well as sterile powders for reconstitution into sterile injectable solutions or dispersions just prior to use. Examples of suitable aqueous and non-aqueous carriers, diluents, solvents or vehicles include water, ethanol, polyols (such as glycerol, propylene glycol, polyethylene glycol, and the like), and suitable mixtures thereof, vegetable oils (such as olive oil), and injectable organic esters such as ethyl oleate. Proper fluidity can be maintained, for example, by the use of coating materials such as lecithin, by the maintenance of the required particle size in the case of dispersions, and by the use of surfactants.

These pharmaceutical compositions may also contain adjuvants such as preservative, wetting agents, emulsifying agents, and dispersing agents. Prevention of the action of micro-organisms may be ensured by the inclusion of various antibacterial and antifungal agents, for example, paraben, chlorobutanol, phenol sorbic acid, and the like. It may also be desirable to include isotonic agents such as sugars, sodium chloride, and the like. Prolonged absorption of the injectable pharmaceutical form may be brought about by the inclusion of agents that delay absorption such as aluminum monostearate and gelatin. The compounds can be incorporated into slow release or targeted delivery systems such as polymer matrices, liposomes, and microspheres. Such formulations may provide more effective distribution of the compounds.

The pharmaceutical compositions that are injectable formulations can be sterilized, for example, by filtration through a bacterial-retaining filter, or by incorporating sterilizing agents in the form of sterile solid pharmaceutical compositions that can be dissolved or dispersed in sterile water or other sterile injectable medium prior to use.

Solid dosage forms of the instant pharmaceutical compositions for oral administration include capsules, tablets, pills, powders, and granules. In such solid dosage forms, the active compound is mixed with at least one inert, pharmaceutically acceptable excipient or carrier such as sodium citrate or dicalcium phosphate and/or a) fillers or extenders such as starches, lactose, sucrose, glucose, mannitol, and silicic acid, b) binders such as, for example, carboxymethylcellulose, alginates, gelatin, polyvinylpyrrolidone, sucrose, and acacia, c) humectants such as glycerol, d) disintegrating agents such as agar-agar, calcium carbonate, potato or tapioca starch, alginic acid, certain silicates, and sodium carbonate, e) solution retarding agents such as paraffin, f) absorption accelerators such as quaternary ammonium compounds, g) wetting agents such as, for example, cetyl alcohol and glycerol monostearate, h) absorbents such as kaolin and bentonite clay, and i) lubricants such as talc, calcium stearate, magnesium stearate, solid polyethylene glycols, sodium lauryl sulfate, and mixtures thereof. In the case of capsules, tablets and pills, the dosage form may also comprise buffering agents.

Solid pharmaceutical compositions of a similar type may also be employed as fillers in soft and hard-filled gelatin capsules using such excipients as lactose or milk sugar as well as high molecular weight polyethylene glycols and the like.

The solid dosage forms of the instant pharmaceutical compositions of tablets, dragées, capsules, pills, and granules can be prepared with coatings and shells such as enteric coatings and other pharmaceutical coatings. They may optionally contain opacifying agents and can also be of a formulation that they release the active ingredient(s) only, or preferentially, in a certain part of the intestinal tract, optionally, in a delayed manner. Examples of embedding pharmaceutical compositions which can be used include polymeric substances and waxes.

The active compounds can also be in microencapsulated form, if appropriate, with one or more of the above-mentioned excipients.

Liquid dosage forms of the instant pharmaceutical compositions for oral administration include pharmaceutically acceptable emulsions, solutions, suspensions, syrups and elixirs. In addition to the active compounds, the liquid dosage forms may contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethyl formamide, oils (in particular, cottonseed, groundnut, corn, germ, olive, castor, and sesame oils), glycerol, tetrahydrofurfuryl alcohol, polyethylene glycols and fatty acid esters of sorbitan, and mixtures thereof.

Besides inert diluents, the oral pharmaceutical compositions can also include adjuvants such as wetting agents, emulsifying and suspending agents, sweetening, flavoring, and perfuming agents.

Suspensions of the instant compounds, in addition to the active compounds, may contain suspending agents as, for example, ethoxylated isostearyl alcohols, polyoxyethylene sorbitol and sorbitan esters, microcrystalline cellulose, aluminum metahydroxide, bentonite, agar-agar, and tragacanth, and mixtures thereof.

The compounds and compositions described herein can, for example, be administered orally or parenterally, with a dosage ranging from about 0.01 milligrams per kilogram (mg/kg) to about 0.05 mg/kg, every 4 to 120 hours, or according to the requirements of the particular drug, dosage form, and/or route of administration. The interrelationship of dosages for animals and humans (based on milligrams per meter squared of body surface) is described by Freireich et al., Cancer Chemother. Rep. 50, 219-244 (1966). Body surface area may be approximately determined from height and weight of the patient. See, e.g., Scientific Tables, Geigy Pharmaceuticals, Ardsley, N.Y., 537 (1970). In certain embodiments, the compositions are administered by oral administration or by injection. The methods herein contemplate administration of an effective amount of compound or compound composition to achieve a desired or stated effect. Typically, the pharmaceutical compositions of the present disclosure will be administered from about 1 to about 6 times per day or alternatively, as a continuous infusion. Such administration can be used as a chronic or acute therapy.

Lower or higher doses than those recited above may be required. Specific dosage and treatment regimens for any particular patient will depend upon a variety of factors, including the activity of the specific compound employed, the age, body weight, general health status, sex, diet, time of administration, rate of excretion, drug combination, the severity and course of the disease, condition or symptoms, the patient's disposition to the disease, and the judgment of the treating physician.

Dosage forms include from about 0.01 mg to about 10 mg (including, from about 0.1 mg to about 5 mg, from about 0.2 mg to about 4 mg, from about 0.3 mg to about 3 mg, from about 0.4 mg to about 2 mg, from about 0.5 mg to about 1.5 mg, or from about 0.6 mg to about 1 mg) of a compound of atrasentan, or a pharmaceutically acceptable salt thereof. In some embodiments, the dosage form include about 0.1 mg, about 0.2 mg, about 0.3 mg, about 0.4 mg, about 0.5 mg, about 0.6 mg, about 0.65, about 0.7 mg, about 0.75, about 0.8 mg, about 0.85, about 0.9 mg, about 1 mg, about 1.1 mg, about 1.2 mg, about 1.3 mg, about 1.4 mg, about 1.5 mg, about 1.6 mg, about 1.7 mg, about 1.8 mg, about 1.9 mg, about 2 mg, or any value in between, of atrasentan, or a pharmaceutically acceptable salt thereof. In some embodiments, the dosage form includes about 0.75 mg of a compound of atrasentan, or a pharmaceutically acceptable salt thereof.

The dosage forms can further include a pharmaceutically acceptable carrier and/or an additional therapeutic agent.

Appropriate dosage levels may be determined by any suitable method. Preferably, the active substance is administered at a frequency of 1 to 4 times per day for topical administration, or less often if a drug delivery system is used. Nevertheless, actual dosage levels and time course of administration of the active ingredients in the pharmaceutical compositions of the present disclosure may be varied so as to obtain an amount of the active ingredient which is effective to achieve a desired therapeutic response for a particular patient, composition and mode of administration, without being intolerably toxic to the patient. In certain cases, dosages may deviate from the stated amounts, in particular as a function of age, gender, body weight, diet and general health status of the patient, route of administration, individual response to the active ingredient, nature of the preparation, and time or interval over which administration takes place. Thus, it may be satisfactory in some cases to manage with less than the aforementioned minimum amount, whereas in other cases the stated upper limit may be exceeded. It may in the event of administration of larger amounts be advisable to divide these into multiple individual doses spread over the day.

Exemplary Dosage Forms of Atrasentan

In some embodiments, provided herein a stable solid pharmaceutical dosage form comprising: (a) about 0.25 mg to about 1.25 mg of atrasentan, or an equivalent amount of a pharmaceutically acceptable salt thereof; wherein the weight percent of atrasentan, or pharmaceutically acceptable salt thereof, in the dosage form is from about 0.05 weight percent to about 2.0 weight percent on an atrasentan free base equivalent weight basis; and (b) a pharmaceutically acceptable diluent.

In some embodiments, provided herein a stable solid pharmaceutical dosage form comprising: (a) about 0.25 mg to about 1.25 mg of atrasentan, or an equivalent amount of a pharmaceutically acceptable salt thereof; wherein the weight percent of atrasentan, or pharmaceutically acceptable salt thereof, in the dosage form is from about 0.05 weight percent to about 2.0 weight percent on an atrasentan free base equivalent weight basis; (b) a pharmaceutically acceptable anti-oxidant; wherein the molar ratio of the anti-oxidant to atrasentan, or pharmaceutically acceptable salt thereof, is from about 10:1 to about 1:10; and (c) a pharmaceutically acceptable diluent.

In certain of these embodiments, degradation of atrasentan in the dosage form is less than degradation of atrasentan in an otherwise identical dosage form lacking the anti-oxidant when the dosage forms are stored for a storage period of six months at about 40° C. and about 75% relative humidity.

In some embodiments, the dosage form is stored during the storage period in a semi-permeable container or a substantially impermeable container. In some embodiments, the dosage form is stored during the storage period in a sealed HDPE bottle or a blister package. In some embodiments, the dosage form is stored during the storage period in a sealed HDPE bottle. In some embodiments, the dosage form is stored during the storage period in a blister package.

(i) Atrasentan

The dosage form can comprise a free base of atrasentan, a pharmaceutically acceptable salt of atrasentan, or a combination thereof. In some embodiments, the dosage form comprises a free base of atrasentan. In some embodiments, the dosage form comprises a pharmaceutically acceptable salt of atrasentan. In some embodiments, the dosage form comprises atrasentan hydrochloride. In some embodiments, the dosage form comprises atrasentan hydrochloride having a polymorph form selected from the group consisting of amorphous atrasentan hydrochloride, Atrasentan Hydrochloride Crystalline Form 1, Atrasentan Hydrochloride Crystalline Form 2, and Atrasentan Hydrochloride Crystalline Form 3. In some embodiments, the dosage form comprises amorphous atrasentan hydrochloride. In some embodiments, the dosage form comprises Atrasentan Hydrochloride Crystalline Form 1. In some embodiments, the dosage form comprises Atrasentan Hydrochloride Crystalline form2. In some embodiments, the dosage form comprises atrasentan hydrochloride crystalline form 3. In some embodiments, the dosage form comprises atrasentan mandelate. In certain embodiments, the dosage form comprises a crystalline atrasentan mandelate (e.g., a crystalline atrasentan (S)-mandelate and/or a crystalline atrasentan (R)-mandelate). In certain embodiments, the dosage form comprises an amorphous atrasentan mandelate (e.g., an amorphous atrasentan (S)-mandelate and/or an amorphous atrasentan (R)-mandelate). In certain of the foregoing embodiments (when the dosage form comprises a crystalline and/or amorphous atrasentan (S)- and/or (R)-mandelate), the molar ratio of atrasentan and mandelate is 1:1. In certain other embodiments, the molar ratio of atrasentan and mandelate is 2:1.

In certain embodiments, the dosage form comprises amorphous atrasentan hydrochloride; and it is substantially free (e.g., contains <10%, <5%, <1%, <0.5%, <0.1%, <0.05%) of other forms (e.g., other salts and/or other polymorphs) of atrasentan. In certain embodiments, the dosage form comprises Atrasentan Hydrochloride Crystalline Form 1; and it is substantially free of (e.g., contains <10%, <5%, <1%, <0.5%, <0.1%, <0.05%) other forms (e.g., other salts and/or other polymorphs) of atrasentan. In certain embodiments, the dosage form comprises Atrasentan Hydrochloride Crystalline form 2; and it is substantially free of other forms (e.g., other salts and/or other polymorphs) of atrasentan. In certain embodiments, the dosage form comprises atrasentan hydrochloride crystalline form 3; and it is substantially free (e.g., contains <10%, <5%, <1%, <0.5%, <0.1%, <0.05%) of other forms (e.g., other salts and/or other polymorphs) of atrasentan. In certain embodiments, the dosage form comprises crystalline atrasentan (S)-mandelate; and it is substantially free (e.g., contains <10%, <5%, <1%, <0.5%, <0.1%, <0.05%) of other forms (e.g., other salts and/or other polymorphs) of atrasentan. In certain embodiments, the dosage form comprises crystalline atrasentan (R)-mandelate; and it is substantially free (e.g., contains <10%, <5%, <1%, <0.5%, <0.1%, <0.05%) of other forms (e.g., other salts and/or other polymorphs) of atrasentan. In certain embodiments, the dosage form comprises amorphous atrasentan (S)-mandelate; and it is substantially free (e.g., contains <10%, <5%, <1%, <0.5%, <0.1%, <0.05%) of other forms (e.g., other salts and/or other polymorphs) of atrasentan. In certain embodiments, the dosage form comprises amorphous atrasentan (R)-mandelate; and it is substantially free (e.g., contains <10%, <5%, <1%, <0.5%, <0.1%, <0.05%) of other forms (e.g., other salts and/or other polymorphs) of atrasentan.

In some embodiments, the weight percent of atrasentan, or pharmaceutically acceptable salt thereof, in the dosage form is from about 0.1 weight percent to about 2.0 weight percent on an atrasentan free base equivalent weight basis. In some embodiments, the weight percent of atrasentan, or pharmaceutically acceptable salt thereof, in the dosage form is from about 0.2 weight percent to about 1.0 weight percent on an atrasentan free base equivalent weight basis. In some embodiments, the weight percent of atrasentan, or pharmaceutically acceptable salt thereof, in the dosage form is from about 0.3 weight percent to about 0.8 weight percent on an atrasentan free base equivalent weight basis. In some embodiments, the weight percent of atrasentan, or pharmaceutically acceptable salt thereof, in the dosage form is from about 0.40 weight percent to about 0.45 weight percent on an atrasentan free base equivalent weight basis. In some embodiments, the weight percent of atrasentan, or pharmaceutically acceptable salt thereof, in the dosage form is from about 0.60 weight percent to about 0.65 weight percent on an atrasentan free base equivalent weight basis.

In some embodiments, the dosage form comprises from about 0.40 mg to about 1.00 mg of atrasentan, or an equivalent amount of a pharmaceutically acceptable salt thereof. In some embodiments, the dosage form comprises from about 0.40 mg to about 0.85 mg of atrasentan, or an equivalent amount of a pharmaceutically acceptable salt thereof. In some embodiments, the dosage form comprises about 0.50 mg of atrasentan, or an equivalent amount of a pharmaceutically acceptable salt thereof. In some embodiments, the dosage form comprises about 0.75 mg of atrasentan, or an equivalent amount of a pharmaceutically acceptable salt thereof.

(ii) Diluent

Suitable diluents for use in the disclosed dosage forms include, but are not limited to, lactose (such as lactose monohydrate, lactose anhydrous, and PHARMATOSE® DCL21), sucrose, glucose, mannitol, sorbitol, isomalt, microcrystalline cellulose (such as AVICEL® PH101 and AVICEL® PH102), silicified microcrystalline cellulose (such as PROSOLV® SMCC 50 and SMCC 90), dicalcium phosphate, starches, and combinations thereof. In some embodiments, the diluent is selected from the group consisting of lactose, mannitol, isomalt, microcrystalline cellulose, dicalcium phosphate, and combinations thereof. In some embodiments, the diluent is lactose.

In some embodiments, the weight percent of the diluent in the dosage form is from about 70 weight percent to about 99 weight percent. In some embodiments, the weight percent of the diluent in the dosage form is from about 80 weight percent to about 99 weight percent. In some embodiments, the weight percent of the diluent in the dosage form is from about 85 weight percent to about 99 weight percent. In certain of the foregoing embodiments, the diluent is selected from the group consisting of lactose, mannitol, isomalt, and combinations thereof. As a non-limiting example, the diluent can be lactose.

(iii) Binder

In some embodiments, the dosage form further comprises a pharmaceutically acceptable binder (e.g., polymeric binder). Suitable binders for use in the disclosed dosage forms include, but are not limited to, celluloses, such as hydroxypropyl methylcellulose (e.g., Hypromellose E5 (Premium LV)), hydroxypropyl ethylcellulose, and hydroxypropyl cellulose, and other pharmaceutically acceptable substances with cohesive properties. In some embodiments, the binder is selected from the group consisting of hydroxymethylpropylcellulose, hydroxymethylpropylcellulose, and hydroxypropylcellulose. In some embodiments, the binder is hydroxypropyl methylcellulose. In some embodiments, the binder is hydroxypropylcellulose. In some embodiments, the binder is hydroxymethylpropylcellulose.

In some embodiments, the dosage form further comprises a pharmaceutically acceptable binder; and the weight percent of the binder in the dosage form is from about 1.0 weight percent to about 10.0 weight percent. In some embodiments, the weight percent of the binder in the dosage form is from about 1.0 weight percent to about 8.0 weight percent. In some embodiments, the weight percent of the binder in the dosage form is from about 1.0 weight percent to about 5.0 weight percent. In certain of the foregoing embodiments, the binder is a polymeric binder selected from the group consisting of hydroxymethylpropylcellulose, hydroxymethylpropylcellulose, and hydroxypropylcellulose In some embodiments, the dosage form further comprises a pharmaceutically acceptable binder; and the weight to weight ratio of the binder to atrasentan, or pharmaceutically acceptable salt thereof, is from about 2:1 to about 25:1 on an atrasentan free base equivalent weight basis. In some embodiments, the weight to weight ratio of the binder to the atrasentan, or pharmaceutically acceptable salt thereof, is from about 1:1 to about 20:1 on an atrasentan free base equivalent weight basis. In some embodiments, the weight to weight ratio of the binder to the atrasentan, or pharmaceutically acceptable salt thereof, is from about 1:1 to about 15:1 on an atrasentan free base equivalent weight basis. In certain embodiments, the binder is a polymeric binder selected from the group consisting of hydroxymethylpropylcellulose, hydroxymethylpropylcellulose, and hydroxypropylcellulose;

(iv) Disintegrant

In some embodiments, the dosage form optionally comprises a pharmaceutically acceptable disintegrant. Suitable disintegrants for use in the disclosed dosage forms include, but are not limited to, cross-linked polyvinyl pyrrolidone (such as POLYPLASDONE™ XL), corn starch, potato starch, maize starch and modified starches (including sodium starch glycolate), agar-agar, alginic acids, microcrystalline cellulose, sodium croscarmellose, and combinations thereof. In some embodiments, the disintegrant is selected from the group consisting of crospovidone, sodium starch glycolate, and sodium croscarmellose. In some embodiments, the disintegrant is a cross-linked polyvinyl pyrrolidone. In some embodiments, the disintegrant is crospovidone.

In some embodiments, the dosage form further comprises a pharmaceutically acceptable disintegrant. In certain embodiments, the weight percent of the disintegrant in the dosage form is from about 1.0 weight percent to about 10.0 weight percent. In some embodiments, the weight percent of the disintegrant in the dosage form is from about 1.0 weight percent to about 6.0 weight percent. In some embodiments, the weight percent of the disintegrant in the dosage form is from about 1.0 weight percent to about 4.0 weight percent. In certain of the foregoing embodiments, the disintegrant is crospovidone.

In some embodiments, the dosage form further comprises a pharmaceutically acceptable disintegrant and the weight to weight ratio of the disintegrant to the anti-oxidant (e.g., L-cysteine), or pharmaceutically acceptable salt or ester thereof, is from about 60:1 to about 3:1. In some embodiments, the weight to weight ratio of the disintegrant to the anti-oxidant (e.g., L-cysteine), or pharmaceutically acceptable salt or ester thereof, is from about 50:1 to about 4:1. In some embodiments, the weight to weight ratio of the disintegrant to the anti-oxidant (e.g., L-cysteine), or pharmaceutically acceptable salt or ester thereof, is from about 35:1 to about 5:1.

(v) Additional Excipients

In further embodiments, the dosage form optionally comprises a pharmaceutically acceptable lubricant and/or glidant. Suitable lubricants and glidants for use in the disclosed dosage forms include, but are not limited to, silicon dioxide (such as SYLOID® 244FP and AEROSIL® 200), glyceryl behenate (such as COMPRITOL®), talc, stearic acid, solid polyethylene glycols, silica gel and mixtures thereof and other substances with lubricating or gliding properties. In certain embodiments, the lubricant is glyceryl behenate (such as COMPRITOL®). In certain embodiments, the glidant is silicon dioxide (such as SYLOID® 244FP). In certain embodiments, the lubricant is glyceryl behenate and the glidant is silicon dioxide.

In some embodiments, the dosage form further comprises a pharmaceutically acceptable glidant. In another aspect, the weight percent of the glidant in the dosage form is from about 0.1 weight percent to about 1.5 weight percent. In some embodiments, the weight percent of the glidant in the dosage form is from about 0.1 weight percent to about 1.0 weight percent. In some embodiments, the weight percent of the glidant in the dosage form is from about 0.1 weight percent to about 0.8 weight percent. In some embodiments, the glidant is silicon dioxide.

In some embodiments, the dosage form further comprises a pharmaceutically acceptable lubricant. In some embodiments, the dosage form further comprises a pharmaceutically acceptable, hydrophobic lubricant. In some embodiments, the weight percent of the lubricant in the dosage form is from about 0.05 weight percent to about 5.0 weight percent. In some embodiments, the weight percent of the lubricant in the dosage form is from about 0.2 weight percent to about 3.0 weight percent. In some embodiments, the weight percent of the lubricant in the dosage form is from about 0.5 weight percent to about 2.0 weight percent. In certain embodiments, the lubricant is glyceryl behenate.

In some embodiments, the dosage form further comprises a disintegrant, a glidant, and a lubricant.

(vi) Anti-Oxidant

Suitable anti-oxidants for use in the disclosed dosage forms include anti-oxidants that function as reducing agents and are oxidized to pharmaceutically acceptable reduced products in the dosage form. In some embodiments, the anti-oxidant has an oxidation reduction potential less than the oxidation reduction potential of atrasentan (i.e., an oxidation reduction potential less than about 900 mV) and greater than about 550 mV. In some embodiments, the anti-oxidant has an oxidation reduction potential less than about 550 mV. In some embodiments, the anti-oxidant has an oxidation reduction potential from about 1 mV to about 550 mV. In some embodiments, the solubility of the anti-oxidant in water at about 25° C. is greater than about 24 mg/mL. In some embodiments, the anti-oxidant is an amino acid, or a pharmaceutically acceptable salt or ester thereof. In some embodiments, the anti-oxidant is cysteine. In some embodiments, the anti-oxidant is L-cysteine, or a pharmaceutically acceptable salt or ester thereof. In some embodiments, the anti-oxidant is selected from the group consisting of L-cysteine hydrochloride monohydrate, L-cysteine hydrochloride anhydrate, and L-cysteine ethyl ester. In some embodiments, the dosage form comprises L-cysteine hydrochloride monohydrate.

In some embodiments, the weight percent of the anti-oxidant in the dosage form is from about 0.05 weight percent to about 1.0 weight percent. In some embodiments, the weight percent of the anti-oxidant in the dosage form is from about 0.07 weight percent to about 0.7 weight percent. In some embodiments, the weight percent of the anti-oxidant in the dosage form is from about 0.09 weight percent to about 0.5 weight percent.

In some embodiments, the molar ratio of the anti-oxidant to atrasentan, or pharmaceutically acceptable salt thereof, is from about 10:1 to about 1:10. In some embodiments, the molar ratio of the anti-oxidant to atrasentan, or pharmaceutically acceptable salt thereof, in the dosage form is from about 5:1 to about 1:5. In some embodiments, the molar ratio of the anti-oxidant to atrasentan, or pharmaceutically acceptable salt thereof, is from about 2:1 to about 1:2. In some embodiments, the molar ratio of the anti-oxidant to atrasentan, or pharmaceutically acceptable salt thereof, is about 1:1.

In some embodiments, the anti-oxidant is L-cysteine, or a pharmaceutically acceptable salt thereof. In certain embodiments, the weight percent of the L-cysteine, or pharmaceutically acceptable salt or ester thereof, in the dosage form is from about 0.05 weight percent to about 1.0 weight percent. In certain embodiments, the weight percent of the L-cysteine, or pharmaceutically acceptable salt or ester thereof, in the dosage form is from about 0.07 weight percent to about 0.7 weight percent. In certain embodiments, the weight percent of the L-cysteine, or pharmaceutically acceptable salt or ester thereof, in the dosage form is from about 0.09 weight percent to about 0.5 weight percent.

In certain embodiments, the molar ratio of the L-cysteine, or pharmaceutically acceptable salt or ester thereof, to atrasentan, or pharmaceutically acceptable salt thereof, in the dosage form is from about 10:1 to about 1:10. In certain embodiments, the molar ratio of the L-cysteine, or pharmaceutically acceptable salt or ester thereof, to atrasentan, or pharmaceutically acceptable salt thereof, in the dosage form is from about 5:1 to about 1:5. In certain embodiments, the molar ratio of the L-cysteine, or pharmaceutically acceptable salt or ester thereof, to atrasentan, or pharmaceutically acceptable salt thereof, is from about 2:1 to about 1:2. In certain embodiments, the molar ratio of the L-cysteine, or pharmaceutically acceptable salt or ester thereof, to atrasentan, or pharmaceutically acceptable salt thereof, about 1:1.

In certain embodiments, the anti-oxidant is selected from the group consisting of L-cysteine hydrochloride monohydrate, L-cysteine hydrochloride anhydrate, and L-cysteine ethyl ester. In some embodiments, the dosage form comprises L-cysteine hydrochloride monohydrate.

(vii) Additional Embodiments

In some embodiments, the dosage form comprises atrasentan or a pharmaceutically acceptable salt thereof and an anti-oxidant. In certain of these embodiments, the anti-oxidant is L-cysteine, or pharmaceutically acceptable salt or ester thereof. In some embodiments, the molar ratio of the anti-oxidant (e.g., L-cysteine, or pharmaceutically acceptable salt or ester thereof) is from about 5:1 to about 1:5. In certain of the foregoing embodiments, the dosage form further comprises a pharmaceutically acceptable polymeric binder selected from the group consisting of hydroxymethylpropylcellulose, hydroxyethylpropylcellulose, and hydroxypropylcellulose; the molar ratio of the anti-oxidant (e.g., L-cysteine, or pharmaceutically acceptable salt or ester thereof) to atrasentan, or pharmaceutically acceptable salt thereof, is from about 5:1 to about 1:5; and the weight to weight ratio of the binder to atrasentan, or pharmaceutically acceptable salt thereof, is from about 1:1 to about 20:1 on an atrasentan free base equivalent weight basis. In some embodiments, this dosage form further comprises a disintegrant and the weight to weight ratio of the disintegrant to the anti-oxidant (e.g., L-cysteine, or pharmaceutically acceptable salt or ester thereof) is from about 60:1 to about 3:1. In some embodiments, the weight percent of atrasentan, or pharmaceutically acceptable salt thereof, in this dosage form is from about 0.2 weight percent to about 1.0 weight percent on an atrasentan free base equivalent weight basis. In some embodiments, this dosage form comprises from about 0.40 mg to about 0.85 mg of atrasentan, or an equivalent amount of a pharmaceutically acceptable salt thereof.

In some embodiments, the dosage form comprises a pharmaceutically acceptable polymeric binder selected from the group consisting of hydroxymethylpropylcellulose, hydroxyethylpropylcellulose, and hydroxypropylcellulose; the molar ratio of the anti-oxidant (e.g., L-cysteine, or a pharmaceutically acceptable salt or ester thereof), to atrasentan, or pharmaceutically acceptable salt thereof, is from about 2:1 to about 1:2; and the weight to weight ratio of the binder to atrasentan, or pharmaceutically acceptable salt thereof, is from about 1:1 to about 15:1 on an atrasentan free base equivalent weight basis. In some embodiments, the dosage form further comprises a disintegrant and the weight to weight ratio of the disintegrant to the anti-oxidant (e.g., L-cysteine, or a pharmaceutically acceptable salt or ester thereof), is from about 50:1 to about 4:1. In some embodiments, the weight percent of atrasentan, or pharmaceutically acceptable salt thereof, in this dosage form is from about 0.2 weight percent to about 1.0 weight percent on an atrasentan free base equivalent weight basis. In some embodiments, this dosage form comprises from about 0.40 mg to about 0.85 mg of atrasentan, or an equivalent amount of a pharmaceutically acceptable salt thereof.

In some embodiments, the dosage form comprises a pharmaceutically acceptable polymeric binder selected from the group consisting of hydroxymethylpropylcellulose, hydroxyethylpropylcellulose, and hydroxypropylcellulose; the molar ratio of the anti-oxidant (e.g., L-cysteine, or pharmaceutically acceptable salt or ester thereof), to atrasentan, or pharmaceutically acceptable salt thereof, is about 1:1; and the weight to weight ratio of the binder to atrasentan, or pharmaceutically acceptable salt thereof, is from about 1:1 to about 15:1 on an atrasentan free base equivalent weight basis. In some embodiments, this dosage form further comprises a disintegrant and the weight to weight ratio of the disintegrant to the anti-oxidant (e.g., L-cysteine, or pharmaceutically acceptable salt or ester thereof), is from about 35:1 to about 5:1. In some embodiments, the weight percent of atrasentan, or pharmaceutically acceptable salt thereof, in this dosage form is from about 0.3 weight percent to about 0.8 weight percent on an atrasentan free base equivalent weight basis. In some embodiments, this dosage form comprises from about 0.40 mg to about 0.85 mg of atrasentan, or an equivalent amount of a pharmaceutically acceptable salt thereof.

In some embodiments, the dosage form comprises a pharmaceutically acceptable polymeric binder selected from the group consisting of hydroxymethylpropylcellulose, hydroxyethylpropylcellulose, and hydroxypropylcellulose; the dosage form comprises from about 0.05 weight percent to about 1.0 weight percent of the anti-oxidant (e.g., L-cysteine, or pharmaceutically acceptable salt or ester thereof); and the dosage form comprises from about 1.0 weight percent to about 10.0 weight percent of the binder. In some embodiments, this dosage form further comprises a disintegrant and the weight percent of the disintegrant in the dosage form is from about 1.0 weight percent to about 10.0 weight percent. In some embodiments, the weight percent of atrasentan, or pharmaceutically acceptable salt thereof, in this dosage form is from about 0.1 weight percent to about 2.0 weight percent on an atrasentan free base equivalent weight basis. In some embodiments, this dosage form comprises from about 0.40 mg to about 0.85 mg of atrasentan, or an equivalent amount of a pharmaceutically acceptable salt thereof.

In some embodiments, the dosage form comprises a pharmaceutically acceptable polymeric binder selected from the group consisting of hydroxymethylpropylcellulose, hydroxyethylpropylcellulose, and hydroxypropylcellulose; the dosage form comprises from about 0.07 weight percent to about 0.70 weight percent of the anti-oxidant (e.g., L-cysteine, or pharmaceutically acceptable salt or ester thereof); and the dosage form comprises from about 1.0 weight percent to about 8.0 weight percent of the binder. In some embodiments, this dosage form further comprises a disintegrant and the weight percent of the disintegrant in the dosage form is from about 1.0 weight percent to about 6.0 weight percent. In some embodiments, the weight percent of atrasentan, or pharmaceutically acceptable salt thereof, in this dosage form is from about 0.2 weight percent to about 1.0 weight percent on an atrasentan free base equivalent weight basis. In some embodiments, this dosage form comprises from about 0.40 mg to about 0.85 mg of atrasentan, or an equivalent amount of a pharmaceutically acceptable salt thereof.

In some embodiments, the dosage form comprises a pharmaceutically acceptable polymeric binder selected from the group consisting of hydroxymethylpropylcellulose, hydroxyethylpropylcellulose, and hydroxypropylcellulose; the dosage form comprises from about 0.09 weight percent to about 0.80 weight percent of the anti-oxidant (e.g., L-cysteine, or pharmaceutically acceptable salt or ester thereof) and the dosage form comprises from about 1.0 weight percent to about 5.0 weight percent of the binder. In some embodiments, this dosage form further comprises a disintegrant and the weight percent of the disintegrant in the dosage form is from about 1.0 weight percent to about 4.0 weight percent. In some embodiments, the weight percent of atrasentan, or pharmaceutically acceptable salt thereof, in this dosage form is from about 0.3 weight percent to about 0.8 weight percent on an atrasentan free base equivalent weight basis. In some embodiments, this dosage form comprises from about 0.40 mg to about 0.85 mg of atrasentan, or an equivalent amount of a pharmaceutically acceptable salt thereof.

In some embodiments, the dosage form comprises:
(a) about 0.1 weight percent to about 2.0 weight percent of atrasentan, or pharmaceutically acceptable salt thereof, on an atrasentan free base equivalent weight basis;
(b) about 0.05 weight percent to about 1.0 weight percent of the anti-oxidant (e.g., L-cysteine, or pharmaceutically acceptable salt or ester thereof);
(c) about 75 weight percent to about 99 weight percent of the diluent;
(d) about 1.0 weight percent to about 10.0 weight percent of a pharmaceutically acceptable binder;
(e) optionally, about 1.0 weight percent to about 10.0 weight percent of a pharmaceutically acceptable disintegrant;
(f) optionally, about 0 weight percent to about 1.5 weight percent of a pharmaceutically acceptable glidant; and
(g) optionally, about 0 weight percent to about 5.0 weight percent of a pharmaceutically acceptable lubricant;
wherein the cumulative weight percent for all components of the dosage form equals 100 percent.

In some embodiments, the dosage form comprises:
(a) about 0.1 weight percent to about 2.0 weight percent of atrasentan, or pharmaceutically acceptable salt thereof, on an atrasentan free base equivalent weight basis;
(b) about 0.05 weight percent to about 1.0 weight percent of the anti-oxidant (L-cysteine, or pharmaceutically acceptable salt or ester thereof);
(c) about 75 weight percent to about 99 weight percent of the diluent;
(d) about 1.0 weight percent to about 10.0 weight percent of a pharmaceutically acceptable binder;
(e) about 1.0 weight percent to about 10.0 weight percent of a pharmaceutically acceptable disintegrant;
(f) optionally, about 0 weight percent to about 1.5 weight percent of a pharmaceutically acceptable glidant; and
(g) optionally, about 0 weight percent to about 5.0 weight percent of a pharmaceutically acceptable lubricant;
wherein the cumulative weight percent for all components of the dosage form equals 100 percent.

In some embodiments, the dosage form comprises:
(a) about 0.2 weight percent to about 1.0 weight percent of atrasentan, or pharmaceutically acceptable salt thereof, on an atrasentan free base equivalent weight basis;
(b) about 0.07 weight percent to about 0.7 weight percent of the anti-oxidant (L-cysteine, or pharmaceutically acceptable salt or ester thereof);
(c) about 82 weight percent to about 99 weight percent of the diluent;
(d) about 1.0 weight percent to about 8.0 weight percent of a pharmaceutically acceptable binder;
(e) optionally, about 1.0 weight percent to about 6.0 weight percent of a pharmaceutically acceptable disintegrant;
(f) optionally, about 0 weight percent to about 1.0 weight percent of a pharmaceutically acceptable glidant; and
(g) optionally, about 0 weight percent to about 3.0 weight percent of a pharmaceutically acceptable lubricant;
wherein the cumulative weight percent for all components of the dosage form equals 100 percent.

In some embodiments, the dosage form comprises:
(a) about 0.2 weight percent to about 1.0 weight percent of atrasentan, or pharmaceutically acceptable salt thereof, on an atrasentan free base equivalent weight basis;
(b) about 0.07 weight percent to about 0.70 weight percent of L-cysteine, or pharmaceutically acceptable salt or ester thereof;
(c) about 82 weight percent to about 99 weight percent of the diluent;
(d) about 1.0 weight percent to about 8.0 weight percent of a pharmaceutically acceptable binder;
(e) about 1.0 weight percent to about 6.0 weight percent of a pharmaceutically acceptable disintegrant;
(f) optionally, about 0 weight percent to about 1.0 weight percent of a pharmaceutically acceptable glidant; and
(g) optionally, about 0 weight percent to about 3.0 weight percent of a pharmaceutically acceptable lubricant;
wherein the cumulative weight percent for all components of the dosage form equals 100 percent.

In some embodiments, the dosage form comprises:
(a) about 0.3 weight percent to about 0.8 weight percent of atrasentan, or pharmaceutically acceptable salt thereof, on an atrasentan free base equivalent weight basis;
(b) about 0.09 weight percent to about 0.50 weight percent of L-cysteine, or pharmaceutically acceptable salt or ester thereof;
(c) about 87 weight percent to about 99 weight percent of a pharmaceutically acceptable diluent;
(d) about 1.0 weight percent to about 5.0 weight percent of a pharmaceutically acceptable binder;
(e) optionally, about 1.0 weight percent to about 4.0 weight percent of a pharmaceutically acceptable disintegrant;
(f) optionally, about 0 weight percent to about 0.75 weight percent of a pharmaceutically acceptable glidant; and
(g) optionally, about 0 weight percent to about 2.0 weight percent of a pharmaceutically acceptable lubricant;
wherein the cumulative weight percent for all components of the dosage form equals 100 percent.

In some embodiments, the dosage form comprises:
(a) about 0.3 weight percent to about 0.8 weight percent of atrasentan, or pharmaceutically acceptable salt thereof, on an atrasentan free base equivalent weight basis;
(b) about 0.09 weight percent to about 0.50 weight percent of L-cysteine, or pharmaceutically acceptable salt or ester thereof;
(c) about 87 weight percent to about 99 weight percent of a pharmaceutically acceptable diluent;
(d) about 1.0 weight percent to about 5.0 weight percent of a pharmaceutically acceptable binder;
(e) about 1.0 weight percent to about 4.0 weight percent of a pharmaceutically acceptable disintegrant;
(f) optionally, about 0 weight percent to about 0.75 weight percent of a pharmaceutically acceptable glidant; and
(g) optionally, about 0 weight percent to about 2.0 weight percent of a pharmaceutically acceptable lubricant;
wherein the cumulative weight percent for all components of the dosage form equals 100 percent.

In some embodiments, the dosage form comprises:
(a) about 0.1 weight percent to about 2.0 weight percent of atrasentan, or pharmaceutically acceptable salt thereof, on an atrasentan free base equivalent weight basis;
(b) about 75 weight percent to about 99 weight percent of the diluent;
(c) about 1.0 weight percent to about 10.0 weight percent of a pharmaceutically acceptable binder;
(d) optionally, about 1.0 weight percent to about 10.0 weight percent of a pharmaceutically acceptable disintegrant;
(e) optionally, about 0 weight percent to about 1.5 weight percent of a pharmaceutically acceptable glidant; and
(f) optionally, about 0 weight percent to about 5.0 weight percent of a pharmaceutically acceptable lubricant;
wherein the cumulative weight percent for all components of the dosage form equals 100 percent.

In some embodiments, the dosage form comprises:
(a) about 0.1 weight percent to about 2.0 weight percent of atrasentan, or pharmaceutically acceptable salt thereof, on an atrasentan free base equivalent weight basis;
(b) about 75 weight percent to about 99 weight percent of the diluent;
(c) about 1.0 weight percent to about 10.0 weight percent of a pharmaceutically acceptable binder;
(d) about 1.0 weight percent to about 10.0 weight percent of a pharmaceutically acceptable disintegrant;
(e) optionally, about 0 weight percent to about 1.5 weight percent of a pharmaceutically acceptable glidant; and
(f) optionally, about 0 weight percent to about 5.0 weight percent of a pharmaceutically acceptable lubricant;
wherein the cumulative weight percent for all components of the dosage form equals 100 percent.

In some embodiments, the dosage form comprises:
(a) about 0.2 weight percent to about 1.0 weight percent of atrasentan, or pharmaceutically acceptable salt thereof, on an atrasentan free base equivalent weight basis;
(b) about 82 weight percent to about 99 weight percent of the diluent;
(c) about 1.0 weight percent to about 8.0 weight percent of a pharmaceutically acceptable binder;
(d) optionally, about 1.0 weight percent to about 6.0 weight percent of a pharmaceutically acceptable disintegrant;
(e) optionally, about 0 weight percent to about 1.0 weight percent of a pharmaceutically acceptable glidant; and
(f) optionally, about 0 weight percent to about 3.0 weight percent of a pharmaceutically acceptable lubricant;
wherein the cumulative weight percent for all components of the dosage form equals 100 percent.

In some embodiments, the dosage form comprises:
(a) about 0.2 weight percent to about 1.0 weight percent of atrasentan, or pharmaceutically acceptable salt thereof, on an atrasentan free base equivalent weight basis;
(b) about 82 weight percent to about 99 weight percent of the diluent;
(c) about 1.0 weight percent to about 8.0 weight percent of a pharmaceutically acceptable binder;
(d) about 1.0 weight percent to about 6.0 weight percent of a pharmaceutically acceptable disintegrant;
(e) optionally, about 0 weight percent to about 1.0 weight percent of a pharmaceutically acceptable glidant; and
(f) optionally, about 0 weight percent to about 3.0 weight percent of a pharmaceutically acceptable lubricant;
wherein the cumulative weight percent for all components of the dosage form equals 100 percent.

In some embodiments, the dosage form comprises:
(a) about 0.3 weight percent to about 0.8 weight percent of atrasentan, or pharmaceutically acceptable salt thereof, on an atrasentan free base equivalent weight basis;
(b) about 87 weight percent to about 99 weight percent of a pharmaceutically acceptable diluent;
(c) about 1.0 weight percent to about 5.0 weight percent of a pharmaceutically acceptable binder;
(d) optionally, about 1.0 weight percent to about 4.0 weight percent of a pharmaceutically acceptable disintegrant;
(e) optionally, about 0 weight percent to about 0.75 weight percent of a pharmaceutically acceptable glidant; and
(f) optionally, about 0 weight percent to about 2.0 weight percent of a pharmaceutically acceptable lubricant;
wherein the cumulative weight percent for all components of the dosage form equals 100 percent.

In some embodiments, the dosage form comprises:
(a) about 0.3 weight percent to about 0.8 weight percent of atrasentan, or pharmaceutically acceptable salt thereof, on an atrasentan free base equivalent weight basis;
(b) about 87 weight percent to about 99 weight percent of a pharmaceutically acceptable diluent;
(c) about 1.0 weight percent to about 5.0 weight percent of a pharmaceutically acceptable binder;
(d) about 1.0 weight percent to about 4.0 weight percent of a pharmaceutically acceptable disintegrant;
(e) optionally, about 0 weight percent to about 0.75 weight percent of a pharmaceutically acceptable glidant; and
(f) optionally, about 0 weight percent to about 2.0 weight percent of a pharmaceutically acceptable lubricant;
wherein the cumulative weight percent for all components of the dosage form equals 100 percent.

In some embodiments, the dosage form satisfies one or more of the following conditions:
(a) the diluent is lactose;
(b) the dosage form comprises a pharmaceutically acceptable binder and the binder is hydroxypropyl methylcellulose;
(c) the dosage form comprises a pharmaceutically acceptable disintegrant and the disintegrant is crospovidone;
(d) the dosage form comprises a pharmaceutically acceptable glidant and the glidant is silicon dioxide;
(e) the dosage form comprises a pharmaceutically acceptable lubricant and the lubricant is glyceryl behenate.

In some embodiments, the dosage form is a solid pharmaceutical dosage form comprising from about 0.25 mg to about 1.25 mg of the atrasentan or a pharmaceutically acceptable salt thereof (e.g., atrasentan hydrochloride) on an atrasentan parent equivalent weight basis. In some embodiments, the pharmaceutical composition comprises from about 0.40 mg to about 1.00 mg of atrasentan or a pharmaceutically acceptable salt thereof (e.g., atrasentan hydrochloride) on an atrasentan parent equivalent weight basis. In some embodiments, the pharmaceutical composition comprises from about 0.40 mg to about 0.85 mg of atrasentan or a pharmaceutically acceptable salt thereof (e.g., atrasentan hydrochloride) on an atrasentan parent equivalent weight basis. In some embodiments, the pharmaceutical composition comprises from about 0.50 mg of atrasentan or a pharmaceutically acceptable salt thereof (e.g., atrasentan hydrochloride) on an atrasentan parent equivalent weight basis. In some embodiments, the pharmaceutical composition comprises from about 0.75 mg of atrasentan or a pharmaceutically acceptable salt thereof (e.g., atrasentan hydrochloride) on an atrasentan parent equivalent weight basis. In certain of the foregoing embodiments, the dosage form is a tablet.

In some embodiments, the dosage form is a tablet. In some embodiments, the tablet has a weight from about 37.5 mg to about 1500 mg. In some embodiments, the tablet has a weight from about 50 mg to about 750 mg. In some embodiments, the tablet has a weight from about 50 mg to about 250 mg. In some embodiments, the tablet has a weight from about 75 mg to about 500 mg. In some embodiments, the tablet has a weight from about 75 mg to about 150 mg. In some embodiments, the tablet has a weight from about 100 mg to about 250 mg. In some embodiments, the tablet has a weight from about 100 mg to about 230 mg. In some embodiments, the tablet has a water content is below about 10%. In certain embodiments, the tablet has a water content of about 4%-6% (e.g., about 4%-5%).

In general, the tablet optionally can be surrounded or coated with at least one non-rate-controlling layer. The non-rate-controlling layer can be formed as a single layer, coating or membrane or a plurality of single layers, coatings or membranes. The functions of the non-rate-controlling layer can include, for example, providing further stability for the atrasentan, serving as a process aid and/or as a cosmetic enhancement for the formulation, and/or acting as a masking agent to reduce any undesired odor associated with the formulation (such as the odor commonly associated with L-cysteine).

When the dosage form comprises a non-rate-controlling layer, the non-rate-controlling layer can be made of one or more polymers, as well as, other ingredients known in the art, such as, but not limited to, plasticizers, pigments/opacifiers, waxes, etc. Examples of polymers that can be used include, but are not limited to, hydroxypropyl methylcellulose, hydroxypropyl cellulose, methylcellulose, polyvinyl alcohol and polyethylene glycol. Examples of plasticizers that can be used include, but are not limited to, polyethylene glycol(s), glycerin, triacetin, triethyl citrate, diethyl phthalate, L-cysteine, and mineral oils. Examples of pigments/opacifiers that can be used include, but are not limited to, water soluble dyes (for example, sunset yellow, quinoline yellow, erythrosine, and tartrazine), pigments (for example, aluminum lakes, titanium oxides, iron oxides and talc), and natural products (for example, riboflavin, carotenoids, chlorophyll, anthocyanins, and carmine). An example of a wax that can be used includes, but is not limited to, a paraffin wax.

In some embodiments, the dosage form is a tablet coated with a pharmaceutically acceptable polymer.

In some embodiments, the dosage form is a capsule.

In some embodiments, the dosage form is packaged in a semi-permeable container. In some embodiments, the semi-permeable container is a blister pack.

In some embodiments, the dosage form is packaged in a substantially impermeable container.

In some embodiments, the dosage form is an immediate release dosage form. In some embodiments, the dosage form is an immediate release tablet and releases at least about 85% of the atrasentan, or pharmaceutically acceptable salt thereof, within about 45 minutes as determined in an in vitro dissolution test conducted using a USP Dissolution Apparatus 2 (Paddle Apparatus), a 0.01N hydrochloric acid dissolution medium, and a paddle rotation of 50 RPM. In some embodiments, the dosage form is an immediate release tablet and releases at least about 75% of the atrasentan, or pharmaceutically acceptable salt thereof, within about 30 minutes.

In some embodiments, the dosage form comprises less than about 1.0 weight percent of total impurities resulting from degradation of the atrasentan, or pharmaceutically acceptable salt thereof, after a storage period of six months at about 40° C. and about 75% relative humidity. In some embodiments, degradation of the atrasentan, or pharmaceutically acceptable salt thereof, is analyzed using high-performance liquid chromatography.

In some embodiments, the dosage form comprises less than about 0.6 weight percent of any single impurity resulting from degradation of the atrasentan, or pharmaceutically acceptable salt thereof, after a storage period of six months at about 40° C. and about 75% relative humidity. In some embodiments, degradation of the atrasentan, or pharmaceutically acceptable salt thereof, is analyzed using high-performance liquid chromatography.

In some embodiments, the dosage form comprises less than about 1.0 weight percent of total impurities and less than about 0.6 weight percent of any single impurity resulting from degradation of the atrasentan, or pharmaceutically acceptable salt thereof, after a storage period of six months at about 40° C. and about 75% relative humidity. In some embodiments, degradation of the atrasentan, or pharmaceutically acceptable salt thereof, is analyzed using high-performance liquid chromatography.

In certain embodiments, the dosage form is selected from the group consisting of:

| Tablet Core Composition | | |
|---|---|---|
| Ingredient | Weight/Weight % | mg/Tablet |
| Atrasentan Monohydrochloride | 0.31 | 0.37[a] |
| Lactose Monohydrate (Regular) | 91.19 | 109.4 |
| Hypromellose E5 (Premium IV) | 3.00 | 3.6 |
| Crospovidone (Polyplasdone™ XL) | 3.50 | 4.2 |
| Silicon Dioxide (SYLOID ®) | 0.50 | 0.6 |
| Glyceryl Behenate (COMPRITOL ®) | 1.50 | 1.8 |
| Purified Water[b] | n/a | n/a |
| Total | 100% | 120 mg |

| Film Coated Table Composition | | |
|---|---|---|
| Ingredient | Weight/Weight %[c] | mg/Tablet[d] |
| PEG1450 | 3 | 0.1 |
| Hypromellose E3 (Premium IV) | 97 | 3.5 |
| Purified Water | n/a | n/a |

[a]Atrasentan monohydrochloride salt factor = 1.07 (i.e., 0.35 mg free base × 1.07 = 0.37 mg salt).
[b]Granulation suspension medium. Less than 2% in final product.
[c]Based on aqueous solution of 10% solids.
[d]Based on a 120 mg tablet weight with a coating weight gain of 3%.

| Tablet Core Composition | | |
|---|---|---|
| Ingredient | Weight/Weight % | mg/Tablet |
| Atrasentan Monohydrochloride | 0.4460 | 0.5350[a] |
| Lactose Monohydrate (Regular) | 91.305 | 109.3 |
| Hypromellose E5 (Premium IV) | 3.000 | 3.600 |
| Crospovidone (Polyplasdone™ XL) | 3.500 | 4.200 |
| Silicon Dioxide (SYLOID ® 244FP) | 0.500 | 0.600 |
| Glyceryl Behenate (COMPRITOL ®) | 1.500 | 1.80 |
| Purified Water[b] | n/a | n/a |
| Total | 100% | 120 mg |

| Film Coated Table Composition | | |
|---|---|---|
| Ingredient | Weight/Weight %[c] | mg/Tablet[d] |
| PEG1450 | 3 | 0.1080 |
| Hypromellose E3 (Premium IV) | 97 | 3.492 |
| Purified Water | n/a | n/a |
| Total | 100% | 123.6 mg |

[a]Atrasentan monohydrochloride salt factor = 1.07 (i.e., 0.50 mg free base × 1.07 = 0.5350 mg salt).
[b]Granulation suspension medium. Less than 2% in final product.
[c]Based on aqueous solution of 10% solids.
[d]Based on a 120 mg tablet weight with a coating weight gain of 3%.

| Tablet Core Composition | | |
|---|---|---|
| Ingredient | Weight/Weight % | mg/Tablet |
| Atrasentan Monohydrochloride | 0.6690 | 0.8025[a] |
| Lactose Monohydrate (Regular) | 90.83 | 109.0 |
| Hypromellose E5 (Premium IV) | 3.000 | 3.600 |
| Crospovidone (Polyplasdone ™ XL) | 3.500 | 4.200 |
| Silicon Dioxide (SYLOID ® 244FP) | 0.500 | 0.600 |
| Glyceryl Behenate (COMPRITOL ®) | 1.500 | 1.80 |
| Purified Water[b] | n/a | n/a |
| Total | 100% | 120 mg |

| Film Coated Table Composition | | |
|---|---|---|
| Ingredient | Weight/Weight %[c] | mg/Tablet[d] |
| PEG1450 | 3 | 0.1080 |
| Hypromellose E3 (Premium IV) | 97 | 3.492 |
| Purified Water | n/a | n/a |
| Total | 100% | 123.6 mg |

[a]Atrasentan monohydrochloride salt factor = 1.07 (i.e., 0.75 mg free base × 1.07 = 0.8025 mg salt).
[b]Granulation suspension medium. Less than 2% in final product.
[c]Based on aqueous solution of 10% solids.
[d]Based on a 120 mg tablet weight with a coating weight gain of 3%.

In certain embodiments, the dosage form is selected from the group consisting of:

| Tablet Core Composition | | |
|---|---|---|
| Ingredient | Weight/Weight % | mg/Tablet |
| Atrasentan Monohydrochloride | 0.4460 | 0.5350[a] |
| Lactose Monohydrate (Regular) | 90.91 | 109.1 |
| L-Cysteine Hydrochloride Monohydrate | 0.1440 | 0.1728 |
| Hypromellose E5 (Premium IV) | 3.000 | 3.600 |
| Crospovidone (Polyplasdone ™ XL) | 3.500 | 4.200 |
| Silicon Dioxide (SYLOID ® 244FP) | 0.500 | 0.600 |
| Glyceryl Behenate (COMPRITOL ®) | 1.500 | 1.800 |
| Purified Water[b] | n/a | n/a |
| Total | 100% | 120 mg |

| Film Coated Table Composition | | |
|---|---|---|
| Ingredient | Weight/Weight %[c] | mg/Tablet[d] |
| PEG1450 | 3 | 0.1 |
| Hypromellose E3 (Premium IV) | 97 | 3.5 |
| Purified Water | n/a | n/a |
| Total | 100% | 123.6 mg |

[a]Atrasentan monohydrochloride salt factor = 1.07 (i.e., 0.5 mg free base × 1.07 = 0.5350 mg salt).
[b]Granulation suspension medium. Less than 2% in final product.
[c]Based on aqueous solution of 10% solids.
[d]Based on a 120 mg tablet weight with a coating weight gain of 3%.

| Tablet Core Composition | | |
|---|---|---|
| Ingredient | Weight/Weight % | mg/Tablet |
| Atrasentan Monohydrochloride | 0.6690 | 0.8025[a] |
| Lactose Monohydrate (Regular) | 90.61 | 108.7 |
| L-Cysteine Hydrochloride Monohydrate | 0.216 | 0.2592 |
| Hypromellose E5 (Premium IV) | 3.000 | 3.600 |
| Crospovidone (Polyplasdone ™ XL) | 3.500 | 4.200 |
| Silicon Dioxide (SYLOID ® 244FP) | 0.500 | 0.600 |
| Glyceryl Behenate (COMPRITOL ®) | 1.500 | 1.800 |
| Purified Water[b] | n/a | n/a |
| Total | 100% | 120 mg |

| Film Coated Table Composition | | |
|---|---|---|
| Ingredient | Weight/Weight %[c] | mg/Tablet[d] |
| PEG1450 | 3 | 0.1080 |
| Hypromellose E3 (Premium IV) | 97 | 3.492 |
| Purified Water | n/a | n/a |
| Total | 100% | 123.6 mg |

[a]Atrasentan monohydrochloride salt factor = 1.07 (i.e., 0.75 mg free base × 1.07 = 0.8025 mg salt).
[b]Granulation suspension medium. Less than 2% in final product.
[c]Based on aqueous solution of 10% solids.
[d]Based on a 120 mg tablet weight with a coating weight gain of 3%.

| Tablet Core Composition | | |
|---|---|---|
| Ingredient | Weight/Weight % | mg/Tablet |
| Atrasentan Monohydrochloride | 0.31 | 0.372[a] |
| Lactose Monohydrate (Regular) | 91.09 | 109.3 |
| L-Cysteine Hydrochloride Monohydrate | 0.0999 | 0.120 |
| Hypromellose E5 (Premium IV) | 3.00 | 3.6 |
| Crospovidone (Polyplasdone ™ XL) | 3.50 | 4.2 |
| Silicon Dioxide (SYLOID ® 244FP) | 0.50 | 0.60 |
| Glyceryl Behenate (COMPRITOL ®) | 1.50 | 1.8 |
| Purified Water[b] | n/a | n/a |
| Total | 100% | 120 mg |

| Film Coated Table Composition | | |
|---|---|---|
| Ingredient | Weight/Weight %[c] | mg/Tablet[d] |
| PEG1450 | 3 | 0.1 |
| Hypromellose E3 (Premium IV) | 97 | 3.5 |
| Purified Water | n/a | n/a |
| Total | 100% | 123.6 mg |

[a]Atrasentan monohydrochloride salt factor = 1.07 (i.e., 0.35 mg free base × 1.07 = 0.37 mg salt).
[b]Granulation suspension medium. Less than 2% in final product.
[c]Based on aqueous solution of 10% solids.
[d]Based on a 120 mg tablet weight with a coating weight gain of 3%.

[d]Based on a 120 mg tablet weight with a coating weight gain of 3%.

The formulations of atrasentan or a pharmaceutically acceptable salt thereof and methods of making the same are further described in U.S. Pat. Nos. 9,364,458 and 10,016,393, each of which is incorporated herein by reference in its entirety.

F. Dosage and Administration

In some embodiments, a dose of atrasentan or a pharmaceutically acceptable salt thereof is between about 0.001 mg and 0.1 mg per kg of the subject's body weight (e.g., about 0.001, about 0.002, about 0.003, about 0.004, about 0.005, about 0.006, about 0.007, about 0.008, about 0.009, about 0.01, about 0.015, about 0.02, about 0.025, about 0.03, about 0.035, about 0.04, about 0.045, about 0.05, about 0.055, about 0.06, about 0.065, about 0.07, about 0.075, about 0.08, about 0.085, about 0.09, about 0.095, or about 0.10 mg per kg, or any value in between, of the subject's body weight) of atrasentan or an equivalent amount of a pharmaceutically acceptable salt thereof.

In some embodiments, a dose of atrasentan or a pharmaceutically acceptable salt thereof is between about 0.1 mg and 10 mg (e.g. about 0.1, about 0.2, about 0.3, about 0.4, about 0.5, about 0.6, about 0.7, about 0.75, about 0.8, about 0.9, about 1.0, about 1.1, about 1.2, about 1.3, about 1.4, about 1.5, about 1.6, about 1.7, about 1.8, about 1.9, about 2.0, about 2.5, about 3.0, about 3.5, about 4.0, about 4.5, about 5.0, about 5.5, about 6.0, about 6.5, about 7.0, about 7.5, about 8.0, about 8.5, about 9.0, about 9.5, or about 10.0 mg, or any value in between) of atrasentan or an equivalent amount of a pharmaceutically acceptable salt thereof. In certain embodiments, a dose of atrasentan or a pharmaceutically acceptable salt thereof is about 0.75 mg (e.g., when administered once per day) of atrasentan or an equivalent amount of a pharmaceutically acceptable salt thereof. In certain embodiments, a dose of atrasentan or a pharmaceutically acceptable salt thereof is about 0.25 mg (e.g., when administered once per day) of atrasentan or an equivalent amount of a pharmaceutically acceptable salt thereof. In certain embodiments, a dose of atrasentan or a pharmaceutically acceptable salt thereof is about 0.35 mg (e.g., when administered once per day) of atrasentan or an equivalent amount of a pharmaceutically acceptable salt thereof. In certain embodiments, a dose of atrasentan or a pharmaceutically acceptable salt thereof is about 1.0 mg (e.g., when administered once per day) of atrasentan or an equivalent amount of a pharmaceutically acceptable salt thereof. In certain embodiments, a dose of atrasentan or a pharmaceutically acceptable salt thereof is about 1.25 mg (e.g., when administered once per day) of atrasentan or an equivalent amount of a pharmaceutically acceptable salt thereof. In certain embodiments, a dose of atrasentan or a pharmaceutically acceptable salt thereof is about 1.5 mg (e.g., when administered once per day) of atrasentan or an equivalent amount of a pharmaceutically acceptable salt thereof. In certain embodiments, a dose of atrasentan or a pharmaceutically acceptable salt thereof is about 1.75 mg (e.g., when administered once per day) of atrasentan or an equivalent amount of a pharmaceutically acceptable salt thereof. In certain of these embodiments, a dose of atrasentan or a pharmaceutically acceptable salt thereof is 0.75 mg (e.g., 1×0.75 mg tablets; or 1.5×0.50 mg tablets) of atrasentan or an equivalent amount of a pharmaceutically acceptable salt thereof, administered once per day.

In some embodiments, a dose of atrasentan, or salt or solvate thereof, contains a therapeutically effective amount of atrasentan, or salt or solvate thereof. In other embodiments, a dose of atrasentan, or salt or solvate thereof, contains less than a therapeutically effective amount of atrasentan, or salt or solvate thereof, (e.g., when multiple doses are given in order to achieve the desired clinical or therapeutic effect).

In some embodiments, the therapeutically effective amount of atrasentan, or a pharmaceutically acceptable salt thereof, is from about 0.20 mg to about 1.5 mg of atrasentan, or an equivalent amount of a pharmaceutically acceptable salt thereof. For example, the therapeutically effective amount of atrasentan, or a pharmaceutically acceptable salt thereof can be about 0.20 mg, about 0.30 mg, about 0.40 mg, about 0.50 mg, about 0.60 mg, about 0.70 mg, about 0.80 mg, about 0.90 mg, about 1.0 mg, about 1.1 mg, about 1.2 mg, about 1.3 mg, about 1.4 mg, or about 1.5 mg of atrasentan or an equivalent amount of a pharmaceutically acceptable salt thereof. In certain embodiments, the therapeutically effective amount of atrasentan, or a pharmaceutically acceptable salt thereof, is from about 0.25 mg to about 1.25 mg of atrasentan, or an equivalent amount of a pharmaceutically acceptable salt thereof. In certain embodiments, the therapeutically effective amount of atrasentan, or a pharmaceutically acceptable salt thereof, is from about 0.40 mg to about 0.85 mg of atrasentan, or an equivalent amount of a pharmaceutically acceptable salt thereof. For example, the therapeutically effective amount of atrasentan, or a pharmaceutically acceptable salt thereof can be about 0.50 mg, about 0.55 mg, about 0.60 mg, about 0.65 mg, about 0.70 mg, about 0.75 mg, about 0.80 mg, or about 0.85 mg of atrasentan or an equivalent amount of a pharmaceutically acceptable salt thereof. As a non-limiting example, the therapeutically effective amount of atrasentan or pharmaceutically acceptable salt thereof can be about 0.75 mg of atrasentan or an equivalent amount of a pharmaceutically acceptable salt thereof.

Atrasentan, or salt or solvate thereof, can be administered by any suitable route and mode. Suitable routes of administering antibodies and/or antibody-drug conjugate of the present disclosure are well known in the art and may be selected by those of ordinary skill in the art. In some embodiments, atrasentan or a pharmaceutically acceptable salt thereof administered parenterally. Parenteral administration refers to modes of administration other than enteral and topical administration, usually by injection, and include epidermal, intravenous, intramuscular, intraarterial, intrathecal, intracapsular, intraorbital, intracardiac, intradermal, intraperitoneal, intratendinous, intratracheal, subcutaneous, subcuticular, intraarticular, subcapsular, subarachnoid, intraspinal, intracranial, intrathoracic, epidural and intrasternal injection and infusion. In some embodiments, the route of administration of atrasentan is intravenous injection or infusion. In some embodiments, the route of administration of atrasentan is intravenous infusion. In some embodiments, the route of administration of atrasentan is intravenous injection or infusion. In some embodiments, the atrasentan is intravenous infusion. In some embodiments, the route of administration of atrasentan is oral.

In one embodiment of the methods or uses or product for uses provided herein, atrasentan is administered to the subject daily, twice daily, three times daily or four times daily. In some embodiments, atrasentan is administered to the subject every other day, once about every week or once about every three weeks. In some embodiments, atrasentan is administered to the subject once per day. In some embodiments, atrasentan is administered to the subject twice per day. In some embodiments, atrasentan is administered to the subject at a dose of about 0.75 mg once per day. In some embodiments, atrasentan is administered to the subject at a dose of 0.75 mg once per day. In some embodiments, atrasentan is administered to the subject at a dose of about 0.25 mg once per day. In some embodiments, atrasentan is administered to the subject at a dose of 0.25 mg once per day. In some embodiments, atrasentan is administered to the subject at a dose of about 0.35 mg once per day. In some embodiments, atrasentan is administered to the subject at a dose of 0.35 mg once per day. In some embodiments, atrasentan is administered to the subject at a dose of about 0.5 mg once per day. In some embodiments, atrasentan is administered to the subject at a dose of 0.5 mg once per day. In some embodiments, atrasentan is administered to the subject at a dose of about 1.0 mg once per day. In some embodiments, atrasentan is administered to the subject at a dose of 1.0 mg once per day. In some embodiments, atrasentan is administered to the subject at a dose of about 1.75 mg once per day. In some embodiments, atrasentan is administered to the subject at a dose of 1.75 mg once per day.

G. Combination Therapy

The methods of the present disclosure also contemplate treatments comprising administering atrasentan or a pharmaceutically acceptable salt thereof, as described in any of the embodiments of the disclosure, in combination with one or more additional therapeutic agents (such as an inhibitor of one or more elements of the renin-angiotensin-aldosterone system). Accordingly, atrasentan or a pharmaceutically acceptable salt thereof as described anywhere herein can be administered alone or in combination with one or more additional therapeutic agents. When administered in combination with one or more additional therapeutic agents, separate dosage forms can be administered to the subject or a single dosage form comprising both atrasentan, or a pharmaceutically acceptable salt thereof, and the additional therapeutic agent(s) can be administered to the subject. If administered as a separate dosage form, the additional therapeutic agent may be administered simultaneously with the atrasentan dosage form of the present disclosure or sequentially (in either order) with the atrasentan dosage form of the present disclosure. Administration of two or more agents in combination can also be referred to herein as "co-administration."

Representative additional therapeutic agents include, for example, diuretics, antihypertensive agents, therapeutic agents for diabetes or diabetic complications, and therapeutic agents for hyperlipidemia.

In some embodiments, atrasentan or a pharmaceutically acceptable salt thereof may be co-administered with one or more diuretics such as hydrochlorothiazide (such as MICROZIDE™ or ORETIC™), hydroflumethiazide (such as SALURON™), bemetanide (such as BUMEX™), torsemide (such as DEMADEX™), metolazone (such as ZAROXOLYN™), chlorothiazide (such as DIURIL™, ESIDRIX™ or HYDRODIURIL™) triamterene (such as DYRENIUM™), ethacrynic acid (such as EDECRIN™), chlorthalidone (such as HYGROTON™), furosemide (such as LASIX™), indapamide (such as LOZOL™) or amiloride (such as MIDAMOR™ or MODURETIC™).

In some embodiments, atrasentan or a pharmaceutically acceptable salt thereof may be co-administered with one or more thiazide diuretics, such as chlorothiazide, chlorthalidone, hydrochlorothiazide, trichloromethiazide, indapamide, or metolazone.

In some embodiments, atrasentan or a pharmaceutically acceptable salt thereof may be co-administered with one or more loop diuretics, such as bumetanide, ethacrynic acid, furosemide, or torsemide.

In some embodiments, atrasentan or a pharmaceutically acceptable salt thereof may be co-administered with one or more potassium-sparing diuretics, such as amiloride, eplerenone, spironolactone, and triamterene.

In some embodiments, atrasentan or a pharmaceutically acceptable salt thereof may be co-administered with one or more angiotensin converting enzyme (ACE) inhibitors such as quinapril (such as ACCUPRIL™), fosinopril, perindopril (such as ACEON™), captopril (such as CAPOTEN™), enalapril (such as VASOTEC™) ENALAPRILAT™, ramipril (such as ALTACE™), cilazapril, delapril, fosenopril (such as MONOPRIL™), zofenopril, indolapril, benazepril (such as LOTENSIN™), lisinopril (such as PRINIVIL™ or ZESTRIL™), spirapril, trandolapril (such as MAVIK™), perindep, pentopril, moexipril (such as UNIVASC™), pivopril, temocapril, omapatrilat, imidapril, rescinnamine, benazeprilat, fosinoprilat, ramiprilat, perindoprilat, quinaprilat, trandolaprilat, moexiprilat, Quinoline Yellow WS, or cilazaprilat. In certain embodiments, the ACE inhibitor is selected from: quinapril, fosinopril perindopril, captopril, enalapril, enalaprilat, ramipril, cilazapril, delapril, fosenopril, zofenopril, indolapril, benazepril, lisinopril, spirapril, trandolapril, perindep, pentopril, moexipril, rescinnamine, and pivopril.

In some embodiments, atrasentan or a pharmaceutically acceptable salt thereof may be co-administered with one or more angiotensin II receptor blockers (ARB) such as candesartan (such as ATACAND™), candesartan cilexetil, eprosartan (such as TEVETEN™), irbesartan (such as AVEPRO™) losartan (such as COZAAR™), olmesartan, olmesartan medoxomil (such as BENICAR™) tasosartan, telmisartan (such as MICARDIS™) valsartan (such as DIOVAN™), zolasartan, azilsartan medoxomil, Fl-6828K, RNH-6270, UR-7198, Way-126227, KRH-594, TAK-536, BRA-657, or TA-606. In certain embodiments, the ARB is selected from: candesartan, candesartan cilexetil, eprosartan, irbesartan, losartan, olmesartan, olmesartan medoxomil, telmisartan, valsartan, azilsartan medoxomil, and BRA-657.

In some embodiments, atrasentan or a pharmaceutically acceptable salt thereof may be co-administered with one or more calcium channel blockers such as nifedipine (such as ADALAT™, ADALAT CC™, or PROCARDIA™), verapamil (such as GALAN™, COVERA-HS™, ISOPTIN SR™, or VERELAN™), diltiazem (such as CARDIZEM™, CARDIZEM CD™, CARDIZEM LA™, CARDIZEM SR™, DILACOR™, TIAMATE™, or TIAZAC™), isradipine (such as DYNACIRC™ or DYNACIRC CR™), amlodipine (such as NORVASC™), felodipine (such as PLENDIL™), nisoldipine (such as SULAR™), bepridil (such as VASCOR™), vatanidipine, clevidipine, lercanidipine, or diltiazem.

In some embodiments, atrasentan or a pharmaceutically acceptable salt thereof may be co-administered with one or more renin inhibitors such as aliskiren (such as TEKTURNA™).

In some embodiments, atrasentan or a pharmaceutically acceptable salt thereof may be co-administered with one or more aldosterone receptor antagonists such as eplerenone (such as INSPRA™) or spironolactone (such as ALDACTONE™).

In some embodiments, atrasentan or a pharmaceutically acceptable salt thereof may be co-administered with one or more alpha blockers such as doxazosin (such as CAR- DURA™) phenoxybenzamine (such as DIBENZYLINE™), terazosin (such as HYTRIN™), CDR1-93/478, or CR-2991.

In some embodiments, atrasentan or a pharmaceutically acceptable salt thereof may be co-administered with one or more beta blockers such as timolol (such as BLO-CARDEN™) carteolol (such as CARTROL™), carvedilol (such as COREG™), nadolol (such as CORGARD™), propranolol (such as INNOPRAN XL™), betaxolol (such as KERLONE™) penbutolol (such as LEVATOL™), metoprolol (such as LOPRESSOR™ or TOPROL-XL™), atenolol (such as TENORMIN™), pindolol (such as VISKEN™), or bisoprolol.

In some embodiments, atrasentan or a pharmaceutically acceptable salt thereof may be co-administered with one or more alpha-beta blockers such as labetalol (such as NOR-MODYNE™ or TRANDATE™).

In some embodiments, atrasentan or a pharmaceutically acceptable salt thereof may be co-administered with one or more central antiadrenergics such as methyldopa (such as ALDOMET™), clonidine (such as CATAPRES™ or CAT-APRES-TTS™) guanfacine (such as TENEX™), or guanabenz (such as WYTENSIN™).

In some embodiments, atrasentan or a pharmaceutically acceptable salt thereof may be co-administered with one or more glycosides/inotropic agents such as digoxin (such as LANOXIN™).

In some embodiments, atrasentan or a pharmaceutically acceptable salt thereof may be co-administered with one or more alpha glucosidase inhibitors, such as miglitol (such as GLYSET™) or acarbose (such as PRECOSE™).

In some embodiments, atrasentan or a pharmaceutically acceptable salt thereof may be co-administered with one or more biguanides, such as rosiglitazone (such as AVAN-DAMET™) or metformin (such as GLUCOPHAGE™ or GLUCOPHAGE XR™).

In some embodiments, atrasentan or a pharmaceutically acceptable salt thereof may be co-administered with one or more insulins, such as HUMALOG™, HUMALOG 50/50™, HUMALOG 75/25™, HUMULIN 50/50™, HUMALIN 75/25™, HUMALIN L™, HUMALIN N™, HUMALIN R™, HUMALIN R U-500™, HUMALIN U™, ILETIN II LENTE™, ILETIN II NPH™, ILETIN II REGULAR™, LANTUS™, NOVOLIN 70/30™, NOVILIN N™, NOVILIN R™, NOVOLOG™, or VELOSULIN BR™, and EXUBERA™.

In some embodiments, atrasentan or a pharmaceutically acceptable salt thereof may be co-administered with one or more meglitinides, such as repaglinide (such as PRAN-DIN™) or nateglinide (such as STARLIX™).

In some embodiments, atrasentan or a pharmaceutically acceptable salt thereof may be co-administered with one or more sulfonylureas, such as glimepiride (such as AMA-RYL™), glyburide (such as DIABETA™, GLYNASE PRESTAB™ or MICRONASE™), or glipizide (such as GLUCOTROL™, or GLUCOTROL XL™).

In some embodiments, atrasentan or a pharmaceutically acceptable salt thereof may be co-administered with one or more thiazolidinediones, such as pioglitazone (such as ACTOS™) or rosiglitazone (such as AVANDIA™).

In some embodiments, atrasentan or a pharmaceutically acceptable salt thereof may be co-administered with niacin or one or more nicotinic acid derivatives, such as NIA-COR™, NIASPAN™, NICOLAR™, or SLO-NIACIN™.

In some embodiments, atrasentan or a pharmaceutically acceptable salt thereof may be co-administered with one or more fabric acid derivatives, such as clofibrate (such as ATROMID-S™), gemfibrozil (such as LOPID™), or fenofibrate (such as TRICOR™).

In some embodiments, atrasentan or a pharmaceutically acceptable salt thereof may be co-administered with one or more bile acid sequestrants, such as colestipol (such as COLESTID™), cholestyramine (such as LOCHOLEST™, PREVALITE™, QUESTRAN™, or QUESTRAN LIGHT™), or colesevelam (such as WELCHOL™).

In some embodiments, atrasentan or a pharmaceutically acceptable salt thereof may be co-administered with one or more cholesterol absorption inhibitors, such as ezetimibe (such as ZETIA™).

In some embodiments, atrasentan or a pharmaceutically acceptable salt thereof may be co-administered with one or more 3-hydroxy-3-methylglutaryl coenzyme A (HMG-CoA) reductase inhibitors (statins) such as fluvastatin (such as LESCOL™) atorvastatin (such as LIPITOR™), lovastatin (such as ALTOCOR™ or MEVACOR™) pravastatin (such as PRAVACHOL™), rosuvastatin (such as CRESTOR™), simvastatin (such as ZOCOR™), or pitavastatin.

In some embodiments, atrasentan or a pharmaceutically acceptable salt thereof may be co-administered with one or more additional agents. In some embodiments, the one or more additional agents is an immunosuppressant. In some embodiments, the one or more additional agents are selected from aminopterin, azathioprine, cyclosporin A, D-penicillamine, gold salts, hydroxychloroquine, leflunomide, methotrexate, minocycline, rapamycin, sulfasalazine, tacrolimus (FK506), and pharmaceutically acceptable salts thereof. As a non-limiting example, the one or more additional agents can be hydroxychloroquine.

In some embodiments, atrasentan or a pharmaceutically acceptable salt thereof may be co-administered with one or more additional therapeutic agents selected group the group consisting of SGLT-2 inhibitor (such as canagliflozin), GR-immunosuppressant (such as budesonide), MASP-2 antibodies (such as OMS721), dual ET1A/ARB inhibitors (such as sparsentan), B cell modulators (e.g., APRIL modulators such as atacicept, APL-2, and VIS649), SYK inhibitor (such as fostamatinib), complement factor 3 convertase inhibitor (such as LNP023), NRF2 activator (such as Bardoxolone), and RNAi therapeutic targeting the C5 component of the complement pathway (e.g., cemdisiram).

In some embodiments, the one or more additional agents are SGLT-2 inhibitors. In some embodiments, the one or more additional agents is a SGLT-2 inhibitor selected from dapagliflozin, canagliflozin, ipragliflozin, empagliflozin, bexagliflozin, licogliflozin, janagliflozin (XZP-5695), tofogliflozin, ertugliflozin, henagliflozin (SHR-3824), enavogliflozin (DWP-16001), TA-1887 (3-(4-cyclopropylbenzyl)-4-fluoro-1-(β-D-glucopyranosyl)-1H-indole), indole-N-glycoside 18 (3-(4-ethylbenzyl)-1-(β-D-glucopyranosyl)-1H-indole), sotagliflozin, luseogliflozin, sergliflozin etabonate, remogliflozin, remogliflozin etabonate, and T-1095 (((2R,3S,4S,5R,6S)-6-(2-(3-(benzofuran-5-yl)propanoyl)-3-hydroxy-5-methylphenoxy)-3,4,5-trihydroxytetrahydro-2H-pyran-2-yl) etabonate). In some embodiments, the one or more additional agents is a SGLT-2 inhibitor selected from bexagliflozin, canagliflozin, dapagliflozin, empagliflozin, ertugliflozin, ipragliflozin, luseogliflozin, remogliflozin, sergliflozin, licogliflozin, sotagliflozin, and tofogliflozin. In some embodiments, the one or more additional agents is bexagliflozin. In some embodiments, the one or more additional agents is canagliflozin. In some embodiments, the one or more additional agents is dapagliflozin. In some embodiments, the one or more additional agents is empagliflozin. In some embodiments, the one or more additional agents is ertugliflozin. In some embodiments, the one or more additional agents is ipragliflozin. In some embodiments, the one or more additional agents is luseogliflozin. In some embodiments, the one or more additional agents is remogliflozin. In some embodiments, the one or more additional agents is serfliflozin. In some embodiments, the one or more additional agents is licofliglozin. In some embodiments, the one or more additional agents is sotagliflozin. In some embodiments, the one or more additional agents is tofogliflozin. In some embodiments, the SGLT-2 inhibitor is dapagliflozin propylene glycol hydrate. In some embodiments, the SGLT-2 inhibitor is canagliflozin hemihydrate.

In some embodiments, the amount of the SGLT-2 inhibitor is from about 1 mg to about 350 mg. For example, about 1 mg to about 175 mg, about 175 mg to about 350 mg, or about 90 mg to about 260 mg. In some embodiments, the amount of the SGLT-2 inhibitor is from about 85 mg to about 325 mg. In some embodiments, the amount of the SGLT-2 inhibitor is from about 1 mg to about 50 mg, about 20 mg to about 70 mg, about 50 mg to about 100 mg, about 70 mg to about 120 mg, about 90 mg to about 140 mg, about 110 mg to about 160 mg, about 130 mg to about 180 mg, about 150 mg to about 200 mg, about 170 mg to about 220 mg, about 190 mg to about 240 mg, about 210 mg to about 260 mg, about 230 mg to about 280 mg, about 250 mg to about 300 mg, about 270 mg to about 320 mg, or about 290 mg to about 350 mg. For example, about 100 mg or about 300 mg. In some embodiments, the amount of the SGLT-2 inhibitor is from about 1 to about 15 mg. For example, about 1 to about 10 mg or about 5 to about 15 mg. In some embodiments, the amount of the SGLT-2 inhibitor is from 1 mg to about 3 mg, about 2 mg to about 4 mg, about 3 mg to about 5 mg, about 4 mg to about 6 mg, about 5 mg to about 7 mg, about 6 mg to about 8 mg, about 7 mg to about 9 mg, about 8 mg to about 10 mg, about 9 mg to about 11 mg, about 10 mg to about 12 mg, about 11 mg to about 13 mg, about 12 mg to about 14 mg, or about 13 mg to about 15 mg.

In some embodiments, the SGLT-2 inhibitor is canagliflozin. In some embodiments, 100 mg or 300 mg of canagliflozin is administered. In some embodiments, 100 mg or 300 mg of canagliflozin hemihydrate is administered. In some embodiments, the SGLT-2 inhibitor is dapagliflozin. In some embodiments, the SGLT-2 inhibitor is dapagliflozin propylene glycol hydrate. In some embodiments, 5 mg or 10 mg of dapagliflozin is administered. In some embodiments, 5 mg or 10 mg of dapagliflozin propylene glycol hydrate is administered. In some embodiments, the SGLT-2 inhibitor is empagliflozin. In some embodiments, 10 mg or 25 mg of empagliflozin is administered. In some embodiments, the SGLT-2 inhibitor is ertugliflozin. In some embodiments, 5 mg or 15 mg of ertugliflozin is administered. In some embodiments, the SGLT-2 inhibitor is ipragliflozin. In some embodiments, 25 mg or 50 mg of ipragliflozin is administered. In some embodiments, the SGLT-2 inhibitor is bexagliflozin. In some embodiments, 20 mg of bexagliflozin is administered. In some embodiments, the SGLT-2 inhibitor is sotagliflozin. In some embodiments, 200 mg or 400 mg of sotagliflozin is administered. In some embodiments, the SGLT-2 inhibitor is licogliflozin. In some embodiments, 15 mg, 50 mg, 75 mg or 150 mg of licogliflozin is administered.

In any of the embodiments described herein, various combinations of atrasentan, or a pharmaceutically acceptable salt thereof, and a SGLT-2 inhibitor, producing an effect, are contemplated. In some embodiments, the effect, for example, any of the beneficial or desired results as described herein, is greater than the sum of the effect observed when the same amount of atrasentan, or a pharmaceutically acceptable salt thereof, when co-administered, and the same amount of the SGLT-2 inhibitor when co-administered, are administered as a monotherapy. In some embodiments, the co-administration of atrasentan, or a pharmaceutically acceptable salt thereof, and a SGLT-2 inhibitor, produce an effect, for example, a therapeutic effect using a smaller dose of either, or both, of the compounds as a monotherapy. For example, producing a therapeutic effect using a smaller dose of atrasentan, or a pharmaceutically acceptable salt thereof, and/or the SGLT-2 inhibitor compared to the amount used in monotherapy. For example, in some embodiments, the dose of atrasentan, or a pharmaceutically acceptable salt thereof, administered in combination with a SGLT-2 inhibitor may be about 50% to about 90% of the dose of atrasentan, or a pharmaceutically acceptable salt thereof, administered as a monotherapy to produce the same therapeutic effect, e.g., any of the beneficial or desired results including described herein. In some embodiments, the dose of the SGLT-2 inhibitor, administered in combination with atrasentan, or a pharmaceutically acceptable salt thereof, may be about 50% to about 90% of the dose of the SGLT-2 inhibitor, administered as a monotherapy to produce the same therapeutic effect, e.g., any of the beneficial or desired results including described herein. For example, treating IgA nephropathy, decreasing renal inflammation and/or fibrosis, decreasing hematuria, decreasing proteinuria, stabilizing eGFR, decreasing the number of IgA-nephropathy associated disease flares, delaying the onset of ESRD, decreasing fatigue, and reducing activation of a mesangial cell.

In some embodiments, the present disclosure relates to the use of atrasentan or a pharmaceutically acceptable salt thereof in combination with a second therapeutic for treating a condition as described in the various embodiments of the disclosure.

In some embodiments, the present disclosure relates to the use of atrasentan or a pharmaceutically acceptable salt thereof, for treating a condition as described in the various embodiments of the disclosure, wherein the use comprises one or more additional therapeutic agent.

In some embodiments, the present disclosure relates to a pharmaceutical composition comprising atrasentan or a pharmaceutically acceptable salt thereof, and further comprising one or more additional therapeutic agent.

In some embodiments, the one or more additional therapeutic agent inhibits one or more elements of the renin-angiotensin-aldosterone system. In some embodiments, the one or more additional therapeutic agent is selected from the group consisting of diuretics, angiotensin converting enzyme (ACE) inhibitors, angiotensin II receptor (ARB) blockers, calcium channel blockers, renin inhibitors, and aldosterone antagonists. In certain particular embodiments, the one or more additional therapeutic agent is selected from the group consisting of angiotensin converting enzyme (ACE) inhibitors and angiotensin II receptor blockers (ARBs). In certain embodiments, the one or more additional therapeutic agent is selected from one or more angiotensin converting enzyme inhibitors. In certain embodiments, the one or more additional therapeutic agent is selected from one or more angiotensin II receptor blockers. In certain embodiments, the one or more additional therapeutic agent comprises one or more ACE inhibitors and one or more ARBs. For example, the one or more inhibitors of the renin-angiotensin system can be ACE inhibitor, ARB, or a combination thereof. For example, the ACE inhibitor can be selected from: quinapril, fosinopril perindopril, captopril, enalapril, enalaprilat, ramipril, cilazapril, delapril, fosenopril, zofenopril, indolapril, benazepril, lisinopril, spirapril, trandolapril, perindep, pentopril, moexipril, rescinnamine, and pivopril. For example, the ARB can be selected from: candesartan, candesartan cilexetil, eprosartan, irbesartan, losartan, olmesartan, olmesartan medoxomil, telmisartan, valsartan, azilsartan medoxomil, and BRA-657.

In some embodiments, atrasentan or a pharmaceutically acceptable salt thereof, may be co-administered with a SGLT-2 inhibitor and one or more ACE inhibitors and/or one or more ARBs. In some embodiments, atrasentan or a pharmaceutically acceptable salt thereof, may be co-administered with a SGLT-2 inhibitor and one or more ACE inhibitors. In some embodiments, atrasentan or a pharmaceutically acceptable salt thereof, may be co-administered with a SGLT-2 inhibitor and one or more ARBs. In some embodiments, atrasentan or a pharmaceutically acceptable salt thereof, may be co-administered with a SGLT-2 inhibitor, an ACE inhibitor, and an ARB.

It is understood that the examples and embodiments described herein are for illustrative purposes only and that various modifications or changes in light thereof will be suggested to persons skilled in the art and are to be included within the spirit and purview of this application and scope of the appended claims. All publications, patents, patent applications, and sequence accession numbers cited herein are hereby incorporated by reference in their entirety for all purposes.

The disclosure will be more fully understood by reference to the following examples. They should not, however, be construed as limiting the scope of the disclosure. It is understood that the examples and embodiments described herein are for illustrative purposes only and that various modifications or changes in light thereof will be suggested to persons skilled in the art and are to be included within the spirit and purview of this application and scope of the appended claims.

SELECTED EMBODIMENTS

Embodiment 1: A method of inhibiting mesangial cell activation in a subject having IgA nephropathy, comprising administering a therapeutically effective amount of atrasentan, or a pharmaceutically acceptable salt thereof, to the subject;
  wherein the subject has not been previously diagnosed with one or more of diabetic nephropathy, HIV/AIDS, or acute kidney failure.

Embodiment 2: A method of treating IgA nephropathy, comprising administering a therapeutically effective amount of atrasentan, or a pharmaceutically acceptable salt thereof, to a subject in need thereof;
  wherein the subject has not been previously diagnosed with one or more of diabetic nephropathy, HIV/AIDS, or acute kidney failure.

Embodiment 3: A method of treating IgA nephropathy, comprising administering a therapeutically effective amount of atrasentan, or a pharmaceutically acceptable salt thereof, to a subject in need thereof;
  wherein the subject does not have one or more of diabetic nephropathy, HIV/AIDS, or acute kidney failure.

Embodiment 4: A method of treating IgA nephropathy, comprising administering a therapeutically effective amount of atrasentan, or a pharmaceutically acceptable salt thereof, to a subject in need thereof;
  wherein the subject does not suffer from one or more of diabetic nephropathy, HIV/AIDS, or acute kidney failure.

Embodiment 5: A method of treating IgA nephropathy, comprising administering a therapeutically effective amount of atrasentan, or a pharmaceutically acceptable salt thereof, to a subject in need thereof;
  wherein the subject has not been previously diagnosed with one or more of diabetic nephropathy, HIV/AIDS, prostate cancer, or acute kidney failure.

Embodiment 6: A method of treating IgA nephropathy, comprising administering a therapeutically effective amount of atrasentan, or a pharmaceutically acceptable salt thereof, to a subject in need thereof;
  wherein the subject has not been previously diagnosed with one or more of diabetic nephropathy, HIV-related nephropathy, prostate cancer, or acute kidney failure.

Embodiment 7: A method of treating IgA nephropathy, comprising administering a therapeutically effective amount of atrasentan, or a pharmaceutically acceptable salt thereof, to a subject in need thereof;
  wherein the subject has not been previously diagnosed with one or more of diabetic nephropathy, HIV-related nephropathy, or acute kidney failure.

Embodiment 8: A method of treating IgA nephropathy, comprising administering a therapeutically effective amount of atrasentan, or a pharmaceutically acceptable salt thereof, to a subject in need thereof;
  wherein the subject is not being treated for one or more of diabetic nephropathy, HIV-related nephropathy, or acute kidney failure.

Embodiment 9: A method of treating IgA nephropathy, comprising administering a therapeutically effective amount of atrasentan, or a pharmaceutically acceptable salt thereof, to a subject in need thereof;
  wherein the subject has been determined to have controlled serum glucose levels; wherein the subject has not been diagnosed with one or more of HIV-related nephropathy or acute kidney failure.

Embodiment 10: A method of decreasing renal inflammation and/or fibrosis in a subject having IgA nephropathy, comprising administering a therapeutically effective amount of atrasentan, or a pharmaceutically acceptable salt thereof, to a subject in need thereof.

Embodiment 11: A method of decreasing the occurrence of hematuria in a subject having IgA nephropathy, comprising administering a therapeutically effective amount of atrasentan, or a pharmaceutically acceptable salt thereof, to a subject in need thereof.

Embodiment 12: A method of stabilizing eGFR in a subject having IgA nephropathy, comprising administering a therapeutically effective amount of atrasentan, or a pharmaceutically acceptable salt thereof, to a subject in need thereof.

Embodiment 13: A method of decreasing the number of IgA-nephropathy associated disease flares in a subject having IgA nephropathy, comprising administering a therapeutically effective amount of atrasentan, or a pharmaceutically acceptable salt thereof, to a subject in need thereof.

Embodiment 14: A method of delaying the onset of ESRD in a subject having IgA nephropathy, comprising administering a therapeutically effective amount of atrasentan, or a pharmaceutically acceptable salt thereof, to a subject in need thereof.

Embodiment 15: A method of decreasing proteinuria in a subject having IgA nephropathy, comprising administering a therapeutically effective amount of atrasentan, or a pharmaceutically acceptable salt thereof, to a subject in need thereof.

Embodiment 16: The method of Embodiment 1, wherein the mesangial activation is induced by IgA immune complexes.

Embodiment 17: The method of Embodiment 1, wherein the mesangial activation is associated with the presence of IgA immune complexes.

Embodiment 18: The method of Embodiment 1, wherein the inhibiting of mesangial cell activation comprises reducing expression and/or activity of one or more biomarkers indicative of mesangial cell proliferation.

Embodiment 19: The method of Embodiment 1, wherein the inhibiting of mesangial cell activation comprises reducing mesangial cell inflammation.

Embodiment 20: The method of Embodiment 19, wherein reducing mesangial cell inflammation comprises reducing expression and/or activity of one or more of IL6, MCP1 or other biomarkers indicative of mesangial cell inflammation.

Embodiment 21: The method of Embodiment 19 or 20, wherein reducing mesangial cell inflammation comprises reducing IL-6 signaling.

Embodiment 22: The method of Embodiment 1, wherein the inhibiting of mesangial cell activation comprises reducing the pro-fibrotic response in the mesangial cells.

Embodiment 23: The method of Embodiment 22, wherein reducing the pro-fibrotic response in the mesangial cells comprises reducing expression and/or activity of one or more of TGF, PDGF, CTGF, MMP, TIMPS, or other biomarkers indicative of mesangial cell fibrosis.

Embodiment 24: The method of Embodiment 22 or 23, wherein reducing the pro-fibrotic response in the mesangial cells comprises reducing expression and/or activity of one or more of ET1, TGF, PDGF, CTGF, MMP, TIMPS, IGF1, DPEP1, ASL, AMN, ALPL, SLC6A19, IL-6, NF-kB, PKC, PI3K, Src, Ras, ERK1/2, Rho, Rac, Akt, mTOR, NAPDH oxidase, MAPK, cPLA$_2$, TNF-α, IL-1, CAM, COX-2, iNOS, JAK, STAT3, PI3K, Akt/PKB, IKKs, IkBs, MAPK, Ras, Raf, MEK, ERK, MCP1, Cntfr, Il1b, Csf1, Il2ra, Map3k8, Il1r1, Pfkfb3, Nr4a1, Gem, Fosl2, Klf4, F3, Nfkbia, Ifit2, Nr4a2, Klf2, Jag1, Dnajb4, Il1b, Spsb1, Btg2, Atf3, Csf1, Trib1, Zbtb10, Btg1, Rhob, Nfat5, Edn1, Rel, Nr4a3, Nfkb1, Serpine1, Ccl20, Per1, Cxcl2, Map3k8, Traf1, Pik3r1, Pdgfra, Nfkbia, Pik3cg, Pla2g4a, Tiam1, and Pdgfb.

Embodiment 25: The method of any one of Embodiments 22-24, wherein reducing the pro-fibrotic response in the mesangial cells comprises reducing expression and/or activity of one or more of ET1, TGF, PDGF, CTGF, MMP, TIMPS, IGF1, DPEP1, ASL, AMN, ALPL, SLC6A19, IL-6, PKC, PI3K, Src, Ras, ERK1/2, Rho, Rac, Akt, mTOR, NAPDH oxidase, MAPK, cPLA$_2$, TNF-α, IL-1, CAM, COX-2, iNOS, JAK, STAT3, PI3K, Akt/PKB, IKKs, IkBs, NF-kB, MAPK, Ras, Raf, MEK, ERK, and MCP1.

Embodiment 26: The method of any one of Embodiments 22-25, wherein reducing the pro-fibrotic response in the mesangial cells comprises reducing expression and/or activity of one or more of Cntfr, Il1b, Csf1, Il2ra, Map3k8, Il1r1, Pfkfb3, Nr4a1, Gem, Fosl2, Klf4, F3, Nfkbia, Ifit2, Nr4a2, Klf2, Jag1, Dnajb4, Il1b, Spsb1, Btg2, Atf3, Csf1, Trib1, Zbtb10, Btg1, Rhob, Nfat5, Edn1, Rel, Nr4a3, Nfkb1, Serpine1, Ccl20, Per1, Cxcl2, Traf1, Pik3r1, Pdgfra, Nfkbia, Pik3cg, Pla2g4a, Tiam1, and Pdgfb.

Embodiment 27: The method of any one of Embodiments 22-25, wherein reducing the pro-fibrotic response in the mesangial cells comprises reducing NF-κB signaling and/or PDGF signaling.

Embodiment 28: The method of any one of Embodiments 23-27, wherein reducing the pro-fibrotic response in the mesangial cells comprises reducing matrix secretion by mesangial cells.

Embodiment 29: The method of Embodiment 28, wherein reducing matrix secretion by mesangial cells comprises reducing expression and/or activity of one or more of excess matrix secretion by mesangial cells.

Embodiment 30: The method of any one of Embodiments 1-29, wherein the subject is not currently receiving one or more immunosuppressants.

Embodiment 31: The method of any one of Embodiments 1-30, wherein the subject is also being administered one or more additional agents.

Embodiment 32: The method of Embodiment 31, wherein the one or more additional agents are selected from alcineurin inhibitors, proteasome inhibitors, aminoquinolines, complement inhibitors, B-cell inhibitors, cytotoxic agents, mTOR inhibitors, and steroids.

Embodiment 33: The method of Embodiment 31 or 32, wherein the one or more additional agents are immunosuppressants.

Embodiment 34: The method of any one of Embodiments 31-33, wherein the one or more additional agents are steroids.

Embodiment 35: The method of Embodiment 34, wherein the steroids are selected from the group consisting of prednisone, dexamethasone, hydrocortisone, ciclosporin, and combinations of any of the foregoing.

Embodiment 36: The method of Embodiment 31 or 32, wherein the one or more additional agents are aminoquinolines.

Embodiment 37: The method of any one of Embodiments 31, 32, or 36, wherein the one or more additional agents is hydroxychloroquine.

Embodiment 38: The method of any one of Embodiments 31-37, wherein the dosage of the one or more additional agents is decreased after between about 15 days to about 30 days of treatment with atrasentan, or a pharmaceutically acceptable salt thereof.

Embodiment 39: The method of any one of Embodiments 33-38, wherein the dosage of the one or more additional agents is decreased by about 25% to about 100%.

Embodiment 40: The method of any one of Embodiments 33-39, wherein the dosage of the one or more additional agents is decreased by about 50% to about 100%.

Embodiment 41: The method of any one of Embodiments 33-40, wherein the dosage of the one or more additional agents is decreased by about 75% to about 100%.

Embodiment 42: A method of decreasing fatigue in a subject having IgA nephropathy, comprising administering a therapeutically effective amount of atrasentan, or a pharmaceutically acceptable salt thereof, to a subject in need thereof,
    wherein the subject has been determined not to suffer from one or more of diabetic nephropathy, HIV-related nephropathy, prostate cancer, or acute kidney failure.

Embodiment 43: The method of Embodiment 42, wherein the fatigue is reduced by about 10% to about 20%.

Embodiment 44: The method of Embodiment 42 or 43, wherein the decrease in fatigue comprises a decrease in the score on one or more of the Fatigue Severity Scale, the Chalder Fatigue Scale, the FACIT Fatigue Scale, the Brief Fatigue Inventory, the FACT-F Subscale, Global Vigor and Affect, the May and Kline Adjective Checklist, the Pearson-Byars Fatigue Feeling Checklist, the Rhoten Fatigue Scale, the Schedule of Fatigue and Anergia, or the Checklist Individual Strength.

Embodiment 45: The method of any one of Embodiments 1-44, wherein the subject is concomitantly receiving an ACE inhibitor, an ARB, a statin, a diuretic, a calcium channel blocker, a beta blocker, an aldosterone antagonist, fish oil, hydroxychloroquine, or a combination of any of the foregoing.

Embodiment 46: The method of any one of Embodiments 1-45, wherein the subject is concomitantly receiving an ACE inhibitor, an ARB, or a combination thereof.

Embodiment 47: The method of Embodiment 45 or 46, wherein the statin is selected from: atorvastatin, fluvastatin, lovastatin, pravastatin, rosuvastatin, simvastatin, and pitavastatin.

Embodiment 48: The method of any one of Embodiments 45-47, wherein the diuretic is selected from: hydrochlorothiazide, trichloromethiazide, hydroflumethiazide, quinethazone, metolazone, chlorothiazide, chlorthalidone, indapamide, methylclothiazide bemetanide, torsemide, piretanide, ethacrynic acid, bumetanide, furosemide, triamterene, spironolactone, eplerenone, and amiloride.

Embodiment 49: The method of any one of Embodiments 45-48, wherein the ACE inhibitor is selected from: quinapril, fosinopril, perindopril, captopril, enalapril, enalaprilat, ramipril, cilazapril, delapril, fosenopril, zofenopril, indolapril, benazepril, lisinopril, spirapril, trandolapril, perindep, pentopril, moexipril, rescinnamine, and pivopril.

Embodiment 50: The method of any one of Embodiments 45-49, wherein the ACE inhibitor is selected from: quinapril, fosinopril, captopril, enalapril, and lisinopril.

Embodiment 51: The method of any one of Embodiments 45-50, wherein the ACE inhibitor is quinapril.

Embodiment 52: The method of any one of Embodiments 45-50, wherein the ACE inhibitor is fosinopril.

Embodiment 53: The method of any one of Embodiments 45-50, wherein the ACE inhibitor is captopril.

Embodiment 54: The method of any one of Embodiments 45-50, wherein the ACE inhibitor is enalapril.

Embodiment 55: The method of any one of Embodiments 45-50, wherein the ACE inhibitor is lisinopril.

Embodiment 56: The method of any one of Embodiments 45-55, wherein the ARB is selected from: candesartan, candesartan cilexetil, eprosartan, irbesartan, losartan, olmesartan, olmesartan medoxomil, telmisartan, valsartan, azilsartan medoxomil, and BRA-657.

Embodiment 57: The method of any one of Embodiments 45-56, wherein the ARB is selected from: candesartan, losartan, olmesartan, and valsartan.

Embodiment 58: The method of any one of Embodiments 45-57, wherein the ARB is candesartan.

Embodiment 59: The method of any one of Embodiments 45-57, wherein the ARB is losartan.

Embodiment 60: The method of any one of Embodiments 45-57, wherein the ARB is olmesartan.

Embodiment 61: The method of any one of Embodiments 45-57, wherein the ARB is valsartan.

Embodiment 62: The method of any one of Embodiments 45-61, wherein the dosage of an ACE inhibitor, an ARB, a statin, a diuretic, a calcium channel blocker, a beta blocker, an aldosterone antagonist, fish oil, hydroxychloroquine, or a combination of any of the foregoing, is decreased after between about 15 days to about 30 days of treatment with atrasentan, or a pharmaceutically acceptable salt thereof.

Embodiment 63: The method of any one of Embodiments 45-62, wherein the dosage is decreased by about 25% to about 100%.

Embodiment 64: The method of any one of Embodiments 45-63, wherein the dosage is decreased by about 50% to about 100%.

Embodiment 65: The method of any one of Embodiments 45-64, wherein the dosage is decreased by about 75% to about 100%.

Embodiment 66: The method of any one of Embodiments 46 or 49-65, wherein the dosage of an ACE inhibitor, an ARB, and/or a diuretic, is decreased after treatment with atrasentan, or a pharmaceutically acceptable salt thereof.

Embodiment 67: The method of any one of Embodiments 46 or 49-66, wherein the dosage of an ACE inhibitor, an ARB, and/or a diuretic, is decreased after between about 15 days to about 30 days of treatment with atrasentan, or a pharmaceutically acceptable salt thereof.

Embodiment 68: The method of any one of Embodiments 46 or 49-67, wherein the dosage of an ACE inhibitor, an ARB, and/or a diuretic, is decreased by about 25% to about 100% after treatment with atrasentan, or a pharmaceutically acceptable salt thereof.

Embodiment 69: The method of any one of Embodiments 46 or 49-68, wherein the dosage of an ACE inhibitor, an ARB, and/or a diuretic, is decreased by about 50% to about 100% after treatment with atrasentan, or a pharmaceutically acceptable salt thereof.

Embodiment 70: The method of any one of Embodiments 46 or 49-69, wherein the dosage of an ACE inhibitor, an ARB, and/or a diuretic, is decreased by about 75% to about 100% after treatment with atrasentan, or a pharmaceutically acceptable salt thereof.

Embodiment 71: The method of Embodiment 66, wherein the dosage of an ACE inhibitor is decreased after treatment with atrasentan, or a pharmaceutically acceptable salt thereof.

Embodiment 72: The method of Embodiment 66, wherein the dosage of an ARB is decreased after treatment with atrasentan, or a pharmaceutically acceptable salt thereof.

Embodiment 73: The method of Embodiment 66, wherein the dosage of a diuretic is decreased after treatment with atrasentan, or a pharmaceutically acceptable salt thereof.

Embodiment 74: The method of any one of Embodiments 1-73, wherein the atrasentan is administered as a pharmaceutically acceptable salt.

Embodiment 75: The method of any one of Embodiments 1-74, wherein the atrasentan is administered as atrasentan hydrochloride or atrasentan mandelate.

Embodiment 76: The method of any one of Embodiments 1-75, wherein the atrasentan is administered as atrasentan hydrochloride.

Embodiment 77: The method of any one of Embodiments 1-76, wherein the atrasentan is administered as the free base.

Embodiment 78: The method of any one of Embodiments 1-77, wherein the subject is at a high risk of progression to ESRD.

Embodiment 79: The method of any one of Embodiments 1-78, wherein the subject has been diagnosed with IgA nephropathy.

Embodiment 80: The method of Embodiment 79, wherein the diagnosis of IgA nephropathy comprises a kidney biopsy, detecting anti-glycan antibodies, detecting deposition of IgA-immune complexes in the kidney, or a combination of any of the foregoing.

Embodiment 81: The method of Embodiment 79 or 80, wherein the diagnosis of IgA nephropathy comprises a kidney biopsy.

Embodiment 82: The method of any one of Embodiments 1-81, wherein the subject is excreting an average of about 0.5 grams or more of protein in the urine per day for at least about 3 months prior to the first administration of atrasentan, or a pharmaceutically acceptable salt thereof.

Embodiment 83: The method of any one of Embodiments 1-82, wherein the subject is excreting an average of about 0.75 grams or more of protein in the urine per day for at least about 3 months prior to the first administration of atrasentan, or a pharmaceutically acceptable salt thereof.

Embodiment 84: The method of any one of Embodiments 1-82, wherein the subject is excreting an average of about 1 gram or more of protein in the urine per day for at least about 3 months prior to the first administration of atrasentan, or a pharmaceutically acceptable salt thereof.

Embodiment 85: The method of any one of Embodiments 1-84, wherein the subject has an average eGFR of about 20 to about 90 mL/min/1.73 m$^2$ for at least about 3 months prior to the first administration of atrasentan, or a pharmaceutically acceptable salt thereof.

Embodiment 86: The method of any one of Embodiments 1-85, wherein the subject has an average eGFR of about 30 to about 90 mL/min/1.73 m$^2$ for at least about 3 months prior to the first administration of atrasentan, or a pharmaceutically acceptable salt thereof.

Embodiment 87: The method of any one of Embodiments 1-85, wherein the subject has an average eGFR of about 20 to about 60 mL/min/1.73 m$^2$ for at least about 3 months prior to the first administration of atrasentan, or a pharmaceutically acceptable salt thereof.

Embodiment 88: The method of any one of Embodiments 1-87, wherein the subject has an average HbA1c of about 4% to about 6% for at least about 3 months prior to the first administration of atrasentan, or a pharmaceutically acceptable salt thereof.

Embodiment 89: The method of any one of Embodiments 1-88, wherein the subject has an average fasting blood glucose level of about 125 mg/dL or less for at least about 3 months prior to the first administration of atrasentan, or a pharmaceutically acceptable salt thereof.

Embodiment 90: The method of any one of Embodiments 1-89, wherein the subject maintains a potassium level within the normal physiologic range.

Embodiment 91: The method of any one of Embodiments 1-90, wherein the subject maintains a sodium level within the normal physiologic range.

Embodiment 92: The method of any one of Embodiments 1-91, wherein the subject has ALT/AST levels during the administration of atrasentan, or a pharmaceutically acceptable salt thereof, that are about the same as the ALT/AST levels prior to the first administration of atrasentan, or a pharmaceutically acceptable salt thereof.

Embodiment 93: The method of any one of Embodiments 1-92, wherein the subject has bilirubin levels during the administration of atrasentan, or a pharmaceutically acceptable salt thereof, that are about the same as the bilirubin levels prior to the first administration of atrasentan, or a pharmaceutically acceptable salt thereof.

Embodiment 94: The method of any one of Embodiments 1-93, wherein the fluid retention in the subject is manageable with diuretics.

Embodiment 95: The method of any one of Embodiments 1-94, wherein the amount of proteins in the urine of the subject is reduced by about 20% to about 80% after between about 15 day and about 30 days of treatment with atrasentan, or a pharmaceutically acceptable salt thereof.

Embodiment 96: The method of Embodiment 95, wherein the amount of proteins in the urine of the subject is reduced by about 35% to about 80%.

Embodiment 97: The method of any one of Embodiments 1-96, wherein the amount of proteins in the urine of the subject is reduced by about 100 mg/dL to about 500 mg/dL after between about 15 days and about 30 days of treatment with atrasentan, or a pharmaceutically acceptable salt thereof.

Embodiment 98: The method of any one of Embodiments 1-97, wherein the amount of proteins in the urine of the subject is reduced by about 500 mg/dL to about 900 mg/dL after between about 15 days and about 30 days of treatment with atrasentan, or a pharmaceutically acceptable salt thereof.

Embodiment 99: The method of any one of Embodiments 1-98, wherein the risk of the subject developing ESRD is reduced by about 20% to about 99% after between about 6 months and about 24 months of treatment with atrasentan, or a pharmaceutically acceptable salt thereof.

Embodiment 100: The method of any one of Embodiments 1-99, wherein the risk of the subject developing ESRD is reduced by about 20% to about 99% after between about 12 months and about 24 months of treatment with atrasentan, or a pharmaceutically acceptable salt thereof.

Embodiment 101: The method of any one of Embodiments 1-100, wherein the average rate of decrease in eGFR is from about 0.75 mL/min/year to about 6 mL/min/year for at least about 3 months prior to the first administration of atrasentan, or a pharmaceutically acceptable salt thereof.

Embodiment 102: The method of any one of Embodiments 1-101, wherein the average rate of decrease in eGFR is from about 3 mL/min/year to about 6 mL/min/year for at least about 3 months prior to the first administration of atrasentan, or a pharmaceutically acceptable salt thereof.

Embodiment 103: The method of any one of Embodiments 1-102, wherein the average rate of decrease in eGFR is from about 4 mL/min/year to about 5 mL/min/year for at least about 3 months prior to the first administration of atrasentan, or a pharmaceutically acceptable salt thereof.

Embodiment 104: The method of any one of Embodiments 1-103, wherein the average rate of decrease in eGFR is reduced by from about 15% to about 30% after between about 6 months and about 24 months of treatment with atrasentan, or a pharmaceutically acceptable salt thereof.

Embodiment 105: The method of any one of Embodiments 1-104, wherein the therapeutically effective amount of atrasentan, or a pharmaceutically acceptable salt thereof, is from about 0.20 mg to about 1.5 mg of atrasentan, or an equivalent amount of a pharmaceutically acceptable salt thereof.

Embodiment 106: The method of any one of Embodiments 1-105, wherein the therapeutically effective amount of atrasentan, or a pharmaceutically acceptable salt thereof, is from about 0.25 mg to about 1.25 mg of atrasentan, or an equivalent amount of a pharmaceutically acceptable salt thereof.

Embodiment 107: The method of any one of Embodiments 1-106, wherein the therapeutically effective amount of atrasentan, or a pharmaceutically acceptable salt thereof, is from about 0.40 mg to about 0.85 mg of atrasentan, or an equivalent amount of a pharmaceutically acceptable salt thereof.

Embodiment 108: The method of any one of Embodiments 1-107, wherein the therapeutically effective amount of atrasentan, or a pharmaceutically acceptable salt thereof, is about 0.75 mg of atrasentan, or an equivalent amount of a pharmaceutically acceptable salt thereof.

Embodiment 109: The method of any one of Embodiments 1-108, further comprising determining expression and/or activity of one or more of ET1, TGF, PDGF, CTGF, MMP, TIMPS, IGF1, DPEP1, ASL, AMN, ALPL, SLC6A19, IL-6, NF-kB, PKC, PI3K, Src, Ras, ERK1/2, Rho, Rac, Akt, mTOR, NAPDH oxidase, MAPK, cPLA$_2$, TNF-α, IL-1, CAM, COX-2, iNOS, JAK, STAT3, PI3K, Akt/PKB, IKKs, IkBs, NF-kB, MAPK, Ras, Raf, MEK, ERK, MCP1, Cntfr, Il1b, Csf1, Il2ra, Map3k8, Il1r1, Pfkfb3, Nr4a1, Gem, Fosl2, Klf4, F3, Nfkbia, Ifit2, Nr4a2, Klf2, Jag1, Dnajb4, Il1b, Spsb1, Btg2, Atf3, Csf1, Trib1, Zbtb10, Btg1, Rhob, Nfat5, Edn1, Rel, Nr4a3, Nfkb1, Serpine1, Ccl20, Per1, Cxcl2, Map3k8, Traf1, Pik3r1, Pdgfra, Nfkbia, Pik3cg, Pla2g4a, Tiam1, and Pdgfb.

Embodiment 110: The method of any one of Embodiments 1-109, further comprising determining expression and/or activity of one or more of ET1, TGF, PDGF, CTGF, MMP, TIMPS, IGF1, DPEP1, ASL, AMN, ALPL, SLC6A19, IL-6, NF-kB, PKC, PI3K, Src, Ras, ERK1/2, Rho, Rac, Akt, mTOR, NAPDH oxidase, MAPK, cPLA$_2$, TNF-α, IL-1, CAM, COX-2, iNOS, JAK, STAT3, PI3K, Akt/PKB, IKKs, IkBs, NF-kB, MAPK, Ras, Raf, MEK, ERK, and MCP1.

Embodiment 111: The method of any one of Embodiments 1-110, further comprising determining expression and/or activity of one or more of Cntfr, Il1b, Csf1, Il2ra, Map3k8, Il1r1, Pfkfb3, Nr4a1, Gem, Fosl2, Klf4, F3, Nfkbia, Ifit2, Nr4a2, Klf2, Jag1, Dnajb4, Il1b, Spsb1, Btg2, Atf3, Csf1, Trib1, Zbtb10, Btg1, Rhob, Nfat5, Edn1, Rel, Nr4a3, Nfkb1, Serpine1, Ccl20, Per1, Cxcl2, Map3k8, Traf1, Pik3r1, Pdgfra, Nfkbia, Pik3cg, Pla2g4a, Tiam1, and Pdgfb.

Embodiment 112: The method of any one of Embodiments 1-108, further comprising determining expression and/or activity of one or more of ET1, TGF, PDGF, CTGF, MMP, TIMPS, IGF1, DPEP1, ASL, AMN, ALPL, SLC6A19, NF-kB, and IL6 in the subject.

Embodiment 113: The method of Embodiment 109, wherein determining the expression and/or activity is performed prior to administration of a therapeutically effective amount of atrasentan, or a pharmaceutically acceptable salt thereof.

Embodiment 114: The method of Embodiment 109, wherein determining the expression and/or activity is performed after administration of a therapeutically effective amount of atrasentan, or a pharmaceutically acceptable salt thereof.

Embodiment 115: The method of any one of Embodiments 1-114, further comprising administering a therapeutically effective amount of a SGLT-2 inhibitor.

Embodiment 116: The method of Embodiment 115, wherein the SGLT-2 inhibitor is selected from dapagliflozin, canagliflozin, ipragliflozin, empagliflozin, bexagliflozin, licogliflozin, janagliflozin (XZP-5695), tofogliflozin, ertugliflozin, henagliflozin (SHR-3824), enavogliflozin (DWP-16001), TA-1887 (3-(4-cyclopropylbenzyl)-4-fluoro-1-(β-D-glucopyranosyl)-1H-indole), indole-N-glycoside 18 (3-(4-ethylbenzyl)-1-(β-D-glucopyranosyl)-1H-indole), sotagliflozin, luseogliflozin, sergliflozin etabonate, remogliflozin, remogliflozin etabonate, and T-1095 (((2R,3S,4S,5R,6S)-6-(2-(3-(benzofuran-5-yl)propanoyl)-3-hydroxy-5-methylphenoxy)-3,4,5-trihydroxytetrahydro-2H-pyran-2-yl) etabonate).

Embodiment 117: The method of Embodiment 115 or 116, wherein the SGLT-2 inhibitor is selected from bexagliflozin, canagliflozin, dapagliflozin, empagliflozin, ertugliflozin, ipragliflozin, luseogliflozin, remogliflozin, serfliflozin, licofligliozin, sotagliflozin, and tofogliflozin.

Embodiment 118: The method of any one of Embodiments 115-117, wherein the SGLT-2 inhibitor is canagliflozin, dapagliflozin, empagliflozin, or ertugliflozin.

Embodiment 119: The method of any one of Embodiments 115-117, wherein the SGLT-2 inhibitor is canagliflozin.

Embodiment 120: The method of any one of Embodiments 115-117, wherein the SGLT-2 inhibitor is dapagliflozin.

Embodiment 121: The method of any one of Embodiments 115-117, wherein the SGLT-2 inhibitor is empagliflozin.

Embodiment 122: The method of any one of Embodiments 115-117, wherein the SGLT-2 inhibitor is ertugliflozin.

Embodiment 123: The method of any one of Embodiments 115-122, wherein the subject is administered a SGLT-2 inhibitor and one or more ACE inhibitors and/or one or more ARBs.

Embodiment 124: The method of any one of Embodiments 115-123, wherein the subject is administered a SGLT-2 inhibitor and one or more ACE inhibitors.

Embodiment 125: The method of any one of Embodiments 115-123, wherein the subject is administered a SGLT-2 inhibitor and one or more ARBs.

Embodiment 126: The method of any one of Embodiments 115-123, wherein the subject is administered a SGLT-2 inhibitor and an ACE inhibitor.

Embodiment 127: The method of any one of Embodiments 115-123, wherein the subject is administered a SGLT-2 inhibitor and an ARB.

Embodiment 128: The method of any one of Embodiments 115-123, wherein the subject is administered a SGLT-2 inhibitor, an ACE inhibitor, and an ARB.

Embodiment 129: A method of inhibiting mesangial cell activation, comprising contacting a mesangial cell with an effective amount of atrasentan, or a pharmaceutically acceptable salt thereof.

Embodiment 130: The method of Embodiment 129, wherein the mesangial activation is induced by IgA immune complexes.

Embodiment 131: The method of Embodiment 129, wherein the mesangial activation is associated with the presence of IgA immune complexes.

Embodiment 132: The method of Embodiment 129, wherein the inhibiting of mesangial cell activation comprises reducing expression and/or activity of one or more biomarkers indicative of mesangial cell proliferation.

Embodiment 133: The method of Embodiment 129, wherein the inhibiting of mesangial cell activation comprises reducing mesangial cell inflammation.

Embodiment 134: The method of Embodiment 133, wherein reducing mesangial cell inflammation comprises reducing expression and/or activity of one or more of IL6, MCP1 or other biomarkers indicative of mesangial cell inflammation.

Embodiment 135: The method of Embodiment 134, wherein reducing mesangial cell inflammation comprises reducing IL-6 signaling.

Embodiment 136: The method of Embodiment 129, wherein the inhibiting of mesangial cell activation comprises reducing the pro-fibrotic response in the mesangial cells.

Embodiment 137: The method of Embodiment 136, wherein reducing the pro-fibrotic response in the mesangial cells comprises reducing expression and/or activity of one or more of TGF, PDGF, CTGF, MMP, TIMPS, or other biomarkers indicative of mesangial cell fibrosis.

Embodiment 138: The method of Embodiment 136 or 137, wherein reducing the pro-fibrotic response in the mesangial cells comprises reducing expression and/or activity of one or more of ET1, TGF, PDGF, CTGF, MMP, TIMPS, IGF1, DPEP1, ASL, AMN, ALPL, SLC6A19, IL-6, NF-kB, PKC, PI3K, Src, Ras, ERK1/2, Rho, Rac, Akt, mTOR, NAPDH oxidase, MAPK, cPLA$_2$, TNF-α, IL-1, CAM, COX-2, iNOS, JAK, STAT3, PI3K, Akt/PKB, IKKs, IkBs, NF-kB, MAPK, Ras, Raf, MEK, ERK, MCP1, Cntfr, Il1b, Csf1, Il2ra, Map3k8, Il1r1, Pfkfb3, Nr4a1, Gem, Fosl2, Klf4, F3, Nfkbia, Ifit2, Nr4a2, Klf2, Jag1, Dnajb4, Il1b, Spsb1, Btg2, Atf3, Csf1, Trib1, Zbtb10, Btg1, Rhob, Nfat5, Edn1, Rel, Nr4a3, Nfkb1, Serpine1, Ccl20, Per1, Cxcl2, Map3k8, Traf1, Pik3r1, Pdgfra, Nfkbia, Pik3cg, Pla2g4a, Tiam1, and Pdgfb.

Embodiment 139: The method of Embodiment 136 or 137, wherein reducing the pro-fibrotic response in the mesangial cells comprises reducing expression and/or activity of one or more of ET1, TGF, PDGF, CTGF, MMP, TIMPS, IGF1, DPEP1, ASL, AMN, ALPL, SLC6A19, IL-6, NF-kB, PKC, PI3K, Src, Ras, ERK1/2, Rho, Rac, Akt, mTOR, NAPDH oxidase, MAPK, cPLA$_2$, TNF-α, IL-1, CAM, COX-2, iNOS, JAK, STAT3, PI3K, Akt/PKB, IKKs, IkBs, NF-kB, MAPK, Ras, Raf, MEK, ERK, and MCP1.

Embodiment 140: The method of Embodiment 136 or 137, wherein reducing the pro-fibrotic response in the mesangial cells comprises reducing expression and/or activity of one or more of Cntfr, Il1b, Csf1, Il2ra, Map3k8, Il1r1, Pfkfb3, Nr4a1, Gem, Fosl2, Klf4, F3, Nfkbia, Ifit2, Nr4a2, Klf2, Jag1, Dnajb4, Il1b, Spsb1, Btg2, Atf3, Csf1, Trib1, Zbtb10, Btg1, Rhob, Nfat5, Edn1, Rel, Nr4a3, Nfkb1, Serpine1, Ccl20, Per1, Cxcl2, Map3k8, Traf1, Pik3r1, Pdgfra, Nfkbia, Pik3cg, Pla2g4a, Tiam1, and Pdgfb.

Embodiment 141: The method of Embodiment 136 or 137, wherein reducing the pro-fibrotic response in the mesangial cells comprises reducing NF-κB signaling and/or PDGF signaling.

Embodiment 142: The method of any one of Embodiment 136-141, wherein reducing the pro-fibrotic response in the mesangial cells comprises reducing matrix secretion by mesangial cells.

Embodiment 143: The method of Embodiment 142, wherein reducing matrix secretion by mesangial cells comprises reducing expression and/or activity of one or more of excess matrix secretion by mesangial cells.

Embodiment 144: A method of reducing activation of a mesangial cell in contact with an IgA immune complex, comprising contacting a mesangial cell with an effective amount of atrasentan, or a pharmaceutically acceptable salt thereof.

Embodiment 145: The method of Embodiment 144, wherein the reducing activation of a mesangial cell comprises reducing expression and/or activity of one or more biomarkers indicative of mesangial cell proliferation.

Embodiment 146: The method of Embodiment 144, wherein the reducing activation of a mesangial cell comprises reducing mesangial cell inflammation.

Embodiment 147: The method of Embodiment 146, wherein reducing mesangial cell inflammation comprises reducing expression and/or activity of one or more of IL6, MCP1, or other biomarkers indicative of mesangial cell inflammation.

Embodiment 148: The method of Embodiment 144, wherein the reducing activation of a mesangial cell comprises reducing the pro-fibrotic response in the mesangial cells.

Embodiment 149: The method of Embodiment 148, wherein reducing the pro-fibrotic response in the mesangial cells comprises reducing expression and/or activity of one or more of TGF, PDGF, CTGF, MMP, TIMPS, or other biomarkers indicative of mesangial cell fibrosis.

Embodiment 150: The method of Embodiment 148 or 149, wherein reducing the pro-fibrotic response in the mesangial cells comprises reducing expression and/or activity of one or more of ET1, TGF, PDGF, CTGF, MMP, TIMPS, IGF1, DPEP1, ASL, AMN, ALPL, SLC6A19, IL-6, NF-kB, PKC, PI3K, Src, Ras, ERKT1/2, Rho, Rac, Akt, mTOR, NAPDH oxidase, MAPK, cPLA$_2$, TNF-α, IL-1, CAM, COX-2, iNOS, JAK, STAT3, PI3K, Akt/PKB, IKKs, IkBs, NF-kB, MAPK, Ras, Raf, MEK, ERK, MCP1, Cntfr, Il1b, Csf1, Il2ra, Map3k8, Il1r1, Pfkfb3, Nr4a1, Gem, Fosl2, Klf4, F3, Nfkbia, Ifit2, Nr4a2, Klf2, Jag1, Dnajb4, Il1b, Spsb1, Btg2, Atf3, Csf1, Trib1, Zbtb10, Btg1, Rhob, Nfat5, Edn1, Rel, Nr4a3, Nfkb1, Serpine1, Ccl20, Per1, Cxcl2, Map3k8, Traf1, Pik3r1, Pdgfra, Nfkbia, Pik3cg, Pla2g4a, Tiam1, and Pdgfb.

Embodiment 151: The method of Embodiment 148 or 149, wherein reducing the pro-fibrotic response in the mesangial cells comprises reducing expression and/or activity of one or more of ET1, TGF, PDGF, CTGF, MMP, TIMPS, IGF1, DPEP1, ASL, AMN, ALPL, SLC6A19, IL-6, NF-kB, PKC, PI3K, Src, Ras, ERK1/2, Rho, Rac, Akt, mTOR, NAPDH oxidase, MAPK, cPLA$_2$, TNF-α, IL-1, CAM, COX-2, iNOS, JAK, STAT3, PI3K, Akt/PKB, IKKs, IkBs, NF-kB, MAPK, Ras, Raf, MEK, ERK, and MCP1.

Embodiment 152: The method of Embodiment 148 or 149, wherein reducing the pro-fibrotic response in the mesangial cells comprises reducing expression and/or activity of one or more of Cntfr, Il1b, Csf1, Il2ra, Map3k8, Il1r1, Pfkfb3, Nr4a1, Gem, Fosl2, Klf4, F3, Nfkbia, Ifit2, Nr4a2, Klf2, Jag1, Dnajb4, Il1b, Spsb1, Btg2, Atf3, Csf1, Trib1, Zbtb10, Btg1, Rhob, Nfat5, Edn1, Rel, Nr4a3, Nfkb1, Serpine1, Ccl20, Per1, Cxcl2, Map3k8, Traf1, Pik3r1, Pdgfra, Nfkbia, Pik3cg, Pla2g4a, Tiam1, and Pdgfb.

Embodiment 153: The method of any one of Embodiments 148-152, wherein reducing the pro-fibrotic response in the mesangial cells comprises reducing matrix secretion by mesangial cells.

Embodiment 154: The method of Embodiment 153, wherein reducing matrix secretion by mesangial cells comprises reducing expression and/or activity of one or more biomarkers indicative of excess matrix secretion by mesangial cells.

Embodiment 155: The method of Embodiment 144, wherein the reducing activation of a mesangial cell comprises reducing undesired mesangial cell migration.

Embodiment 156: The method of any one of Embodiments 129-155, wherein the contacting occurs in vitro.

Embodiment 157: The method of any one of Embodiments 129-155, wherein the contacting occurs in vivo.

Embodiment 158: A method of treating IgA nephropathy in a subject in need thereof, comprising:
 a) determining that the subject has IgA-immune complex deposition in the kidney; and b) administering a therapeutically effective amount of atrasentan, or a pharmaceutically acceptable salt thereof, to the subject.

Embodiment 159: The method of Embodiment 158, wherein the subject has not been previously diagnosed with one or more of diabetic nephropathy, HIV/AIDS, or acute kidney failure.

Embodiment 160: The method of Embodiment 158, wherein the subject has not been previously diagnosed with HIV-related nephropathy.

Embodiment 161: The method of any one of Embodiments 158-160, wherein the subject is not currently diagnosed with cancer.

Embodiment 162: The method of any one of Embodiments 158-160, wherein the subject is not currently being treated for cancer.

Embodiment 163: The method of any one of Embodiments 158-160, wherein the subject has not been previously diagnosed with cancer.

Embodiment 164: The method of Embodiment 163, wherein the cancer is lung cancer or prostate cancer.

Embodiment 165: A method of treating IgA nephropathy in a subject in need thereof, comprising:
a) determining that the subject has elevated levels of mesangial activation; and
b) administering a therapeutically effective amount of atrasentan, or a pharmaceutically acceptable salt thereof, to the subject.

Embodiment 166: The method of Embodiment 165, wherein determining of elevated levels of mesangial activation comprises obtaining a sample from the subject and assessing the level of mesangial activation in the same.

Embodiment 167: The method of Embodiment 166, wherein the sample is a kidney biopsy sample.

Embodiment 168: The method of Embodiment 166 or 167, wherein the sample exhibits elevated levels of one or more of: matrix secretion by the mesangial cells, IgA-immune complex deposition, mesangial cell proliferation, and endocapillary cell proliferation.

Embodiment 169: The method of any one of Embodiments 166-168, wherein the sample exhibits elevated levels of IgA-immune complex deposition.

Embodiment 170: The method of any one of Embodiments 165-169, wherein the subject has been determined to have proteinuria of at least 1 g/day in at least two of three consecutive readings over the year prior to administration of a therapeutically effective amount of atrasentan, or a pharmaceutically acceptable salt thereof.

Embodiment 171: The method of any one of Embodiments 165-170, wherein the subject has been administered a maximally tolerated stable dose of a RAS inhibitor for at least 12 weeks prior to administration of a therapeutically effective amount of atrasentan, or a pharmaceutically acceptable salt thereof.

Embodiment 172: The method of any one of Embodiments 165-171, wherein the subject is concurrently administered a maximally tolerated stable dose of a RAS inhibitor and a therapeutically effective amount of atrasentan, or a pharmaceutically acceptable salt thereof.

Embodiment 173: The method of any one of Embodiments 165-171, wherein the subject has been determined to have hematuria prior to administration of a therapeutically effective amount of atrasentan, or a pharmaceutically acceptable salt thereof.

Embodiment 174: The method of Embodiment 173, wherein the hematuria is microhematuria.

Embodiment 175: The method of Embodiment 173, wherein the hematuria is gross hematuria.

Embodiment 176: The method of any one of Embodiments 165-175, wherein the subject has been determined to have an eGFR of at least 30 mL/min/1.73 m$^2$ prior to administration of a therapeutically effective amount of atrasentan, or a pharmaceutically acceptable salt thereof.

Embodiment 177: The method of any one of Embodiments 165-176, wherein the subject has not been previously diagnosed with one or more of diabetic nephropathy, HIV/AIDS, or acute kidney failure.

Embodiment 178: The method of any one of Embodiments 165-177, wherein the subject has not been previously diagnosed with HIV-related nephropathy.

Embodiment 179: The method of any one of Embodiments 165-178, wherein the subject is not currently diagnosed with cancer.

Embodiment 180: The method of any one of Embodiments 165-178, wherein the subject is not currently being treated for cancer.

Embodiment 181: The method of any one of Embodiments 165-178, wherein the subject has not been previously diagnosed with cancer.

Embodiment 182: The method of Embodiment 181, wherein the cancer is lung cancer or prostate cancer.

Embodiment 183: The method of any one of Embodiments 165-182, wherein assessing the level of mesangial activation in the sample comprises one or more of serum analysis, urinalysis, light microscopy and immunofluorescence microscopy.

Embodiment 184: A method of treating IgA nephropathy in a subject in need thereof, comprising:
a) determining that the subject has elevated levels of IgA-immune complexes in the kidney; and
b) administering a therapeutically effective amount of atrasentan, or a pharmaceutically acceptable salt thereof, to the subject.

Embodiment 185: The method of Embodiment 184, wherein determining of elevated levels of IgA-immune complexes in the kidney comprises obtaining a kidney biopsy sample from the subject and assessing the level of IgA-immune complexes in the same.

Embodiment 186: The method of Embodiment 184 or 185, wherein the sample exhibits elevated levels of one or more of: matrix secretion by the mesangial cells, mesangial cell activation, mesangial cell proliferation, and endocapillary cell proliferation.

Embodiment 187: The method of any one of Embodiments 184-186, wherein the subject has been determined to have proteinuria of at least 1 g/day in at least two of three consecutive readings over the year prior to administration of a therapeutically effective amount of atrasentan, or a pharmaceutically acceptable salt thereof.

Embodiment 188: The method of any one of Embodiments 184-187, wherein the subject has been administered a maximally tolerated stable dose of a RAS inhibitor for at least 12 weeks prior to administration of a therapeutically effective amount of atrasentan, or a pharmaceutically acceptable salt thereof.

Embodiment 189: The method of any one of Embodiments 184-188, wherein the subject is concurrently administered a maximally tolerated stable dose of a RAS inhibitor and a therapeutically effective amount of atrasentan, or a pharmaceutically acceptable salt thereof.

Embodiment 190: The method of any one of Embodiments 184-189, wherein the subject has been determined to have hematuria prior to administration of a therapeutically effective amount of atrasentan, or a pharmaceutically acceptable salt thereof.

Embodiment 191: The method of Embodiment 190, wherein the hematuria is microhematuria.

Embodiment 192: The method of Embodiment 190, wherein the hematuria is gross hematuria.

Embodiment 193: The method of any one of Embodiments 184-192, wherein the subject has been determined to have an eGFR of at least 30 mL/min/1.73 m$^2$ prior to administration of a therapeutically effective amount of atrasentan, or a pharmaceutically acceptable salt thereof.

Embodiment 194: The method of any one of Embodiments 184-193, wherein the subject has not been previously diagnosed with one or more of diabetic nephropathy, HIV/AIDS, or acute kidney failure.

Embodiment 195: The method of any one of Embodiments 184-194, wherein the subject has not been previously diagnosed with HIV-related nephropathy.

Embodiment 196: The method of any one of Embodiments 184-195, wherein the subject is not currently diagnosed with cancer.

Embodiment 197: The method of any one of Embodiments 184-196, wherein the subject is not currently being treated for cancer.

Embodiment 198: The method of any one of Embodiments 184-197, wherein the subject has not been previously diagnosed with cancer.

Embodiment 199: The method of any one of Embodiments 196-198, wherein the cancer is lung cancer or prostate cancer.

Embodiment 200: The method of any one of Embodiments 185-199, wherein assessing the level of IgA-immune complexes in the sample comprises one or more of serum analysis, urinalysis, light microscopy and immunofluorescence microscopy.

Embodiment 201: The method of any one of Embodiments 158-200, further comprising administering a SGLT-2 inhibitor.

Embodiment 202: The method of Embodiment 201, wherein the SGLT-2 inhibitor is selected from dapagliflozin, canagliflozin, ipragliflozin, empagliflozin, bexagliflozin, licogliflozin, janagliflozin (XZP-5695), tofogliflozin, ertugliflozin, henagliflozin (SHR-3824), enavogliflozin (DWP-16001), TA-1887 (3-(4-cyclopropylbenzyl)-4-fluoro-1-(β-D-glucopyranosyl)-1H-indole), indole-N-glycoside 18 (3-(4-ethylbenzyl)-1-(β-D-glucopyranosyl)-1H-indole), sotagliflozin, luseogliflozin, sergliflozin etabonate, remogliflozin, remogliflozin etabonate, and T-1095 (((2R,3S,4S,5R,6S)-6-(2-(3-(benzofuran-5-yl)propanoyl)-3-hydroxy-5-methylphenoxy)-3,4,5-trihydroxytetrahydro-2H-pyran-2-yl) etabonate).

Embodiment 203: The method of Embodiment 200 or 201, wherein the SGLT-2 inhibitor is selected from bexagliflozin, canagliflozin, dapagliflozin, empagliflozin, ertugliflozin, ipragliflozin, luseogliflozin, remogliflozin, serfliflozin, licofliglozin, sotagliflozin, and tofogliflozin.

Embodiment 204: The method of any one of Embodiments 201-203, wherein the SGLT-2 inhibitor is canagliflozin, dapagliflozin, empagliflozin, or ertugliflozin.

EXAMPLES

Example 1. In Vitro Study Using a Cellular Model of Human IgA Nephropathy

Primary human mesangial cells in a culture are stimulated with pathogenic dgIgA immune complexes isolated from human IgA nephropathy patients or generated in vitro. Proliferation as well as pro-inflammatory and pro-fibrotic responses to these disease causing immune complexes are observed in mesangial cells within 48 hours. The cells are treated with atrasentan or a pharmaceutically acceptable salt thereof (e.g., atrasentan hydrochloride) in an appropriate medium. Changes in proliferation, pro-inflammatory responses, and/or pro-fibrotic responses are measured. The result of this study will indicate the extent to which atrasentan attenuates underlying disease processes in IgA nephropathy in an in vitro model.

Example 2. A Randomized, Double-Blind, Placebo-Controlled Efficacy and Safety Study of Atrasentan in Patients with IgA Nephropathy This example describes a Randomized, Double-Blind, Placebo-Controlled Efficacy and Safety Study of Atrasentan on IgA nephropathy patients on renin angiotensin system (RAS) inhibitors with persistent proteinuria and risk of rapid renal progression.

Study Overview

This protocol encompasses 2 periods. The first period involves the open-label treatment of approximately 20-30 patients with IgA nephropathy to confirm the safety and tolerability of atrasentan 0.75 mg daily over 6 weeks. After all patients have completed at least 6 weeks of treatment, an independent Data Monitoring Committee (DMC) reviews all available safety data including adverse events, laboratory studies, and vital signs and makes a recommendation as to whether the safety profile is consistent with prior clinical experience, and safety data supports continued evaluation in the larger randomized study. If the DMC recommends proceeding to the randomized study, the initial open-label patients continue to receive open-label treatment for 110 weeks (approximately two years).

The second period involves a double-blind, placebo-controlled study of approximately 350-400 patients randomized 1:1 to receive atrasentan 0.75 mg daily or a matched placebo for 110 weeks. Patients are followed regularly with blood and urine markers of renal function as well as safety assessments.

Both the initial open-label cohort and the randomized double-blind cohort receive assigned treatment up through week 110. All patients subsequently discontinue study drug at week 110 and return for a safety follow up/study completion visit at week 114. Any patients that discontinue treatment prior to week 114 undergo a safety follow-up visit approximately four weeks after last dose of study drug. After the safety follow-up visit, patients that discontinue treatment prematurely are encouraged to remain on study for quarterly efficacy assessments in order to provide data for the study endpoints.

Objectives:

The primary objectives of this study are:

(1) To confirm the short-term safety and tolerability of atrasentan 0.75 mg daily in IgA nephropathy patients; and (2) To evaluate the effect of atrasentan on proteinuria levels at week 24 compared to placebo.

The Secondary Objectives are:

(3) To evaluate the effect of atrasentan on slowing estimated glomerular filtration rate (eGFR) loss between baseline and week 114 (4 weeks post cessation of randomized treatment);

(4) To compare two-year on-treatment rates of change in eGFR between atrasentan and placebo (eGFR slope week 6 to 110 of randomized treatment); and (5) To compare the percentage of patients achieving a partial clinical response with proteinuria reduction to less than 1 g/day at week 24 between atrasentan and placebo.

The Exploratory Objectives are:

(6) To evaluate the percentage of patients achieving partial and complete responses at each time point between week 6 and 114;

(7) To evaluate quality of life (QOL) of patients receiving atrasentan compared to placebo; and (8) To evaluate the steady-state pharmacokinetics of atrasentan that support exploratory exposure-response analyses.

Number of Subjects

Approximately 20-30 patients are enrolled into the phase 2 safety period and approximately 350-400 patients are enrolled into the randomized double-blind period.

Patients who discontinue the initial open-label period for reasons other than safety may be replaced at the discretion of the sponsor to ensure adequate safety data review after at least 6 weeks of treatment.

Number of Study Sites: Approximately 120 sites worldwide

Criteria for Inclusion:

The following are the inclusion criteria. Patients must meet ALL of the following inclusion criteria to be enrolled:

(1) male and female patients aged 18 and older;

(2) biopsy-proven diagnosis of IgA nephropathy not due to secondary causes;

(3) receiving a maximally tolerated stable dose of a RAS inhibitor for at least 12 weeks prior to screening;

(4) proteinuria of at least 1 g/day at screening and on at least two of three consecutive readings over the previous year;

(5) eGFR of at least 30 mL/min/1.73 m$^2$ at screening;

(6) willing to abide with highly effective forms of contraception as specified in the protocol throughout the study; and (7) willing and able to provide written informed consent and comply with all study visits and study procedures.

Exclusion Criteria

The following are the exclusion criteria; patients must meet NONE of the following exclusion criteria to be enrolled:

(1) concurrent diagnosis of another cause of chronic kidney disease including diabetic kidney disease, hypertensive kidney disease or another primary glomerulopathy. A history of well controlled hypertension is acceptable;

(2) presence of cellular glomerular crescents in >25% of glomeruli on kidney biopsy (if biopsy available within 6 months of screening) or clinical suspicion of rapidly progressive glomerulonephritis (RPGN);

(3) history of organ transplantation;

(4) use of systemic immunosuppressant medications (or investigational agents) for at least 2 weeks in the past 6 months;

(5) blood pressure of >160 systolic or >100 diastolic at screening;

(6) history of heart failure or prior hospital admissions for conditions relating to fluid overload such as uncontrolled peripheral edema, pleural effusion, or ascites;

(7) history of clinically significant liver disease and transaminase or bilirubin values more than twice the upper limit of normal;

(8) hemoglobin below 9 g/dL at screening or prior history of blood transfusion for anemia within 3 months of screening;

(9) history of malignancy unless cancer free for at least 5 years or nonmelanoma skin cancer not requiring ongoing treatment;

(10) pregnancy, breast feeding, or intent to become pregnant during the study period for females;

(11) intent to father a child during the study period for males;

(12) have received any investigational or biologic agent within 1 month (or 5 half-lives of the agent, whichever is longer) prior to screening;

(13) concurrent clinically significant, unstable, or uncontrolled cardiovascular, pulmonary, hepatic, renal, gastrointestinal, genitourinary, haematological, coagulation, immunological, endocrine/metabolic, or other medical disorder that, in the opinion of the Investigator, might confound the results of the study or pose additional risk to the patient by their participation in the study; or

(14) history of an alcohol or illicit drug-related disorder.

Note: Screening of a previously ineligible patient may be repeated with medical monitor approval.

Test Product(s), Dose, and Mode of Administration:

Patients in the open label period receive atrasentan 0.75 mg once daily by oral administration. Patients in the randomized double-blind period receive either: atrasentan 0.75 mg once daily by oral administration; or matching placebo once daily by oral administration.

Treatment assignment during the randomized study period is determined by an interactive voice/web response system (IXRS). Patients, investigators, and the sponsor do have access to the assigned study treatment. In the event of a medical emergency the investigator is able to receive the treatment assignment through the IXRS system if required to provide optimal care of the patient. Randomization is stratified by region (North America vs all other regions) and baseline urinary protein levels at screening (>2 g/day vs<2 g/day).

Duration of Treatment:

Screening Duration: up to 4 weeks
Treatment Duration: 110 weeks
Safety Follow up: 4 weeks
Total study duration for an individual patient: Up to 118 weeks (approximately 2.3 years)

Criteria for Evaluation: Efficacy

The primary efficacy endpoint is the change in proteinuria (urine protein/creatinine ratio based on 24-hour urine collection) from baseline to week 24 in atrasentan-treated patients as compared to placebo-treated patients.

The key secondary efficacy endpoint is the rate of change in eGFR as measured through a slope calculated from values at baseline through to the safety follow up/study completion visit (week 114) in atrasentan-treated patients as compared to placebo-treated patients.

Additional secondary efficacy endpoints include: rate of change in eGFR during two years on treatment as measured through a chronic slope calculated from values at week 6 through to week 110 in atrasentan-treated patients as compared to placebo-treated patients, and the percent of patients achieving partial and complete clinical responses.

Criteria for Evaluation: Safety

Safety Endpoints Include:

(1) frequency and severity of adverse events and serious adverse events;

(2) Frequency and severity of adverse events of special interest including events of cardiac failure and/or fluid overload; and (3) Clinically significant changes in safety labs, ECGs, or physical examination findings (including vital signs).

Stopping Criteria

An independent data monitoring committee (DMC) is appointed to monitor the study. The DMC meets periodically to review the safety data and makes recommendations regarding continuation, modification, suspension or termination of the study. The DMC also makes a formal recommendation to proceed to the randomized study following completion of at least 6 weeks of treatment for all patients in the open-label period.

The only required study drug stopping criteria is evidence of pregnancy or noncompliance with protocol-specified contraception or pregnancy monitoring. Other study drug stopping criteria may be based on investigator and patient discretion that may include fluid overload syndromes uncontrolled with diuretics and medical management and any suspected study drug-related adverse event that represents unacceptable toxicity.

All patients that stop study drug prior to week 110 are encouraged to continue quarterly visits through week 114 for efficacy assessments only.

Criteria for Evaluation: Pharmacokinetics and Pharmacodynamics

The pharmacokinetic and pharmacodynamic endpoints are:
(1) atrasentan plasma levels; and
(2) exploratory biomarkers.

Note: PK sampling is sparse to support development of a population PK.

Statistical Methods

Treatment Population Definitions:
All open-label participants comprise the Open Label Population for safety analyses and descriptive noncomparative efficacy analyses
All randomised participants who receive any amount of study drug comprise the Safety Population for safety and exposure analyses
All randomised participants comprise the Intent-to-Treat Population for efficacy analyses
All randomised participants who receive any amount of study drug and who have at least one post-baseline PK sample comprise the PK Population Safety and Tolerability:

Continuous safety data are summarised with descriptive statistics (arithmetic mean, standard deviation [SD], median, minimum, and maximum) by treatment group. Categorical safety data are summarised with frequency counts and percentages by treatment group. Adverse events are coded using the most current Medical Dictionary for Regulatory Activities (MedDRA) version available. The number of participants experiencing treatment-emergent adverse events as well as maximum severity and relationship to study drug are summarized.

Laboratory evaluations, vital signs assessments, and ECG parameters are summarised by treatment group and protocol-specified collection time point. A summary of change-from-baseline at each protocol-specified time point by treatment group are also presented. Concomitant medications are listed by participant and coded using the most current World Health Organization drug dictionary. Medical history is listed by subject. Further details regarding presentation and analysis of safety data is detailed in the Statistical Analysis Plan (SAP).

Pharmacokinetics:

Individual steady state atrasentan concentration data is listed and summarised with descriptive statistics (sample size, arithmetic mean, SD, median, minimum, maximum, geometric mean, and geometric coefficient of variation). These data may be fed into a larger population PK model of atrasentan. Correlations between atrasentan drug levels and safety or efficacy responses may be explored. Details regarding the statistical analyses of pharmacokinetic data are provided in the SAP.

Efficacy Evaluations:

Descriptive statistics are used to evaluate differences in demographic and baseline characteristics. The primary efficacy endpoint is the change from baseline to each postbaseline visit up to week 24 in urinary protein to creatinine ratio as determined from 24-hour urine collection samples. The primary analysis is carried out using log transformed data and a repeated measures analysis using all data collected at baseline, week 12, and week 24. Additional sensitivity analyses are performed on the primary endpoint to evaluate robustness and the impact of missing data. Subgroup analyses are performed as specified in the SAP. Following the collection and analysis of primary endpoint data at week 24, patients in the randomized study continue to receive their assigned study treatment up until study completion at week 114.

Example 3. In Vitro Study Using a Cellular Model of Human IgA Nephropathy

Primary human mesangial cells in a culture were stimulated with pathogenic galactose deficient (Gd)-IgA containing immune complexes isolated from human IgA nephropathy patients. Proliferation as well as pro-inflammatory and pro-fibrotic responses to these disease causing immune complexes were observed in mesangial cells within 48-72 hours. The cells were treated with atrasentan and changes in proliferation, pro-inflammatory responses, and/or pro-fibrotic responses were measured.

Specifically, pathogenic IgA-containing immune complexes were isolated from serum from either IgA nephropathy patients or age, gender and ethnicity-matched healthy individuals. Frozen serum was purchased from BioIVT and IgA-containing immune complexes were purified using jacalin affinity chromatography. In brief, 2 mL of serum was applied to a jacalin-agarose affinity column (ThermoFisher) and IgA was eluted with 0.1 M melibiose (Sigma Aldrich). Purified IgA-containing immune complexes were concentrated using a 100K Amicon filtration unit and the amount of total IgA and galactose-deficient IgA (Gd-IgA) in the immune complexes was measured by ELISA (ThermoFisher and IBL America, respectively). Primary human renal mesangial cells (HRMCs) from a 23-year-old male donor were purchased from ScienCell Research Laboratories. HRMCs were cultured as recommended by the supplier in MCM media containing 2% FBS and proprietary growth factors. For proliferation and cytokine production experiments, 5,000 cells per well were plated in 96 well plates, cultured overnight in complete media, then switched to MCM media containing 0.5% FBS in the absence of growth factors. Following one day of low serum treatment, media was replaced with MCM containing 0.5% FBS in the presence of purified immune complexes with or without atrasentan for up to 72 hours. See, e.g., Novak et. al., *Kidney International*, 67, pp. 504-516; 2005; Novak et. al., *Nephrol. Dial. Transplant*, 26, pp. 3451-3457; 2011; Liang et. al., *Cell Physiol. Biochem.*, 36, pp. 1793-1808; 2015; Nguyen et. al., *Clin. Kidney J.*, 12 (2), pp, 232-238; 2019. Mesangial cell activation was assessed by measuring proliferation with BrdU incorporation (Abcam) and secretion of inflammatory cytokines including IL-6 was measured by ELISA (R&D Systems).

Figure 1B:
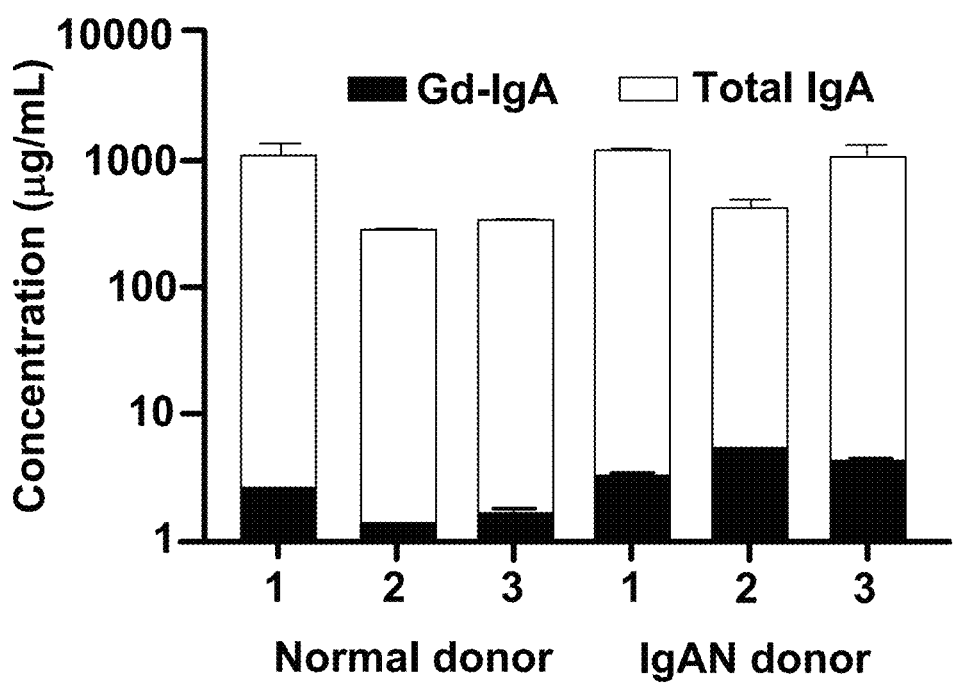
FIG. 1B illustrates the content of galactose-deficient (Gd)-IgA and total IgA following purification of immune complexes from IgAN or healthy control serum.

Compared to the IgA containing serum fractions from healthy controls, HRMCs treated with IgA containing immune complexes purified from three separate patients with IgA nephropathy showed increased cell proliferation, a hallmark of mesangial cell activation in response to pathogenic IgA immune complexes (FIG. 1A). Atrasentan had no effect on basal cell proliferation in HRMCs treated with IgA containing serum fractions from healthy controls, however, atrasentan significantly attenuated the hyperproliferation of HRMCs induced by IgA containing immune complexes purified from three separate patients with IgA nephropathy (FIG. 1A). The purified immune complexes from normal and IgAN donors contained a mean of 1.9 and 4.4 μg/mL Gd-IgA, respectively (FIG. 1B).

Example 4. Atrasentan Inhibits ET-1 Induced Proliferation and IL-6 Production in Primary Human Mesangial Cells Primary human renal mesangial cells (HRMCs) from a 23-year-old male donor were purchased from ScienCell Research Laboratories. HRMCs were cultured as recommended by the supplier in MCM media containing 2% FBS and proprietary growth factors (ScienCell). For proliferation and cytokine production experiments, 5,000 cells per well were plated in 96 well plates, cultured overnight in complete media, then switched to MCM media containing 0.5% FBS in the absence of growth factors. Following one day of low serum treatment, media was replaced with MCM containing 0.5% FBS in the presence or absence of 10 ng/mL ET-1 and a range of atrasentan concentrations for up to 72 hours. Mesangial cell activation was assessed by measuring proliferation with bromodeoxyuridine (BrdU) incorporation (Abcam) and secretion of inflammatory cytokines including IL-6 was measured by ELISA (R&D Systems). $IC_{50}$ values were calculated in GraphPad Prism using a variable slope four-parameter fit.

Figure 2A:
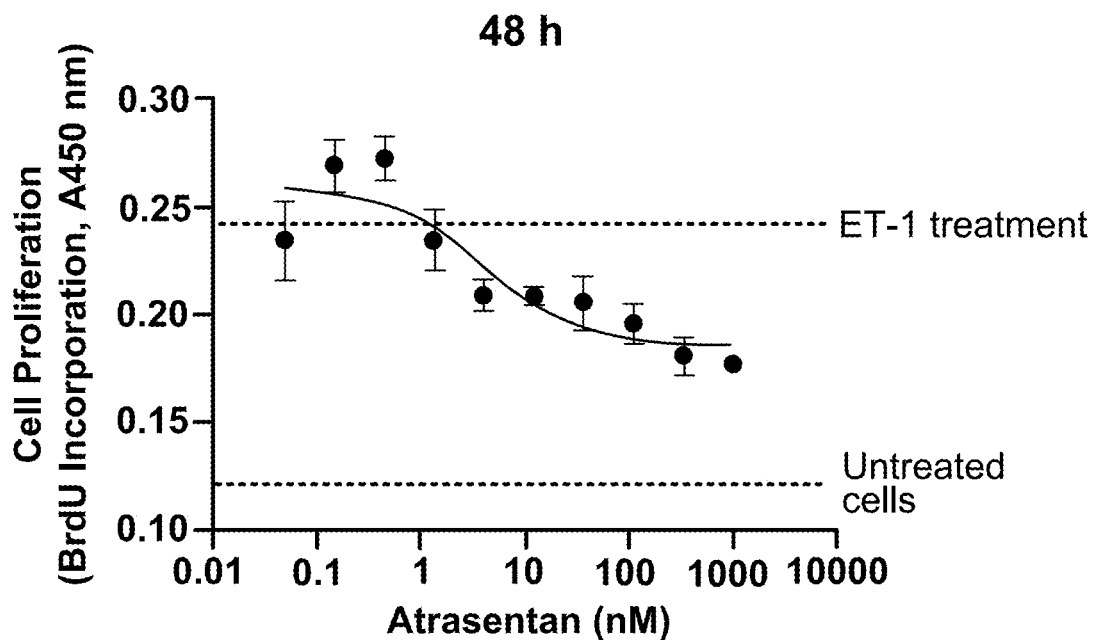
FIG. 2A illustrates the decrease in proliferation (after 48 hours) of primary human mesangial cells stimulated with endothelin 1 (ET-1) upon treatment with increasing concentrations of atrasentan shown in log scale, demonstrating an $IC_{50}$ of about 5.1 nM.
Figure 2B:
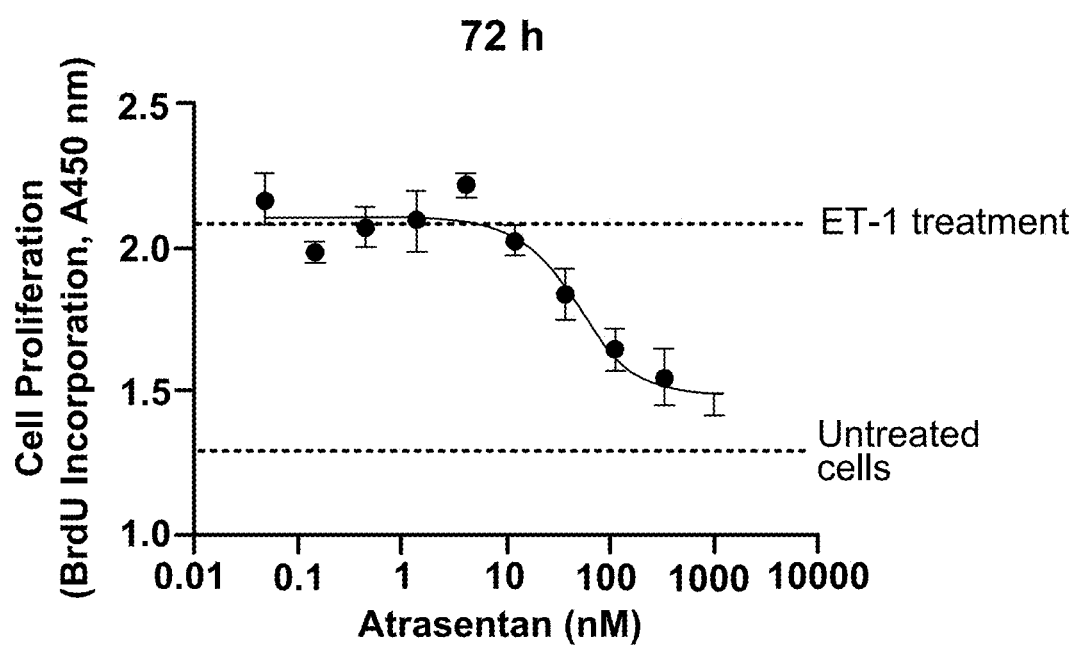
FIG. 2B illustrates the decrease in proliferation (after 72 hours) of primary human mesangial cells stimulated with endothelin 1 (ET-1) upon treatment with increasing concentrations of atrasentan shown in log scale, demonstrating an $IC_{50}$ of about 50.8 nM.
Figure 3A:
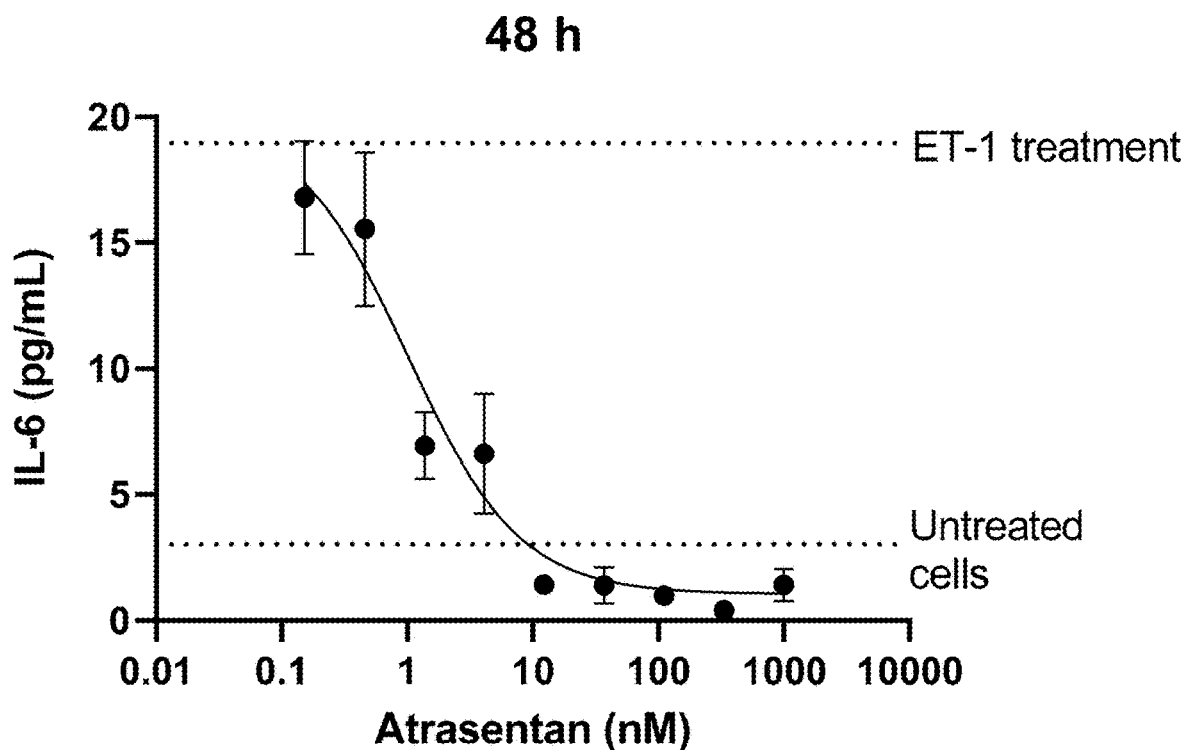
FIG. 3A illustrates the increase in IL-6 production by primary human mesangial cells exposed to ET-1 over 48 hours (about a 6-fold increase) and the decrease in IL-6 levels upon treatment with increasing concentrations of atrasentan shown in log scale, demonstrating an $IC_{50}$ of about 1 nM.
Figure 3B:
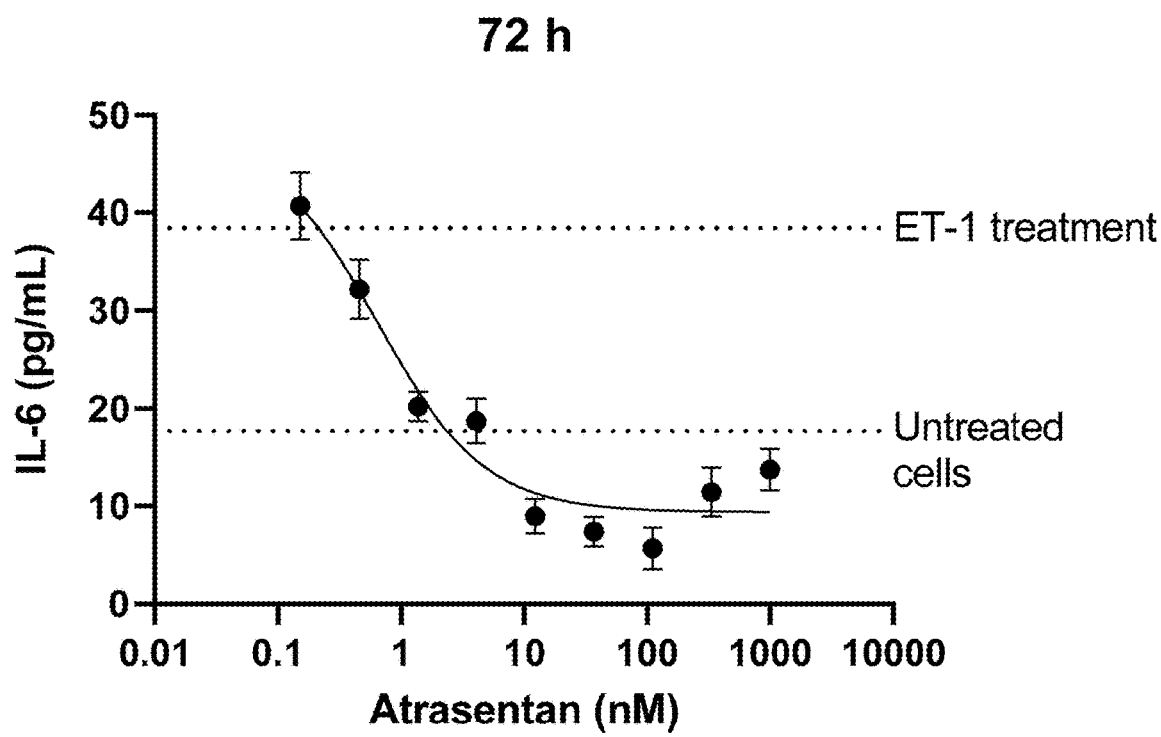
FIG. 3B illustrates the increase in IL-6 production by primary human mesangial cells exposed to ET-1 over 72 hours (about a 2.2-fold increase) and the decrease in IL-6 levels upon treatment with increasing concentrations of atrasentan shown in log scale, demonstrating an $IC_{50}$ of about 1 nM.

ET-1 induced HRMC proliferation at both 48 (FIG. 2A) and 72 hours (FIG. 2B). ET-1 induced HRMC proliferation was blocked in a concentration-dependent manner by atrasentan with $IC_{50}$ values of 4.2 nM and 50.8 nM after 48 (FIG. 2A) and 72 hours (FIG. 2B) of treatment, respectively. ET-1 also stimulated the production of IL-6 in HRMCs at 48 (FIG. 3A) and 72 hours (FIG. 3B), which was inhibited in a concentration-dependent manner by atrasentan with $IC_{50}$ values of 1.0 nM and 0.65 nM at 48 and 72 hour timepoints, respectively (FIGS. 3A and 3B).

Example 5. A Phase 3, Randomized, Double-Blind, Placebo-Controlled Study of Atrasentan in Patients with IgA Nephropathy at Risk of Progressive Loss of Renal Function (the ALIGN Study)

This example describes a Phase 3, Randomized, Double-Blind, Placebo-Controlled Study of Atrasentan in patients with IgA nephropathy) at risk of progressive loss of renal function despite treatment with a maximally tolerated and stable dose of a RAS inhibitor.

Study Overview

Approximately 320 patients with IgA nephropathy will be randomized 1:1 to receive atrasentan 0.75 mg once daily (QD) or a matched placebo for 132 weeks. Randomization will be stratified according to region and screening UPCR levels. Subjects will be evaluated for safety as well as changes in proteinuria and eGFR from baseline. Total duration for study participation per subject is expected to be up to 140 weeks including 4 weeks for screening, 132 weeks of treatment, and 4 weeks follow-up.

An independent data monitoring committee (IDMC) will periodically convene to review unblinded overall safety and emerging efficacy results. As well, an interim re-estimation of sample size supporting the key secondary endpoint may result in an increase of enrollment up to 450 total subjects Subjects who complete the study may be eligible to enroll in an extension study to receive open-label treatment with atrasentan under a separate protocol.

Objectives:

The Primary Objective of this Study is:

(1) To evaluate the effect of atrasentan on proteinuria levels at week 24 compared to placebo.

The Secondary Objectives are:

(2) To evaluate the effect of atrasentan versus placebo on change from baseline to Week 136 (4 weeks post cessation of randomized treatment) in estimated glomerular filtration rate (eGFR);

(3) To compare 2-year on-treatment rates of change in eGFR between atrasentan and placebo (eGFR slope Week 12 to Week 120 of randomized treatment); and (4) To compare the total on-study rates of change in eGFR between atrasentan and placebo (eGFR slope from baseline to Week 136).

The Exploratory Objectives are:

(5) To evaluate quality of life (QOL) of patients receiving atrasentan compared to placebo; and (6) To evaluate the steady-state pharmacokinetics of atrasentan that support exploratory exposure-response analyses.

Number of Subjects

Approximately 320 patients will be enrolled.

Number of Study Sites: Approximately 150 sites worldwide

Criteria for Inclusion:

The following are the inclusion criteria. Patients must meet all of the following inclusion criteria to be enrolled:

1. Male and female subjects aged 18 and older at the time of signing the ICF prior to initiation of any study specific activities/procedures.
2. Biopsy-proven IgAN that, in the opinion of the Investigator, is not due to secondary causes.
   Biopsy could have occurred at any point in time prior to study.
   A diagnostic report must be available for review by the Sponsor or designee.
3. Receiving a maximally tolerated and optimized dose of a RAS inhibitor that has been stable for at least 12 weeks prior to screening.
   Investigator discretion should be used in determining maximally tolerated and optimized dose.
   Subjects who are intolerant to RAS inhibitors are eligible, but will not exceed ~5% of total population randomized.
4. UPCR≥1 g/g based on a central laboratory assessment of first morning void urine collected at screening.
5. eGFR of at least 30 mL/min/1.73 m² at screening based on the CKD-EPI equation.
6. Willing to abide with highly effective forms of contraception, as specified in the protocol, throughout the study and for 1 month afterward. In WOCBP, use of hormonal contraceptive agents
7. Willing and able to provide written informed consent and comply with all study visits and study procedures.

Exclusion Criteria

The following are the exclusion criteria; patients must meet none of the following exclusion criteria to be enrolled:

1. Concurrent diagnosis of another cause of chronic kidney disease including diabetic kidney disease or another primary glomerulopathy.
2. Clinical suspicion of rapidly progressive glomerulonephritis (RPGN) based on KDIGO guidelines or clinical suspicion of Henoch-Schonlein Purpura.
3. Diagnosis of nephrotic syndrome with serum albumin <3 g/dL at screening.
4. BNP value of >200 pg/mL at screening.
5. Platelet count <80,000 per μL at screening
6. History of organ transplantation (subjects with history of corneal transplant are not excluded).
7. Use of systemic immunosuppressant medications including mycophenolate, azathioprine, cyclosporine, tacrolimus, etc.; use of herbs such as Tripterygium Wilfordii Hook F, Caulis sinomenii and *Sinomenium acutum*; for >2 weeks in the past 3 months. Use of rituximab within the past 6 months.
8. Confirmed blood pressure >150 mmHg systolic or >95 mmHg diastolic based on a mean of 3 measurements obtained at screening.
9. Known history of heart failure or prior hospital admissions for conditions relating to fluid overload such as pulmonary edema, uncontrolled peripheral edema, pleural effusion, or ascites.
10. Known history of clinically significant liver disease or transaminase or bilirubin values more than twice the upper limit of normal. Subjects with treated hepatitis C can be considered for inclusion into the study upon consultation with the Sponsor's Medical Monitor (or designee).
11. Hemoglobin below 9 g/dL at screening or prior history of blood transfusion for anemia within 3 months of screening.
12. History of malignancy unless cancer free for at least 5 years or nonmelanoma skin cancer not requiring ongoing treatment. A subject with curatively treated cervical carcinoma in situ is eligible for this study.
13. Pregnancy, breast feeding, or intent to become pregnant during the study period and at least 1 month afterward for females.
14. Intent to father a child or donate sperm during the study period and at least 1 month afterward for males.
15. Have received any investigational agent within 1 month (or 5 half-lives of the agent, whichever is longer) prior to screening. If the investigational agent is a cytotoxic or immunosuppressive agent then this washout period is 6 months.
16. Concurrent clinically significant, unstable, or uncontrolled cardiovascular, pulmonary, hepatic, renal, gastrointestinal, genitourinary, hematological, coagulation, immunological, endocrine/metabolic, or other medical disorder that, in the opinion of the Investigator or Sponsor's Medical Monitor (or designee), might confound the results of the study or pose additional risk to the subject by their participation in the study.
17. History of an alcohol or illicit drug-related disorder within the past 3 years.

Test Product(s), Dose, and Mode of Administration:
  Subjects will receive either atrasentan 0.75 mg once daily by oral administration or matching placebo once daily by oral administration.
  Treatment assignment is determined by an interactive voice/web response system (IXRS). Patients, investigators, and the sponsor do have access to the assigned study treatment. In the event of a medical emergency the investigator is able to receive the treatment assignment through the IXRS system if required to provide optimal care of the patient. Randomization is stratified by region (Asia vs. all other regions) and UPCR levels at screening (≥2 g/day vs. <2 g/day).

Duration of Treatment:
  Screening Duration: up to 4 weeks
  Treatment Duration: 132 weeks
  Safety Follow up: 4 weeks
  Total study duration for an individual patient: Up to 140 weeks (approximately 2.3 years)

Criteria for Evaluation: Efficacy
  The primary efficacy endpoint is the change in proteinuria (urine protein/creatinine ratio based on 24-hour urine collection) from baseline to week 24 in atrasentan-treated patients as compared to placebo-treated patients.
  The key secondary endpoint, change from baseline in eGFR for each subject, will be determined by the difference in eGFR at Week 136 from baseline. The eGFR change from baseline will be analyzed using an MMRM model.
  Additional secondary efficacy endpoints include:
    Rate of change in eGFR during 2 years on treatment as measured through a chronic slope calculated from values at Week 12 through to Week 120
    Rate of change in eGFR during the study as measured through a total slope calculated from values at baseline to Week 136
    Percent of subjects achieving proteinuria reduction to <1 g/day at Week 24 and 40% decrease in UPCR from baseline
    Percent of subjects experiencing at least a 30% reduction in eGFR or reach ESKD during the study
    Percent of subjects experiencing at least a 40% reduction in eGFR or reach ESKD during the study. Secondary endpoints will to be tested in hierarchical fashion at the final analysis at Week 136 after approximately 320 subjects in the ITT analysis set complete the Week 136 visit or discontinue from the study. Secondary analyses will be tested in hierarchical fashion (as listed above) based on a 2-sided significance level of 0.05.

Criteria for Evaluation: Safety
  Safety Endpoints Include:
  (1) frequency and severity of adverse events and serious adverse events;
  (2) Frequency and severity of adverse events of special interest including events of cardiac failure and/or fluid overload; and
  (3) Clinically significant changes in safety labs, ECGs, or physical examination findings (including vital signs).

Stopping Criteria
  An independent data monitoring committee (DMC) is appointed to monitor the study. The DMC meets periodically to review the safety data and makes recommendations regarding continuation, modification, suspension or termination of the study.
  Subjects will be required to permanently discontinue study drug for the following reasons:
    Evidence of pregnancy or noncompliance with protocol-specified contraception or pregnancy monitoring
    Chronic dialysis or kidney transplantation for ESKD
    Other study drug stopping criteria may be based on investigator and subject discretion that may include fluid overload syndromes uncontrolled with diuretics and medical management, and any suspected study drug-related adverse event that represents unacceptable toxicity.
  All subjects who discontinue study drug prior to Week 132 will have an EoT visit at the time of study drug discontinuation, followed by a visit 2 weeks after study drug discontinuation and a safety follow up visit 4 weeks after study drug discontinuation. Thereafter, subjects should continue quarterly efficacy assessments for visits through Week 136/EoS.

Criteria for Evaluation: Pharmacokinetics and Pharmacodynamics

The pharmacokinetic and pharmacodynamic endpoints are:

(1) atrasentan plasma levels; and (2) Proteomic, metabolomic and transcriptomic analysis of the blood and urine for potential biomarkers of IgAN disease activity (such as galactose deficient IgA (gd-IgA) and gd-IgA auto antibodies) or factors contributing to the subject's response to atrasentan in terms of efficacy, tolerability and safety will be conducted.

(3) Pharmacogenetic (PGx) analyses may be performed on any bio-sample from subjects who have consented for PGx sampling. Subject confidentiality will be maintained. This analysis is optional.

Statistical Methods

Treatment Population Definitions:

Enrolled: All subjects who sign the informed consent form (ICF).

Intent-to-treat: All subjects randomly assigned to study drug. Subjects will be analyzed according to the intervention to which they have been randomly assigned.

Safety All subjects randomly assigned to study drug and who take at least 1 dose of study drug. Subjects will be analyzed according to the intervention they actually received Pharmacokinetic (PK) Population All randomized subjects who receive any amount of study drug and who have at least one post-baseline PK sample will comprise the PK Population. Data will be analyzed based on treatment received Safety and Tolerability:

Continuous safety data are summarised with descriptive statistics (arithmetic mean, standard deviation [SD], median, minimum, and maximum) by treatment group. Categorical safety data are summarised with frequency counts and percentages by treatment group. Adverse events are coded using the most current Medical Dictionary for Regulatory Activities (MedDRA) version available. The number of participants experiencing treatment-emergent adverse events as well as maximum severity and relationship to study drug are summarized.

Laboratory evaluations, vital signs assessments, and ECG parameters are summarised by treatment group and protocol-specified collection time point. A summary of change-from-baseline at each protocol-specified time point by treatment group are also presented. Concomitant medications are listed by participant and coded using the most current World Health Organization drug dictionary. Medical history is listed by subject. Further details regarding presentation and analysis of safety data is detailed in the Statistical Analysis Plan (SAP).

Pharmacokinetics:

Individual steady state atrasentan concentration data is listed and summarised with descriptive statistics (sample size, arithmetic mean, SD, median, minimum, maximum, geometric mean, and geometric coefficient of variation). These data may be fed into a larger population PK model of atrasentan. Correlations between atrasentan drug levels and safety or efficacy responses may be explored. Details regarding the statistical analyses of pharmacokinetic data are provided in the SAP.

Efficacy Evaluations:

Descriptive statistics are used to evaluate differences in demographic and baseline characteristics.

The primary efficacy endpoint is the change in proteinuria (UPCR) based on 24-hour urine collection) from baseline to Week 24. The primary analysis will be conducted after approximately 270 subjects in the intent-to-treat (ITT) analysis set complete the Week 24 visit or discontinue from the study. The primary analysis will be tested based on a 2-sided significance level of 0.01. Baseline and Week 24 UPCR values will be estimated as the mean of the natural log of two separate samples collected within 14 days apart prior to any study drug values.

The primary endpoint will be analyzed using a mixed-effects model repeated-measures (MMRM) model. The MMRM model will include change from baseline of natural log UPCR at each postbaseline measurement as outcomes. The model will also include the fixed effects of treatment, visit, and treatment-by-visit interaction, with covariates of baseline natural log UPCR and baseline eGFR as continuous variables and region randomization stratification factors (region: Asia vs all other regions). The covariance structure is assumed to be unstructured. Missing data will be assumed to be missing at random. UPCR data collected after dialysis, use of SGLT-2 inhibitor, or use of prohibited systemic corticosteroids will not be included in the analysis. The resulting analysis at 24-weeks will be used to assess efficacy.

Supportive and sensitivity analyses of the primary endpoint will be conducted to assess the robustness of the data and to evaluate the impact of missing data. A supportive analysis will be conducted using the analysis of covariance (ANCOVA) methodology on the point estimate of the change from baseline to Week 24 in natural log UPCR. Missing data will not be imputed and therefore assumed to be missing at random. Sensitivity analyses will be conducted including all on- and off-treatment data through the 24-week endpoint analysis with an MMRM model as described in the primary analysis. Additionally, a tipping point analysis will be conducted to assess the impact of missing data on the final endpoint. These sensitivity analyses will be further described in the SAP. Subjects missing baseline UPCR will be excluded from efficacy analyses. Subgroup analyses for clinically relevant demographic and baseline disease characteristics may be performed as specified in the SAP.

Example 6. A Randomized, Double-Blind, Placebo-Controlled Study of Atrasentan in Patients with IgA Nephropathy at Risk of Progressive Loss of Renal Function Study Overview This study is a Phase 3, double-blind, placebo-controlled study to compare the efficacy and safety of atrasentan, a selective endothelin-A receptor antagonist, to placebo in patients with IgA nephropathy at risk of progressive loss of renal function. Approximately 320 patients will be randomized 1:1 to receive atrasentan 0.75 mg daily or a matched placebo for 132 weeks while on a maximally tolerated and stable dose of a RAS inhibitor (physician choice). Patients who are unable to tolerate RAS inhibition (up to 5% of study population) may be included Study arms will be stratified according to region, and baseline urinary protein levels.

Patients will have a telephone contact for safety evaluation at week 1 and then return to clinic at week 2, 4, 6, 12, and then every 12 weeks through the completion of treatment at week 132 for safety and efficacy assessments. Pregnancy testing and patient counseling on contraception requirements will occur monthly throughout the study for women of child-bearing potential. A negative pregnancy test result will be verified by a health care provider prior to the patient being approved for continued dosing. A positive or indeterminate pregnancy test result will lead to immediate hold of study medication and a repeat serum test at the clinical trial site within 2 days. Any positive serum pregnancy test will lead to permanent treatment discontinuation. In certain regions, with approval of the lead investigator and arrangement with the sponsor, patients may have an option for monthly urine pregnancy testing at a local point of care facility/lab or at-home urine pregnancy testing with a virtual site-visit enabled by video/audio.

Patients that discontinue treatment prematurely before week 132 should remain on study for quarterly efficacy assessments to provide data for the study endpoints. Patients will return to the clinic approximately 4 weeks after the last dose of study drug. An additional blood draw should be collected approximately 2 weeks after last dose of study drug. The final study visit will occur at approximately week 136. Patients completing the study through Week 136 may be eligible to enroll in an extension study to receive open-label treatment with atrasentan under a separate protocol.

Objectives:

The primary objective of this study is:

(1) To evaluate the effect of atrasentan versus placebo on proteinuria levels at week 24 compared to placebo.

The Secondary Objectives are:

(2) To evaluate the effect of atrasentan versus placebo on change from baseline to week 136 (4 weeks post cessation of randomized treatment) in estimated glomerular filtration rate (eGFR);

(3) To compare two-year on-treatment rates of change in eGFR between atrasentan and placebo (eGFR slope week 12 to 120 of randomized treatment); and (4) To compare the total on study rates of change in eGFR between atrasentan and placebo (eGFR slope from baseline to week 136).

The Exploratory Objectives are:

(5) To compare the percentage of patients achieving a proteinuria reduction of at least 50% from baseline and to a value less than 1 g/day at week 24 between atrasentan and placebo;

(6) To evaluate the percentage of patients achieving a proteinuria level of less than 0.3 g/day at week 24;

(7) To evaluate the percentage of patients experiencing at least a 30% reduction in eGFR during the study;

(8) To evaluate the percentage of patients experiencing at least a 40% reduction in eGFR during the study;

(9) To evaluate quality of life (QOL) of patients receiving atrasentan compared to placebo; and

(10) To evaluate the steady-state pharmacokinetics of atrasentan that support exploratory exposure-response analyses.

Number of Subjects

Approximately 320 patients will be enrolled. Patients who discontinue for reasons other than safety may be replaced at the discretion of the sponsor to ensure adequate data review after at least 6 weeks of treatment.

Number of Study Sites: Approximately 120 sites worldwide Criteria for Inclusion:

The following are the inclusion criteria. Patients must meet ALL of the following inclusion criteria to be enrolled:

(1) male and female patients aged 18 and older;

(2) biopsy-proven diagnosis of IgA nephropathy not due to secondary causes;

(3) receiving a maximally tolerated stable dose of a RAS inhibitor for at least 12 weeks prior to screening;

(4) Urine protein to creatinine (UPCR) of at least 1 g/g at screening.

(5) eGFR of at least 30 mL/min/1.73 m$^2$ at screening;

(6) willing to abide with highly effective forms of contraception as specified in the protocol throughout the study; and (7) willing and able to provide written informed consent and comply with all study visits and study procedures.

Exclusion Criteria

The following are the exclusion criteria; patients must meet NONE of the following exclusion criteria to be enrolled:

(1) concurrent diagnosis of another cause of chronic kidney disease including diabetic kidney disease, hypertensive kidney disease or another primary glomerulopathy. A history of well controlled hypertension is acceptable;

(2) presence of cellular glomerular crescents in >25% of glomeruli on kidney biopsy (if biopsy available within 6 months of screening) or clinical suspicion of rapidly progressive glomerulonephritis (RPGN);

(3) history of organ transplantation;

(4) use of systemic immunosuppressant medications (or investigational agents) for at least 2 weeks in the past 6 months;

(5) blood pressure of >160 systolic or >100 diastolic at screening;

(6) history of heart failure or prior hospital admissions for conditions relating to fluid overload such as uncontrolled peripheral edema, pleural effusion, or ascites;

(7) history of clinically significant liver disease and transaminase or bilirubin values more than twice the upper limit of normal;

(8) hemoglobin below 9 g/dL at screening or prior history of blood transfusion for anemia within 3 months of screening;

(9) history of malignancy unless cancer free for at least 5 years or nonmelanoma skin cancer not requiring ongoing treatment;

(10) pregnancy, breast feeding, or intent to become pregnant during the study period for females;

(11) intent to father a child during the study period for males;

(12) have received any investigational or biologic agent within 1 month (or 5 half-lives of the agent, whichever is longer) prior to screening. If the investigational agent is a cytotoxic or immunosuppressive agent then this washout period is 6 months;

(13) concurrent clinically significant, unstable, or uncontrolled cardiovascular, pulmonary, hepatic, renal, gastrointestinal, genitourinary, haematological, coagulation, immunological, endocrine/metabolic, or other medical disorder that, in the opinion of the Investigator, might confound the results of the study or pose additional risk to the patient by their participation in the study;

(14) history of an alcohol or illicit drug-related disorder;

(15) Ongoing diagnosis of nephrotic syndrome with serum albumin <3 g/dL at screening; or

(16) Brain natriuretic peptide (BNP) value of >200 pg/mL at screening.

Note: Screening of a previously ineligible patient may be repeated with medical monitor approval.

Test Product(s), Dose, and Mode of Administration:

Patients receive either: atrasentan 0.75 mg once daily by oral administration; or matching placebo once daily by oral administration.

Atrasentan or placebo tablets will be supplied in a blinded manner in bottles with a 4-week supply (35 tablets to accommodate visit window). Patients will be instructed to take one tablet daily at approximately the same time, preferably in the morning. On days with study visits, patients should hold dosing until in clinic to enable pharmacokinetic sampling prior to dose administration as applicable. Medication can be taken with or without food. No study drug dose reductions are permitted during the study. Study drug should be temporarily halted or permanently discontinued in the event of unacceptable toxicity that cannot be managed through supportive measures.

Treatment assignment will be determined by an interactive voice/web response system (IXRS). Patients, investigators, and the sponsor will not have access to the assigned study treatment. In the event of a medical emergency the investigator will be able to receive the treatment assignment through the IXRS system if required to provide optimal care of the patient. Randomization will be stratified by region (Asia vs all other regions), baseline urinary protein levels at screening ($\geq 2$ g/day vs<2 g/day) and baseline eGFR ($\geq 60$ mL/min/1.73 m$^2$ vs<60 mL/min/1.73 m$^2$). All patients will continue to receive a maximally tolerated and stable dose of RAS inhibitor (angiotensin converting enzyme inhibitor or angiotensin-receptor blocker) of the physician's choice as per standard of care. All efforts should be made to maintain a stable dosing regimen throughout the study.

Duration of Treatment:

The study duration for an individual patient is approximately 2 years and 7 months (136 weeks) to include up to 4 weeks for screening, 132 weeks of blinded study treatment, and 4 weeks for off-treatment follow-up. Patients may provide additional consent for pre-screening to occur up to 6 months prior to the anticipated baseline visit; however, pre-screening assessments will have to be repeated for screening if performed outside of the 28-day screening window. The total duration of the study is expected to be 4-5 years. Enrolment is anticipated to last 2 to 2.5 years with the last patient completing treatment and safety follow-up approximately 2 years and 7 months later.

Criteria for Evaluation: Efficacy

The primary efficacy endpoint is the change in proteinuria (urine protein/creatinine ratio based on 24-hour urine collection) from baseline to week 24 in atrasentan-treated patients as compared to placebo-treated patients.

The key secondary efficacy endpoint is the rate of change in eGFR using the CKD-EPI creatinine equation from values at baseline through to the study completion visit (week 136) in atrasentan-treated patients as compared to placebo-treated patients. Additional secondary efficacy endpoints include: rate of change in eGFR during two years on treatment calculated from values at baseline to week 136 in atrasentan-treated patients as compared to placebo-treated patients.

Exploratory endpoints include the percent of patients achieving proteinuria reduction to less than 1 g/day at week 24 and 50% decrease from baseline, percent of patients achieving proteinuria reduction to less than 0.3 g/day at week 24, percent of patients experiencing at least a 30% reduction in eGFR during the study, and percent of patients experiencing at least a 40% reduction in eGFR during the study.

Criteria for Evaluation: Safety

Safety Endpoints Include:

(1) Type, incidence, severity, grading, seriousness, and relatedness of adverse events;

(2) Incidence, severity, seriousness, and relatedness of adverse events of special interest including events of fluid overload; and (3) Clinically significant changes in safety labs, ECGs, or physical examination findings (including vital signs).

Stopping Criteria

An independent data monitoring committee (DMC) will be appointed to monitor the study. The DMC will meet periodically to review the safety and will make recommendations regarding continuation, modification, suspension or termination of the study.

Patients will be required to discontinue study drug for the following reasons:

(1) Evidence of pregnancy or noncompliance with protocol-specified contraception or pregnancy monitoring;

(2) Initiation of high-dose steroids or other immunosuppressants or cytotoxic agents for treatment of IgAN; or (3) Chronic dialysis for ESRD.

Other study drug stopping criteria may be based on investigator and patient discretion that may include fluid overload syndromes uncontrolled with diuretics and medical management, and any suspected study drug-related adverse event that represents unacceptable toxicity. All patients who stop study drug prior to week 132 will have blood draw 2 weeks after discontinuation and a safety follow up visit after 4 weeks. Patients should continue quarterly visits through week 136 for efficacy assessments only.

Statistical Methods

Treatment Population Definitions:

Safety Population: All randomised participants who receive any amount of study drug comprise the Safety Population for safety and exposure analyses. Data will be analysed based on treatment received.

Intent-to-Treat: All randomised participants comprise the Intent-to-Treat Population for efficacy analyses. Data will be analysed based on randomized treatment assignment.

PK Population: All randomised participants who receive any amount of study drug and who have at least one post-baseline PK sample will comprise the PK Population. Data will be analysed based on treatment received.

Safety and Tolerability:

Continuous safety data are summarised with descriptive statistics (arithmetic mean, standard deviation [SD], median, minimum, and maximum) by treatment group. Categorical safety data are summarised with frequency counts and percentages by treatment group. Adverse events are coded using the most current Medical Dictionary for Regulatory Activities (MedDRA) version available. The number of participants experiencing treatment-emergent adverse events as well as maximum severity and relationship to study drug are summarized.

Laboratory evaluations, vital signs assessments, and ECG parameters are summarised by treatment group and protocol-specified collection time point. A summary of change-from-baseline at each protocol-specified time point by treatment group are also presented. Concomitant medications are listed by participant and coded using the most current World Health Organization drug dictionary. Medical history is listed by subject. Further details regarding presentation and analysis of safety data is detailed in the Statistical Analysis Plan (SAP).

Pharmacokinetics:

Individual steady state atrasentan concentration data is listed and summarised with descriptive statistics (sample size, arithmetic mean, SD, median, minimum, maximum, geometric mean, and geometric coefficient of variation). These data may be fed into a larger population PK model of atrasentan. Correlations between atrasentan drug levels and safety or efficacy responses may be explored.

Efficacy Evaluations:

The primary and key secondary efficacy endpoints of the trial will be ordered hierarchically and tested sequentially with gatekeeping procedures. The primary endpoint will be tested first, acting as the gatekeeper, and if the null hypothesis is rejected at the 1% significance level (alpha=0.01), the key secondary endpoint will be tested. The study will be deemed positive if the key secondary endpoint null hypothesis is rejected at the 5% significance level (alpha=0.05).

The primary efficacy endpoint is the change from baseline to each postbaseline visit up to week 24 in urinary protein to creatinine ratio (UPCR) as determined from 24-hour urine collection samples. As the primary analysis is considering longitudinal results, the analysis methodology will be a mixed-effects model repeated-measures (MMRM) analysis of change from baseline to each postbaseline measurement of log UPCR. The model will include the fixed effects of treatment, visit, and treatment-by-visit interaction, with covariates including randomization stratification factors (region: Asia vs all other regions; baseline urinary protein levels at screening: ≥2 g/day vs<2 g/day, and baseline eGFR≥60 mL/min/1.73 m$^2$ vs<60 mL/min/1.73 m$^2$). The covariance structure is assumed to be unstructured. The resulting analysis at 24-weeks will be used to assess efficacy. A supportive analysis will be conducted using the analysis of covariance (ANCOVA) methodology on the point estimate of the change from baseline to Week 24 in log UPCR. This analysis will be performed on the primary endpoint to evaluate the robustness of the data. Missing data will not be imputed and therefore assumed to be missing at random. Patients missing baseline UPCR will be excluded from efficacy analyses. Further sensitivity analyses may be performed to assess the impact of missing data. Subgroup analyses for clinically relevant demographic and baseline disease characteristics will be performed as specified in the statistical analysis plan.

Following the collection and analysis of primary endpoint data at week 24, patients will continue to receive their assigned blinded study treatment up until week 132 and be followed off of study drug for an additional 4 weeks to study completion at week 136 to collect additional data on eGFR decline.

The baseline and final eGFR values will be estimated as the mean of two samples at each time point to reduce variability. The baseline reference eGFR value will be determined from the mean of the screening and baseline (prior to any study drug) values and the final eGFR value will be estimated as the mean of two separate samples taken between 7 days and 35 days (inclusive of visit windows) after last dose of study drug. Estimated GFR will be determined using the Chronic Kidney Disease Epidemiology Collaboration equation. The change from baseline in eGFR for each patient will be determined by the absolute difference in values averaged at baseline and Week 136, and then normalized for individual time on study to decrease risk of bias from any differences between groups in the incidence of timing of early discontinuations from study. The endpoint will be analyzed by means of an ANCOVA with factors such as treatment group and randomization stratification factors included as independent variables.

Example 7. A Phase 3, Randomized Placebo-Controlled Study of Atrasentan and Dapagliflozin in Patients with IgA Nephropathy This example describes a Phase 3, Randomized, Double-Blind, Placebo-Controlled Study of Atrasentan in patients with IgA nephropathy) at risk of progressive loss of renal function despite treatment with a maximally tolerated and stable dose of a RAS inhibitor.

Study Overview

This example describes a randomized placebo-controlled efficacy and safety study of atrasentan, a selective endothelin-A receptor antagonist, in combination with dapagliflozin, a sodium-glucose linked transporter 2 (SGLT-2) inhibitor, in patients with IgA nephropathy. Approximately 36 patients will be randomized 1:1:1 to receive atrasentan 0.75 mg daily, atrasentan 0.75 mg daily and dapagliflozin 10 mg daily, or a matched placebo (for both atrasentan and dapagliflozin) for 4 weeks (plus a two week washout period), in addition to a maximally tolerated dose of a RAS inhibitor.

Patients will have a telephone contact for safety evaluation at week 1 and will return to clinic at week 3 and at the end of the washout period (week 6) for safety and efficacy assessments.

Objectives:

The primary objective of this study is:

(1) To evaluate the effect of atrasentan in combination with dapagliflozin versus atrasentan alone on proteinuria levels compared to placebo.

The secondary objectives are:

(2) To evaluate the effect on change from baseline in albumin to creatinine ratio over the active treatment period and washout period;

(3) To evaluate the effect on change from baseline in body weight over the active treatment period and washout period;

(4) To evaluate the effect on change from baseline in extracellular fluid (for example, measured by bio-impedance spectroscopy (Impedimed)) over the active treatment period and washout period;

(5) To evaluate the effect on change from baseline in brain natriuretic peptide (BNP) levels over the active treatment period and washout period; and (6) To evaluate the effect on change from baseline in systolic blood pressure over the active treatment period and washout period.

The exploratory objectives are:

(7) To compare the change in hematocrit from baseline to end of active treatment;

(8) To compare the change in eGFR from baseline to end of active treatment; and (9) To compare the change in eGFR from baseline to end of wash out period (2 weeks after last dose of study drug).

Number of Subjects

Approximately 36 patients will be enrolled. Patients who discontinue for reasons other than safety may be replaced at the discretion of the sponsor to ensure adequate data review after at least 6 weeks of treatment.

Number of Study Sites: Approximately 6 sites worldwide

Criteria for Inclusion:

The following are the inclusion criteria. Patients must meet ALL of the following inclusion criteria to be enrolled:

(1) male and female patients aged 18 and older;

(2) biopsy-proven diagnosis of IgA nephropathy not due to secondary causes;

(3) receiving a maximally tolerated stable dose of a RAS inhibitor for at least 4 weeks prior to screening;

(4) eGFR of at least 30 mL/min/1.73 m$^2$ at screening;

(5) willing to abide with highly effective forms of contraception as specified in the protocol throughout the study; and (6) willing and able to provide written informed consent and comply with all study visits and study procedures.

Exclusion Criteria

The following are the exclusion criteria; patients must meet NONE of the following exclusion criteria to be enrolled:

(1) concurrent diagnosis of another cause of chronic kidney disease including diabetic kidney disease, hypertensive kidney disease or another primary glomerulopathy. A history of well controlled hypertension is acceptable;

(2) concurrent diagnosis of type 1 diabetes or type 2 diabetes;

(3) brain natriuretic peptide (BNP) value of >200 pg/mL at screening;

(4) cardiovascular event within 3 months prior to screening;

(5) history of heart failure or prior hospital admissions for conditions relating to fluid overload such as uncontrolled peripheral edema, pleural effusion, or ascites;

(6) use of systemic immunosuppressant medications (or investigational agents) for at least 2 weeks in the past 6 months;

(7) blood pressure of >160 systolic or >100 diastolic at screening;

(8) history of clinically significant liver disease and transaminase or bilirubin values more than twice the upper limit of normal;

(9) hemoglobin below 9 g/dL at screening or prior history of blood transfusion for anemia within 3 months of screening;

(10) history of malignancy unless cancer free for at least 5 years or nonmelanoma skin cancer not requiring ongoing treatment;

(11) have received any investigational or biologic agent within 1 month (or 5 half-lives of the agent, whichever is longer) prior to screening. If the investigational agent is a cytotoxic or immunosuppressive agent then this washout period is 6 months;

(12) concurrent clinically significant, unstable, or uncontrolled cardiovascular, pulmonary, hepatic, renal, gastrointestinal, genitourinary, haematological, coagulation, immunological, endocrine/metabolic, or other medical disorder that, in the opinion of the Investigator, might confound the results of the study or pose additional risk to the patient by their participation in the study;

(13) history of an alcohol or illicit drug-related disorder; or

(14) Ongoing diagnosis of nephrotic syndrome with serum albumin <3 g/dL at screening.

Note: Screening of a previously ineligible patient may be repeated with medical monitor approval.

Test Product(s), Dose, and Mode of Administration:

Patients receive either: atrasentan 0.75 mg once daily by oral administration; or atrasentan 0.75 mg and dapagliflozin 10 mg, each once daily by oral administration; or matching placebo once daily by oral administration.

Treatment assignment will be determined by an interactive voice/web response system (IXRS). Patients, investigators, and the sponsor will not have access to the assigned study treatment. In the event of a medical emergency the investigator will be able to receive the treatment assignment through the IXRS system if required to provide optimal care of the patient. Randomization will be stratified by region (Asia vs all other regions), baseline urinary protein levels at screening ($\geq 2$ g/day vs<2 g/day) and baseline eGFR ($\geq 60$ mL/min/1.73 m$^2$ vs<60 mL/min/1.73 m$^2$). All patients will continue to receive a maximally tolerated and stable dose of RAS inhibitor (angiotensin converting enzyme inhibitor or angiotensin-receptor blocker) of the physician's choice as per standard of care. All efforts should be made to maintain a stable dosing regimen throughout the study.

Criteria for Evaluation: Efficacy

The primary efficacy endpoint is the change in proteinuria (urine protein/creatinine ratio based on 24-hour urine collection) from baseline to week 4 in atrasentan-treated patients and in atrasentan+dapagliflozin treated patients as compared to placebo-treated patients.

Criteria for Evaluation: Safety

Safety endpoints include:

(1) Type, incidence, severity, grading, seriousness, and relatedness of adverse events;

(2) Incidence, severity, seriousness, and relatedness of adverse events of special interest including events of fluid overload; and (3) Clinically significant changes in safety labs, ECGs, or physical examination findings (including vital signs).

Stopping Criteria

An independent data monitoring committee (DMC) will be appointed to monitor the study. The DMC will meet periodically to review the safety and will make recommendations regarding continuation, modification, suspension or termination of the study.

Safety and Tolerability:

Continuous safety data are summarised with descriptive statistics (arithmetic mean, standard deviation [SD], median, minimum, and maximum) by treatment group. Categorical safety data are summarised with frequency counts and percentages by treatment group. Adverse events are coded using the most current Medical Dictionary for Regulatory Activities (MedDRA) version available. The number of participants experiencing treatment-emergent adverse events as well as maximum severity and relationship to study drug are summarized.

Laboratory evaluations, vital signs assessments, and ECG parameters are summarised by treatment group and protocol-specified collection time point. A summary of change-from-baseline at each protocol-specified time point by treatment group are also presented. Concomitant medications are listed by participant and coded using the most current World Health Organization drug dictionary. Medical history is listed by subject.

Efficacy Evaluations:

The primary efficacy endpoint is the change from baseline to end of study proteinuria levels as determined from 24-hour urine collection samples. Following the collection and analysis of primary endpoint data at week 4, patients will be followed off of study drug for an additional 2 weeks (the washout period) to collect additional data on proteinuria levels.

Example 8. In Vivo Study Using a Mouse Model of IgA Nephropathy

The grouped ddY (g-ddY) mouse is a spontaneous model of early-onset IgA nephropathy characterized by IgA immune complex deposition in the mesangium of the kidney, leading to significant proteinuria, glomerular hypercellularity, mesangioproliferative glomerular lesions, glomerular sclerosis and reduced kidney function, all hallmarks of human IgA nephropathy (*J Am Soc Nephrol* 23: 1364-1374, 2012). Consistent with human IgA nephropathy, the mesangial IgA deposits in the g-ddY mouse are also accompanied by deposition of IgG and complement C3.

Methods

Approximately 6-week-old g-ddY mice were administered varying doses of atrasentan hydrochloride (10, 20, or 30 mg/kg/day, n=3/group) in drinking water for a duration of approximately 5 days. A separate group of 6-week-old male control g-ddY mice (n=2) received regular drinking water without atrasentan. Proteinuria was assessed as urine albumin to creatinine ratio (UACR), at baseline prior to atrasentan administration and on the final day of atrasentan administration. The effect of atrasentan on UACR was compared relative to baseline, within an individual mouse, and also to the control group who did not receive atrasentan.

RNA-sequencing (RNA-seq) was used to assess changes in gene expression in kidney tissue following administration of atrasentan to g-ddY mice at 0 (control), 10, 20, or 30 mg/kg/day. RNA isolation and sequencing libraries were generated using standard protocols. Sequencing was performed using an Illumina NextSeq500 using manufacturer's instructions with a read length of 75 bp and a read depth of 30 million. Raw data was assembled to FASTQ files. Following QC analysis, high quality sequencing reads (e.g., reads with a Phred quality score >36) were aligned to the mouse reference genome (GRCm38—mm10) using the default parameters of the align algorithm and transcript count tables of each library was generated using the default parameters of the featureCounts algorithm of the RSubread package (Liao Y, Smyth G K, Shi W, 2019). High quality sequencing reads mapped to 27,129 genes. Following additional QC of low count filtering (i.e. transcripts <10 counts across all samples), 16,207 genes were identified and used for further analysis. The remaining sequencing read counts of the included 16,207 genes were normalized to library size, log-transformed, and were quantified as counts per million (CPM). Select RNA-seq counts were validated using qPCR.

Sequencing read counts (CPM) were used for identification of differential gene expression between specified populations using the quasi-likelihood methodology of the edgeR package. Genes were considered differentially expressed between populations if they had an adjusted p-value (FDR of less than 0.05). MA plots were generated using edgeR. Heatmaps and other plots were generated using the gplots and ggplot2 package.

Analysis of gene pathways was performed using Qiagen's Ingenuity Pathway Analysis (IPA) and Gene Set Enrichment Analysis (Subramanian, et al., Gene set enrichment analysis: A knowledge-based approach for interpreting genome-wide expression profiles. Proc. Nat. Acad. Sci. USA, 102(43), 15545-15550 (2005). The outcome from the differential gene expression analysis was uploaded into the IPA system for core analysis and then overlaid with the global molecular network in the Ingenuity pathway knowledge base (IPKB). IPA was performed to identify canonical pathways and gene networks that are most significant to the differentially expressed genes identified using the analysis above. Gene expression data input into IPA did not include a fold-change threshold and the P-value filter was set at <0.001. The resulting enriched gene pathways were considered significant with Benjamin-Hochberg adjusted p-value <0.001. IPA analysis output was summarized in a heatmap with activation z-scores representing pathway enrichment in different populations. See FIG. 6. For GSEA, the differentially expressed gene list from edgeR (Robinson et al., A Bioconductor package for differential expression analysis of digital gene expression data. Bioinformatics, 26(1), 139-140 (2009) was rank ordered based on the F-statistic without arbitrary log FC or p-value thresholds. GSEA was implemented using the fgsea package (Korotkevich, et al., BioRxiv 2016, Fast gene set enrichment analysis. 1-29. https://doi.org/10.1101/060012) and the Hallmark gene set collection of MSigDB (Liberzon et al., The Molecular Signatures Database Hallmark Gene Set Collection. Cell Systems, 1(6), 417-425 (2015)).

Results

Healthy Balb/c mice without IgA nephropathy (the appropriate control strain for the g-ddY mouse) have very low, nearly undetectable levels of UACR, even through 2 years of age (Tsaih et al., 2010, Kidney International). At baseline, the grouped g-ddY mice used in this study had substantial proteinuria, with a mean (±standard error of the mean (SEM)) UACR level of 293.1±16 mg/g. The baseline albuminuria was well matched across treatment groups, with no significant differences between any groups (FIG. 4).

Effect of Atrasentan on UACR: Comparison to Baseline

Figure 4:
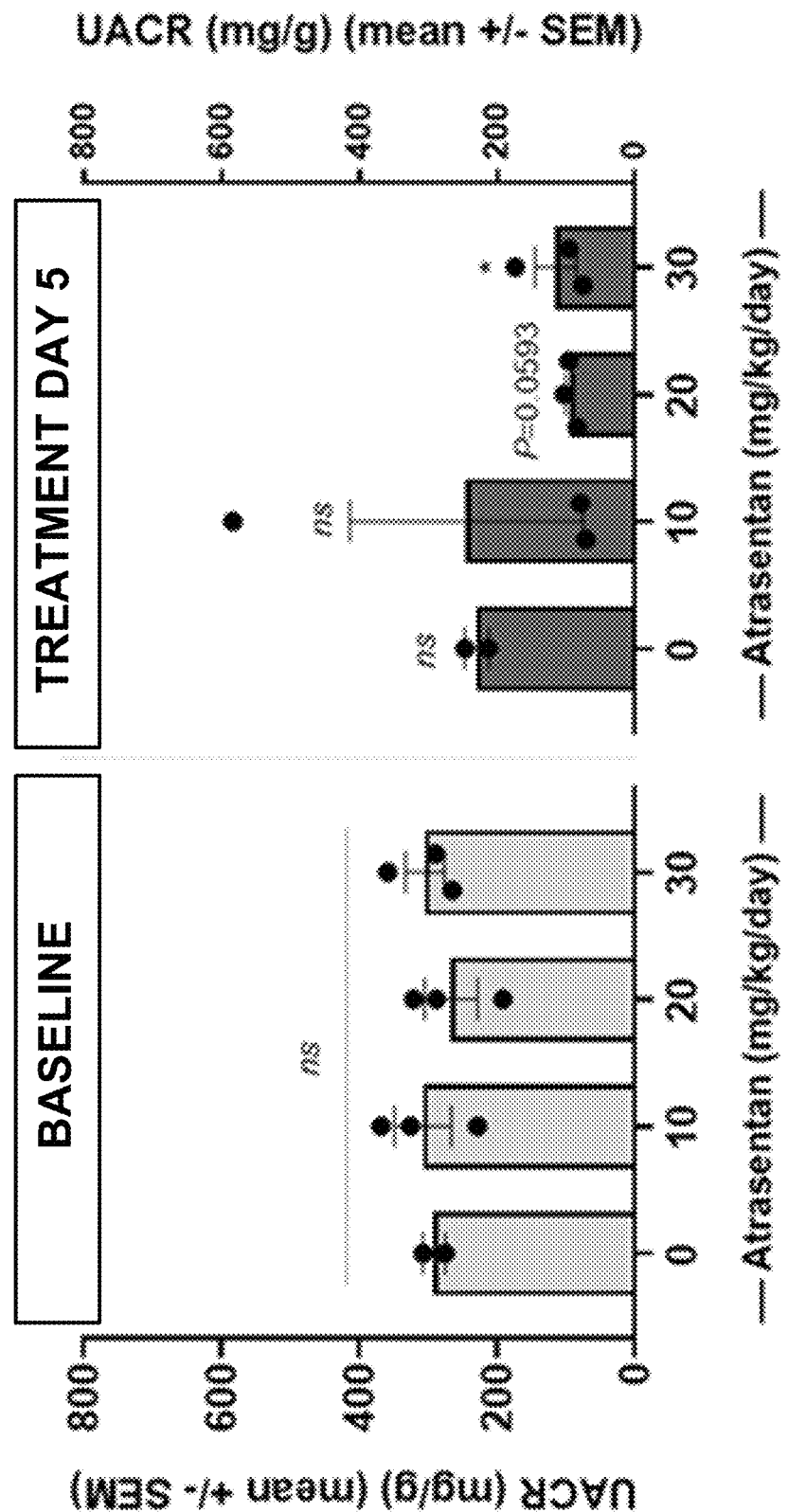
FIG. 4 illustrates UACR levels in g-ddY mice, at baseline, prior to atrasentan administration, and following approximately 5 days of treatment with atrasentan at 0 (control), 10, 20 or 30 mg/kg/day in the drinking water. (*$P<0.05$ compared to baseline levels, paired t-test).

Atrasentan treatment for approximately 5 days, at 30 mg/kg/day significantly (P=0.0002, paired two-sided t-test) reduced albuminuria from baseline (FIG. 4). Albuminuria was reduced from baseline to a similar extent by treatment with atrasentan at 20 mg/kg/day, however this effect just failed to reach statistical significance (P=0.0593) (FIG. 4). Albuminuria was not significantly changed from baseline in control g-ddY mice who did not receive atrasentan, or in the group of mice treated with atrasentan at 10 mg/kg/day; although albuminuria was reduced in ⅔ mice in this 10 mg/kg/day group (FIG. 4).

Effect of Atrasentan on UACR: Comparison to Control

Figure 5:
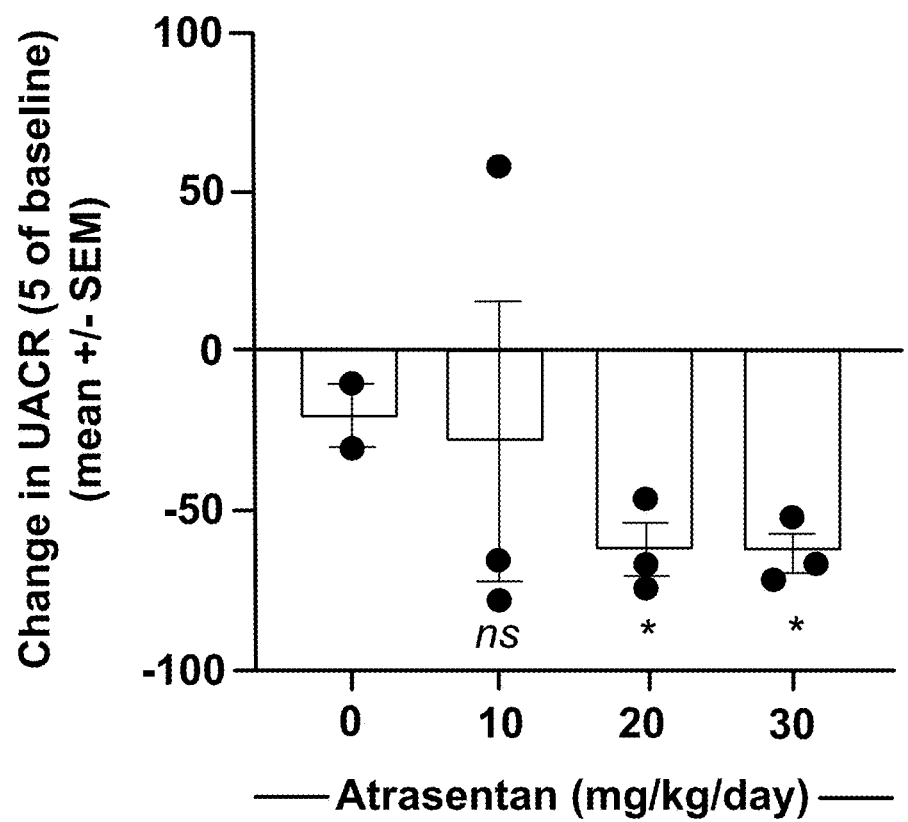
FIG. 5 illustrates the change in UACR levels (% of baseline) in g-ddY mice, following approximately 5 days of treatment with atrasentan at 0 (control), 10, 20 or 30 mg/kg/day in the drinking water. (*$P<0.05$ compared to control group (0 mg/kg/day), unpaired t-test).

The change in albuminuria from baseline (percent (%) change from baseline), following approximately 5 days of treatment with atrasentan or control is shown in FIG. 5. Atrasentan reduced UACR from baseline by 28±44%, 62±8% and 63±6% at 10, 20 and 30 mg/kg/day, respectively. The effect of atrasentan to reduce UACR from baseline at 20 mg/kg/day (P=0.0498, un-paired t-test) and 30 mg/kg/day (P=0.029), was statistically significant compared to the control group (0 mg/kg/day) (FIG. 5). However, the effect of atrasentan at 10 mg/kg/day was not significant, although again proteinuria was reduced in ⅔ mice in this 10 mg/kg/day group (FIG. 5).

Gene Expression Analysis Following Treatment with Atrasentan

Figure 6:
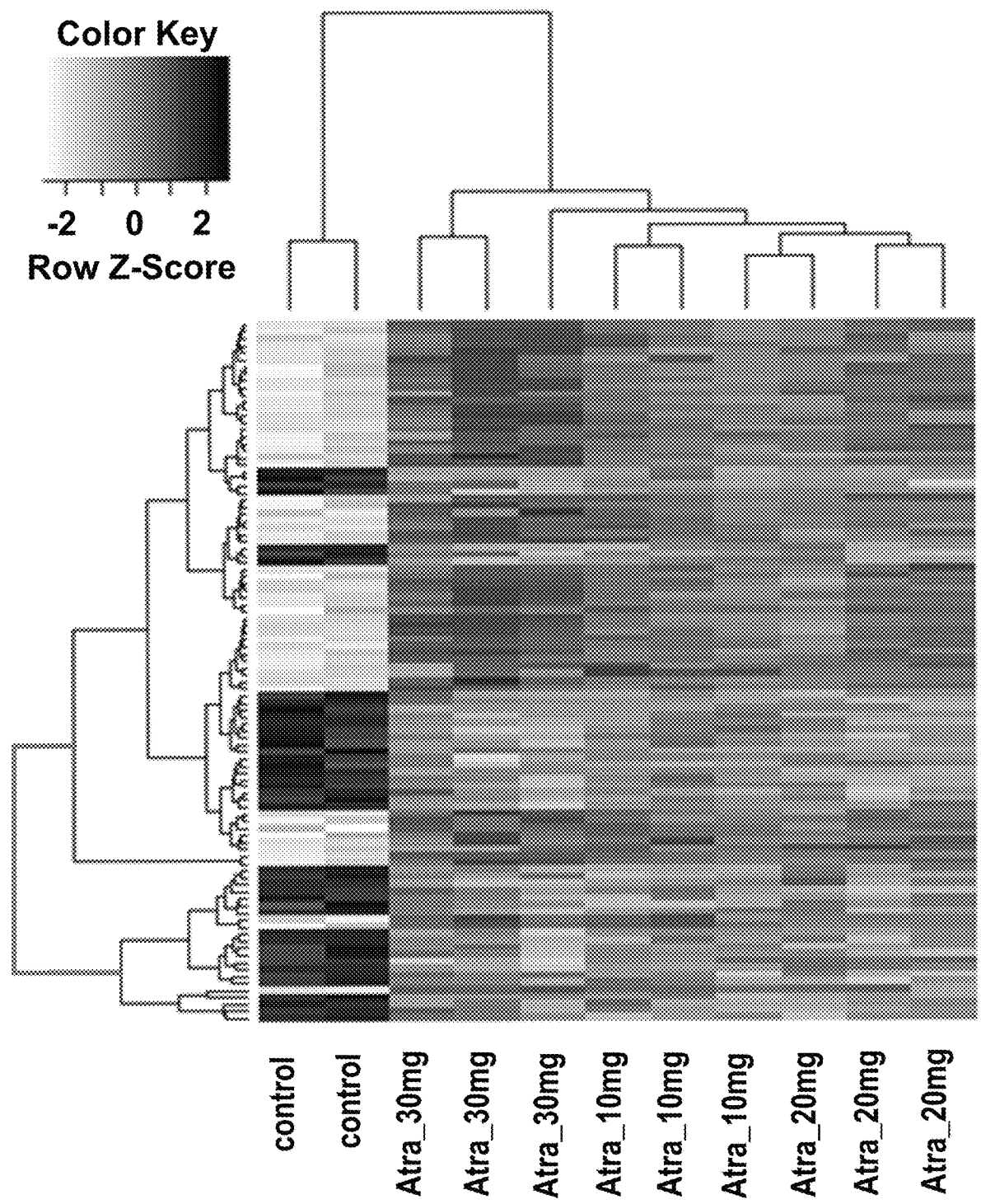
FIG. 6 illustrates the top 100 differentially expressed genes in kidney tissue following treatment of g-ddY mice with atrasentan at 0 (control), 10, 20, or 30 mg/kg/day. Heatmap shows row-wise z-transformed counts per million (CPM) values for each of the top 100 differentially expressed genes.
Figure 7A:
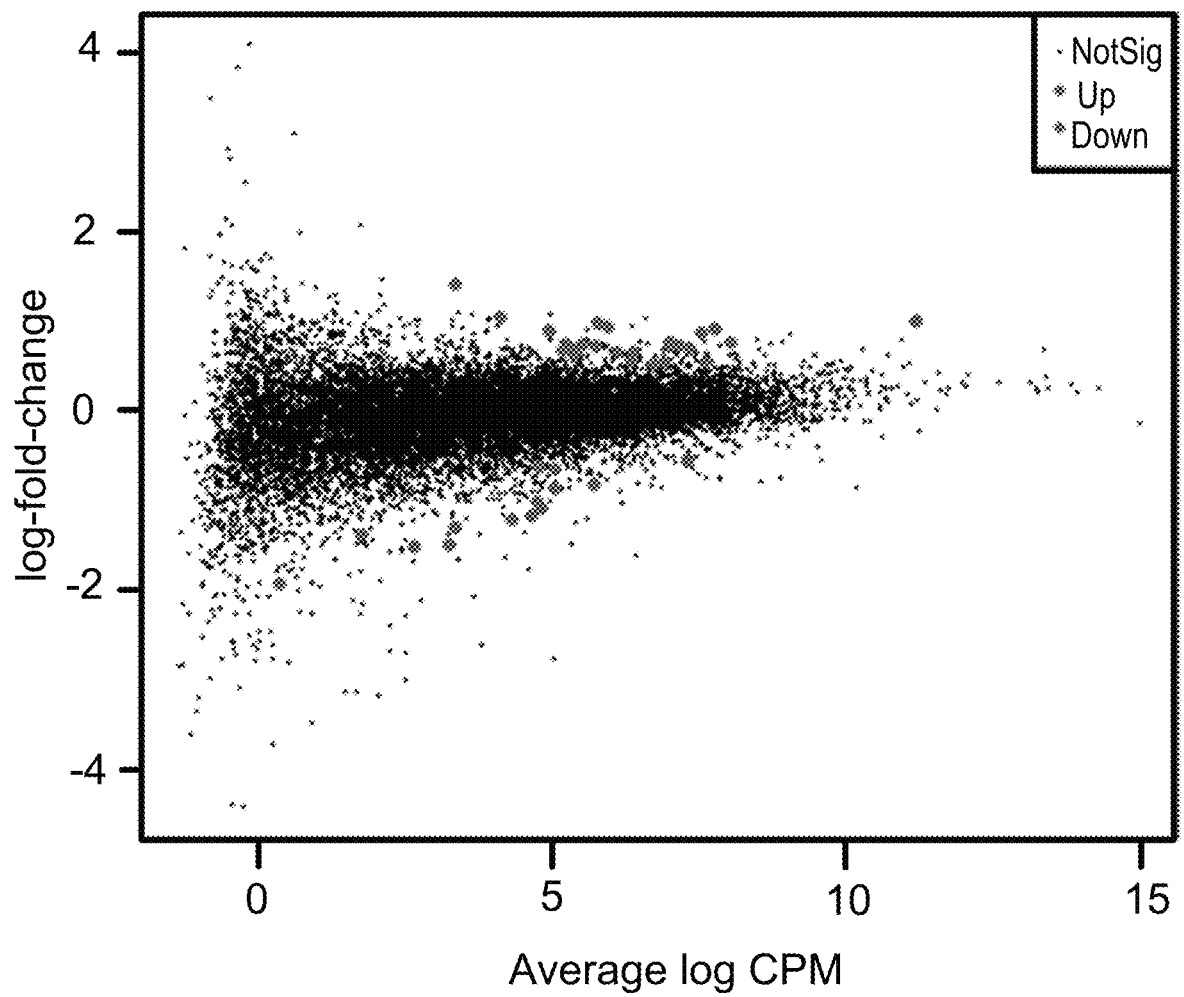
FIG. 7A illustrates differential gene expression in kidney tissue following treatment of g-ddY mice with atrasentan at 0 (control) and 10 mg/kg/day. Black dots indicate genes not significantly differentially expressed. Gray dots above 0 log-fold-change indicate upregulated genes. Gray dots below 0 log-fold change indicate downregulated genes.
Figure 7B:
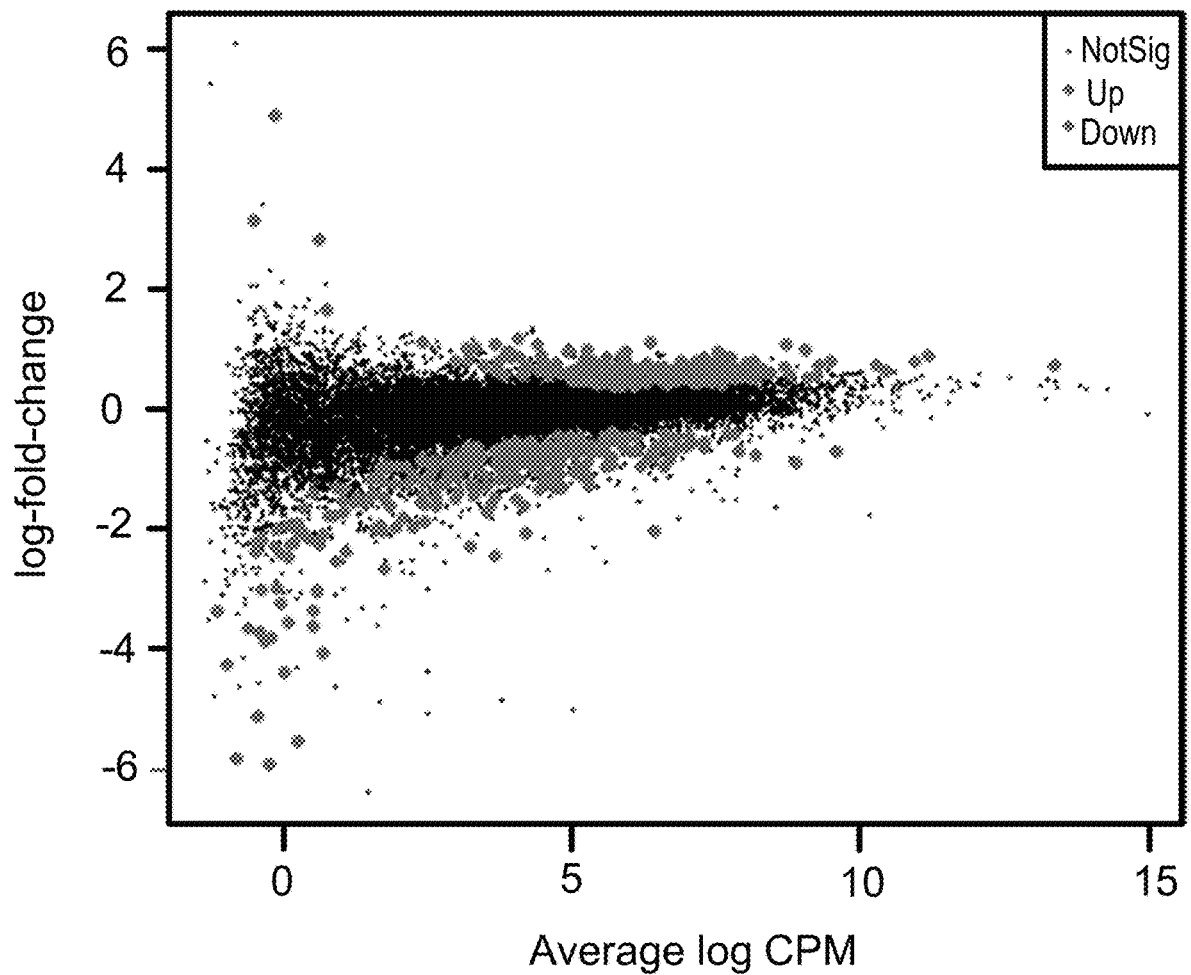
FIG. 7B illustrates differential gene expression in kidney tissue following treatment of g-ddY mice with atrasentan at 0 (control) and 20 mg/kg/day. Black dots indicate genes not significantly differentially expressed. Gray dots above 0 log-fold-change indicate upregulated genes. Gray dots below 0 log-fold change indicate downregulated genes.
Figure 7C:
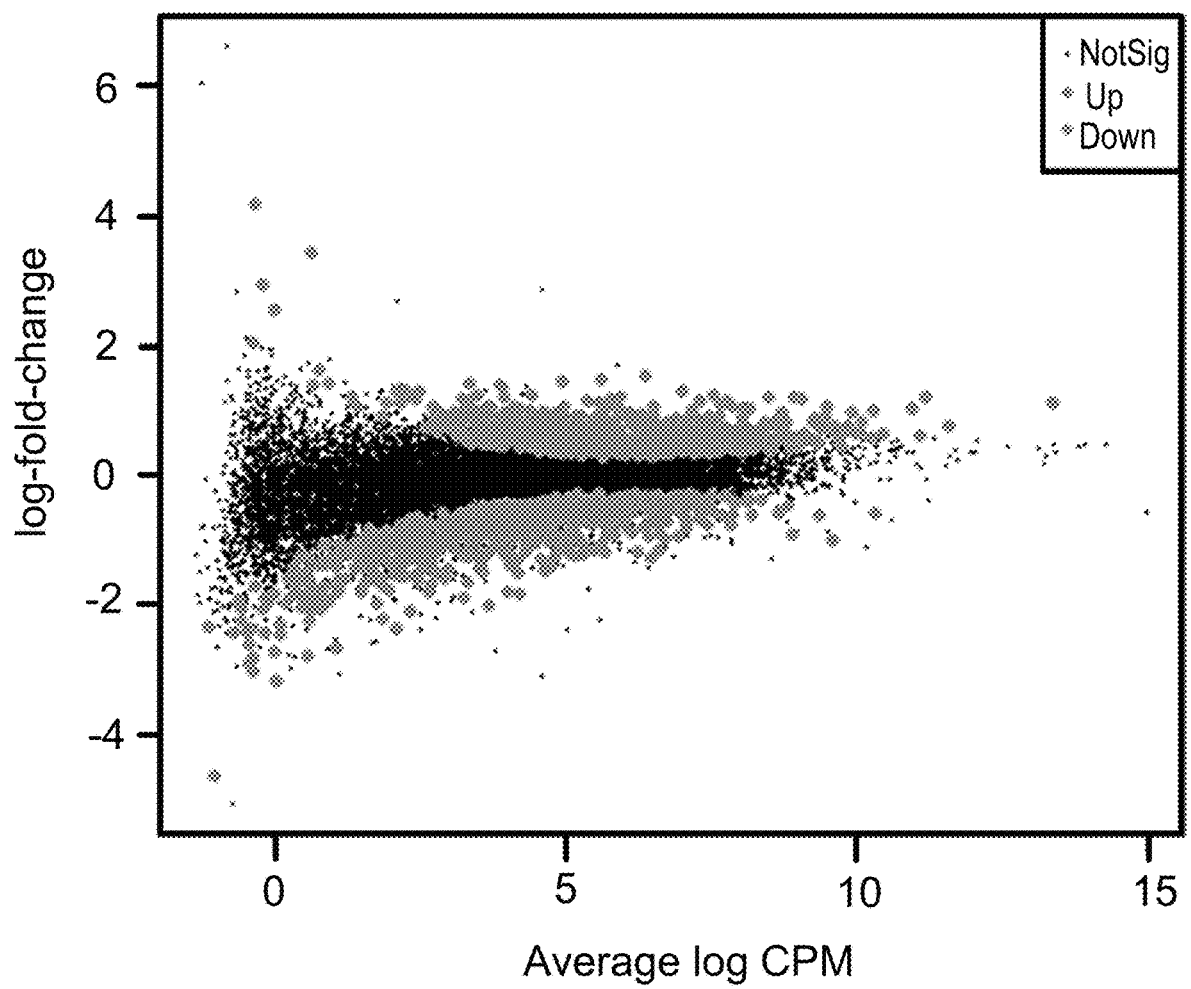
FIG. 7C illustrates differential gene expression in kidney tissue following treatment of g-ddY mice with atrasentan at 0 (control) and 30 mg/kg/day. Black dots indicate genes not significantly differentially expressed. Gray dots above 0 log-fold-change indicate upregulated genes. Gray dots below 0 log-fold change indicate downregulated genes.

Analysis of RNA-seq data provided the top 100 differentially expressed genes in kidney tissue following administration of atrasentan to g-ddY mice at 0 (control), 10, 20, or 30 mg/kg/day clustered according to disease and atrasentan treatment condition, as shown in FIG. 6 and Table 5. Pairwise comparison between 10 mg/kg/day versus control, 20 mg/kg/day versus control, and 30 mg/kg/day versus control showed dose-dependent gene expression changes (FIGS. 7A-7C). FIG. 7A shows differentially expressed genes for 10 mg/kg/day versus control where 25 genes are upregulated (+log-fold-change) and 15 genes are downregulated (−log-fold-change). Upregulated and downregulated genes from FIG. 7A are shown in Table 1. FIG. 7B shows differentially expressed genes for 20 mg/kg/day versus control where 214 genes are upregulated (+log-fold-change) and 281 genes are downregulated (−log-fold-change). The top 25 upregulated and top 25 downregulated genes from FIG. 7B are shown in Table 2. FIG. 7C shows differentially expressed genes for 30 mg/kg/day versus control where 910 genes are upregulated (+log-fold-change) and 768 genes are downregulated (−log-fold-change). The top 25 upregulated and top 25 down regulated genes from FIG. 7C are shown in Table 3.

Figure 8A:
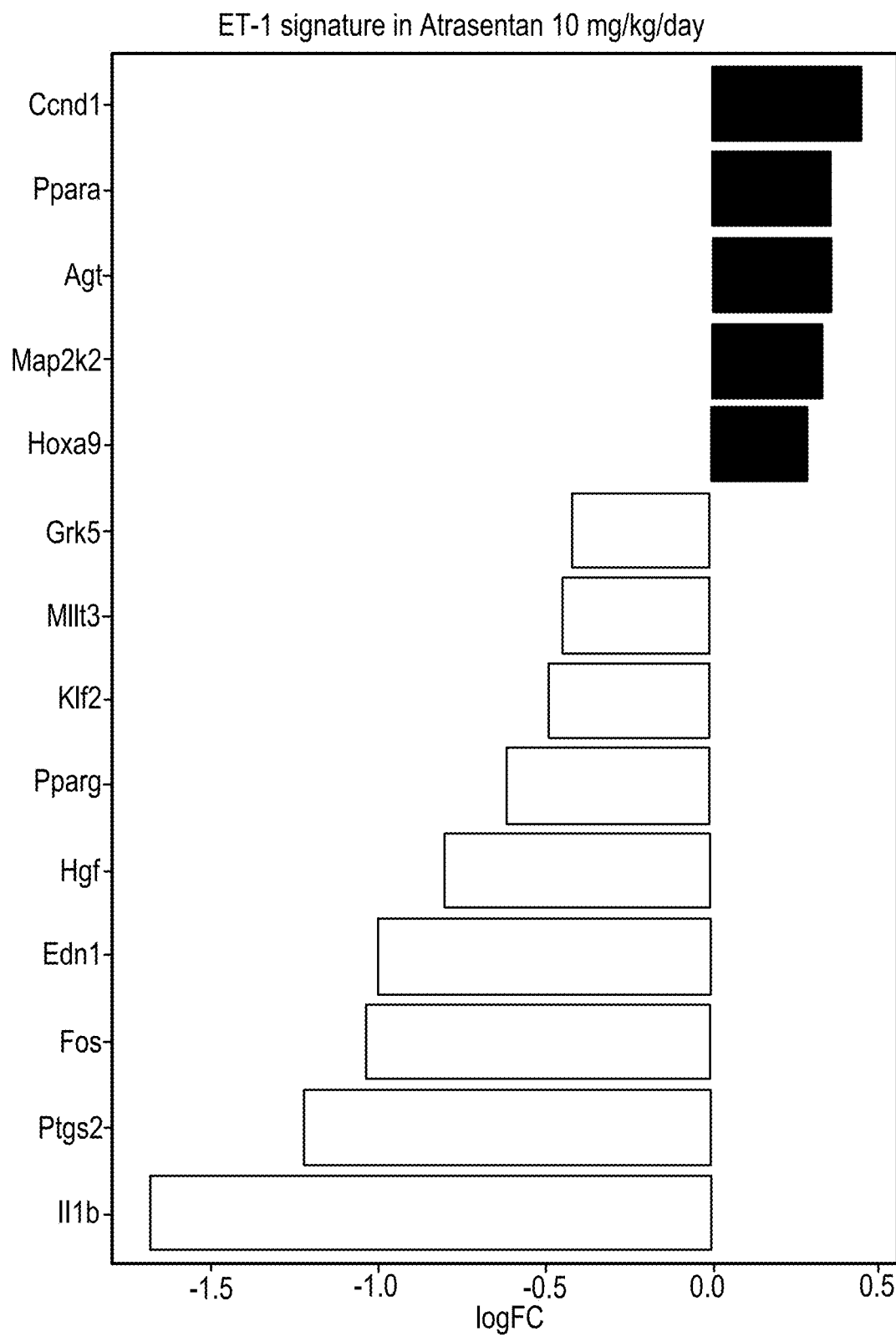
FIG. 8A illustrates differentially expressed genes in kidney tissue in a subset of genes associated with an ET1 gene signature following treatment of g-ddY mice with atrasentan at 0 (control) and 10 mg/kg/day.
Figure 8B:
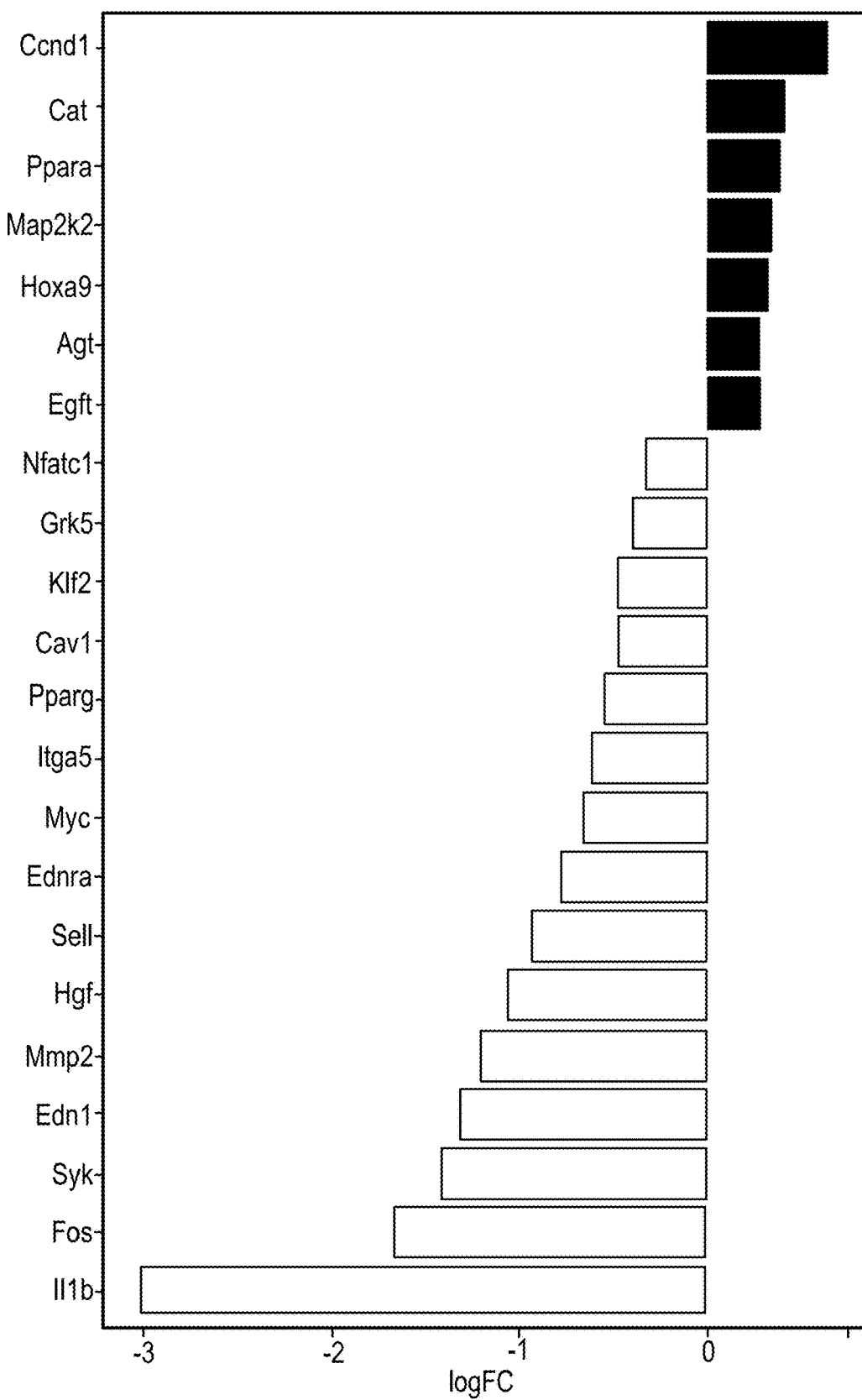
FIG. 8B illustrates differentially expressed genes in kidney tissue in a subset of genes associated with an ET1 gene signature following treatment of g-ddY mice with atrasentan at 0 (control) and 20 mg/kg/day.
Figure 8C:
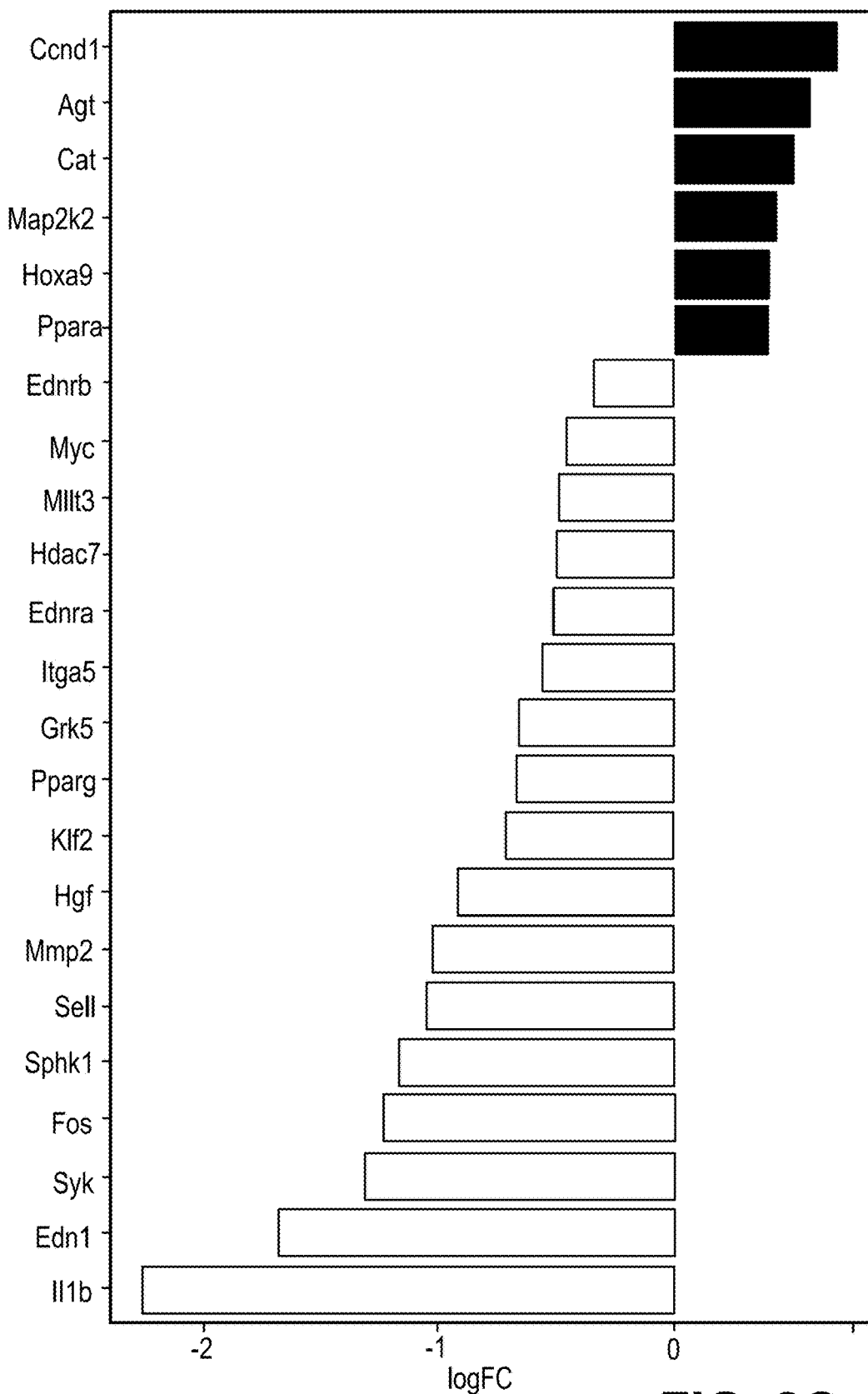
FIG. 8C illustrates differentially expressed genes in kidney tissue for a subset of genes associated with an ET1 gene signature following treatment of g-ddY mice with atrasentan at 0 (control) and 30 mg/kg/day.

Comparing gene expression changes in atrasentan treated mice with a human specific Atra/ET1 gene signature showed that 53 of 60 genes overlapped. Specifically, FIGS. 8A-8C show differential gene expression genes (p-value <0.05)

annotated as being part of the 60 genes associated with an ET1 gene signature and that are differentially expressed in mice treated with atrasentan. Gene expression analysis showed ET1 (End1) was downregulated across all three doses (FIGS. 8A-8C). In addition, Ednra and Ednrb were downregulated at 30 mg/kg/day. Of the genes that overlapped between mouse and human and were differentially expressed when comparing 10 mg/kg/day atrasentan treatment to untreated control, Ccnd1, Ppara, Agt, Map2k2 and Hoxa9 were upregulated while Grk5, M1lt3, Klf2, Pparg, Hgf, Edn1, Fos, Ptgs2, and IL-1b were downregulated (FIG. 8A). Looking at the overlapping genes that were differentially expressed when comparing 20 mg/kg/day atrasentan treatment to untreated control, FIG. 8B shows Ccdn1, Cat, Ppara, Map2k2, Hoxa9, Agt, and Egfr were upregulated while Nfatc1, Grk5, Klf2, Cav1, Pparg, Itga5, Myc, Ednra, Sell, Hgf, Mmp2, Edn1, Syk, Fos, and IL-1b were downregulated. Finally, differentially expressed genes that overlapped between species when comparing 30 mg/kg/day atrasentan treatment to untreated controls included upregulated genes Ccnd1, Agt, Cat, Map2k2, Hoxa9, and Ppara and downregulated genes Ednrb, Myc, M1lt3, Hdac7, Ednra, Itga5, Grk5, Pparg, Klf2, Hgf, Mmp2, Sell, Sphk1, Fos, Syk, Edn1, and IL-1b (FIG. 8C).

Ingenuity pathway analysis (IPA) and Gene Set Enrichment Analysis (GSEA) were applied to systematically identify pathways associated with genes differentially expressed at different dosages of atrasentan. In IPA, canonical pathways significantly enriched that include an adjusted p-value less than 0.001 without a filter on the activation z-score are shown in Table 4. IPA analysis revealed that atrasentan treatment at 30 mg/kg/day reduced NF-κB signaling, IL-6 pathway signaling (e.g., STAT3), and PDGF signaling. Tables 9-11 show specific signaling components impacted by atrasentan treatment for each of NF-κB signaling (Table 9), IL-6 signaling (Table 10), and PDGF signaling (Table 11). In addition, IPA demonstrated that atrasentan treatment induced gene expression changes that work synergistically in pathways of rescue including, for example, reduction in inflammatory and proliferative pathways. The positive and negative enriched gene sets from GSEA following atrasentan treatment are shown in Table 5. As shown in Table 5, GSEA identified concordant negative enrichment (NES<− 1.5 and adjusted p-value <0.05) indicating under-expression of hallmark signaling pathways including TNFα signaling via NF-κB, epithelial mesenchymal transition, inflammatory response, IL6-JAK-STAT3 signaling, and gene sets associated with cell-proliferation (mitotic spindle and G2M checkpoint) following treatment of g-ddY mice with atrasentan at 10, 20, and 30 mg/kg/day.

Upstream regulator analysis using Ingenuity Pathway identified the predicted activation/inactivation state of potential upstream regulatory molecules in relation to the biological processes and pathways found to be differentially regulated in the 30 mg/kg/day of atrasentan (Tables 6, 7 and 8). Tables 6, 7 and 8 show the reduction in pro-inflammation, fibrosis, and cell proliferation was the result of predicted inhibition of one or more positive regulators of inflammation, fibrosis, and cell proliferation and/or predicted activation of one or more negative regulators of inflammation, fibrosis, and cell proliferation. Predicted inhibition and activation of cytokines, growth factors, transcriptional regulators, ligand-dependent nuclear receptors, transmembrane receptors, and G-coupled protein receptors, can include, without limitation, EDN1, CCL5, CD40LG, CSF2, CSF3, CXCL2, IFNA2, IFNG, OSM, PF4, PRL, tumor necrosis family (TNF, TNFSF11, TNFSF12), TSLP, WNT3 Å, the interleukin cytokine family (IL1 Å, IL1B, IL2, IL3, IL6, IL10, IL21, IL33), TGFB1, TGFB2, TGFB3, IGF1, HGF, AGT, EGF, NRG1, PDGFB, VEGFA, FGF23, BMP2, GDF2, FGF2, IL6R, EDNRA, toll-like receptor family (TLR3, TLR4, TLR9), JUNB, YAP1, TEAD1, TEAD2, TEAD3, TEAD4, NFKB1, JUNB, STAT1, STAT3, STAT4, SMAD2, SMAD3, and SMAD4.

As shown in Table 4, 5, and 8, treatment with 30 mg/kg/day of atrasentan reduced NF-κB signaling. Components of NF-κB signaling differentially expressed following treatment with 30 mg/kg/day of atrasentan can be found in Table 9. Table 9 shows that the reduction in NK-κB signaling was the result of a decrease of one or more positive regulators of NF-κB signaling and/or increase of one or more negative regulators of NF-κB signaling. Table 9 also shows that the reduction in NK-κB signaling was also the result of modulation of one or more core components of NF-κB signaling such that NF-κB signaling was reduced. NF-κB signaling pathway components can include, without limitation, CHUK, FADD, IKBKB, IKBKG, IL1A, IL1R1, MAP3K1, MAP3K14, MAP3K7, MYD88, NFKB1, NFKBIA, RELA, RIPK1, TAB1, TNF, TNFAIP3, TNFRSF1A, TNFRSF1B, TRADD, and TRAF6 (see, e.g., BIOCARTA NFKB_PATHWAY).

As shown in Tables 5 and 10, treatment with 30 mg/kg/day of atrasentan reduced IL-6 signaling. Components of IL-6 signaling differentially expressed following treatment with 30 mg/kg/day of atrasentan can be found in Table 10. Table 10 shows the reduction in IL-6 signaling was the result of a decrease of one or more positive regulators of IL-6 signaling and/or increase of one or more negative regulators of IL-6 signaling. Table 10 also shows the reduction in IL-6 signaling was also the result of modulation of one or more core components of IL-6 signaling such that IL-6 signaling was reduced. IL-6 signaling pathway components can include, without limitation, AGT, AKT1, BAD, BCL2L1, CREBBP, CRP, GAB1, GRB2, GSK3B, HCK, HDAC1, IL6, IL6R, IL6ST, IRF1, JAK1, JAK2, JUNB, MAP2K1, MAP2K2, MAP2K4, MAP2K7, MAPK1, MAPK3, NCOA1, NLK, NR2F6, PIK3R1, PIK3R2, PRDM1, PRKCD, PTPN11, RAC1, RPS6KB1, SHC1, SOCS3, SOS1, STAT1, STAT3, TIMP1, TYK2, VAV1, and VIP (see, e.g., Wiki Pathway IL6_SIGNALING_PATHWAY).

As shown in Tables 4 and 11, treatment with 30 mg/kg/day of atrasentan reduced PDGF signaling. Components of PDGF signaling differentially expressed following treatment with 30 mg/kg/day of atrasentan can be found in Table 11. Table 11 shows the reduction in PDGF signaling was the result of a decrease of one or more positive regulators of PDGF signaling and/or an increase of one or more negative regulators of PDGF signaling. Table 11 also shows the reduction in PDGF signaling was also the result of modulation of one or more core components of PDGF signaling such that PDGF signaling was reduced. PDGF signaling pathway components can include, without limitation, ARFIP2CDC42, CHUK, ELK1, FOS, GRB2, HRAS, JAK1, JUN, MAP2K1, MAP2K4, MAP3K1, MAPK1, MAPK3, MAPK8, MT-CO2, NFKB1, NFKBIA, PAK1, PDGFA, PDGFB, PDGFRB, PIK3R1, PLA2G4 Å, PLCG1, PTPN11, RAC1, RAF1, RASA1, RHOA, SHC1, SOS1, SRC, SRF, STAT1, STAT3, TIAM1, VAV1, VAV2, and WASL (see, e.g., Wiki Pathway PDGF_PATHWAY). For example, atrasentan can inhibit the expression and/or activity of one or more PDGF signaling pathway components selected from the group of ARFIP2CDC42, CHUK, ELK1, FOS, GRB2, HRAS, JAK1, JUN, MAP2K1, MAP2K4, MAP3K1, MAPK1, MAPK3, MAPK8, MT-CO2, NFKB1, NFKBIA, PAK1, PDGFA, PDGFB, PDGFRA, PDGFRB, PIK3CG, PIK3R1, PLA2G4 Å, PLCG1, PTPN11, RAC1, RAF1, RASA1, RHOA, SHC1, SOS1, SRC, SRF, STAT1, STAT3, TIAM1, VAV1, VAV2, and WASL.

As shown in Tables 5 and 12, treatment with 30 mg/kg/day of atrasentan reduced cell proliferation associated signaling. Components of cell proliferation associated signaling (mitotic spindle and G2M checkpoint) differentially expressed following treatment with 30 mg/kg/day of atrasentan can be found in Table 12. Table 12 shows the reduction in cell proliferation associated signaling (mitotic spindle and G2M checkpoint) was the result of a decrease of one or more positive regulators of cell proliferation associated signaling (mitotic spindle and G2M checkpoint) and/or an increase of one or more negative regulators of cell proliferation associated signaling (mitotic spindle and G2M checkpoint). Table 12 also shows the reduction in cell proliferation associated signaling (mitotic spindle and G2M checkpoint) was also the result of modulation of one or more core components of cell proliferation associated signaling (mitotic spindle and G2M checkpoint) such that cell proliferation associated signaling (mitotic spindle and G2M checkpoint) was reduced. Cell proliferation associated signaling pathway (mitotic spindle and G2M checkpoint) components can include, without limitation, CCDC88A, SORBS2, RHOT2, EPB41L2, CEP192, BCAR1, PPP4R2, TUBA4A, OPHN1, CNTRL, TIAM1, NIN, MYH10, FLNA, RAPGEF5, FGD6, MYO1E, VCL, ITSN1, SMC3, MYH9, SLC12A2, DMD, CCND1, ARID4A, KMT5 Å, ATRX, SLC38A1, SLC7A1, YTHDC1, and MEIS1 (see, e.g., MSigDB HALLMARK_G2M_CHECKPOINT and HALLMARK_MITOTIC_SPINDLE).

As shown in Tables 5 and 13, treatment with 30 mg/kg/day of atrasentan reduced inflammatory response signaling. Components of inflammatory response signaling differentially expressed following treatment with 30 mg/kg/day of atrasentan can be found in Table 13. Table 13 shows the reduction in inflammatory response signaling was the result of a decrease of one or more positive regulators of cell proliferation associated signaling inflammatory response signaling and/or an increase of one or more negative regulators of inflammatory response signaling. Table 13 also shows the reduction in inflammatory response signaling was also the result of modulation of one or more core components of inflammatory response signaling such that inflammatory response signaling was reduced. inflammatory response signaling pathway components can include, without limitation, RNF144B, ROS1, SLC7A2, F3, NFKBIA, HPN, SLC4A4, CHST2, IL1B, CDKN1A, BTG2, CSF1, SLC11A2, EIF2AK2, EDN1, NFKB1, SERPINE1, SLC7A1, CCL20, IL1R1, LY6E, and GABBR1 (see, e.g., MSigDB HALLMARK_INFLAMMATORY_RESPONSE).

Figure 10:
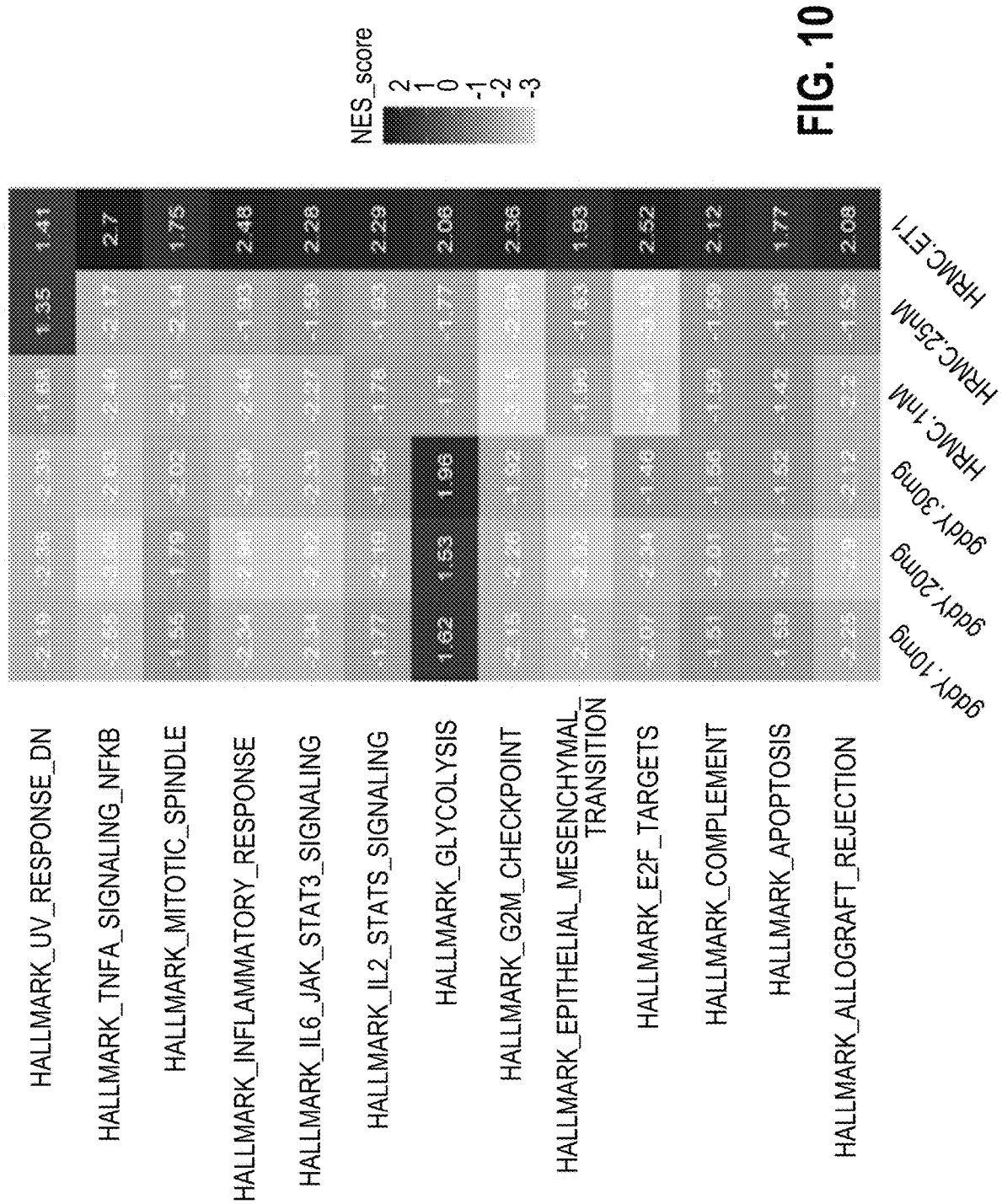
FIG. 10 illustrates the concordance of significantly enriched (FDR<0.05) hallmark gene set pathways following treatment of g-ddY mice with 10, 20 or 30 mg/kg/day compared to atrasentan at 0 (control), following treatment of ET-1 stimulated HRMC with atrasentan at 1 nM and 25 nM, and ET-1 stimulated HRMC compared to untreated HRMC (control).

Cross-validation of the impact of atrasentan treatment on hallmark gene sets across two models (g-ddY mouse model of IgAN and ET-1 treated HRMC) is shown in FIG. 10. FIG. 10 illustrates the concordance in negative enrichment scores indicating the under-expression of hallmark gene sets (i.e. TNFα signaling via NF-κB, mitotic spindle, inflammatory response, epithelial mesenchymal transition, IL2-STAT5 signaling, IL6-JAK-STAT3 signaling, G2M checkpoint, E2F targets, complement, apoptosis, and allograft rejection) as a result of atrasentan treatment in the g-ddY and HRMC model systems. Enriched gene sets following the treatment of HRMC with ET-1 compared to untreated HRMC (control) shows positive enrichment scores indicating the over-expression of the same hallmark gene sets (i.e. TNFα signaling via NF-κB, mitotic spindle, inflammatory response, epithelial mesenchymal transition, IL2-STAT5 signaling, IL6-JAK-STAT3 signaling, G2M checkpoint, E2F targets, complement, apoptosis, and allograft rejection).

Figure 11A:
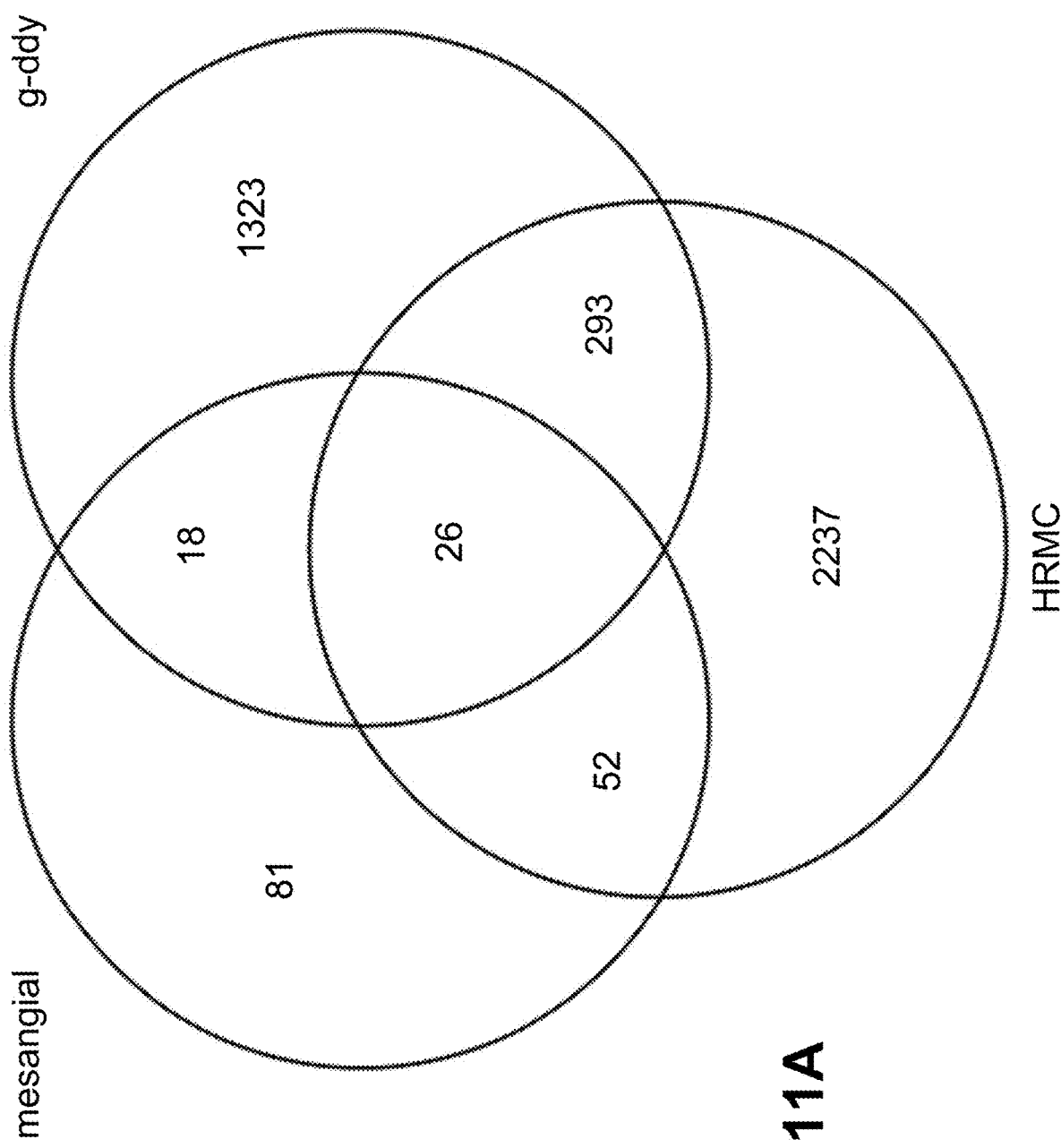
FIG. 11A illustrates the overlap in gene signature between published human mesangial single cell signature (Lake et al., A single-nucleus RNA-sequencing pipeline to decipher the molecular anatomy and pathophysiology of human kidneys. Nat. Comm., 10(1), 1-15 (2018); labeled as mesangial), differentially expressed genes following treatment of g-ddY mice with atrasentan at 30 mg/kg/day (labeled as g-ddY), and differentially expressed genes following treatment of HRMC with atrasentan at 25 nM in the presence of ET1 (labeled as HRMC).
Figure 11B:
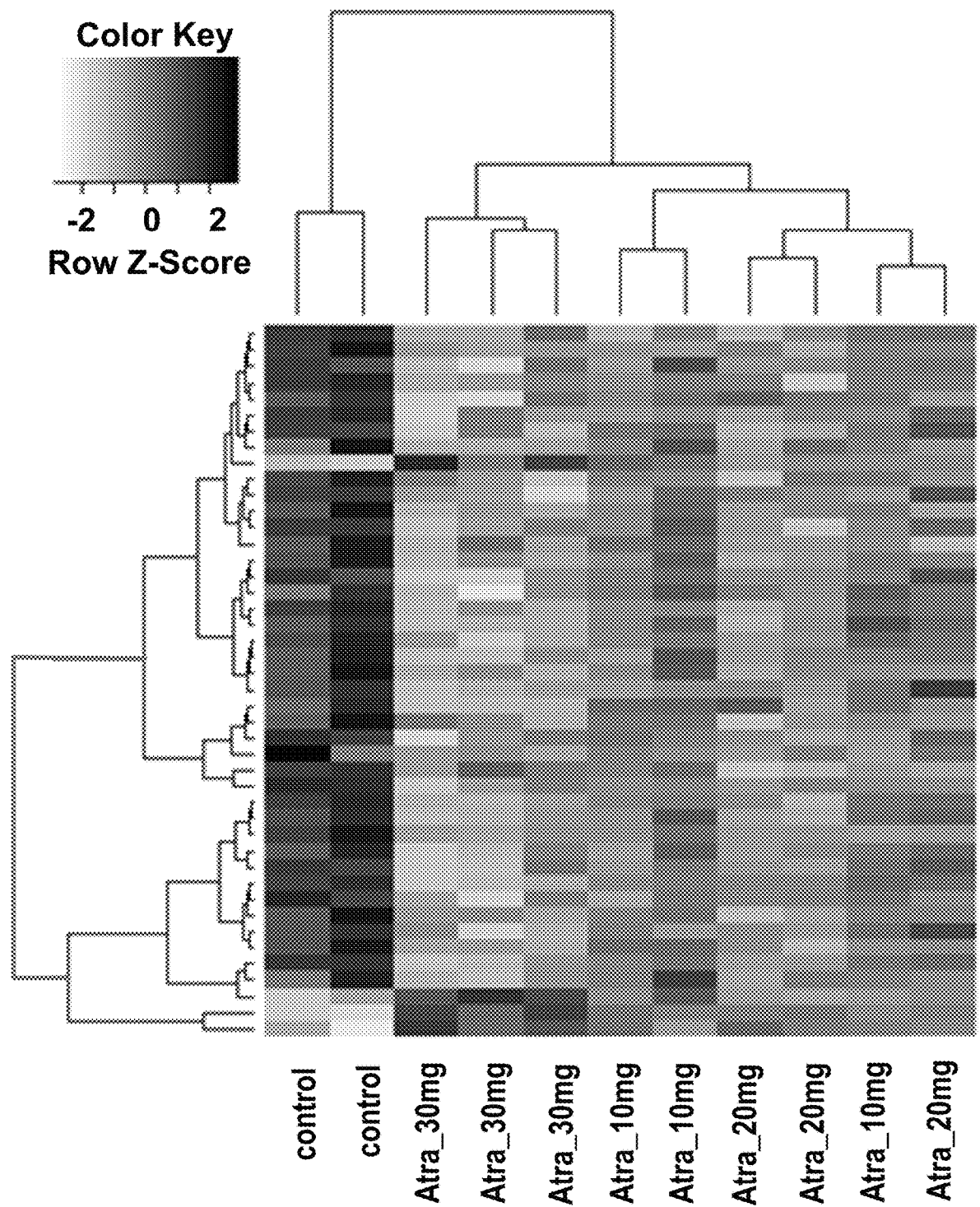
FIG. 11B illustrates the expression levels (row wise z-transformed values of log 2 counts per million) of 44 genes overlapped between human mesangial single cell signature and differentially expressed genes following treatment of g-ddY mice with atrasentan at 30 mg/kg/day.

Analysis of mesangial cell associated gene signature is shown in FIG. 11A and FIG. 11B. FIG. 11A shows the overlapping genes between differentially expressed genes following treatment of g-ddY mice with atrasentan at 30 mg/kg/day compared to treatment of atrasentan at 0 mg/kg/day (control), differentially expressed genes following treatment of HRMC with atrasentan at 25 nM in the presence of ET-1, and a published human mesangial single cell signature (Lake et al., 2018). FIG. 11B illustrates the increased and/or decreased expression levels of 44 genes associated with mesangial cell signature in g-ddY mice treated with atrasentan at 0 mg/kg/day (control) and decreased and/or increased expression levels following treatment of g-ddY mice with atrasentan at 10, 20, and 30 mg/kg/day. Components of the mesangial cell associated gene signature is shown in Table 14.

Figure 12B:
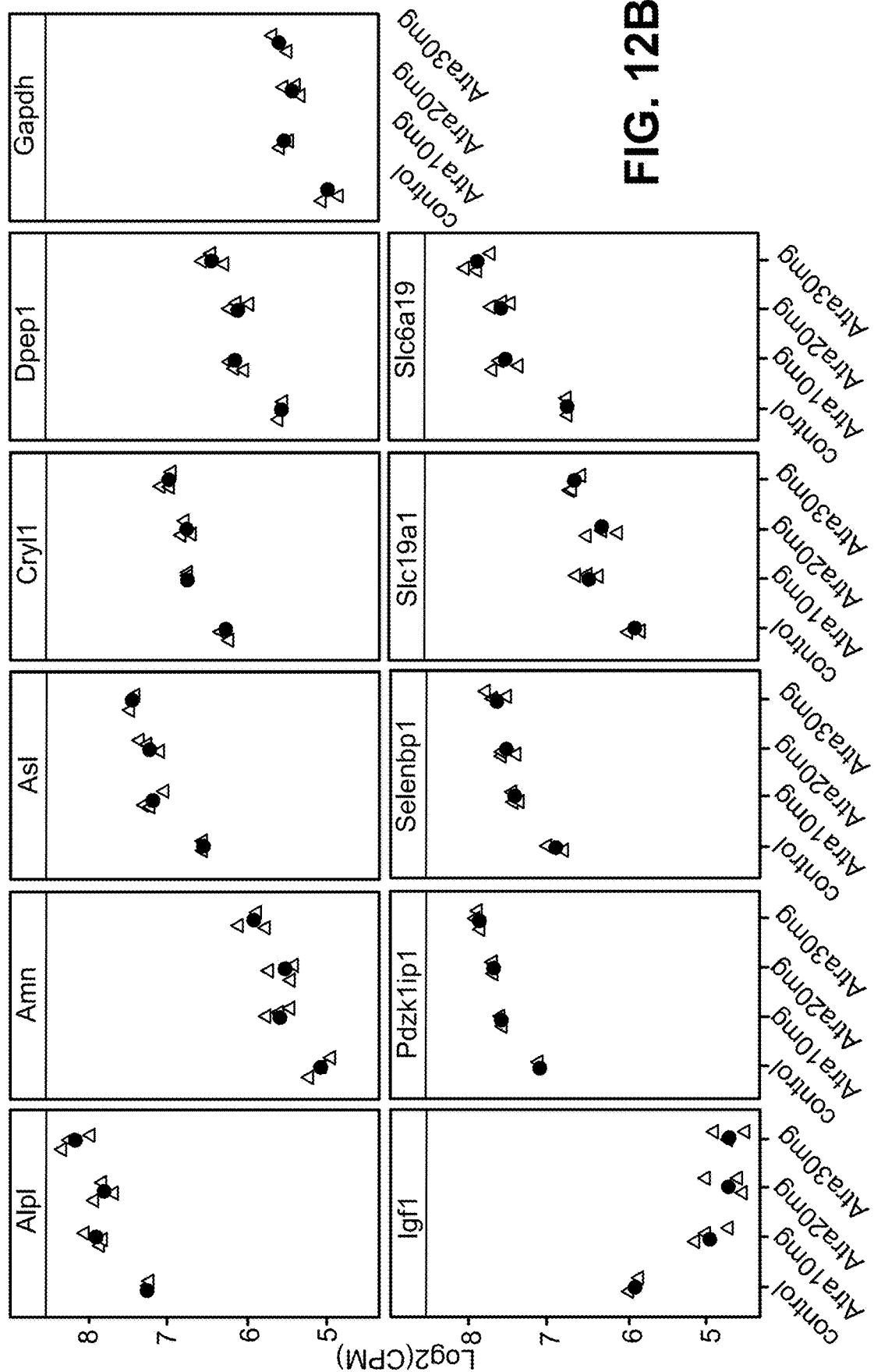
FIG. 12B illustrates log 2 (CPM) for each potential biomarker following treatment of g-ddY mice with atrasentan at 0 (control), 10, 20 or 30 mg/kg/day.

Assessment of potential biomarkers based on the RNA-seq data is shown in FIGS. 12A-12B. FIG. 12A summarizes mouse versus human translatability among the selected biomarkers: ALPL, AMN, ASL, CRYL1, DPEP1, GAPDH, IGF1, PDZK1IP1, PEBP1, SELENBP1, SLC19A1, and SLC6A19. FIG. 12A shows which of the potential biomarkers were present in plasma/serum and/or urine and whether the potential biomarker was expressed in both mouse and human. As the RNA-seq data was generated in mouse, filtering potential biomarkers based on a set of criteria, as seen in FIG. 12A, was used to limit potential future issue with lack of translatability. Gene expression changes (log 2 (CPM)) for each potential biomarker was plotted for control and atrasentan treatment at 10 mg/kg/day, 20 mg/kg/day and 30 mg/kg/day (FIG. 12B). Based on the criteria in FIG. 12A and the RNA-seq data in FIG. 12B, IGF1, DPEP1, ASL, AMN, ALPL and SLC6A19 were identified as potential biomarkers.

In summary, the gene expression analysis following atrasentan treatment showed treatment induced changes in genes that work synergistically in pathways of rescue (e.g., reduction in inflammatory and proliferative pathways). In addition, the RNA-seq data identified potential biomarkers (e.g., IGF1, DPEP1, ASL, AMN, ALPL, and SLC6A19) that can be used alongside ET-1 (EDN1), TNF, and FGF-2. Note that the overall dose-dependent changes in gene expression following treatment suggest that biomarkers and functional UACR readout can be used in conjunction.

Tables

TABLE 1

Top 40 DEGs (25 upregulated and 15 downregulated) in Atrasentan 10 mg/kg/day vs. control.

| Top 25 Upregulated Genes | | | | Top 15 Downregulated Genes | | | |
|---|---|---|---|---|---|---|---|
| Symbol | logFC | PValue | FDR | Symbol | logFC | PValue | FDR |
| Ciyl1 | 0.520646 | 7.06E-05 | 0.035738 | Apoc1 | -1.92878 | 0.000107 | 0.045268 |
| Pdzk1ipl | 0.530754 | 6.24E-05 | 0.034124 | Nr4a1 | -1.52471 | 1.11E-05 | 0.02068 |
| Slc7a9 | 0.545579 | 9.00E-05 | 0.040481 | Gem | -1.50783 | 4.30E-05 | 0.028806 |
| Bckdha | 0.549172 | 3.73E-05 | 0.028796 | Gm15910 | -1.39721 | 3.43E-05 | 0.027787 |
| Gapdh | 0.625688 | 1.93E-05 | 0.021512 | Cish | -1.30133 | 2.79E-06 | 0.015098 |
| Slc19a1 | 0.645059 | 7.31E-05 | 0.035903 | Dbp | -1.20474 | 1.42E-05 | 0.020966 |
| Dpep1 | 0.647598 | 4.23E-05 | 0.028806 | Pfkfb3 | -1.16606 | 5.04E-06 | 0.016337 |
| Mnt | 0.666881 | 2.82E-05 | 0.025402 | Ccn1 | -1.08749 | 6.74E-05 | 0.035252 |
| Hacl1 | 0.680475 | 0.000118 | 0.047742 | Mmd | -1.01248 | 1.02E-06 | 0.008642 |
| Frmd4b | 0.686272 | 5.76E-05 | 0.034124 | Igf1 | -0.87229 | 2.12E-05 | 0.021512 |
| Mapt | 0.703518 | 8.51E-05 | 0.040481 | Filip1l | -0.81857 | 2.44E-05 | 0.023255 |
| As1 | 0.707013 | 1.15E-05 | 0.02068 | Pde3b | -0.66114 | 4.28E-05 | 0.028806 |
| Bmp6 | 0.714133 | 1.99E-05 | 0.021512 | Mef2c | -0.62169 | 9.17E-05 | 0.040481 |
| Pdzd3 | 0.726782 | 2.05E-05 | 0.021512 | Zeb2 | -0.56382 | 0.000109 | 0.045268 |
| Sirt3 | 0.737604 | 9.11E-06 | 0.02068 | Ccn2 | -0.53791 | 5.98E-05 | 0.034124 |
| Slc5a2 | 0.747833 | 3.07E-05 | 0.026184 | | | | |
| S100g | 0.754604 | 5.84E-05 | 0.034124 | | | | |
| Slc6a19 | 0.85668 | 1.82E-05 | 0.021512 | | | | |
| Slc34a3 | 0.89234 | 9.24E-05 | 0.040481 | | | | |
| Acnat2 | 0.917366 | 4.44E-05 | 0.028806 | | | | |
| Ethe1 | 0.941025 | 7.89E-06 | 0.02068 | | | | |
| Slc16a1 | 0.980825 | 1.07E-06 | 0.008642 | | | | |
| Ndrg1 | 0.988732 | 4.13E-06 | 0.016337 | | | | |
| Arntl | 1.039427 | 6.32E-05 | 0.034124 | | | | |
| Npas2 | 1.41519 | 1.37E-05 | 0.020966 | | | | |

TABLE 2

Top 50 DEGs (25 upregulated and 25 downregulated) in Atrasentan 20 mg/kg/day vs. control

| Top 25 Unregulated Genes | | | | Top 25 Downregulated Genes | | | |
|---|---|---|---|---|---|---|---|
| Symbol | logFC | PValue | FDR | Symbol | logFC | PValue | FDR |
| Glis1 | 0.877569 | 0.000497 | 0.033022 | Lep | -5.90482 | 0.000285 | 0.027287 |
| Klf15 | 0.87985 | 9.74E-05 | 0.020853 | Otop1 | -5.80751 | 0.000198 | 0.026094 |
| Ndrg1 | 0.894577 | 1.19E-05 | 0.011184 | Para1l | -5.13251 | 0.000207 | 0.026429 |
| Prodh | 0.898674 | 5.01E-05 | 0.0167936 | Sprr2a3 | -4.40323 | 0.00025 | 0.026639 |
| Lhx1 | 0.925842 | 0.000382 | 0.029887 | C5ar2 | -4.27061 | 0.000429 | 0.031245 |
| Pfn3 | 0.93398 | 0.000559 | 0.033736 | Bche | -4.06216 | 0.000249 | 0.026639 |
| Slc34a3 | 0.934522 | 5.82E-05 | 0.017159 | Ivl | -3.8887 | 0.000596 | 0.034028 |
| Cndp1 | 0.937324 | 0.000184 | 0.025434 | Dio2 | -3.82328 | 5.45E-05 | 0.016936 |
| Morn2 | 0.937472 | 0.000256 | 0.026639 | Ebf2 | -3.71451 | 0.000316 | 0.028532 |
| Tmem37 | 0.943864 | 8.88E-05 | 0.019978 | Plekhs1 | -3.66111 | 0.000155 | 0.023432 |
| Pvalb | 0.944123 | 0.001322 | 0.047017 | Apol6 | -3.61598 | 2.86E-05 | 0.016936 |
| Slc6a19 | 0.958468 | 5.59E-06 | 0.009287 | Ccl20 | -3.56331 | 0.000567 | 0.033736 |
| Aspdh | 0.964605 | 0.000115 | 0.021249 | Ankef1 | -3.38241 | 0.000347 | 0.029573 |
| Hao2 | 0.985461 | 0.00074 | 0.037501 | Ly6d | -3.37673 | 0.000848 | 0.040407 |
| Cyp4b1-ps2 | 1.004361 | 0.000176 | 0.025048 | Nat8l | -3.26334 | 0.000359 | 0.029887 |
| Npas2 | 1.011763 | 0.000377 | 0.029887 | Krt5 | -3.04126 | 0.001278 | 0.046755 |
| Clec2h | 1.077782 | 0.000267 | 0.026652 | Il1b | -3.02945 | 0.000263 | 0.026639 |
| Dnase1 | 1.085844 | 0.000173 | 0.024747 | A530016L24Rik | -3.02722 | 0.000155 | 0.023432 |
| Ftcd | 1.086278 | 0.000998 | 0.042127 | | | | |
| Frs3 | 1.093787 | 0.000444 | 0.031697 | Ccl8 | -2.99918 | 0.000577 | 0.033797 |
| Ren1 | 1.117496 | 0.000566 | 0.033736 | Abcd2 | -2.68553 | 9.78E-06 | 0.011184 |
| Fcamr | 1.182032 | 1.22E-05 | 0.011184 | Lgals12 | -2.53645 | 5.63E-05 | 0.016936 |
| 1700101I11Rik | 1.65775 | 0.000966 | 0.041578 | Adcy2 | -2.48445 | 0.000234 | 0.026429 |
| Igfbp1 | 2.820036 | 0.000497 | 0.033022 | Prkar2b | -2.46803 | 0.000194 | 0.026008 |
| Hrg | 4.888319 | 0.000192 | 0.025954 | Cadm3 | -2.43878 | 0.001079 | 0.04323 |
| | | | | Tns4 | -2.38111 | 0.00111 | 0.043442 |

TABLE 3

Top 50 DEGs (25 upregulated and 25 downregulated) in Atrasentan 30 mg/kg/day vs. control

| Top 25 Upregulated Genes | | | | Top 25 Downregulated Genes | | | |
|---|---|---|---|---|---|---|---|
| Symbol | logFC | PValue | FDR | Symbol | logFC | PValue | FDR |
| Frs3 | 1.17584 | 0.000241 | 0.01131 | Clec4d | −4.65021 | 0.004497 | 0.046687 |
| Slc16a1 | 1.178285 | 1.26E-07 | 0.000796 | Adamts17 | −3.19106 | 0.001153 | 0.023207 |
| Ndrg1 | 1.197276 | 5.02E-07 | 0.000796 | A530016L24Rik | −3.0348 | 0.000191 | 0.010045 |
| G6pc | 1.206971 | 0.000984 | 0.021884 | Arhgap36 | −2.90784 | 0.00497 | 0.04903 |
| Ethe1 | 1.210571 | 4.78E-07 | 0.000796 | Rnf182 | −2.81664 | 0.00456 | 0.046915 |
| Calb1 | 1.211236 | 1.55E-05 | 0.003454 | Fam163b | −2.78491 | 5.34E-05 | 0.00548 |
| Clec2h | 1.21514 | 9.25E-05 | 0.00704 | Igkv3-5 | −2.72187 | 0.004931 | 0.048844 |
| Slc6a19 | 1.238229 | 3.26E-07 | 0.000796 | Cxcl2 | −2.6664 | 0.004478 | 0.04664 |
| Pgam2 | 1.24014 | 1.46E-05 | 0.003454 | Xirp2 | −2.61909 | 0.002983 | 0.037627 |
| Mogat2 | 1.285346 | 0.000444 | 0.015136 | Ccl20 | −2.47108 | 0.004346 | 0.045771 |
| Nepn | 1.290765 | 0.000594 | 0.017346 | Tns4 | −2.44271 | 0.001081 | 0.022699 |
| Nkx3-1 | 1.29376 | 0.002691 | 0.035636 | Kcnk2 | −2.43099 | 0.001377 | 0.025337 |
| S100g | 1.295748 | 1.68E-07 | 0.000796 | Plch2 | −2.42276 | 0.003667 | 0.041761 |
| Misp3 | 1.307023 | 0.000755 | 0.019283 | Ebf2 | −2.38601 | 0.003955 | 0.043366 |
| Cyp27b1 | 1.350092 | 0.00012 | 0.008122 | E030018B13Rik | −2.37324 | 5.79E-07 | 0.000796 |
| Pvalb | 1.388586 | 4.38E-05 | 0.004946 | Ankef1 | −2.3582 | 0.003009 | 0.037799 |
| Npas2 | 1.393557 | 1.65E-05 | 0.003454 | Adcy2 | −2.32735 | 0.000415 | 0.014673 |
| Chadl | 1.409504 | 0.003796 | 0.042633 | Il1b | −2.26303 | 0.001846 | 0.029185 |
| Slc34a3 | 1.435992 | 5.69E-07 | 0.000796 | Stx1b | −2.24452 | 0.000525 | 0.016224 |
| Cyp2d26 | 1.463625 | 0.00016 | 0.00927 | Alf3 | −2.21952 | 0.002193 | 0.031678 |
| Ren1 | 1.530684 | 4.64E-05 | 0.005079 | Kif1a | −2.10828 | 0.000147 | 0.008889 |
| 1700101I11Rik | 1.613376 | 0.00129 | 0.024488 | 1700003D09Rik | −2.08702 | 0.003352 | 0.039918 |
| Cyp2d37-ps | 2.922005 | 0.002459 | 0.033932 | Gm20026 | −2.0755 | 0.002092 | 0.031103 |
| Igibp1 | 3.447021 | 5.49E-05 | 0.005512 | Wnt10a | −2.07117 | 0.003982 | 0.043533 |
| Bhmt | 4.173438 | 0.000315 | 0.012685 | Fat3 | −2.06711 | 0.000583 | 0.017174 |

TABLE 4

The enriched signaling pathways following treatment of g-ddY mice with atrasentan at 0 (control), 10, 20 or 30 mg/kg/day. Z-score values indicate the magnitude of the effect seen at each dosage.

| Canonical Pathways | Atra_10 mg | Atra_20 mg | Atra_30 mg |
|---|---|---|---|
| Oxidative Phosphorylation | −0.309 | −0.283 | 7.02 |
| Folate Polyglutamylation | −1 | 0.447 | 1.342 |
| PTEN Signaling | −0.426 | 1.029 | 2.214 |
| Apelin Cardiac Fibroblast Signaling Pathway | 1.134 | 0.577 | 1.732 |
| NRF2-mediated Oxidative Stress Response | 0.471 | −0.392 | 1.3 |
| Glutathione Redox Reactions I | −0.302 | −0.277 | 2.496 |
| Tryptophan Degradation III (Eukaryotic) | 0.378 | −1.265 | 3.742 |
| TCA Cycle II (Eukaryotic) | 0.277 | −0.535 | 3.207 |
| Glycolysis I | 0.577 | 0 | 3.051 |
| Gluconeogenesis I | 0.905 | −0.302 | 3.464 |
| Cardiac Hypertrophy Signaling (Enhanced) | 0.361 | −0.396 | −6.236 |
| Hepatic Fibrosis Signaling Pathway | −0.25 | −3.181 | −5.058 |
| PDGF Signaling | −0.5 | −2.353 | −3.528 |
| GP6 Signaling Pathway | 0 | −1.715 | −4.938 |
| NF-KB Signaling | 0.507 | −1.313 | −4.636 |
| PI3K Signaling in B Lymphocytes | 0.426 | −1.333 | −4.041 |
| NF-KB Activation by Viruses | 0 | −0.816 | −3.9 |
| PEDF Signaling | 0 | −1.043 | −3.922 |
| Sperm Motility | 1.213 | 1.633 | −2.263 |
| Sirtuin Signaling Pathway | 0.849 | 0.62 | −1.254 |
| Xenobiotic Metabolism General Signaling Pathway | −0.577 | −1.581 | −0.152 |
| Ga12/13 Signaling | −1.279 | −0.707 | −0.949 |
| TNFR2 Signaling | −1.89 | 0 | −1.291 |
| Relaxin Signaling | −0.535 | −0.853 | −2.449 |
| Paxillin Signaling | −1 | −0.626 | −2.268 |
| Integrin Signaling | −0.928 | −1.342 | −3.311 |
| Acute Phase Response Signaling | −1.177 | −1.298 | −2.832 |
| Small Cell Lung Cancer Signaling | −0.905 | −1.886 | −2.236 |
| Lymphotoxin f3 Receptor Signaling | −1.508 | −1.291 | −2.183 |
| GM-CSF Signaling | −0.243 | −1.46 | −1.225 |
| Acute Myeloid Leukemia Signaling | −0.258 | −0.853 | −1.134 |
| Sphingosine-1-phosphate Signaling | −0.218 | −0.73 | −1.808 |
| PI3K/AKT Signaling | 0.447 | −0.18 | −1.947 |
| IGF-1 Signaling | 0.243 | −0.408 | −1.633 |
| Glioblastoma Multiforme Signaling | 1 | −0.16 | −3.464 |
| Thrombin Signaling | 1.3 | −0.926 | −2.828 |
| Gαq Signaling | 1 | −0.822 | −2.16 |
| Glioma Signaling | 0.5 | −0.816 | −2.353 |
| IL-8 Signaling | 0.365 | −0.905 | −2.828 |
| HGF Signaling | −0.688 | 0 | −3.182 |
| Toll-like Receptor Signaling | −0.302 | −0.258 | −2.982 |
| Macropinocytosis Signaling | 0.277 | 0.243 | −2.828 |
| LPS/IL-1 Mediated Inhibition of RXR Function | 0.535 | 0.626 | −2.746 |
| STAT3 Pathway | −0.218 | 0.192 | −2.556 |
| CXCR4 Signaling | 0 | 0.333 | −2.214 |

TABLE 5

Gene Set Enrichment Analysis showing enrichment in hallmark gene sets following treatment of g-ddY mice with atrasentan at 0 (control), 10, 20 or 30 mg/kg/day. NES is the normalized enrichment score indicating accounting for gene set size. NES of <−1.5 or <1.5 was considered to be biologically significant. Adj p-value is the estimated probability that the results of the given enriched gene set is a false positive finding.

| Pathway | Atrasentan 10 mg/kg/day vs. control | | Atrasentan 20 mg/kg/day vs. control | | Atrasentan 30 mg/kg/day vs. control | |
| --- | --- | --- | --- | --- | --- | --- |
| | Adj p-value | NES | Adj p-value | NES | Adj p-value | NES |
| HALLMARK_ADIPOGENESIS | 6.03E-09 | 2.15 | 3.57E-10 | 2.26 | 6.25E-10 | 2.64 |
| HALLMARK_ALLOGRAFT_REJECTION | 1.42E-09 | −2.25 | 3.57E-10 | −2.90 | 2.41E-07 | −2.12 |
| HALLMARK_ANDROGEN_RESPONSE | 0.75 | 0.88 | 0.46 | 1.03 | 0.67 | 0.92 |
| HALLMARK_ANGIOGENESIS | 7.37E-04 | −1.94 | 1.80E-05 | −2.19 | 3.42E-03 | −1.86 |
| HALLMARK_APICAL_JUNCTION | 1.06E-04 | −1.79 | 3.57E-10 | −2.24 | 1.23E-06 | −2.00 |
| HALLMARK_APICAL_SURFACE | 5.06E-02 | −1.52 | 8.79E-03 | −1.67 | 0.03 | −1.65 |
| HALLMARK_APOPTOSIS | 2.22E-03 | −1.59 | 1.04E-08 | −2.17 | 6.12E-03 | −1.52 |
| HALLMARK_BILE_ACID_METABOLISM | 6.97E-06 | 2.08 | 4.69E-09 | 2.39 | 1.42E-08 | 2.40 |
| HALLMARK_CHOLESTEROL_HOMEOSTASIS | 0.47 | 1.03 | 0.46 | −1.03 | 0.27 | 1.14 |
| HALLMARK_COAGULATION | 1.38E-2 | −1.53 | 4.51E-07 | −2.11 | 6.12E-03 | −1.56 |
| HALLMARK_COMPLEMENT | 7.80E-03 | −1.51 | 3.81E-07 | −2.01 | 3.50E-03 | −1.56 |
| HALLMARK_DNA_REPAIR | 0.94 | 0.79 | 0.93 | 0.83 | 3.50E-03 | 1.52 |
| HALLMARK_E2F_TARGETS | 3.92E-08 | −2.07 | 3.57E-10 | −2.34 | 1.19E-02 | −1.46 |
| HALLMARK_EPITHELIAL_MESENCHYMAL_TRANSITION | 8.33E-10 | −2.47 | 3.57E-10 | −2.92 | 6.25E-10 | −2.60 |
| HALLMARK_ESTROGEN_RESPONSE_EARLY | 0.09 | −1.27 | 3.84E-03 | −1.52 | 0.10 | −1.22 |
| HALLMARK_ESTROGEN_RESPONSE_LATE | 0.18 | −1.18 | 2.80E-02 | −1.37 | 0.18 | 1.16 |
| HALLMARK_FATTY_ACID_METABOLISM | 5.83E-09 | 2.25 | 3.57E-10 | 2.51 | 6.25E-10 | 2.90 |
| HALLMARK_G2M_CHECKPOINT | 4.73E-09 | −2.15 | 3.57E-10 | −2.26 | 4.82E-06 | −1.92 |
| HALLMARK_GLYCOLYSIS | 3.80E-04 | 1.62 | 1.52E-03 | 1.53 | 1.10E-06 | 1.96 |
| HALLMARK_HEDGEHOG_SIGNALING | 5.56E-02 | −1.51 | 8.79E-03 | −1.72 | 1.76E-03 | −1.94 |
| HALLMARK_HEME_METABOLISM | 1.38E-04 | 1.57 | 4.00E-06 | 1.92 | 2.51E-07 | 1.99 |
| HALLMARK_HYPDXIA | 2.81E-02 | −1.38 | 1.65E-02 | −1.62 | 0.17 | −1.18 |
| HALLMARK_IL2_STATS_SIGNALING | 1.28E-04 | −1.77 | 1.38E-09 | −2.20 | 3.44E-03 | −1.56 |
| HALLMARK_L6_JAK_STAT3_SIGNALING | 9.50E-08 | −2.34 | 3.57E-10 | −2.92 | 1.07E-07 | −2.33 |
| HALLMARK_INFLAMMATORY_RESPONSE | 8.33E-10 | −2.34 | 3.57E-10 | −2.96 | 6.25E-10 | −2.40 |
| HALLMARK_INTERFERON_ALPHA_RESPONSE | 4.12E-05 | −1.96 | 1.48E-09 | −2.44 | 5.93E-04 | −1.80 |
| HALLMARK_INTERFERON_GAMMA RESPONSE | 8.33E-10 | −2.26 | 3.57E-10 | −2.88 | 8.95E-10 | −2.26 |
| HALLMARK_KRAS_SIGNALING_DN | 0.10 | 1.28 | 0.08 | 1.32 | 0.26 | −1.12 |
| HALLMARK_KRAS_SIGNALING_UP | 8.33E-10 | −2.24 | 3.57E-10 | −2.65 | 7.40E-10 | −2.31 |
| HALLMARK_MITOTIC_SPINDLE | 3.13E-03 | −1.55 | 1.61E-05 | −1.79 | 9.54E-08 | −2.02 |
| HALLMARK_MTORC1_SIGNALING | 0.28 | 1.11 | 0.11 | 1.23 | 2.36E-05 | 1.81 |
| HALLMARK_MYC_TARGETSV1 | 0.18 | −1.17 | 0.94 | −0.81 | 0.09 | 1.26 |
| HALLMARK_MYC_TARGETSV2 | 0.88 | −0.780 | 0.94 | 0.76 | 0.64 | 0.92 |
| HALLMARK_MYOGENESIS | 0.18 | −1.19 | 2.82E-03 | −1.60 | 0.07 | −1.30 |
| HALLMARK_NOTCH_SIGNALING | 0.76 | 0.83 | 0.94 | 0.69 | 0.29 | −1.15 |
| HALLMARK_OXIDATIVE_PHOSPHORYLATION | 8.33E-10 | 3.06 | 3.57E-10 | 3.38 | 6.25E-10 | 3.69 |
| HALLMARK_P53_PATHWAY | 0.25 | −1.12 | 0.06 | −1.3 | 0.27 | 1.10 |
| HALLMARK_PANCREAS_BETA_CELLS | 0.75 | 0.85 | 0.51 | 0.98 | 0.39 | 1.07 |
| HALLMARK_PEROXISOME | 3.55E-03 | 1.68 | 2.66E-04 | 1.88 | 6.93E-08 | 2.39 |
| HALLMARK_PI3K_AKT_MTOR_SIGNALING | 0.73 | −0.92 | 0.12 | −1.24 | 0.86 | 0.83 |
| HALLMARK_PROTEIN_SECRETION | 0.42 | 1.06 | 0.34 | 1.08 | 2.75E-03 | 1.73 |
| HALLMARK_REACTIVE_OXYGEN_SPECIES_PATHWAY | 0.02 | 1.59 | 9.30E-04 | 1.61 | 6.02E-04 | 1.98 |
| HALLMARK_SPERMATOGENESIS | 0.74 | 0.89 | 0.21 | 1.17 | 0.20 | 1.21 |
| HALLMARK_TGF_BETA_SIGNALING | 7.80E-03 | −1.72 | 2.66E-04 | −1.96 | 0.03 | −1.55 |
| HALLMARK_TNFA_SIGNALING_VIA_NFKB | 8.33E-10 | −2.55 | 3.57E-10 | −3.06 | 6.25E-10 | −2.63 |
| HALLMARK_UNFOLDED_PROTEIN_RESPONSE | 0.73 | −0.91 | 0.99 | −0.64 | 0.90 | 0.78 |

TABLE 5-continued

Gene Set Enrichment Analysis showing enrichment in hallmark gene sets following treatment of g-ddY mice with atrasentan at 0 (control), 10, 20 or 30 mg/kg/day. NES is the normalized enrichment score indicating accounting for gene set size. NES of <−1.5 or <1.5 was considered to be biologically significant. Adj p-value is the estimated probability that the results of the given enriched gene set is a false positive finding.

| Pathway | Atrasentan 10 mg/kg/day vs. control | | Atrasentan 20 mg/kg/day vs. control | | Atrasentan 30 mg/kg/day vs. control | |
|---|---|---|---|---|---|---|
| | Adj p-value | NES | Adj p-value | NES | Adj p-value | NES |
| HALLMARK_UV_RESPONSEDN | 1.64E-08 | −2.19 | 3.57E-10 | −2.36 | 6.25E-10 | −2.39 |
| HALLMARK_UV_RESPONSEUP | 0.08 | 1.28 | 0.22 | 1.15 | 2.13E-03 | 1.63 |
| HALLMARK_WNT_BETA_CATENIN_SIGNALING | 0.50 | −1.02 | 0.13 | −1.57 | 0.02 | −1.63 |
| HALLMARK_XENOBIOTIC_METABOLISM | 4.98E-07 | 1.95 | 9.17E-09 | 2.16 | 6.25E-10 | 2.38 |

TABLE 6

List of upstream regulators grouped by cytokine and growth factor molecular types. P-value of overlap indicates the significance of enrichment based on the number of overlapping genes between the dataset and the gene targets in IPKB. Activation z-score threshold of <−2 or >2 and p-value of overlap threshold of <0.05 was considered significant.

| Upstream Regulator | Molecule Type | Predicted Activation State | Activation z-score | p-value of overlap |
|---|---|---|---|---|
| VEGFB | growth factor | Activated | 3.128 | 0.0183 |
| CCN5 | growth factor | Activated | 2.45 | 0.000199 |
| DKK1 | growth factor | Activated | 2.113 | 0.0264 |
| GDF2 | growth factor | Inhibited | −2.055 | 0.0000181 |
| PF4 | cytokine | Inhibited | −2.219 | 0.0331 |
| CCL5 | cytokine | Inhibited | −2.268 | 0.00286 |
| BMP2 | growth factor | Inhibited | −2.435 | 0.00524 |
| FGF23 | growth factor | Inhibited | −2.497 | 0.000088 |
| VEGFA | growth factor | Inhibited | −2.501 | 5.6E-09 |
| TNFSF11 | cytokine | Inhibited | −2.519 | 0.000579 |
| TSLP | cytokine | Inhibited | −2.533 | 0.0371 |
| PDGFB | growth factor | Inhibited | −2.622 | 0.0453 |
| TGFB2 | growth factor | Inhibited | −2.631 | 0.0000392 |
| TGFB3 | growth factor | Inhibited | −2.663 | 0.00265 |
| IGF1 | growth factor | Inhibited | −2.676 | 0.0000051 |
| IL10 | cytokine | Inhibited | −2.775 | 0.000086 |
| CXCL12 | cytokine | Inhibited | −2.851 | 0.000837 |
| IL21 | cytokine | Inhibited | −2.886 | 0.0482 |
| CSF3 | cytokine | Inhibited | −3.116 | 0.000333 |
| TNFSF12 | cytokine | Inhibited | −3.271 | 0.0184 |
| IFNA2 | cytokine | Inhibited | −3.465 | 0.0171 |
| NRG1 | growth factor | Inhibited | −3.478 | 0.000000103 |
| PRL | cytokine | Inhibited | −3.529 | 1.13E-10 |
| CD4OLG | cytokine | Inhibited | −3.607 | 0.0000006 |
| EGF | growth factor | Inhibited | −3.649 | 7.11E-09 |
| WNT3A | cytokine | Inhibited | −3.711 | 3.78E-08 |
| IL33 | cytokine | Inhibited | −3.781 | 0.00000473 |
| IL6 | cytokine | Inhibited | −3.872 | 0.00000371 |
| IL3 | cytokine | Inhibited | −3.894 | 6.97E-08 |
| IL2 | cytokine | Inhibited | −4.023 | 0.00000511 |
| EDN1 | cytokine | Inhibited | −4.26 | 0.00012 |
| FGF2 | growth factor | Inhibited | −4.33 | 3.56E-09 |
| IFNG | cytokine | Inhibited | −4.604 | 1.34E-12 |
| AGT | growth factor | Inhibited | −4.741 | 5.66E-13 |
| IL1A | cytokine | Inhibited | −4.942 | 0.00513 |
| HGF | growth factor | Inhibited | −5.138 | 1.15E-10 |
| TGFB1 | growth factor | Inhibited | −5.163 | 1.87E-26 |
| CSF2 | cytokine | Inhibited | −5.645 | 7.08E-10 |
| OSM | cytokine | Inhibited | −5.912 | 0.000000269 |
| TNF | cytokine | Inhibited | −6.593 | 5.21E-21 |
| IL1B | cytokine | Inhibited | −7.154 | 4.35E-09 |

TABLE 7

List of upstream regulators grouped by transmembrane receptor, G-protein coupled receptor, and protein complexes molecular types. P-value of overlap indicates the significance of enrichment based on the number of overlapping genes between the dataset and the gene targets in IPKB. Activation z-score threshold of <−2 or >2 and p-value of overlap threshold of <0.05 was considered significant.

| Upstream Regulator | Molecule Type | Predicted Activation State | Activation z-score | p-value of overlap |
|---|---|---|---|---|
| PLA2R1 | transmembrane receptor | Activated | 2.917 | 0.0000325 |
| FAS | transmembrane receptor | Activated | 2.887 | 0.000000264 |
| SMO | G-protein coupled receptor | Activated | 2.621 | 0.043 |
| IGF1R | transmembrane receptor | Activated | 2.165 | 0.00206 |
| LGR5 | transmembrane receptor | Activated | 2.137 | 0.000486 |
| Laminin (complex) | complex | Activated | 2.043 | 0.00105 |
| PTGER4 | G-protein coupled receptor | Activated | 2.017 | 0.000049 |
| ADGRF5 | G-protein coupled receptor | Activated | 2 | 0.0437 |
| PROKR1 | G-protein coupled receptor | Activated | 2 | 0.0437 |
| 26s Proteasome | complex | Inhibited | −2.122 | 0.0000336 |
| IL6R | transmembrane receptor | Inhibited | −2.179 | 0.0213 |
| FCGR1A | transmembrane receptor | Inhibited | −2.201 | 0.000821 |
| HTR7 | G-protein coupled receptor | Inhibited | −2.219 | 0.0141 |
| TCR | complex | Inhibited | −2.362 | 8.88E−11 |
| TYROBP | transmembrane receptor | Inhibited | −2.376 | 0.048 |
| CHRM3 | G-protein coupled receptor | Inhibited | −2.425 | 0.0079 |
| TNFRSF1A | transmembrane receptor | Inhibited | −2.449 | 0.0455 |
| EDNRA | transmembrane receptor | Inhibited | −2.449 | 0.0119 |
| Pdgf (complex) | complex | Inhibited | −2.779 | 0.015 |
| F2R | G-protein coupled receptor | Inhibited | −3.04 | 0.00000844 |
| IFNAR1 | transmembrane receptor | Inhibited | −3.094 | 0.0185 |
| PI3K (complex) | complex | Inhibited | −3.293 | 0.0000027 |
| Ifn gamma | complex | Inhibited | −3.354 | 0.0476 |
| GPER1 | G-protein coupled receptor | Inhibited | −3.527 | 0.000000242 |
| LDL | complex | Inhibited | −3.568 | 0.000272 |
| TREM1 | transmembrane receptor | Inhibited | −3.62 | 0.000494 |
| CCR2 | G-protein coupled receptor | Inhibited | −3.791 | 0.00113 |
| F3 | transmembrane receptor | Inhibited | −3.862 | 0.0113 |
| PDGF BB | complex | Inhibited | −3.976 | 6.87E−14 |
| CG | complex | Inhibited | −4.34 | 1.58E−10 |
| TLR4 | transmembrane receptor | Inhibited | −4.561 | 0.000392 |
| Ige | complex | Inhibited | −4.883 | 0.00000228 |
| TLR9 | transmembrane receptor | Inhibited | −4.894 | 0.00697 |
| TLR3 | transmembrane receptor | Inhibited | −5.02 | 0.0158 |
| NFκB (complex) | complex | Inhibited | −5.503 | 0.0000354 |

TABLE 8

List of upstream regulators grouped by transcription regulator and ligand-dependent nuclear receptor molecular types. P-value of overlap indicates the significance of enrichment based on the number of overlapping genes between the dataset and the gene targets in IPKB. Activation z-score threshold of <−2 or >2 and p-value of overlap threshold of <0.05 was considered significant.

| Upstream Regulator | Molecule Type | Predicted Activation State | Activation z-score | p-value of overlap |
|---|---|---|---|---|
| PPARGC1A | transcription regulator | Activated | 8.123 | 1.65E−14 |
| HNF4A | transcription regulator | Activated | 4.856 | 3.88E−27 |
| MYCN | transcription regulator | Activated | 4.584 | 1.75E−10 |
| RB1 | transcription regulator | Activated | 4.435 | 1.57E−09 |
| SPDEF | transcription regulator | Activated | 4.415 | 0.000000425 |
| LHX1 | transcription regulator | Activated | 4.214 | 3.15E−15 |
| HNF1A | transcription regulator | Activated | 4.107 | 0.0000186 |
| PITX2 | transcription regulator | Activated | 3.976 | 0.000000278 |
| PPARG | ligand-dependent nuclear receptor | Activated | 3.581 | 3.16E−10 |
| XBP1 | transcription regulator | Activated | 3.505 | 0.00651 |
| SMAD7 | transcription regulator | Activated | 3.504 | 0.0218 |
| IKZF1 | transcription regulator | Activated | 3.472 | 0.0000024 |

TABLE 8-continued

List of upstream regulators grouped by transcription regulator and ligand-dependent nuclear receptor molecular types. P-value of overlap indicates the significance of enrichment based on the number of overlapping genes between the dataset and the gene targets in IPKB. Activation z-score threshold of <−2 or >2 and p-value of overlap threshold of <0.05 was considered significant.

| Upstream Regulator | Molecule Type | Predicted Activation State | Activation z-score | p-value of overlap |
|---|---|---|---|---|
| KLF15 | transcription regulator | Activated | 3.401 | 0.000534 |
| NFE2L2 | transcription regulator | Activated | 3.389 | 2.21E−08 |
| RUNX3 | transcription regulator | Activated | 3.355 | 0.0000332 |
| PPARA | ligand-dependent nuclear receptor | Activated | 3.182 | 3.79E−17 |
| IKZF3 | transcription regulator | Activated | 3.165 | 0.000634 |
| NEUROG1 | transcription regulator | Activated | 3 | 0.0000441 |
| RXRA | ligand-dependent nuclear receptor | Activated | 2.96 | 0.00000779 |
| HNF1B | transcription regulator | Activated | 2.944 | 0.0000399 |
| TFAP2C | transcription regulator | Activated | 2.899 | 0.00026 |
| MLXIPL | transcription regulator | Activated | 2.871 | 0.00638 |
| GFI1 | transcription regulator | Activated | 2.82 | 0.000832 |
| KLF2 | transcription regulator | Activated | 2.742 | 0.00107 |
| PPARGC1B | transcription regulator | Activated | 2.664 | 0.000802 |
| IEEE | transcription regulator | Activated | 2.587 | 0.000232 |
| MEOX2 | transcription regulator | Activated | 2.54 | 0.0197 |
| ESRRA | ligand-dependent nuclear receptor | Activated | 2.517 | 0.0189 |
| BCL6 | transcription regulator | Activated | 2.514 | 9.52E−09 |
| GPS2 | transcription regulator | Activated | 2.51 | 0.00975 |
| TCF7L1 | transcription regulator | Activated | 2.373 | 0.0384 |
| CBX5 | transcription regulator | Activated | 2.355 | 0.0000488 |
| DACH1 | transcription regulator | Activated | 2.354 | 0.0243 |
| FOX03 | transcription regulator | Activated | 2.338 | 9.92E−08 |
| SRSF2 | transcription regulator | Activated | 2.328 | 0.00808 |
| PRDM1 | transcription regulator | Activated | 2.281 | 0.000765 |
| SREBF2 | transcription regulator | Activated | 2.277 | 0.0488 |
| SMYD1 | transcription regulator | Activated | 2.213 | 1.71E−11 |
| AHR | ligand-dependent nuclear receptor | Activated | 2.092 | 3.17E−13 |
| PCGF2 | transcription regulator | Activated | 2 | 0.0127 |
| Msx3 | transcription regulator | Inhibited | −2 | 0.0128 |
| SPZ1 | transcription regulator | Inhibited | −2.022 | 0.0283 |
| HIF1A | transcription regulator | Inhibited | −2.042 | 5.35E−08 |
| ARNT2 | transcription regulator | Inhibited | −2.079 | 0.00156 |
| ETS1 | transcription regulator | Inhibited | −2.096 | 0.00125 |
| TEAD4 | transcription regulator | Inhibited | −2.143 | 0.00305 |
| NCOA3 | transcription regulator | Inhibited | −2.143 | 0.0176 |
| ELK1 | transcription regulator | Inhibited | −2.151 | 0.00543 |
| CEBPD | transcription regulator | Inhibited | −2.154 | 0.00211 |
| NR3C2 | ligand-dependent nuclear receptor | Inhibited | −2.191 | 0.000655 |
| KMT2A | transcription regulator | Inhibited | −2.246 | 0.000564 |
| FOXF1 | transcription regulator | Inhibited | −2.253 | 0.00866 |
| NRIP1 | transcription regulator | Inhibited | −2.267 | 0.0000719 |
| FOXM1 | transcription regulator | Inhibited | −2.307 | 0.000132 |
| SMAD2 | transcription regulator | Inhibited | −2.323 | 0.00988 |
| HOXC6 | transcription regulator | Inhibited | −2.35 | 0.000765 |
| SOX4 | transcription regulator | Inhibited | −2.397 | 0.0000114 |
| STAT4 | transcription regulator | Inhibited | −2.401 | 7.22E−08 |
| SMAD4 | transcription regulator | Inhibited | −2.417 | 0.00000815 |
| MECP2 | transcription regulator | Inhibited | −2.419 | 0.0155 |
| ESR1 | ligand-dependent nuclear receptor | Inhibited | −2.439 | 7.07E−18 |
| SP1 | transcription regulator | Inhibited | −2.444 | 7.53E−10 |
| MESP2 | transcription regulator | Inhibited | −2.449 | 0.0255 |
| REL | transcription regulator | Inhibited | −2.451 | 0.0000517 |
| NR4A1 | ligand-dependent nuclear receptor | Inhibited | −2.488 | 7.08E−13 |
| FOXCl | transcription regulator | Inhibited | −2.563 | 0.0227 |
| IRF8 | transcription regulator | Inhibited | −2.577 | 0.0237 |
| MESP1 | transcription regulator | Inhibited | −2.646 | 0.0178 |
| SNAI1 | transcription regulator | Inhibited | −2.699 | 6.16E−08 |
| ECSIT | transcription regulator | Inhibited | −2.72 | 0.00604 |
| EGR1 | transcription regulator | Inhibited | −2.766 | 0.00543 |
| TCF4 | transcription regulator | Inhibited | −2.836 | 0.00000487 |
| PAX7 | transcription regulator | Inhibited | −2.883 | 0.00101 |
| SPIB | transcription regulator | Inhibited | −2.933 | 0.00407 |
| MTPN | transcription regulator | Inhibited | −2.942 | 0.000223 |
| SMAD3 | transcription regulator | Inhibited | −2.952 | 0.000126 |
| PDX1 | transcription regulator | Inhibited | −2.958 | 0.0000197 |

TABLE 8-continued

List of upstream regulators grouped by transcription regulator and ligand-dependent nuclear receptor molecular types. P-value of overlap indicates the significance of enrichment based on the number of overlapping genes between the dataset and the gene targets in IPKB. Activation z-score threshold of <−2 or >2 and p-value of overlap threshold of <0.05 was considered significant.

| Upstream Regulator | Molecule Type | Predicted Activation State | Activation z-score | p-value of overlap |
|---|---|---|---|---|
| TWIST1 | transcription regulator | Inhibited | −2.987 | 0.000114 |
| CCND1 | transcription regulator | Inhibited | −3.003 | 1.83E−08 |
| TEAD1 | transcription regulator | Inhibited | −3.036 | 0.00192 |
| MEF2D | transcription regulator | Inhibited | −3.056 | 0.000802 |
| FOXL2 | transcription regulator | Inhibited | −3.108 | 0.00539 |
| TEAD2 | transcription regulator | Inhibited | −3.153 | 0.00127 |
| SMARCA4 | transcription regulator | Inhibited | −3.211 | 1.99E−09 |
| NFKB1 | transcription regulator | Inhibited | −3.239 | 0.0000117 |
| SRF | transcription regulator | Inhibited | −3.269 | 0.000056 |
| GATA1 | transcription regulator | Inhibited | −3.309 | 0.00268 |
| FOXC2 | transcription regulator | Inhibited | −3.361 | 0.048 |
| TP53 | transcription regulator | Inhibited | −3.365 | 1.2E−36 |
| CTNNB1 | transcription regulator | Inhibited | −3.373 | 2.83E−14 |
| SPI1 | transcription regulator | Inhibited | −3.51 | 0.0135 |
| TEAD3 | transcription regulator | Inhibited | −3.638 | 0.0102 |
| FEV | transcription regulator | Inhibited | −3.651 | 0.000117 |
| ERG | transcription regulator | Inhibited | −3.672 | 0.0000583 |
| JUNE | transcription regulator | Inhibited | −3.721 | 0.00172 |
| MRTFA | transcription regulator | Inhibited | −3.84 | 0.0491 |
| STAT1 | transcription regulator | Inhibited | −3.918 | 0.00156 |
| KLF4 | transcription regulator | Inhibited | −3.94 | 0.0148 |
| Tcf7 | transcription regulator | Inhibited | −3.984 | 0.0000319 |
| YAP1 | transcription regulator | Inhibited | −4.255 | 0.0000177 |
| RELA | transcription regulator | Inhibited | −4.344 | 0.0000969 |
| IRF7 | transcription regulator | Inhibited | −4.492 | 0.00811 |
| STAT3 | transcription regulator | Inhibited | −4.716 | 5.94E−09 |
| MRTFB | transcription regulator | Inhibited | −4.734 | 0.000158 |
| KDM5A | transcription regulator | Inhibited | −5.858 | 1.92E−13 |

TABLE 9

Gene expression of the components of the NF-kB signaling pathways following treatment of g-ddY mice with atrasentan at 10, 20 or 30 mg/kg/day compared to atrasentan at 0 mg/kg/day (control).

| | Atrasentan 10 mg/kg/day | | Atrasentan 20 mg/kg/day | | Atrasentan 30 mg/kg/day | |
|---|---|---|---|---|---|---|
| Symbol | logFC | FDR | logFC | FDR | logFC | FDR |
| Pfkfb3 | −1.16606 | 0.016337 | −1.12478 | 0.009909 | −1.48475 | 0.000796 |
| Nr4a1 | −1.52471 | 0.02068 | −1.62096 | 0.009287 | −1.80272 | 0.001473 |
| Gem | −1.50783 | 0.028806 | −1.23709 | 0.026639 | −1.91184 | 0.002183 |
| Ccn1 | −1.08749 | 0.035252 | −1.08727 | 0.018504 | −0.91985 | 0.012547 |
| Fos12 | −0.86618 | 0.067384 | −1.12215 | 0.016936 | −1.20525 | 0.003639 |
| Klf4 | −0.54933 | 0.083567 | −0.90396 | 0.009287 | −0.94744 | 0.001843 |
| Efna1 | 0.693762 | 0.098009 | 0.286021 | 0.359139 | 0.727762 | 0.021668 |
| F3 | −0.49627 | 0.122022 | −0.52346 | 0.05148 | −0.564 | 0.021548 |
| Nfkbia | −0.5525 | 0.123145 | −0.70406 | 0.029887 | −0.73071 | 0.011919 |
| Ifit2 | −0.47104 | 0.143064 | −0.63233 | 0.030246 | −0.61195 | 0.016546 |
| Snn | 0.351718 | 0.143092 | 0.475301 | 0.029887 | 0.472482 | 0.014513 |
| Nr4a2 | −1.3802 | 0.150927 | −1.11098 | 0.124988 | −1.72799 | 0.022984 |
| Klf2 | −0.4894 | 0.156952 | −0.48163 | 0.080629 | −0.71822 | 0.011835 |
| Jag1 | −0.41987 | 0.163479 | −0.39391 | 0.100075 | −0.67841 | 0.008592 |
| Dnajb4 | −0.36834 | 0.172404 | −0.35475 | 0.099555 | −0.75343 | 0.003454 |
| Il1b | −1.68357 | 0.193146 | −3.02945 | 0.026639 | −2.26303 | 0.029185 |
| Cdkn1a | 0.558282 | 0.20458 | 0.254616 | 0.471505 | 0.636882 | 0.049691 |
| Spsb1 | −0.61566 | 0.206032 | −0.65404 | 0.094579 | −1.09671 | 0.009718 |
| Btg2 | −0.42396 | 0.209991 | −0.69738 | 0.029887 | −0.66894 | 0.016296 |
| Ccnd1 | 0.452977 | 0.214814 | 0.643985 | 0.047017 | 0.69473 | 0.01924 |
| Alf3 | −1.51365 | 0.22778 | −2.10661 | 0.060485 | −2.21952 | 0.031678 |
| Csf1 | −0.83319 | 0.237302 | −1.08925 | 0.072389 | −1.26006 | 0.027904 |
| Trib1 | −0.64809 | 0.240117 | −0.76678 | 0.091587 | −1.07401 | 0.019758 |
| Zbtb10 | −0.23348 | 0.242089 | −0.25865 | 0.10667 | −0.29122 | 0.049691 |
| Btg1 | −0.37446 | 0.250264 | −0.51866 | 0.060738 | −0.48249 | 0.046956 |
| Ehd1 | 0.256254 | 0.260538 | 0.271542 | 0.132492 | 0.413845 | 0.022598 |
| Rhob | −0.53303 | 0.261164 | −0.54187 | 0.148633 | −0.72645 | 0.045084 |
| Nfat5 | −0.31176 | 0.298987 | −0.32299 | 0.17069 | −0.58448 | 0.017517 |
| Tnfaip8 | 0.273019 | 0.300195 | 0.399971 | 0.072756 | 0.516997 | 0.017659 |
| Pnrc1 | 0.263462 | 0.304842 | 0.041556 | 0.870084 | 0.485627 | 0.020041 |

TABLE 9-continued

Gene expression of the components of the NF-kB signaling pathways following treatment of g-ddY mice with atrasentan at 10, 20 or 30 mg/kg/day compared to atrasentan at 0 mg/kg/day (control).

| Symbol | Atrasentan 10 mg/kg/day | | Atrasentan 20 mg/kg/day | | Atrasentan 30 mg/kg/day | |
|---|---|---|---|---|---|---|
|  | logFC | FDR | logFC | FDR | logFC | FDR |
| Edn1 | −1.00599 | 0.306986 | −1.32804 | 0.10522 | −1.68836 | 0.035952 |
| Rel | −0.72185 | 0.315094 | −1.0782 | 0.075629 | −1.29814 | 0.026258 |
| Nr4a3 | −1.14299 | 0.340486 | −1.11302 | 0.234364 | −1.93865 | 0.047968 |
| Nfkbl | −0.34242 | 0.36235 | −0.61603 | 0.059621 | −0.64981 | 0.028263 |
| Serpine1 | −0.71692 | 0.365608 | −1.50107 | 0.049438 | −1.38665 | 0.034662 |
| Ackr3 | 0.285126 | 0.37038 | 0.491654 | 0.069748 | 0.548488 | 0.028167 |
| Ccl20 | −1.27345 | 0.384854 | −3.56331 | 0.033736 | −2.47108 | 0.045771 |
| Per1 | −0.41615 | 0.408249 | −0.12155 | 0.798223 | −0.93068 | 0.025478 |
| Cxcl2 | −1.18965 | 0.446123 | −2.5772 | 0.075629 | −2.6664 | 0.04664 |
| Map3k8 | −0.35577 | 0.45048 | −0.82217 | 0.050202 | −0.86644 | 0.022718 |
| Traf1 | −0.51819 | 0.570487 | −1.48546 | 0.059621 | −1.37067 | 0.046862 |
| Id2 | 0.166343 | 0.656887 | 0.222761 | 0.421533 | 0.539366 | 0.040736 |

TABLE 10

Expression of the components of the IL6 signaling pathways following treatment of g-ddY mice with atrasentan at 10, 20 or 30 mg/kg/day compared to atrasentan at 0 mg/kg/day (control).

| Symbol | Atrasentan 10 mg/kg/day | | Atrasentan 20 mg/kg/day | | Atrasentan 30 mg/kg/day | |
|---|---|---|---|---|---|---|
|  | logFC | FDR | logFC | FDR 20mg | logFC | FDR |
| Cntfr | −0.86692 | 0.099624 | −0.85744 | 0.049966 | −0.93652 | 0.019879 |
| Il1b | −1.68357 | 0.193146 | −3.02945 | 0.026639 | −2.26303 | 0.029185 |
| Csf1 | −0.83319 | 0.237302 | −1.08925 | 0.072389 | −1.26006 | 0.027904 |
| Il2ra | −0.85988 | 0.372724 | −0.95904 | 0.206119 | −1.57951 | 0.042633 |
| Map3k8 | −0.35577 | 0.45048 | −0.82217 | 0.050202 | −0.86644 | 0.022718 |
| Il1r1 | −0.29875 | 0.455743 | −0.82629 | 0.029887 | −0.60782 | 0.044115 |

TABLE 11

Gene expression of the components of the PDGF signaling pathways following treatment of g-ddY mice with atrasentan at 10, 20 or 30 mg/kg/day compared to atrasentan at 0 mg/kg/day (control).

| Symbol | Atrasentan 10 mg/kg/day | | Atrasentan 20 mg/kg/day | | Atrasentan 30 mg/kg/day | |
|---|---|---|---|---|---|---|
|  | logFC | FDR | logFC | FDR_20 mg | logFC | FDR |
| Pik3r1 | −0.42534 | 0.07447 | −0.42839 | 0.033132 | −0.62233 | 0.003454 |
| Pdgfra | −0.51003 | 0.113814 | −0.658 | 0.026639 | −0.70937 | 0.008179 |
| Nfkbia | −0.5525 | 0.123145 | −0.70406 | 0.029887 | −0.73071 | 0.011919 |
| Pik3cg | −0.58823 | 0.193255 | −1.09598 | 0.019436 | −0.72874 | 0.034335 |
| Pla2g4a | −0.69994 | 0.201471 | −0.83808 | 0.067311 | −0.9024 | 0.031577 |
| Tiam1 | −0.74555 | 0.280074 | −0.94943 | 0.098932 | −1.22717 | 0.029267 |
| Pdgfb | −0.34145 | 0.351246 | −0.83749 | 0.023432 | −0.54241 | 0.049074 |
| Nfkbl | −0.34242 | 0.36235 | −0.61603 | 0.059621 | −0.64981 | 0.028263 |
| Map3k1 | −0.38251 | 0.413587 | −0.72028 | 0.072782 | −0.76362 | 0.036915 |
| Hras | 0.188685 | 0.470644 | 0.068017 | 0.780401 | 0.435389 | 0.030337 |

TABLE 12

Expression of the components of the cell proliferation signaling pathways (mitotic spindle and G2M cell cycle checkpoint) following treatment of g-ddY mice with atrasentan at 10, 20 or 30 mg/kg/day compared to atrasentan at 0 mg/kg/day (control).

| | Atrasentan 10 mg/kg/day | | Atrasentan 20 mg/kg/day | | Atrasentan 30 mg/kg/day | |
|---|---|---|---|---|---|---|
| Symbol | logFC | FDR | logFC | FDR_20mg | logFC | FDR |
| Ccdc88a | −0.560213108 | 0.064307704 | −0.63737 | 0.019436 | −0.72059 | 0.003971 |
| Sorbs2 | −0.395795452 | 0.094299303 | −0.47171 | 0.026652 | −0.36011 | 0.033932 |
| Rhot2 | 0.472719618 | 0.118416595 | 0.457604 | 0.061542 | 0.543154 | 0.019524 |
| Epb4112 | −0.437552327 | 0.123145067 | −0.6149 | 0.023432 | −0.70213 | 0.004946 |
| Cep192 | −0.421092775 | 0.150917991 | −0.41731 | 0.07457 | −0.43003 | 0.043366 |
| Bcar1 | 0.337889791 | 0.184961955 | 0.346027 | 0.092736 | 0.41824 | 0.031186 |
| Ppp4r2 | −0.421363936 | 0.186488374 | −0.39924 | 0.113169 | −0.50412 | 0.036549 |
| Tuba4a | 0.273786265 | 0.207446205 | 0.28609 | 0.100847 | 0.495831 | 0.008518 |
| Ophn1 | −0.499897642 | 0.209990532 | −0.7587 | 0.036699 | −0.71292 | 0.023569 |
| Cntrl | −0.289023549 | 0.264775176 | −0.39629 | 0.069769 | −0.55688 | 0.011835 |
| Tiam1 | −0.745550285 | 0.280074251 | −0.94943 | 0.098932 | −1.22717 | 0.029267 |
| Nin | −0.339329706 | 0.291537075 | −0.42364 | 0.104354 | −0.7352 | 0.00911 |
| Myh10 | −0.306833953 | 0.291537075 | −0.1801 | 0.445837 | −0.52418 | 0.023157 |
| Flna | −0.416208801 | 0.29963401 | −0.78417 | 0.03471 | −0.61835 | 0.042633 |
| Rapgef5 | −0.273198499 | 0.310608123 | −0.38035 | 0.087682 | −0.42253 | 0.039906 |
| Fgd6 | −0.236922692 | 0.318947872 | −0.34192 | 0.082731 | −0.69833 | 0.003454 |
| Myo1e | −0.234884513 | 0.327254691 | −0.29201 | 0.127987 | −0.41769 | 0.02663 |
| Vcl | −0.200128517 | 0.335661912 | −0.33173 | 0.061542 | −0.36045 | 0.026782 |
| Itsn1 | −0.227594667 | 0.384854101 | −0.27517 | 0.181905 | −0.51285 | 0.01799 |
| Smc3 | −0.230373555 | 0.410052693 | −0.16956 | 0.458127 | −0.4558 | 0.034583 |
| Myh9 | −0.209349487 | 0.631442809 | −0.45434 | 0.154803 | −0.61714 | 0.04296 |
| Slc12a2 | −0.250697945 | 0.207446205 | −0.33735 | 0.051461 | −0.33063 | 0.029395 |
| Dmd | −0.333454644 | 0.211421937 | −0.34846 | 0.104532 | −0.40498 | 0.043352 |
| Ccnd1 | 0.452977372 | 0.214813934 | 0.643985 | 0.047017 | 0.69473 | 0.01924 |
| Arid4a | −0.277719336 | 0.264775176 | −0.19604 | 0.315402 | −0.57195 | 0.00866 |
| Kmt5a | 0.260119308 | 0.291940817 | 0.287339 | 0.144023 | 0.416918 | 0.030303 |
| Atrx | −0.246276232 | 0.322185047 | −0.21876 | 0.258831 | −0.40313 | 0.034743 |
| Slc38a1 | −0.497099916 | 0.335090449 | −0.69888 | 0.099211 | −0.81081 | 0.041274 |
| Slc7a1 | −0.396018735 | 0.366958406 | −0.73041 | 0.057987 | −0.79523 | 0.02442 |
| Ythdc1 | −0.193613498 | 0.408636337 | −0.0815 | 0.701193 | −0.35794 | 0.043485 |
| Meis1 | −0.250703773 | 0.445700579 | −0.35928 | 0.161072 | −0.49344 | 0.045256 |

TABLE 13

Expression of the components of the inflammatory response signaling pathways following treatment of g-ddY mice with atrasentan at 10, 20 or 30 mg/kg/day compared to atrasentan at 0 mg/kg/day (control).

| | Atrasentan 10 mg/kg/day | | Atrasentan 20 mg/kg/day | | Atrasentan 30 mg/kg/day | |
|---|---|---|---|---|---|---|
| Symbol | logFC | FDR | logFC | FDR | logFC | FDR |
| Rn1144b | −0.71083 | 0.093159 | −0.97649 | 0.018504 | −0.88478 | 0.009694 |
| Ros1 | −2.07792 | 0.107948 | −1.99181 | 0.057987 | −1.98547 | 0.034335 |
| Slc7a2 | −0.83149 | 0.120432 | −1.33578 | 0.016936 | −0.98085 | 0.018794 |
| F3 | −0.49627 | 0.122022 | −0.52346 | 0.05148 | −0.564 | 0.021548 |
| Nfkbia | −0.5525 | 0.123145 | −0.70406 | 0.029887 | −0.73071 | 0.011919 |
| Hpn | 0.400668 | 0.134179 | 0.418714 | 0.057987 | 0.619746 | 0.006798 |
| Slc4a4 | 0.512324 | 0.172404 | 0.524475 | 0.085406 | 0.614581 | 0.03148 |
| Chst2 | −0.52123 | 0.191357 | −0.36799 | 0.22704 | −0.92143 | 0.008518 |
| Il1b | −1.68357 | 0.193146 | −3.02945 | 0.026639 | −2.26303 | 0.029185 |
| Cdkn1a | 0.558282 | 0.20458 | 0.254616 | 0.471505 | 0.636882 | 0.049691 |
| Btg2 | −0.42396 | 0.209991 | −0.69738 | 0.029887 | −0.66894 | 0.016296 |
| Csf1 | −0.83319 | 0.237302 | −1.08925 | 0.072389 | −1.26006 | 0.027904 |
| Slc11a2 | 0.319159 | 0.264775 | 0.350018 | 0.12506 | 0.420512 | 0.049481 |
| Eif2ak2 | −0.27199 | 0.27558 | −0.30022 | 0.130897 | −0.5033 | 0.015208 |
| Edn1 | −1.00599 | 0.306986 | −1.32804 | 0.10522 | −1.68836 | 0.035952 |
| Nfkb1 | −0.34242 | 0.36235 | −0.61619 | 0.059621 | −0.64981 | 0.028263 |
| Serpine1 | −0.71692 | 0.365608 | −1.50107 | 0.049438 | −1.38665 | 0.034662 |
| Slc7a1 | −0.39602 | 0.366958 | −0.73041 | 0.057987 | −0.79523 | 0.02442 |
| Ccl20 | −1.27345 | 0.384854 | −3.56331 | 0.033736 | −2.47108 | 0.045771 |
| Il1r1 | −0.29875 | 0.455743 | −0.82629 | 0.029887 | −0.60782 | 0.044115 |
| Ly6e | 0.166615 | 0.73244 | 0.243601 | 0.496099 | 0.685667 | 0.041805 |
| Gabbr1 | −0.02473 | 0.964627 | −0.13161 | 0.701936 | −0.57619 | 0.046381 |

TABLE 14

Gene expression of the 44 genes associated with mesangial cell signature following treatment of g-ddY with atrasentan at 10, 20, or 30 mg/kg/day compared to atrasentan at 0 mg/kg/day (control).

| Symbol | Atrasentan 10 mg/kg/day | | Atrasentan 20 mg/kg/day | | Atrasentan 30 mg/kg/day | |
|---|---|---|---|---|---|---|
| | logFC | FDR | logFC | FDR | logFC | FDR |
| Nr4a1 | −1.52471 | 0.02068 | −1.62096 | 0.009287 | −1.80272 | 0.001473 |
| Mef2c | −0.62169 | 0.040481 | −0.6302 | 0.019436 | −0.6869 | 0.004544 |
| Zeb2 | −0.56382 | 0.045268 | −0.64921 | 0.016936 | −0.67777 | 0.003454 |
| Postn | −1.38468 | 0.064308 | −2.29303 | 0.009287 | −1.24718 | 0.017778 |
| Stard13 | −0.72235 | 0.070757 | −0.63665 | 0.047017 | −0.84655 | 0.008122 |
| Rbms3 | −0.57488 | 0.074375 | −0.71922 | 0.018674 | −0.88947 | 0.002755 |
| Gpx3 | 0.680189 | 0.094299 | 0.710044 | 0.040407 | 1.122196 | 0.003454 |
| Ahnak | −0.57555 | 0.103546 | −0.71282 | 0.026639 | −1.01336 | 0.002755 |
| Nfkbia | −0.5525 | 0.123145 | −0.70406 | 0.029887 | −0.73071 | 0.011919 |
| Epb4112 | −0.43755 | 0.123145 | −0.6149 | 0.023432 | −0.70213 | 0.004946 |
| Gata3 | −0.48215 | 0.141854 | −0.49245 | 0.06467 | −0.52161 | 0.031516 |
| Akt3 | −0.38631 | 0.143064 | −0.46726 | 0.041092 | −0.48434 | 0.018794 |
| Cald1 | −0.37193 | 0.159141 | −0.53608 | 0.028056 | −0.50596 | 0.015786 |
| Unc5c | 0.561795 | 0.160194 | 0.36849 | 0.224278 | 0.951658 | 0.00669 |
| Psd3 | −0.35444 | 0.172404 | −0.52273 | 0.029887 | −0.58428 | 0.00866 |
| Pparg | −0.61292 | 0.172404 | −0.56156 | 0.112215 | −0.67808 | 0.042887 |
| Robo1 | −0.48025 | 0.180027 | −0.7261 | 0.029888 | −0.60087 | 0.029099 |
| C7 | −0.77671 | 0.201471 | −1.277 | 0.031245 | −1.07912 | 0.026221 |
| Raph1 | −0.29653 | 0.202275 | −0.38519 | 0.054865 | −0.53579 | 0.008122 |
| Lama2 | −0.29553 | 0.206144 | −0.4437 | 0.035116 | −0.48948 | 0.011923 |
| Tjp1 | −0.24892 | 0.242617 | −0.30541 | 0.081209 | −0.39891 | 0.019552 |
| Utrn | −0.49005 | 0.247838 | −0.51434 | 0.126507 | −0.76971 | 0.022718 |
| Aldob | 0.419369 | 0.259564 | 0.492327 | 0.102004 | 0.747988 | 0.015448 |
| Fchsd2 | −0.25643 | 0.262979 | −0.18823 | 0.292954 | −0.37722 | 0.032457 |
| Nbea | −0.28187 | 0.270291 | −0.19334 | 0.334672 | −0.43202 | 0.029267 |
| Ebf1 | −0.33006 | 0.274512 | −0.35124 | 0.142697 | −0.45065 | 0.047835 |
| Tcf4 | −0.21758 | 0.286673 | −0.22405 | 0.162797 | −0.30548 | 0.046576 |
| Ppp1r12a | −0.19949 | 0.294247 | −0.21354 | 0.15604 | −0.38255 | 0.015257 |
| Ankrd12 | −0.28245 | 0.298987 | −0.24628 | 0.245564 | −0.4726 | 0.026737 |
| Ptprm | −0.26142 | 0.298987 | −0.2678 | 0.175547 | −0.54534 | 0.011636 |
| Etsl | −0.21985 | 0.308571 | −0.30649 | 0.086114 | −0.33787 | 0.040012 |
| Rapgef5 | −0.2732 | 0.310608 | −0.38035 | 0.087682 | −0.42253 | 0.039906 |
| Myo1e | −0.23488 | 0.327255 | −0.29201 | 0.127987 | −0.41769 | 0.02663 |
| Tns3 | −0.2638 | 0.340113 | −0.30431 | 0.162366 | −0.45216 | 0.033592 |
| Tacc1 | −0.24487 | 0.354586 | −0.3693 | 0.090837 | −0.49245 | 0.020907 |
| Piezo2 | −0.40781 | 0.391686 | −0.61479 | 0.113663 | −0.8237 | 0.030578 |
| Maml2 | −0.23179 | 0.42616 | −0.23109 | 0.309113 | −0.44408 | 0.043294 |
| Akap12 | −0.2687 | 0.445264 | −0.54041 | 0.068209 | −0.8211 | 0.008226 |
| Meis1 | −0.2507 | 0.445701 | −0.35928 | 0.161072 | −0.49344 | 0.045256 |
| Frmd4a | −0.28382 | 0.446123 | −0.39548 | 0.171443 | −0.57422 | 0.041274 |
| Igfbp7 | 0.205172 | 0.45523 | 0.108837 | 0.648747 | 0.425852 | 0.040662 |
| Prkg1 | −0.21871 | 0.488645 | −0.32796 | 0.180294 | −0.63558 | 0.015208 |
| Myh9 | −0.20935 | 0.631443 | −0.45434 | 0.154803 | −0.61714 | 0.04296 |
| Cblb | −0.082 | 0.788712 | −0.20682 | 0.316455 | −0.42884 | 0.034058 |

CONCLUSION

Thus, in the g-ddY mouse model of spontaneous IgA nephropathy, atrasentan treatment at 20 and 30 mg/kg/day significantly reduced albuminuria following approximately 5-days of treatment compared to control g-ddY mice not treated with atrasentan. The magnitude of albuminuria lowering observed at these doses (>60% reduction from baseline) is considered highly clinically meaningful, demonstrating that atrasentan reduces albuminuria in a mouse model of IgA nephropathy.

What is claimed:

1. A method of improving kidney function in a subject in need thereof,
   comprising administering to the subject a therapeutically effective amount of atrasentan, or a pharmaceutically acceptable salt thereof;
   wherein the subject has been previously diagnosed with IgA nephropathy; and
   wherein the diagnosis of IgA nephropathy comprises a kidney biopsy, detecting anti-glycan antibodies, detecting deposition of IgA-immune complexes in the kidney, or a combination of any of the foregoing.

2. The method of claim 1, wherein the therapeutically effective amount of atrasentan, or a pharmaceutically acceptable salt thereof, is from about 0.20 mg to about 1.5 mg of atrasentan, or an equivalent amount of a pharmaceutically acceptable salt thereof.

3. The method of claim 2, wherein the therapeutically effective amount of atrasentan, or a pharmaceutically acceptable salt thereof, is from about 0.25 mg to about 1.25 mg of atrasentan, or an equivalent amount of a pharmaceutically acceptable salt thereof.

4. The method of claim 3, wherein the therapeutically effective amount of atrasentan, or a pharmaceutically acceptable salt thereof, is from about 0.40 mg to about 0.85 mg of atrasentan, or an equivalent amount of a pharmaceutically acceptable salt thereof.

5. The method of claim 4, wherein the therapeutically effective amount of atrasentan, or a pharmaceutically acceptable salt thereof, is about 0.75 mg of atrasentan, or an equivalent amount of a pharmaceutically acceptable salt thereof.

6. The method of claim 1, wherein the atrasentan is administered as a pharmaceutically acceptable salt.

7. The method of claim 6, wherein the atrasentan is administered as atrasentan hydrochloride or atrasentan mandelate.

8. The method of claim 7, wherein the atrasentan is administered as atrasentan hydrochloride.

9. The method of claim 7, wherein the atrasentan is administered as atrasentan mandelate.

10. The method of claim 1, wherein the atrasentan is administered as the free base.

11. The method of claim 1, wherein the subject is excreting an average of about 0.5 grams or more of protein in the urine per day for at least about 3 months prior to the first administration of atrasentan, or a pharmaceutically acceptable salt thereof.

12. The method of claim 11, wherein the subject is excreting an average of about 0.3 grams to 2.0 grams of protein in the urine per day for at least about 3 months prior to the first administration of atrasentan, or a pharmaceutically acceptable salt thereof.

13. The method of claim 11, wherein the subject is excreting an average of about 0.5 grams to 1.5 grams of protein in the urine per day for at least about 3 months prior to the first administration of atrasentan, or a pharmaceutically acceptable salt thereof.

14. The method of claim 11, wherein the subject is excreting an average of about 0.75 grams to 1.5 grams of protein in the urine per day for at least about 3 months prior to the first administration of atrasentan, or a pharmaceutically acceptable salt thereof.

15. The method of claim 1, wherein the subject has an average eGFR of about 20 to about 90 mL/min/1.73 m$^2$ for at least about 3 months prior to the first administration of atrasentan, or a pharmaceutically acceptable salt thereof.

16. The method of claim 15, wherein the subject has an average eGFR of about 30 to about 90 mL/min/1.73 m$^2$ for at least about 3 months prior to the first administration of atrasentan, or a pharmaceutically acceptable salt thereof.

17. The method of claim 15, wherein the subject has an average eGFR of about 20 to about 60 mL/min/1.73 m$^2$ for at least about 3 months prior to the first administration of atrasentan, or a pharmaceutically acceptable salt thereof.

18. The method of claim 11, wherein the therapeutically effective amount of atrasentan, or a pharmaceutically acceptable salt thereof, is from about 0.20 mg to about 1.5 mg of atrasentan, or an equivalent amount of a pharmaceutically acceptable salt thereof.

19. The method of claim 18, wherein the therapeutically effective amount of atrasentan, or a pharmaceutically acceptable salt thereof, is from about 0.25 mg to about 1.25 mg of atrasentan, or an equivalent amount of a pharmaceutically acceptable salt thereof.

20. The method of claim 19, wherein the therapeutically effective amount of atrasentan, or a pharmaceutically acceptable salt thereof, is from about 0.40 mg to about 0.85 mg of atrasentan, or an equivalent amount of a pharmaceutically acceptable salt thereof.

21. The method of claim 20, wherein the therapeutically effective amount of atrasentan, or a pharmaceutically acceptable salt thereof, is about 0.75 mg of atrasentan, or an equivalent amount of a pharmaceutically acceptable salt thereof.

22. The method of claim 18, wherein the atrasentan is administered as a pharmaceutically acceptable salt.

23. The method of claim 22, wherein the atrasentan is administered as atrasentan hydrochloride or atrasentan mandelate.

24. The method of claim 18, wherein the atrasentan is administered as the free base.

25. The method of claim 15, wherein the therapeutically effective amount of atrasentan, or a pharmaceutically acceptable salt thereof, is from about 0.20 mg to about 1.5 mg of atrasentan, or an equivalent amount of a pharmaceutically acceptable salt thereof.

26. The method of claim 25, wherein the therapeutically effective amount of atrasentan, or a pharmaceutically acceptable salt thereof, is from about 0.25 mg to about 1.25 mg of atrasentan, or an equivalent amount of a pharmaceutically acceptable salt thereof.

27. The method of claim 26, wherein the therapeutically effective amount of atrasentan, or a pharmaceutically acceptable salt thereof, is from about 0.40 mg to about 0.85 mg of atrasentan, or an equivalent amount of a pharmaceutically acceptable salt thereof.

28. The method of claim 27, wherein the therapeutically effective amount of atrasentan, or a pharmaceutically acceptable salt thereof, is about 0.75 mg of atrasentan, or an equivalent amount of a pharmaceutically acceptable salt thereof.

29. The method of claim 25, wherein the atrasentan is administered as a pharmaceutically acceptable salt.

30. The method of claim 29, wherein the atrasentan is administered as atrasentan hydrochloride or atrasentan mandelate.

* * * * *

UNITED STATES PATENT AND TRADEMARK OFFICE
CERTIFICATE OF CORRECTION

Page 1 of 4

PATENT NO. : 11,491,137 B2
APPLICATION NO. : 17/826843
DATED : November 8, 2022
INVENTOR(S) : Philip Thomas Frohlich et al.

It is certified that error appears in the above-identified patent and that said Letters Patent is hereby corrected as shown below:

On the Title Page

Page 2, Column 1, Line 44 (Other Publications), delete "nonfanrilial" and insert -- nonfamilial --.
Page 2, Column 2, Line 40 (Other Publications), delete "Acession" and insert -- Accession --.
Page 3, Column 1, Line 35 (Other Publications), delete "Dmg" and insert -- Drug --.
Page 3, Column 1, Line 68 (Other Publications), delete "andImmunofluorescence" and insert -- and Immunofluorescence --.
Page 3, Column 2, Line 17 (Other Publications), delete "body weight,"" and insert -- bodyweight," --.
Page 3, Column 2, Line 35 (Other Publications), delete "brain,"Nat." and insert -- brain," Nat. --.
Page 4, Column 1, Line 43 (Other Publications), delete "PCTUS2020/65311," and insert -- PCT/US2020/65311, --.
Page 4, Column 2, Line 4 (Other Publications), delete "retrived" and insert -- retrieved --.
Page 4, Column 2, Line 5 (Other Publications), delete "fromURL:" and insert -- from URL: --.
Page 4, Column 2, Line 42 (Other Publications), delete "diabetickidney" and insert -- diabetic kidney --.
Page 5, Column 1, Line 10 (Other Publications), delete "bv" and insert -- by --.

In the Drawings

Figure 9A:
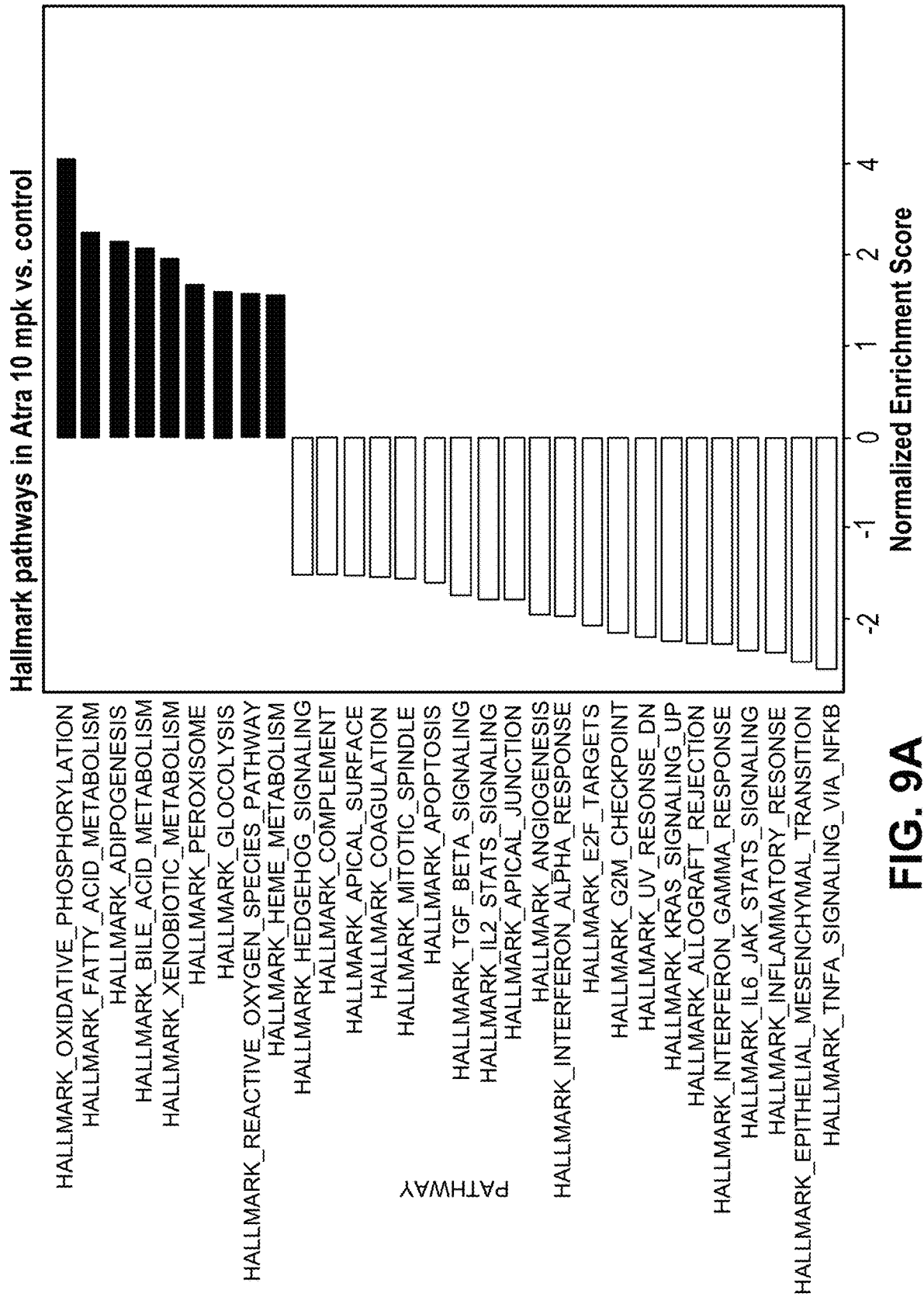
FIG. 9A illustrates the significantly enriched (FDR<0.05) hallmark gene sets following treatment of g-ddY mice with atrasentan 10 mg/kg/day compared to treatment of atrasentan at 0 mg/kg/day (control). Negative normalized enrichment score (NES) indicates under-expression and positive NES indicates over-expression.
Figure 9B:
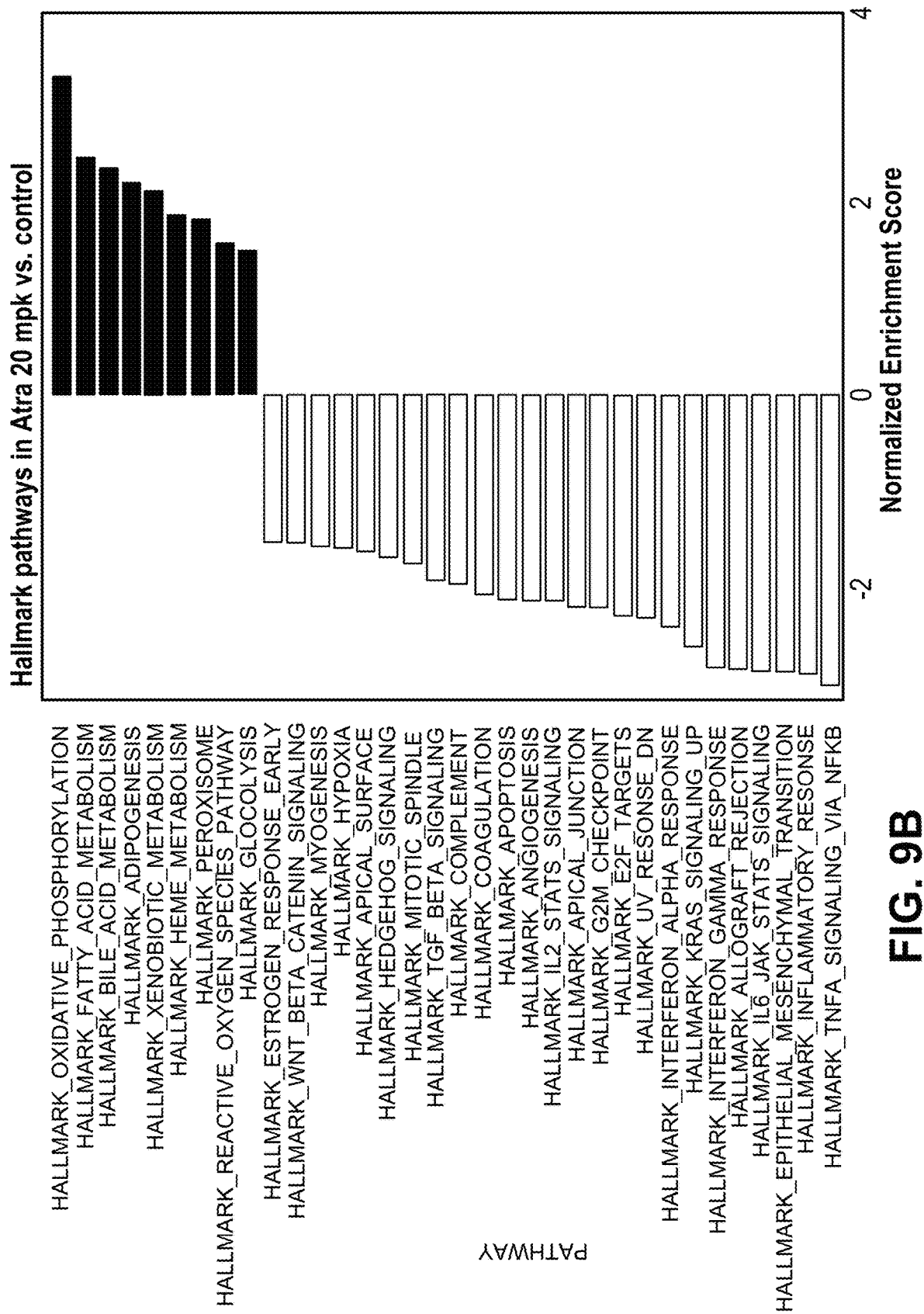
FIG. 9B illustrates the significantly enriched (FDR<0.05) hallmark gene sets following treatment of g-ddY mice with atrasentan 20 mg/kg/day compared to treatment of atrasentan at 0 mg/kg/day (control). Negative normalized enrichment score (NES) indicates under-expression and positive NES indicates over-expression.
Figure 9C:
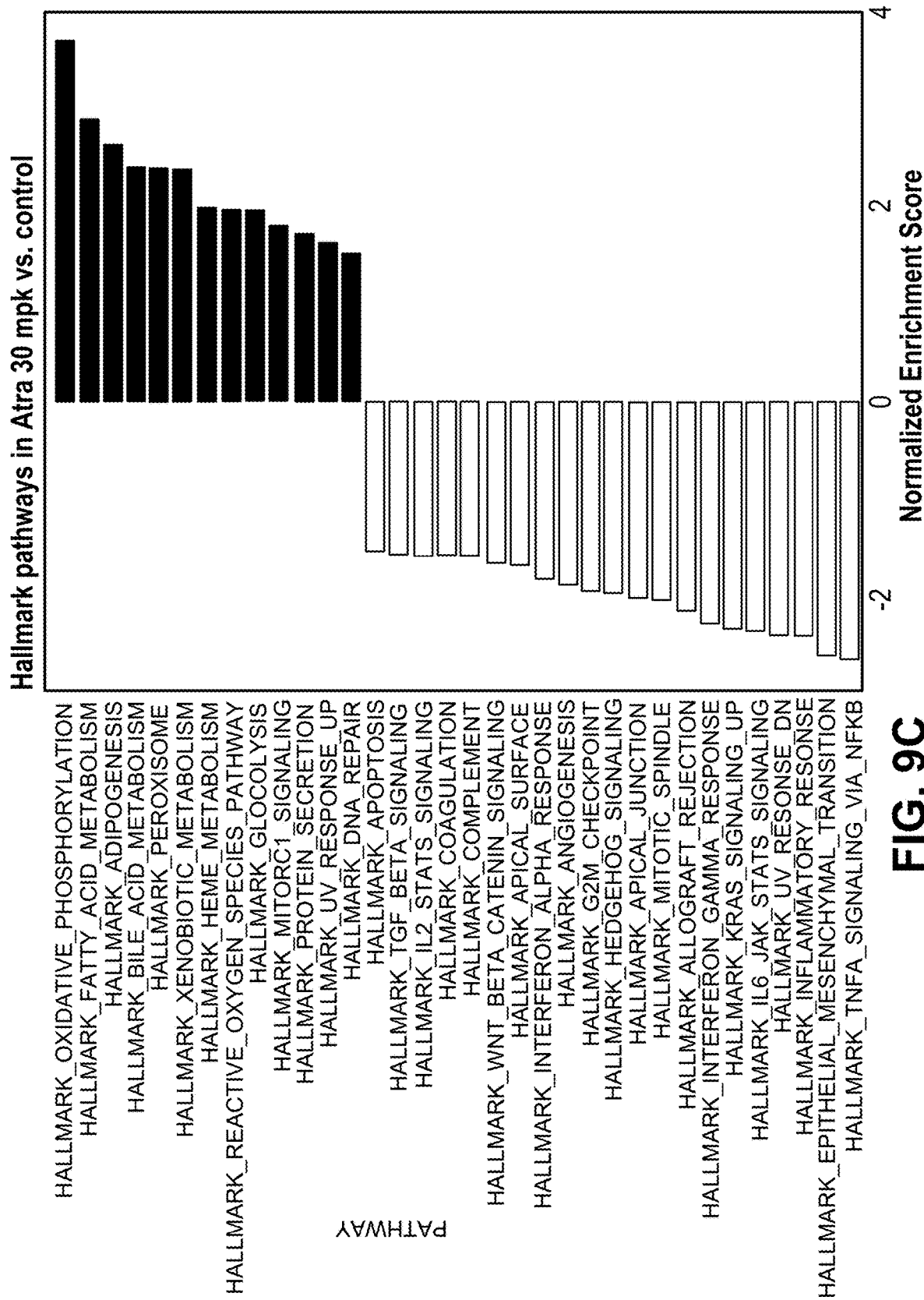
FIG. 9C illustrates the significantly enriched (FDR<0.05) hallmark gene sets following treatment of g-ddY mice with atrasentan 30 mg/kg/day compared to treatment of atrasentan at 0 mg/kg/day (control). Negative normalized enrichment score (NES) indicates under-expression and positive NES indicates over-expression.

Sheet 13 of 20, Line 8 (FIG. 9A), delete "GLOCOLYSIS" and insert -- GLYCOLYSIS --.
Sheet 13 of 20, Line 24 (FIG. 9A), delete "RESONSE" and insert -- RESPONSE --.
Sheet 13 of 20, Line 29 (FIG. 9A), delete "RESONSE" and insert -- RESPONSE --.
Sheet 14 of 20, Line 10 (FIG. 9B), delete "GLOCOLYSIS" and insert -- GLYCOLYSIS --.
Sheet 14 of 20, Line 27 (FIG. 9B), delete "RESONSE" and insert -- RESPONSE --.
Sheet 14 of 20, Line 34 (FIG. 9B), delete "RESONSE" and insert -- RESPONSE --.
Sheet 15 of 20, Line 10 (FIG. 9C), delete "GLOCOLYSIS" and insert -- GLYCOLYSIS --.
Sheet 15 of 20, Line 32 (FIG. 9C), delete "RESONSE" and insert -- RESPONSE --.
Sheet 15 of 20, Line 33 (FIG. 9C), delete "RESONSE" and insert -- RESPONSE --.
Sheet 19 of 20, Line 5 (FIG. 12A), delete "crystallin lamda" and insert -- crystallin lambda --.

Signed and Sealed this
Seventh Day of March, 2023

Katherine Kelly Vidal
*Director of the United States Patent and Trademark Office*

CERTIFICATE OF CORRECTION (continued)
U.S. Pat. No. 11,491,137 B2

In the Specification

Column 1, Line 61, delete "107s-111" and insert -- 107s-111s --.
Column 3, Line 9, delete "PLA2G4 Å," and insert -- PLA2G4A, --.
Column 3, Line 26, delete "thereof," and insert -- thereof; --.
Column 3, Line 59, delete "thereof," and insert -- thereof; --.
Column 6, Line 49, delete "log 2" and insert -- log2 --.
Column 6, Line 59, delete "log 2 (CPM)" and insert -- log2(CPM) --.
Column 6, Line 62, below "mg/kg/day." insert -- SUMMARY OF TABLES --.
Column 11, Line 60, delete "ERKT1/2," and insert -- ERK1/2, --.
Column 12, Line 16, delete "(STEGLATRO™)" and insert -- (STEGLATRO™), --.
Column 15, Line 28, delete ""microalbuminuria")" and insert -- "macroalbuminuria") --.
Column 32, Line 40, delete "fosenopril," and insert -- fosinopril, --.
Column 34, Lines 33-34, delete "trichloromethiazide," and insert -- trichlormethiazide, --.
Column 34, Line 35, delete "methylclothiazide" and insert -- methyclothiazide --.
Column 34, Line 36, delete "bemetanide," and insert -- bumetanide, --.
Column 34, Line 44, delete "fosenopril," and insert -- fosinopril, --.
Column 42, Line 18, delete "450%," and insert -- 450%, --.
Column 43, Line 47, delete "day" and insert -- days --.
Column 46, Line 28, delete "PLA2G4 Å," and insert -- PLA2G4A, --.
Column 47, Line 18, delete "mesanial" and insert -- mesangial --.
Column 47, Line 51, delete "the the" and insert -- the --.

Column 54, Lines 27-41, delete " 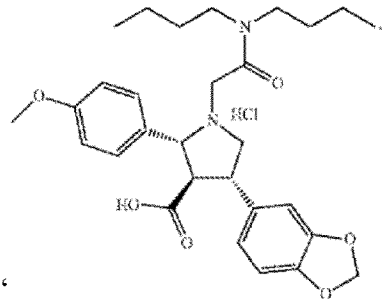 " insert
-- 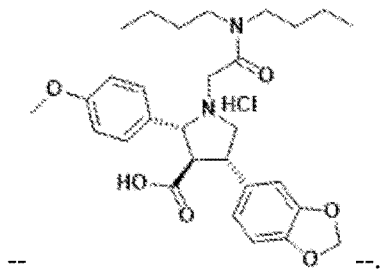 --.

Column 55, Line 47, delete "Cu-Ku" and insert -- Cu-Kα --.
Column 55, Line 49, delete "20" and insert -- 2θ --.
Column 55, Line 66, delete "20," and insert -- 2θ, --.
Column 55, Line 67, delete "Cu-Ku" and insert -- Cu-Kα --.
Column 56, Line 41, delete "22.050" and insert -- 22.05° --.
Column 56, Line 48, delete "Cu-Ku" and insert -- Cu-Kα --.
Column 56, Line 50, delete "22.050" and insert -- 22.05° --.
Column 56, Line 58, delete "22.050" and insert -- 22.05° --.

CERTIFICATE OF CORRECTION (continued)
U.S. Pat. No. 11,491,137 B2

Column 57, Line 14, delete "21.950" and insert -- 21.95° --.
Column 57, Line 21, delete "Cu-Ku" and insert -- Cu-Kα --.
Column 57, Line 23, delete "21.950" and insert -- 21.95° --.
Column 57, Line 31, delete "21.950" and insert -- 21.95° --.
Column 59, Line 8, delete "Kul" and insert -- Kα1 --.
Column 59, Line 12, delete "Kul" and insert -- Kα1 --.
Column 59, Line 54, delete "Kul" and insert -- Kα1 --.
Column 59, Line 58, delete "Kul" and insert -- Kα1 --.
Column 64, Line 23, delete "form2." and insert -- form 2. --.
Column 66, Lines 8-9, delete "hydroxymethylpropylcellulose, hydroxymethylpropylcellulose," and insert -- hydroxymethylpropylcellulose, hydroxyethylpropylcellulose, --.
Column 66, Line 12, delete "hydroxymethylpropylcellulose." and insert -- hydroxyethylpropylcellulose. --.
Column 66, Lines 24-25, delete "hydroxymethylpropylcellulose, hydroxymethylpropylcellulose," and insert -- hydroxymethylpropylcellulose, hydroxyethylpropylcellulose, --.
Column 66, Line 25, delete "hydroxypropylcellulose" and insert -- hydroxypropylcellulose. --.
Column 66, Lines 40-41, delete "hydroxymethylpropylcellulose, hydroxymethylpropylcellulose," and insert -- hydroxymethylpropylcellulose, hydroxyethylpropylcellulose, --.
Column 66, Lines 41-42, delete "hydroxypropylcellulose;" and insert -- hydroxypropylcellulose. --.
Column 76, Line 45 (Approx.), delete "91.305" and insert -- 91.05 --.
Column 78, Lines 63-64 (Approx.), above "The" delete "dBased on a 120 mg tablet weight with a coating weight gain of 3%.".
Column 81, Line 54 (Approx.), delete "bemetanide" and insert -- bumetanide --.
Column 81, Line 57 (Approx.), delete "HYDRODIURIL™)" and insert -- HYDRODIURIL™), --.
Column 81, Line 66, delete "trichloromethiazide," and insert -- trichlormethiazide, --.
Column 82, Line 14, delete "VASOTEC™)" and insert -- VASOTEC™), --.
Column 82, Lines 15-16, delete "fosenopril" and insert -- fosinopril --.
Column 82, Line 26, delete "fosenopril," and insert -- fosinopril, --.
Column 82, Line 35, delete "BENICAR™)" and insert -- BENICAR™), --.
Column 82, Line 36, delete "MICARDIS™)" and insert -- MICARDIS™), --.
Column 82-83, Line 67, delete "CARDURA™)" and insert -- CARDURA™), --.
Column 83, Lines 5-6, delete "BLOCARDEN™)" and insert -- BLOCARDEN™), --.
Column 83, Line 9, delete "KERLONE™)" and insert -- KERLONE™), --.
Column 83, Lines 21-22, delete "CATAPRES-TTS™)" and insert -- CATAPRES-TTS™), --.
Column 83, Line 42, delete "HUMALIN" and insert -- HUMULIN --.
Column 83, Line 42, delete "HUMALIN" and insert -- HUMULIN --.
Column 83, Line 42, delete "HUMALIN" and insert -- HUMULIN --.
Column 83, Line 43, delete "HUMALIN" and insert -- HUMULIN --.
Column 83, Line 43, delete "HUMALIN" and insert -- HUMULIN --.
Column 83, Line 43, delete "HUMALIN" and insert -- HUMULIN --.
Column 83, Line 45, delete "NOVILIN" and insert -- NOVOLIN --.
Column 83, Line 46, delete "NOVILIN" and insert -- NOVOLIN --.
Column 84, Line 18, delete "LESCOL™)" and insert -- LESCOL™), --.
Column 84, Line 19, delete "MEVACOR™)" and insert -- MEVACOR™), --.
Column 84, Line 44, delete "cemdisiram)." and insert -- cemdisiran). --.
Column 84, Line 62, delete "serfliflozin, licofliglozin," and insert -- sergliflozin, licogliflozin, --.

CERTIFICATE OF CORRECTION (continued)
U.S. Pat. No. 11,491,137 B2

Column 85, Line 7, delete "serfliflozin." and insert -- sergliflozin. --.
Column 85, Line 8, delete "licofliglozin." and insert -- licogliflozin. --.
Column 87, Lines 2-3, delete "fosenopril," and insert -- fosinopril, --.
Column 90, Line 5, delete "of Embodiment" and insert -- of Embodiments --.
Column 90, Lines 20-21, delete "alcineurin" and insert -- calcineurin --.
Column 90, Line 58, delete "thereof," and insert -- thereof; --.
Column 91, Line 21, delete "trichloromethiazide," and insert -- trichlormethiazide, --.
Column 91, Line 23, delete "methylclothiazide" and insert -- methyclothiazide --.
Column 91, Line 23, delete "bemetanide," and insert -- bumetanide, --.
Column 91, Line 29, delete "fosenopril," and insert -- fosinopril, --.
Column 94, Line 1, delete "day" and insert -- days --.
Column 96, Lines 4-5, delete "serfliflozin, licofliglozin," and insert -- sergliflozin, licogliflozin, --.
Column 97, Line 48, delete "of Embodiment" and insert -- of Embodiments --.
Column 98, Line 20, delete "ERKT1/2," and insert -- ERK1/2, --.
Column 101, Lines 55-56, delete "serfliflozin, licofliglozin," and insert -- sergliflozin, licogliflozin, --.
Column 108, Line 7, delete "subjects" and insert -- subjects. --.
Column 108, Line 62, delete "agents" and insert -- agents. --.
Column 109, Line 10, delete "screening" and insert -- screening. --.
Column 111, Line 31, delete "received" and insert -- received. --.
Column 111, Line 36, delete "received" and insert -- received. --.
Column 121, Line 15, delete "NextSeq500" and insert -- NextSeq 500 --.
Column 121, Line 64, delete "log FC" and insert -- logFC --.
Column 124, Line 4, delete "WNT3 Å," and insert -- WNT3A, --.
Column 124, Line 5, delete "(IL1 Å," and insert -- (IL1A, --.
Column 125, Line 2, delete "PLA2G4 Å," and insert -- PLA2G4A, --.
Column 125, Line 13 (Approx.), delete "PLA2G4 Å," and insert -- PLA2G4A, --.
Column 125, Line 44, delete "KMT5 Å," and insert -- KMT5A, --.
Column 126, Lines 50-51, delete "(log 2 (CPM))" and insert -- (log2(CPM)) --.
Column 129, Line 1 (Table 4), delete "emiched" and insert -- enriched --.
Column 129, Line 15 (Table 4), delete "(Eukalyotic)" and insert -- (Eukaryotic) --.
Column 130, Line 15 (Table 4-continued), delete "emiched" and insert -- enriched --.
Column 131-132, Line 11 (Table 5), delete "HALLMARK_ ADIPOGENESIS" and insert
-- HALLMARK_ADIPOGENESIS --.
Column 131-132, Line 28 (Table 5), delete "HALLMARK_ ESTROGEN_" and insert
-- HALLMARK_ESTROGEN_ --.
Column 131-132, Line 39 (Table 5), delete "HYPDXIA" and insert -- HYPOXIA --.